United States Patent
Squire et al.

(10) Patent No.: US 11,807,671 B2
(45) Date of Patent: Nov. 7, 2023

(54) METHODS FOR PROTEIN LIGATION AND USES THEREOF

(71) Applicant: AUCKLAND UNISERVICES LIMITED, Auckland (NZ)

(72) Inventors: Christopher John Squire, Auckland (NZ); Edward Neill Baker, Auckland (NZ); Paul Gary Young, Auckland (NZ); Yuliana Yosaatmadja, Auckland (NZ)

(73) Assignee: AUCKLAND UNISERVICES LIMITED, Auckland (NZ)

( * ) Notice: Subject to any disclaimer, the term of this patent is extended or adjusted under 35 U.S.C. 154(b) by 0 days.

(21) Appl. No.: 16/349,674

(22) PCT Filed: Nov. 16, 2017

(86) PCT No.: PCT/NZ2017/050147
§ 371 (c)(1),
(2) Date: May 14, 2019

(87) PCT Pub. No.: WO2018/093274
PCT Pub. Date: May 24, 2018

(65) Prior Publication Data
US 2019/0352343 A1    Nov. 21, 2019

(30) Foreign Application Priority Data
Nov. 16, 2016    (NZ) ........................ 726413

(51) Int. Cl.
*C07K 14/33* (2006.01)
*C07K 14/195* (2006.01)

(52) U.S. Cl.
CPC ............ *C07K 14/33* (2013.01); *C07K 14/195* (2013.01); *C07K 2319/21* (2013.01); *C07K 2319/24* (2013.01); *C07K 2319/50* (2013.01)

(58) Field of Classification Search
CPC .......... A61K 38/00; A61K 2039/55516; A61K 38/02; A61K 47/65; A61K 8/37; C07K 2319/50; C07K 1/306; C07K 1/1075; C07K 1/1136; C07K 2317/34; C07K 5/06069; C07K 5/081; C07K 7/04; C12N 2533/50
See application file for complete search history.

(56) References Cited

FOREIGN PATENT DOCUMENTS

WO    WO2002039268 A2  *  4/2002
WO    2011098772 A1        8/2011

OTHER PUBLICATIONS

Kwon et al. Autocatalytically generated Thr-Gln ester bond crosslinks stabilize the repetitive Ig-domain shaft of a bacterial cell surface adhesin. Proc Natl Acad Sci U S A. Jan. 28, 2014;111(4):1367-72. (Year: 2014).*
Zakeri et al. Peptide tag forming a rapid covalent bond to a protein, through engineering a bacterial adhesin. Proc Natl Acad Sci U S A. Mar. 20, 2012; 109(12): E690-E697. (Year: 2012).*
Kwon et al. Chain A, Putative Surface Anchored Protein. Feb. 12, 2014. https://www.ncbi.nlm.nih.gov/protein/4MKM_A. (Year: 2014).*
Proschel et al. Engineering of metabolic pathways by artificial enzyme channels. Front. Bioeng. Biotechnol. 2015; 3:168. (Year: 2015).*
Kang et al. Stabilizing Isopeptide Bonds Revealed in Gram-Positive Bacterial Pilus Structure. Science. Dec. 7, 2007;318(5856):1625-8. (Year: 2007).*
Kwon et al. "Autocatalytically generated Thr-Gln ester bond cross-links stabilizethe repetitive Ig-domain shaft of a bacterial cell surface adhesin." Proceedings of the National Academy of Sciences 2014, 111(4), 1367-1372.
Proschel et al. "Engineering of metabolic pathways by artificial enzyme channels." Frontiers in Bioengineering and Biotechnology. Oct. 21, 2015, 3 (168), 13 pages.
Horn et al. "Synthetic protein scaffolds based on peptide motifs and cognate adaptor domains for improving metabolic productivity", Frontiers in Bioengineering and Biotechnology. Nov. 23, 2015, 3(191), 7 pages.
Baker et al. "Self-generated covalent cross-links in the cell-surface adhesins of gram-positive bacteria." Biochemical Society Transactions. 2015, 43(5), 787-794.
Veggiani al. "programmable polyproteams built using twin peptide superglues." Proceedings of the National Academy of Sciences. Feb. 2, 2016, 113(5), 1202-1207.
Young et al. "Harnessing ester bond chemistry for protein ligation." Chemical Communications. 2017 53, 1502-1502.
International Search Report and Written Opinion in corresponding International Patent Application No. PCT/NZ2017/050147 dated Mar. 2, 2018. 15 pages.

(Continued)

*Primary Examiner* — Sudhakar Katakam
(74) *Attorney, Agent, or Firm* — Leason Ellis LLP

(57) ABSTRACT

The invention relates to protein ligation technologies, purified or recombinant peptides, methods for making peptides and proteins with covalent bonds including reversible covalent bonds such as reversible intermolecular covalent bonds, and uses thereof. In particular, this invention relates to intermolecular ester bonds, particularly reversible ester bonds between the hydroxyl and amide groups of amino acid side chains present in recombinant chimeric peptides and proteins and the use of such peptides and proteins in protein engineering, for example in the preparation of multimeric protein complexes, including functionalised multimeric protein complexes.

15 Claims, 28 Drawing Sheets

Specification includes a Sequence Listing.

(56) References Cited

OTHER PUBLICATIONS

International Preliminary Report on Patentability in corresponding International Patent Application No. PCT/NZ2017/050147 dated May 21, 2019. 9 pages.

Lee et al., "Spatial organization of enzymes for metabolic engineering", Metabolic Engineering 14 (2012) 242-251.

Chen et al., "Biomolecular scaffolds for enhanced signaling and catalytic efficiency", Current Opinion Biotechnology 2014, 28, 59-68.

Ting et al., "Expression, purification and crystallization of a membrane-associated, catalytically active type I signal peptidase from *Staphylococcus aureus*", Acta crystallographica, Section F. Structural biology communications 2015, 71, 61-65.

Wu et al., "Rapid pulse length determination in high-resolution NMR". Journal of Magnetic Resonance, 2005, 176, 115.

\* cited by examiner

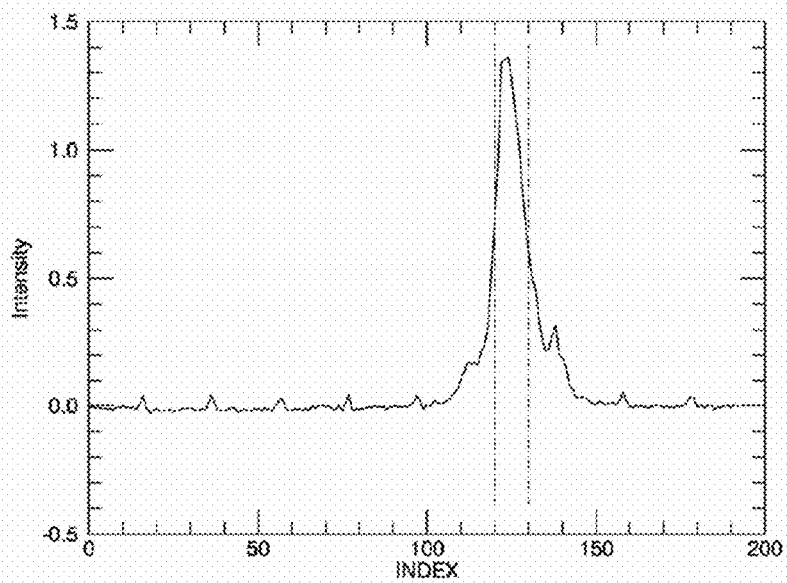
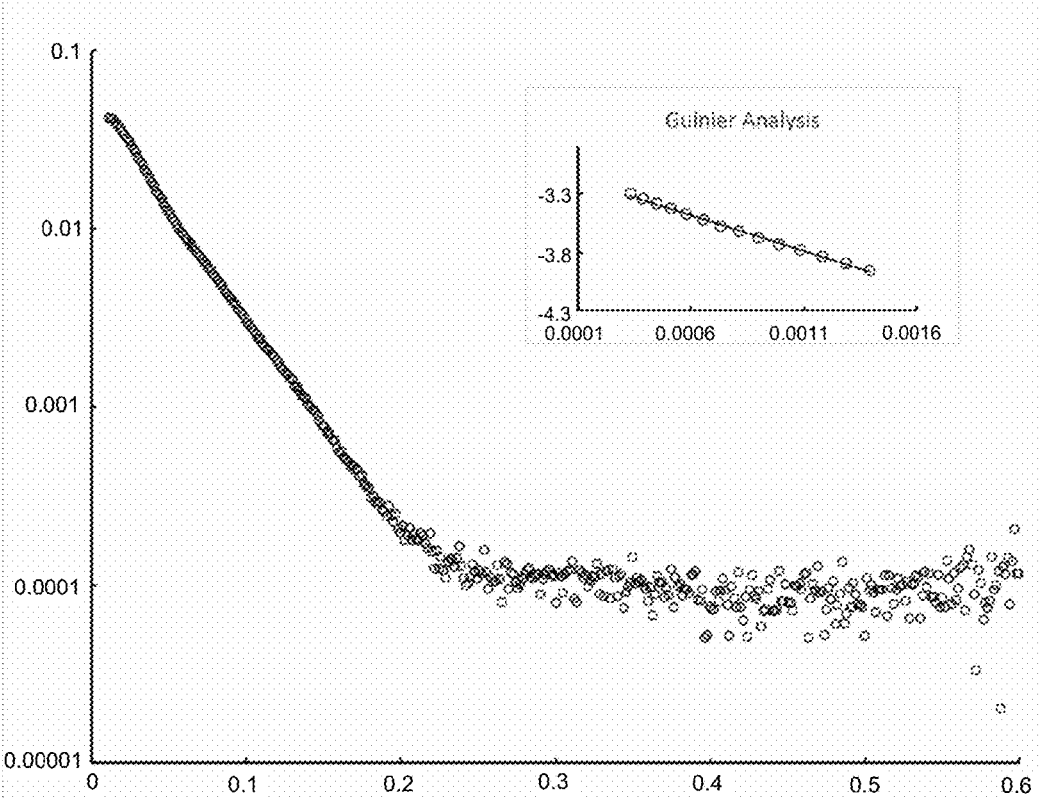
Figure 14

```
MOL10     --------HNPGITTTLTDAQAAKGTDGK--VISLTRDAQLKDVVRVIQTGLI-EGAKYH-
MOL4      ----------GGLKTKAVDAADEN-------QAMVPGQKSAAVVDTVTFNGRFEKSHSYT-
MOL6      ----------PSLRTLATVNGAKV-------IQMKKDSKENLTVIDQITWANLA-PGT-YT-
MOL9      -------GTSPSLKTVL-SADGKREWVENNTNIPTVPHASDSLIDTVLYTGLT-EGVSYR-
MOL11     ---------APKIGTTLKYGQSKTVWVADKVE-----------LIDTVEYFNLQ-PKTKYT-
MOL8      ----------PSVKTQARVDSERNL---------LLADKDSTIKDTVTLSGLK-TGETYV-
MOL7      --------SLDTTATDA--ADGNKH---------ADNAAAVTINDKVDYSGLN-LAATYPD
MOL3      ----------PGVTTDATDGDGDKY---------VDSSQNFTIKDTVIATGLI-PGKTYD-
MOL5      EVEITTTAYDGAAGDKSDPKDKNL---------DASKETVIIYDQVDYKGLN-VGEEYT-
                 :   .                              :    .       *

MOL10     --------VFSKLVNQANPDQVVSAGMQEFT----------------------ATGDQLRSV
MOL4      --------LVGELHYVNGTVV-PGTKTE------------------------TKTFQSDQDGAIAAQ
MOL6      --------LEGSLMEVKDGQLVSNTP-VAKGQTQ---KV--------EVAAGKAGATTSTGEA
MOL9      --------LDAKLMEINPVTG-----KVSET-PVAT-----------GYTEFIAKTSDGTA
MOL11     --------LSGNLMGGTSAESLSDTGVKATT-EFTT-----------PAAANGAQTVSGTA
MOL8      --------LSGVLMDKATGQPVLGKDMQAIT-AV-------------SEPLKAESGAFVKTD
MOL7      GTLKAYLVRGELMDKATGKPVAGVAPVERVIGAANSVYRVGD--QNRPVEEEITSGAGSV
MOL3      --------VSGELMVDNGTP-QGATTGIKQTGTI-------------TA-----KADGTGET
MOL5      --------ITGTLHYQADAT-LADGTQVKRGDEVPAQYVNVTPVKITANKASSDESGAVKA
                 :   .  *

MOL10     TVKFTVPKETLQELAGSDPSAEFKLVAYEYLALDSDTDIVNKEATSEIEAVGFKTG---K
MOL4      KMTFTVPAEYI----K----AGQNMVVFEKLFDAK----------------KKDGTPV-
MOL6      QMTFKLPVDKV----K----SGSQFVVYQILKDKS----------------GQVV-
MOL9      QVTFNGITGKL----K----AGYKYVAYEKMTRP-----------------GQPDK
MOL11     VVKFTVPREVL----E----RNEKLVAYEYLTID-----------------GNPV-
MOL8      AVSFTVPAGTV----K----ADTELVVFEKLWVANEVTVDTKTKTVTPKDTKTGKSQPA-
MOL7      VLSFQVPAK-----LT----QGKVLVAFETVYEE-----------------GREF-
MOL3      VLEFPVTAQQAQDLGL----VGKPIVVFEDLSLD-----------------GKKV-
MOL5      IVKF-----EVQKTAL----ATAPVVVFETLYQG-----------------TVEV-
             : *                   *.:: :

MOL10     TWAATHADPNDAGQTVTVVK
MOL4      ---ASHEDPNDPDQTITVQ-
MOL6      ---ATHADPKSDDQTVTVG-
MOL9      PVPPPHEDPKDPNQTVVSE-
MOL11     ---ASHEDPKDENQTVTSKK
MOL8      ---ASHEDITDENQTVKS--
MOL7      ---LIHHDINDDAQTVYT--
MOL3      ---AVHHDIKDEKQTVYN--
MOL5      ---ATHQDIDDGSQVVYH--
             *  *  .  *.:
```

Figure 19

Mol7a

*MSYYHHHHHHDYDIPTTENLYFQ*GAVGSLDTTATDAADGNKHADNAAAVTINDKVDY
SGLNLAATYPDGTLKAYLVRGELMDKATGKPVAGVAPVERVIGAANSVYRVGDQNRP
VEEEITSGAGSVVLSFQVPAKLTQGKVLVAFETVYEE*

Mol8

*MSYYHHHHHHDYDIPTTENLYFQ*GAGREFLIHHDINDDAQTVYTPSVKTQARVDSER
NLLLADKDSTIKDTVTLSGLKTGETYVLSGVLMDKATGQPVLGKDMQAITAVSEPLK
AESGAFVKTDAVSFTVPAGTVKADTELVVFEKLWVANEVTVDAKTKTVTPKDTK*

Mol9

*MSYYHHHHHHDYDIPTTENLYFQ*GAGKSQPAASHEDITDENQTVKSGTSPSLKTVLS
ADGKREWVENNTNIPTVPHASDSLIDTVLYTGLTEGVSYRLDAKLMEINPVTGKVSE
TPVATGYTEFTAKTSDGTAQVTFNGITGKLKAGYKYVAYEKMTRPG*

Mol10

*MSYYHHHHHHDYDIPTTENLYFQ*GAPDKPVPPPHEDPKDPNQTVVSEHNPGITTTLT
DAQAAKGTDGKVISLTRDAQLKDVVRVTQTGLIEGAKYHVFSKLVNQANPDQVVSAG
MQEFTATGDQLRSVTVKFTVPKETLQELAGSDPSAEFKLVAYEYLALDSDTDIVNKE
ATSEIEAVGFK*

Mol11

*MSYYHHHHHHDYDIPTTENLYFQ*GAGKTWAATHADPNDAGQTVTVVKAPKIGTTLKY
GQSKTVWVADKVELTDTVEYFNLQPKTKYTLSGNLMGGTSAESLSDTGVKATTEFTT
PAAANGAQTVSGTAVVKFTVPREVLERNEKLVAYEYLTIDGNPVASHEDPKDENQTV
TSKKP*

Figure 23

Cpe2-HL-Mo17b
*MSYYHHHHHHDYDIPTTENLYFQ*<u>GANLPEVKDGTLRTTVIADGVNGSSEKEALVSFE
NSKDGVDVKDTINYEGLVANQNYTLTGTLMHVKADGSLEEIATKTTNVTAGENGNGT
WGLDFGNQKLQVGEKYVVFENAESVENLIDTDKDYN</u>*SHGKAEAAAKEAAAKEAAAKE
AAAKEAAAKAAAPTSA*GQVVATHADPKSDDQTVTVGSLDTTATDAADGNKHADNAAA
VTINDKVDYSGLNLAATYPDGTLKAYLVRGELMDKATGKPVAGVAPVERVIGAANSV
YRVGDQNRPVEEEITSGAGSVVLSFQVPAKLTQGKVLVAFETVYEE

Cpe2-HL-Mo18
*MSYYHHHHHHDYDIPTTENLYFQ*<u>GANLPEVKDGTLRTTVIADGVNGSSEKEALVSFE
NSKDGVDVKDTINYEGLVANQNYTLTGTLMHVKADGSLEEIATKTTNVTAGENGNGT
WGLDFGNQKLQVGEKYVVFENAESVENLIDTDKDYN</u>*SHGKAEAAAKEAAAKEAAAKE
AAAKEAAAKAAAPTSA*GREFLIHHDINDDAQTVYTPSVKTQARVDSERNLLLADKDS
TIKDTVTLSGLKTGETYVLSGVLMDKATGQPVLGKDMQAITAVSEPLKAESGAFVKT
DAVSFTVPAGTVKADTELVVFEKLWVANEVTVDAKTKTVTPKDTK

Cpe2-HL-Mo19
*MSYYHHHHHHDYDIPTTENLYFQ*<u>GANLPEVKDGTLRTTVIADGVNGSSEKEALVSFE
NSKDGVDVKDTINYEGLVANQNYTLTGTLMHVKADGSLEEIATKTTNVTAGENGNGT
WGLDFGNQKLQVGEKYVVFENAESVENLIDTDKDYN</u>*SHGKAEAAAKEAAAKEAAAKE
AAAKEAAAKAAAPTSA*GKSQPAASHEDITDENQTVKSGTSPSLKTVLSADGKREWVE
NNTNIPTVPHASDSLIDTVLYTGLTEGVSYRLDAKLMEINPVTGKVSETPVATGYTE
FTAKTSDGTAQVTFNGITGKLKAGYKYVAYEKMTRPG

CpeC2-HL-Mo110
*MSYYHHHHHHDYDIPTTENLYFQ*<u>GANLPEVKDGTLRTTVIADGVNGSSEKEALVSFE
NSKDGVDVKDTINYEGLVANQNYTLTGTLMHVKADGSLEEIATKTTNVTAGENGNGT
WGLDFGNQKLQVGEKYVVFENAESVENLIDTDKDYN</u>*SHGKAEAAAKEAAAKEAAAKE
AAAKEAAAKAAAPTSA*PDKPVPPHEDPKDPNQTVVSEHNPGITTTLTDAQAAKGTD
GKVISLTRDAQLKDVVRVTQTGLIEGAKYHVFSKLVNQANPDQVVSAGMQEFTATGD
QLRSVTVKFTVPKETLQELAGSDPSAEFKLVAYEYLALDSDTDIVNKEATSEIEAVG
FK

JT-Mo111
*MSYYHHHHHHDYDIPTTENLYFQ*GAGKTWAATHADPNDAGQTVTVVKAPKIGTTLKY
GQSKTVWVADKVELTDTVEYFNLQPKTKYTLSGNLMGGTSAESLSDTGVKATTEFTT
PAAANGAQTVSGTAVVKFTVPREVLERNEKLVAYEYLTIDGNPVASHEDPKDENQTV
TSKKP

Figure 28

C2pept-T1
*MSYYHHHHHHDYDIPTTENLYFQ*GADTKQVVKHEDKNDKAQTLVVEKPTGSGSGAET
VVNGAKLTVTKNLDLVNSNALIPNTDFTFKIEPDTTVNEDGNKFKGVALNTPMTKVT
YTNSDKGGSNTKTAEFDFSEVTFEKPGVYYYKVTEEKIDKVPGVSYDTTSYTVQVHV
LWNEEQQKPVATYIVGYKEGSKVPIQFKNSLDSTTLTVKKKVSGTGGDRSKDFNFGL
TLKANQYYKASEKVMIEKTTKGGQAPVQTEASIDQLYHFTLKDGESIKVTNLPVGVD
YVVTEDDYKSEKYTTNVEVSPQDGAVKNIAGNSTEQETSTDKDMTITFTNKKFE

C2pept-T3.2
*MSYYHHHHHHDYDIPTTENLYFQ*GADTKQVVKHEDKNDKAQTLVVEKPTGSGSGAET
AGVSENAKLIVKKTFDSYTDNEVLMPKADYTFKVEADSTASGKTKDGLEIKPGIVNG
LTEQIISYTNTDKPDSKVKSTEFDFSKVVFPGIGVYRYIVSEKQGDVEGITYDTKKW
TVDVYVGNKEGGGFEPKFIVSKEQGTDVKKPVNFNNSFATTSLKVKKNVSGNTGELQ
KEFDFTLTLNESTNFKKDQIVSLQKGNEKFEVKIGTPYKFKLKNGESIQLDKLPVGI
TYKVNEMEANKDGYKTTASLKEGDGQSKMYQLDMEQKTDESADEIVVTNKRD

C2pept-T13
*MSYYHHHHHHDYDIPTTENLYFQ*GADTKQVVKHEDKNDKAQTLVVEKPTGSGSGAET
AGVVTGKTLPITKSMIYTDNEILMPKTTFTFTIEPDTTASGKTKDGLEIKSGETTGL
TTKAIVSYDNTDKESAKNKTSNFNFETVTFSGIGIYRYTVSEQNDGIEGIQYDGKKW
TVDVYVGNKEGGGFEPKYVVSKEVNSDVKKPIRFENSFKTTSLKIEKQVTGNTGELQ
KDFNFTLILEASALYEKGQVVKIIQDGQTKDVVIGQEYKFTLHDHQSIMLAKLPIGI
SYKLTEDKADGYTTTATLKEGEIDAKEYVLGNLQKTDESADEIVVTNKRD

C2pept-T18
*MSYYHHHHHHDYDIPTTENLYFQ*GADTKQVVKHEDKNDKAQTLVVEKPTGSGSGAET
AGVIDGSTLVVKKTFPSYTDDKVLMPKADYTFKVEADDNAKGKTKDGLDIKPGVIDG
LENTKTIHYGNSDKTTAKEKSVNFDFANVKFPGVGVYRYTVSEVNGNKAGIAYDSQQ
WTVDVYVVNREDGGFEAKYIVSTEGGQSDKKPVLFKNFFDTTSLKVTKKVTGNTGEH
QRSFSFTLLLTPNECFEKGQVVNILQGGETKKVVIGEEYSFTLKDKESVTLSQLPVG
IEYKVTEEDVTKDGYKTSATLKDGDVTDGYNLGDSKTTDKSTDEIVVTNKRD

Figure 29

Corio-HL-Mo17b
*MSYYHHHHHHDYDIPTTENLYFQ*GAGGEEPFVPGNGDTPSLKTTVKAASSTASSEAA
AKLTASEAAKGASVVDTIDYANLYGGKQYEVTARLMPVKDGVVTGDPLVTVTVRRTA
DLSGSGSWTVPLGTVEGLEKDTSYVVFEKAVSIDNLVDRDGDGN*SHGKAEAAAKEAA
AKEAAAKEAAAKEAAAKAAAPTSA*GQVVATHADPKSDDQTVTVGSLDTTATDAADGN
KHADNAAAVTINDKVDYSGLNLAATYPDGTLKAYLVRGELMDKATGKPVAGVAPVER
VIGAANSVYRVGDQNRPVEEEITSGAGSVVLSFQVPAKLTQGKVLVAFETVYEE

Gberg1-HL-Mo18
*MSYYHHHHHHDYDIPTTENLYFQ*GATVTDQDKYVNPKGELKTTVEADGQSSTTEKSV
EVTENKDGVKVVDTIKYKGLVEGKDYTVTGQLYEVKDGKIVGEAKATKTETKKADKD
EGNWNLDFGTVKGLEAGKSYVVYETATSLENLVDTDNDNK*SHGKAEAAAKEAAAKEA
AAKEAAAKEAAAKAAAPTSA*GREFLIHHDINDDAQTVYTPSVKTQARVDSERNLLLA
DKDSTIKDTVTLSGLKTGETYVLSGVLMDKATGQPVLGKDMQAITAVSEPLKAESGA
FVKTDAVSFTVPAGTVKADTELVVFEKLWVANEVTVDAKTKTVTPKDTK

Gberg2-HL-Mo19
*MSYYHHHHHHDYDIPTTENLYFQ*GARVTNKKIVSSLQTTVEADGQSSTAEKSAEVTE
NKDGVNVVDTIHYKGLIPKQKYEVVGILYEVKDGKLVDPNKPITISNGTGEYTVSDS
GEGEWKLNFGKIDGVEARKSYVVYEEVTSVENLVDTDNDGN*SHGKAEAAAKEAAAKE
AAAKEAAAKEAAAKAAAPTSA*GKSQPAASHEDITDENQTVKSGTSPSLKTVLSADGK
REWVENNTNIPTVPHASDSLIDTVLYTGLTEGVSYRLDAKLMEINPVTGKVSETPVA
TGYTEFTAKTSDGTAQVTFNGITGKLKAGYKYVAYEKMTRPG

CpeC2-HL-Mo110
*MSYYHHHHHHDYDIPTTENLYFQ*GANLPEVKDGTLRTTVIADGVNGSSEKEALVSFE
NSKDGVDVKDTINYEGLVANQNYTLTGTLMHVKADGSLEEIATKTTNVTAGENGNGT
WGLDFGNQKLQVGEKYVVFENAESVENLIDTKDYN*SHGKAEAAAKEAAAKEAAAKE
AAAKEAAAKAAAPTSA*PDKPVPPPHEDPKDPNQTVVSEHNPGITTTLTDAQAAKGTD
GKVISLTRDAQLKDVVRVTQTGLIEGAKYHVFSKLVNQANPDQVVSAGMQEFTATGD
QLRSVTVKFTVPKETLQELAGSDPSAEFKLVAYEYLALDSDTDIVNKEATSEIEAVG
FK

JT-Mo111
*MSYYHHHHHHDYDIPTTENLYFQ*GAGKTWAATHADPNDAGQTVTVVKAPKIGTTLKY
GQSKTVWVADKVELTDTVEYFNLQPKTKYTLSGNLMGGTSAESLSDTGVKATTEFTT
PAAANGAQTVSGTAVVKFTVPREVLERNEKLVAYEYLTIDGNPVASHEDPKDENQTV
TSKKP

Figure 33

Coriopept-GFP
*MSYYHHHHHHDYDIPTTENLYFQ*GGGDELQTGSHEDPRDSSQTVTVASDPGSGSGAM
VSKGEELFTGVVPILVELDGDVNGHKFSVSGEGEGDATYGKLTLKFICTTGKLPVPW
PTLVTTLTYGVQCFSRYPDHMKQHDFFKSAMPEGYVQERTIFFKDDGNYKTRAEVKF
EGDTLVNRIELKGIDFKEDGNILGHKLEYNYNSHNVYIMADKQKNGIKVNFKIRHNI
EDGSVQLADHYQQNTPIGDGPVLLPDNHYLSTQSALSKDPNEKRDHMVLLEFVTAAG
ITLGMDELYK

Gberg2pept-GFP
*MSYYHHHHHHDYDIPTTENLYFQ*GGGDKKHEVEHKDPKDKSQTFVVKPKTPGSGSAM
VSKGEELFTGVVPILVELDGDVNGHKFSVSGEGEGDATYGKLTLKFICTTGKLPVPW
PTLVTTLTYGVQCFSRYPDHMKQHDFFKSAMPEGYVQERTIFFKDDGNYKTRAEVKF
EGDTLVNRIELKGIDFKEDGNILGHKLEYNYNSHNVYIMADKQKNGIKVNFKIRHNI
EDGSVQLADHYQQNTPIGDGPVLLPDNHYLSTQSALSKDPNEKRDHMVLLEFVTAAG
ITLGMDELYK

Gberg1pept-GFP
*MSYYHHHHHHDYDIPTTENLYFQ*GGGDKKQEVEHKDPKDKSQTFVVKPKTPGSGSGA
MVSKGEELFTGVVPILVELDGDVNGHKFSVSGEGEGDATYGKLTLKFICTTGKLPVP
WPTLVTTLTYGVQCFSRYPDHMKQHDFFKSAMPEGYVQERTIFFKDDGNYKTRAEVK
FEGDTLVNRIELKGIDFKEDGNILGHKLEYNYNSHNVYIMADKQKNGIKVNFKIRHN
IEDGSVQLADHYQQNTPIGDGPVLLPDNHYLSTQSALSKDPNEKRDHMVLLEFVTAA
GITLGMDELYK

C2pept-GFP
*MSYYHHHHHHDYDIPTTENLYFQ*GADTKQVVKHEDKNDKAQTLVVEKPTGSGSGAMV
SKGEELFTGVVPILVELDGDVNGHKFSVSGEGEGDATYGKLTLKFICTTGKLPVPWP
TLVTTLTYGVQCFSRYPDHMKQHDFFKSAMPEGYVQERTIFFKDDGNYKTRAEVKFE
GDTLVNRIELKGIDFKEDGNILGHKLEYNYNSHNVYIMADKQKNGIKVNFKIRHNIE
DGSVQLADHYQQNTPIGDGPVLLPDNHYLSTQSALSKDPNEKRDHMVLLEFVTAAGI
TLGMDELYK

Figure 34

SEQUENCE LISTING

<160> NUMBER OF SEQ ID NOS: 58

<210> SEQ ID NO 1
<211> LENGTH: 148
<212> TYPE: PRT
<213> ORGANISM: Clostridium perfringens B str. ATCC 3626

<400> SEQUENCE: 1

Leu Pro Glu Val Lys Asp Gly Thr Leu Arg Thr Thr Val Ile Ala Asp
1               5                   10                  15

Gly Val Asn Gly Ser Ser Glu Lys Glu Ala Leu Val Ser Phe Glu Asn
            20                  25                  30

Ser Lys Asp Gly Val Asp Val Lys Asp Thr Ile Asn Tyr Glu Gly Leu
        35                  40                  45

Val Ala Asn Gln Asn Tyr Thr Leu Thr Gly Thr Leu Met His Val Lys
    50                  55                  60

Ala Asp Gly Ser Leu Glu Glu Ile Ala Thr Lys Thr Thr Asn Val Thr
65                  70                  75                  80

Ala Gly Glu Asn Gly Asn Gly Thr Trp Gly Leu Asp Phe Gly Asn Gln
                85                  90                  95

Lys Leu Gln Val Gly Glu Lys Tyr Val Val Phe Glu Asn Ala Glu Ser
            100                 105                 110

Val Glu Asn Leu Ile Asp Thr Asp Lys Asp Tyr Asn Leu Asp Thr Lys
        115                 120                 125

Gln Val Val Lys His Glu Asp Lys Asn Asp Lys Ala Gln Thr Leu Val
    130                 135                 140

Val Glu Lys Pro
145

<210> SEQ ID NO 2
<211> LENGTH: 124
<212> TYPE: PRT
<213> ORGANISM: Clostridium perfringens B str. ATCC 3626

<400> SEQUENCE: 2

Leu Pro Glu Val Lys Asp Gly Thr Leu Arg Thr Thr Val Ile Ala Asp
1               5                   10                  15

Gly Val Asn Gly Ser Ser Glu Lys Glu Ala Leu Val Ser Phe Glu Asn
            20                  25                  30

Ser Lys Asp Gly Val Asp Val Lys Asp Thr Ile Asn Tyr Glu Gly Leu
        35                  40                  45

Val Ala Asn Gln Asn Tyr Thr Leu Thr Gly Thr Leu Met His Val Lys
    50                  55                  60

Ala Asp Gly Ser Leu Glu Glu Ile Ala Thr Lys Thr Thr Asn Val Thr
65                  70                  75                  80

Ala Gly Glu Asn Gly Asn Gly Thr Trp Gly Leu Asp Phe Gly Asn Gln
                85                  90                  95

Lys Leu Gln Val Gly Glu Lys Tyr Val Val Phe Glu Asn Ala Glu Ser
            100                 105                 110

Val Glu Asn Leu Ile Asp Thr Asp Lys Asp Tyr Asn
        115                 120

<210> SEQ ID NO 3
<211> LENGTH: 23
<212> TYPE: PRT
<213> ORGANISM: Clostridium perfringens B str. ATCC 3626

<400> SEQUENCE: 3

Asp Thr Lys Gln Val Val Lys His Glu Asp Lys Asn Asp Lys Ala Gln
1               5                   10                  15

Thr Leu Val Val Glu Lys Pro
            20

<210> SEQ ID NO 4
<211> LENGTH: 23
<212> TYPE: PRT
<213> ORGANISM: Clostridium perfringens B str. ATCC 3626

<400> SEQUENCE: 4

Asp Thr Lys Gln Val Val Lys His Glu Asp Lys Asn Asp Lys Ala Gln
1               5                   10                  15

Thr Leu Ile Val Glu Lys Pro
            20

<210> SEQ ID NO 5
<211> LENGTH: 32
<212> TYPE: DNA
<213> ORGANISM: Artificial
<220> FEATURE:
<223> OTHER INFORMATION: Synthetic oligonucleotide

<400> SEQUENCE: 5
aaaggcgcca atctgcctga agtgaaagat gg                               32

<210> SEQ ID NO 6
<211> LENGTH: 36
<212> TYPE: DNA
<213> ORGANISM: Artificial
<220> FEATURE:
<223> OTHER INFORMATION: Synthetic oligonucleotide

<400> SEQUENCE: 6
tttgaattct cagttgtaat ctttatccgt atcgat                           36

<210> SEQ ID NO 7
<211> LENGTH: 31
<212> TYPE: DNA
<213> ORGANISM: Artificial
<220> FEATURE:
<223> OTHER INFORMATION: Synthetic oligonucleotide

<400> SEQUENCE: 7
aaaggcgccg ataccaaaca ggtggtgaaa c                                31

<210> SEQ ID NO 8
<211> LENGTH: 76
<212> TYPE: DNA
<213> ORGANISM: Artificial
<220> FEATURE:
<223> OTHER INFORMATION: Synthetic oligonucleotide

<400> SEQUENCE: 8
gcgccgacac aaaacaggtt gtcaaacatg aggacaaaaa cgacaaagca cagacactgg   60
tggttgaaaa accgac                                                  76

<210> SEQ ID NO 9
<211> LENGTH: 76
<212> TYPE: DNA
<213> ORGANISM: Artificial
<220> FEATURE:
<223> OTHER INFORMATION: Synthetic oligonucleotide

<400> SEQUENCE: 9
catggtcggt ttttcaacca ccagtgtctg tgctttgtcg tttttgtcct catgtttgac    60
aacctgtttt gtgtcg    76

<210> SEQ ID NO 10
<211> LENGTH: 22
<212> TYPE: DNA
<213> ORGANISM: Artificial
<220> FEATURE:
<223> OTHER INFORMATION: Synthetic oligonucleotide

<400> SEQUENCE: 10
agcaccgtta ttgcagatgg cg    22

<210> SEQ ID NO 11
<211> LENGTH: 21
<212> TYPE: DNA
<213> ORGANISM: Artificial
<220> FEATURE:
<223> OTHER INFORMATION: Synthetic oligonucleotide

<400> SEQUENCE: 11
acgcagtgta ccatctttca c    21

<210> SEQ ID NO 12
<211> LENGTH: 34
<212> TYPE: DNA
<213> ORGANISM: Artificial
<220> FEATURE:
<223> OTHER INFORMATION: Synthetic oligonucleotide

<400> SEQUENCE: 12
aaaggcgccc ccggtgtcac cacggatgcc accg    34

<210> SEQ ID NO 13
<211> LENGTH: 38
<212> TYPE: DNA
<213> ORGANISM: Artificial
<220> FEATURE:
<223> OTHER INFORMATION: Synthetic oligonucleotide

<400> SEQUENCE: 13
aaactcgagt cacaggctcg ggtggtacac gacctggg    38

<210> SEQ ID NO 14
<211> LENGTH: 39
<212> TYPE: DNA
<213> ORGANISM: Artificial
<220> FEATURE:
<223> OTHER INFORMATION: Synthetic oligonucleotide

<400> SEQUENCE: 14
aaaggcgccg tgcaagaggt agagattacc accacggcc    39

<210> SEQ ID NO 15
<211> LENGTH: 42
<212> TYPE: DNA
<213> ORGANISM: Artificial
<220> FEATURE:
<223> OTHER INFORMATION: Synthetic oligonucleotide

<400> SEQUENCE: 15
aaactcgagt caactcgggg tgtaaaccgt ctgggcgtca tc    42

<210> SEQ ID NO 16
<211> LENGTH: 40
<212> TYPE: DNA
<213> ORGANISM: Artificial
<220> FEATURE:
<223> OTHER INFORMATION: Synthetic oligonucleotide

<400> SEQUENCE: 16
aaaggcgccg ttggttctct ggataccacc gctaccgatg                    40

<210> SEQ ID NO 17
<211> LENGTH: 42
<212> TYPE: DNA
<213> ORGANISM: Artificial
<220> FEATURE:
<223> OTHER INFORMATION: Synthetic oligonucleotide

<400> SEQUENCE: 17
aaactcgagt caatgctccg acaccaccgt ttggttcgga tc                 42

<210> SEQ ID NO 18
<211> LENGTH: 36
<212> TYPE: DNA
<213> ORGANISM: Artificial
<220> FEATURE:
<223> OTHER INFORMATION: Synthetic oligonucleotide

<400> SEQUENCE: 18
aaaggcgccg gcacgagccc gtctctaaag accgtg                       36

<210> SEQ ID NO 19
<211> LENGTH: 46
<212> TYPE: DNA
<213> ORGANISM: Artificial
<220> FEATURE:
<223> OTHER INFORMATION: Synthetic oligonucleotide

<400> SEQUENCE: 19
aaactcgagt caaggcttct tggacgtaac cgtctggttt tcatcc             46

<210> SEQ ID NO 20
<211> LENGTH: 148
<212> TYPE: PRT
<213> ORGANISM: Clostridium perfringens B str. ATCC 3626

<400> SEQUENCE: 20

Leu Pro Glu Val Lys Asp Gly Thr Leu Arg Ser Thr Val Ile Ala Asp
1               5                   10                  15

Gly Val Asn Gly Ser Ser Glu Lys Glu Ala Leu Val Ser Phe Glu Asn
            20                  25                  30

Ser Lys Asp Gly Val Asp Val Lys Asp Thr Ile Asn Tyr Glu Gly Leu
        35                  40                  45

Val Ala Asn Gln Asn Tyr Thr Leu Thr Gly Thr Leu Met His Val Lys
    50                  55                  60

Ala Asp Gly Ser Leu Glu Glu Ile Ala Thr Lys Thr Thr Asn Val Thr
65                  70                  75                  80

Ala Gly Glu Asn Gly Asn Gly Thr Trp Gly Leu Asp Phe Gly Asn Gln
                85                  90                  95

Lys Leu Gln Val Gly Glu Lys Tyr Val Val Phe Glu Asn Ala Glu Ser
            100                 105                 110

Val Glu Asn Leu Ile Asp Thr Asp Lys Asp Tyr Asn Leu Asp Thr Lys
        115                 120                 125

```
Gln Val Val Lys His Glu Asp Lys Asn Asp Lys Ala Gln Thr Leu Val
    130                 135                 140

Val Glu Lys Pro
145

<210> SEQ ID NO 21
<211> LENGTH: 124
<212> TYPE: PRT
<213> ORGANISM: Mobiluncus mulieris ATCC 35239

<400> SEQUENCE: 21

Pro Gly Val Thr Thr Asp Ala Thr Asp Gly Asp Gly Asp Lys Tyr Val
1               5                   10                  15

Asp Ser Ser Gln Asn Phe Thr Ile Lys Asp Thr Val Thr Ala Thr Gly
            20                  25                  30

Leu Ile Pro Gly Lys Thr Tyr Asp Val Ser Gly Glu Leu Met Val Asp
        35                  40                  45

Asn Gly Thr Pro Gln Gly Ala Thr Thr Gly Ile Lys Gln Thr Gly Thr
    50                  55                  60

Ile Thr Ala Lys Ala Asp Gly Thr Gly Glu Thr Val Leu Glu Phe Pro
65                  70                  75                  80

Val Thr Ala Gln Gln Ala Gln Asp Leu Gly Leu Val Gly Lys Pro Ile
                85                  90                  95

Val Val Phe Glu Asp Leu Ser Leu Asp Gly Lys Lys Val Ala Val His
            100                 105                 110

His Asp Ile Lys Asp Glu Lys Gln Thr Val Tyr Asn
        115                 120

<210> SEQ ID NO 22
<211> LENGTH: 127
<212> TYPE: PRT
<213> ORGANISM: Mobiluncus mulieris ATCC 35239

<400> SEQUENCE: 22

Gly Gly Leu Lys Thr Lys Ala Val Asp Ala Ala Asp Glu Asn Gln Ala
1               5                   10                  15

Met Val Pro Gly Gln Lys Ser Ala Ala Val Val Asp Thr Val Thr Phe
            20                  25                  30

Asn Gly Arg Phe Glu Lys Ser His Ser Tyr Thr Leu Val Gly Glu Leu
        35                  40                  45

His Tyr Val Asn Gly Thr Val Val Pro Gly Lys Thr Glu Thr Lys
    50                  55                  60

Thr Phe Gln Ser Asp Gln Asp Gly Ala Ile Ala Ala Lys Met Thr
65                  70                  75                  80

Phe Thr Val Pro Ala Glu Tyr Ile Lys Ala Gly Gln Asn Met Val Val
                85                  90                  95

Phe Glu Lys Leu Phe Asp Ala Lys Lys Lys Asp Gly Thr Pro Val Ala
            100                 105                 110

Ser His Glu Asp Pro Asn Asp Pro Asp Gln Thr Ile Thr Val Gln
        115                 120                 125

<210> SEQ ID NO 23
<211> LENGTH: 145
<212> TYPE: PRT
<213> ORGANISM: Mobiluncus mulieris ATCC 35239

<400> SEQUENCE: 23

Glu Val Glu Ile Thr Thr Thr Ala Tyr Asp Gly Ala Ala Gly Asp Lys
```

```
                1               5                   10                  15
Ser Asp Pro Lys Asp Lys Asn Leu Asp Ala Ser Lys Glu Thr Val Thr
                20                  25                  30

Ile Tyr Asp Gln Val Asp Tyr Lys Gly Leu Asn Val Gly Glu Glu Tyr
                35                  40                  45

Thr Ile Thr Gly Thr Leu His Tyr Gln Ala Asp Ala Thr Leu Ala Asp
    50                  55                  60

Gly Thr Gln Val Lys Arg Gly Asp Glu Val Pro Ala Gln Tyr Val Asn
65                  70                  75                  80

Val Thr Pro Val Lys Ile Thr Ala Asn Lys Ala Ser Ser Asp Glu Ser
                85                  90                  95

Gly Ala Val Lys Ala Ile Val Lys Phe Glu Val Gln Lys Thr Ala Leu
                100                 105                 110

Ala Thr Ala Pro Val Val Val Phe Glu Thr Leu Tyr Gln Gly Thr Val
                115                 120                 125

Glu Val Ala Thr His Gln Asp Ile Asp Asp Gly Ser Gln Val Val Tyr
                130                 135                 140

His
145
```

<210> SEQ ID NO 24
<211> LENGTH: 132
<212> TYPE: PRT
<213> ORGANISM: Mobiluncus mulieris ATCC 35239

<400> SEQUENCE: 24

```
Pro Ser Leu Arg Thr Leu Ala Thr Val Asn Gly Ala Lys Val Ile Gln
1               5                   10                  15

Met Lys Lys Asp Ser Lys Glu Asn Leu Thr Val Thr Asp Gln Ile Thr
                20                  25                  30

Trp Ala Asn Leu Ala Pro Gly Thr Tyr Thr Leu Glu Gly Ser Leu Met
                35                  40                  45

Glu Val Lys Asp Gly Gln Leu Val Ser Asn Thr Pro Val Ala Lys Gly
    50                  55                  60

Gln Thr Gln Lys Val Glu Val Ala Ala Gly Lys Ala Gly Ala Thr Thr
65                  70                  75                  80

Ser Thr Gly Glu Ala Gln Met Thr Phe Lys Leu Pro Val Asp Lys Val
                85                  90                  95

Lys Ser Gly Ser Gln Phe Val Val Tyr Gln Ile Leu Lys Asp Lys Ser
                100                 105                 110

Gly Gln Val Val Ala Thr His Ala Asp Pro Lys Ser Asp Gln Thr
                115                 120                 125

Val Thr Val Gly
    130
```

<210> SEQ ID NO 25
<211> LENGTH: 143
<212> TYPE: PRT
<213> ORGANISM: Mobiluncus mulieris ATCC 35239

<400> SEQUENCE: 25

```
Ser Leu Asp Thr Thr Ala Thr Asp Ala Ala Asp Gly Asn Lys His Ala
1               5                   10                  15

Asp Asn Ala Ala Ala Val Thr Ile Asn Asp Lys Val Asp Tyr Ser Gly
                20                  25                  30

Leu Asn Leu Ala Ala Thr Tyr Pro Asp Gly Thr Leu Lys Ala Tyr Leu
```

```
                 35                  40                  45

Val Arg Gly Glu Leu Met Asp Lys Ala Thr Gly Lys Pro Val Ala Gly
 50                  55                  60

Val Ala Pro Val Glu Arg Val Ile Gly Ala Ala Asn Ser Val Tyr Arg
 65                  70                  75                  80

Val Gly Asp Gln Asn Arg Pro Val Glu Glu Ile Thr Ser Gly Ala
                 85                  90                  95

Gly Ser Val Val Leu Ser Phe Gln Val Pro Ala Lys Leu Thr Gln Gly
                100                 105                 110

Lys Val Leu Val Ala Phe Glu Thr Val Tyr Glu Glu Gly Arg Glu Phe
                115                 120                 125

Leu Ile His His Asp Ile Asn Asp Ala Gln Thr Val Tyr Thr
                130                 135                 140

<210> SEQ ID NO 26
<211> LENGTH: 146
<212> TYPE: PRT
<213> ORGANISM: Mobiluncus mulieris ATCC 35239

<400> SEQUENCE: 26

Pro Ser Val Lys Thr Gln Ala Arg Val Asp Ser Glu Arg Asn Leu Leu
 1               5                  10                  15

Leu Ala Asp Lys Asp Ser Thr Ile Lys Asp Thr Val Thr Leu Ser Gly
                 20                  25                  30

Leu Lys Thr Gly Glu Thr Tyr Val Leu Ser Gly Val Leu Met Asp Lys
                 35                  40                  45

Ala Thr Gly Gln Pro Val Leu Gly Lys Asp Met Gln Ala Ile Thr Ala
 50                  55                  60

Val Ser Glu Pro Leu Lys Ala Glu Ser Gly Ala Phe Val Lys Thr Asp
 65                  70                  75                  80

Ala Val Ser Phe Thr Val Pro Ala Gly Thr Val Lys Ala Asp Thr Glu
                 85                  90                  95

Leu Val Val Phe Glu Lys Leu Trp Val Ala Asn Glu Val Thr Val Asp
                100                 105                 110

Thr Lys Thr Lys Thr Val Thr Pro Lys Asp Thr Lys Gly Lys Ser
                115                 120                 125

Gln Pro Ala Ala Ser His Glu Asp Ile Thr Asp Glu Asn Gln Thr Val
                130                 135                 140

Lys Ser
145

<210> SEQ ID NO 27
<211> LENGTH: 146
<212> TYPE: PRT
<213> ORGANISM: Mobiluncus mulieris ATCC 35239

<400> SEQUENCE: 27

Pro Ser Val Lys Ser Gln Ala Arg Val Asp Ser Glu Arg Asn Leu Leu
 1               5                  10                  15

Leu Ala Asp Lys Asp Ser Thr Ile Lys Asp Thr Val Thr Leu Ser Gly
                 20                  25                  30

Leu Lys Thr Gly Glu Thr Tyr Val Leu Ser Gly Val Leu Met Asp Lys
                 35                  40                  45

Ala Thr Gly Gln Pro Val Leu Gly Lys Asp Met Gln Ala Ile Thr Ala
 50                  55                  60

Val Ser Glu Pro Leu Lys Ala Glu Ser Gly Ala Phe Val Lys Thr Asp
```

```
                65                  70                  75                  80
Ala Val Ser Phe Thr Val Pro Ala Gly Thr Val Lys Ala Asp Thr Glu
                    85                  90                  95

Leu Val Val Phe Glu Lys Leu Trp Val Ala Asn Glu Val Thr Val Asp
                100                 105                 110

Thr Lys Thr Lys Thr Val Thr Pro Lys Asp Thr Lys Thr Gly Lys Ser
                115                 120                 125

Gln Pro Ala Ala Ser His Glu Asp Ile Thr Asp Glu Asn Gln Thr Val
            130                 135                 140

Lys Ser
145

<210> SEQ ID NO 28
<211> LENGTH: 158
<212> TYPE: PRT
<213> ORGANISM: Mobiluncus mulieris ATCC 35239

<400> SEQUENCE: 28

His Asn Pro Gly Ile Thr Thr Thr Leu Thr Asp Ala Gln Ala Ala Lys
1               5                   10                  15

Gly Thr Asp Gly Lys Val Ile Ser Leu Thr Arg Asp Ala Gln Leu Lys
            20                  25                  30

Asp Val Val Arg Val Thr Gln Thr Gly Leu Ile Glu Gly Ala Lys Tyr
        35                  40                  45

His Val Phe Ser Lys Leu Val Asn Gln Ala Asn Pro Asp Gln Val Val
    50                  55                  60

Ser Ala Gly Met Gln Glu Phe Thr Ala Thr Gly Asp Gln Leu Arg Ser
65                  70                  75                  80

Val Thr Val Lys Phe Thr Val Pro Lys Glu Thr Leu Gln Glu Leu Ala
                85                  90                  95

Gly Ser Asp Pro Ser Ala Glu Phe Lys Leu Val Ala Tyr Glu Tyr Leu
            100                 105                 110

Ala Leu Asp Ser Asp Thr Asp Ile Val Asn Lys Glu Ala Thr Ser Glu
        115                 120                 125

Ile Glu Ala Val Gly Phe Lys Thr Gly Lys Thr Trp Ala Ala Thr His
    130                 135                 140

Ala Asp Pro Asn Asp Ala Gly Gln Thr Val Thr Val Val Lys
145                 150                 155

<210> SEQ ID NO 29
<211> LENGTH: 128
<212> TYPE: PRT
<213> ORGANISM: Mobiluncus mulieris ATCC 35239

<400> SEQUENCE: 29

Ala Pro Lys Ile Gly Thr Thr Leu Lys Tyr Gly Gln Ser Lys Thr Val
1               5                   10                  15

Trp Val Ala Asp Lys Val Glu Leu Thr Asp Thr Val Glu Tyr Phe Asn
            20                  25                  30

Leu Gln Pro Lys Thr Lys Tyr Thr Leu Ser Gly Asn Leu Met Gly Gly
        35                  40                  45

Thr Ser Ala Glu Ser Leu Ser Asp Thr Gly Val Lys Ala Thr Thr Glu
    50                  55                  60

Phe Thr Thr Pro Ala Ala Ala Asn Gly Ala Gln Thr Val Ser Gly Thr
65                  70                  75                  80

Ala Val Val Lys Phe Thr Val Pro Arg Glu Val Leu Glu Arg Asn Glu
```

```
                     85                  90                  95

Lys Leu Val Ala Tyr Glu Tyr Leu Thr Ile Asp Gly Asn Pro Val Ala
                100                 105                 110

Ser His Glu Asp Pro Lys Asp Glu Asn Gln Thr Val Thr Ser Lys Lys
            115                 120                 125

<210> SEQ ID NO 30
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: VARIANT
<222> LOCATION: (9)..(9)
<223> OTHER INFORMATION: Q or E

<400> SEQUENCE: 30

His Xaa Asp Xaa Xaa Asp Xaa Xaa Gln
1               5

<210> SEQ ID NO 31
<211> LENGTH: 137
<212> TYPE: PRT
<213> ORGANISM: Artificial Sequence
<220> FEATURE:
<223> OTHER INFORMATION: Synthetic

<400> SEQUENCE: 31

Gly Thr Ser Pro Ser Leu Lys Thr Val Leu Ser Ala Asp Gly Lys Arg
1               5                   10                  15

Glu Trp Val Glu Asn Asn Thr Asn Ile Pro Thr Val Pro His Ala Ser
            20                  25                  30

Asp Ser Leu Ile Asp Thr Val Leu Tyr Thr Gly Leu Thr Glu Gly Val
        35                  40                  45

Ser Tyr Arg Leu Asp Ala Lys Leu Met Glu Ile Asn Pro Val Thr Gly
    50                  55                  60

Lys Val Ser Glu Thr Pro Val Ala Thr Gly Tyr Thr Glu Phe Thr Ala
65                  70                  75                  80

Lys Thr Ser Asp Gly Thr Ala Gln Val Thr Phe Asn Gly Ile Thr Gly
                85                  90                  95

Lys Leu Lys Ala Gly Tyr Lys Tyr Val Ala Tyr Glu Lys Met Thr Arg
                100                 105                 110

Pro Gly Gln Pro Asp Lys Pro Val Pro Pro His Glu Asp Pro Lys
            115                 120                 125

Asp Pro Asn Gln Thr Val Val Ser Glu
        130                 135

<210> SEQ ID NO 32
<211> LENGTH: 151
<212> TYPE: PRT
<213> ORGANISM: Artificial Sequence
```

```
<220> FEATURE:
<223> OTHER INFORMATION: Synthetic

<400> SEQUENCE: 32

Met Ser Tyr Tyr His His His His His His Asp Tyr Asp Ile Pro Thr
1               5                   10                  15

Thr Glu Asn Leu Tyr Phe Gln Gly Ala Val Gly Ser Leu Asp Thr Thr
            20                  25                  30

Ala Thr Asp Ala Ala Asp Gly Asn Lys His Ala Asp Asn Ala Ala Ala
        35                  40                  45

Val Thr Ile Asn Asp Lys Val Asp Tyr Ser Gly Leu Asn Leu Ala Ala
    50                  55                  60

Thr Tyr Pro Asp Gly Thr Leu Lys Ala Tyr Leu Val Arg Gly Glu Leu
65                  70                  75                  80

Met Asp Lys Ala Thr Gly Lys Pro Val Ala Gly Val Ala Pro Val Glu
                85                  90                  95

Arg Val Ile Gly Ala Ala Asn Ser Val Tyr Arg Val Gly Asp Gln Asn
            100                 105                 110

Arg Pro Val Glu Glu Glu Ile Thr Ser Gly Ala Gly Ser Val Val Leu
        115                 120                 125

Ser Phe Gln Val Pro Ala Lys Leu Thr Gln Gly Lys Val Leu Val Ala
    130                 135                 140

Phe Glu Thr Val Tyr Glu Glu
145                 150

<210> SEQ ID NO 33
<211> LENGTH: 168
<212> TYPE: PRT
<213> ORGANISM: Artificial Sequence
<220> FEATURE:
<223> OTHER INFORMATION: Synthetic

<400> SEQUENCE: 33

Met Ser Tyr Tyr His His His His His His Asp Tyr Asp Ile Pro Thr
1               5                   10                  15

Thr Glu Asn Leu Tyr Phe Gln Gly Ala Gly Arg Glu Phe Leu Ile His
            20                  25                  30

His Asp Ile Asn Asp Asp Ala Gln Thr Val Tyr Thr Pro Ser Val Lys
        35                  40                  45

Thr Gln Ala Arg Val Asp Ser Glu Arg Asn Leu Leu Leu Ala Asp Lys
    50                  55                  60

Asp Ser Thr Ile Lys Asp Thr Val Thr Leu Ser Gly Leu Lys Thr Gly
65                  70                  75                  80

Glu Thr Tyr Val Leu Ser Gly Val Leu Met Asp Lys Ala Thr Gly Gln
                85                  90                  95

Pro Val Leu Gly Lys Asp Met Gln Ala Ile Thr Ala Val Ser Glu Pro
            100                 105                 110

Leu Lys Ala Glu Ser Gly Ala Phe Val Lys Thr Asp Ala Val Ser Phe
        115                 120                 125

Thr Val Pro Ala Gly Thr Val Lys Ala Asp Thr Glu Leu Val Val Phe
    130                 135                 140

Glu Lys Leu Trp Val Ala Asn Glu Val Thr Val Asp Ala Lys Thr Lys
145                 150                 155                 160

Thr Val Thr Pro Lys Asp Thr Lys
                165
```

```
<210> SEQ ID NO 34
<211> LENGTH: 160
<212> TYPE: PRT
<213> ORGANISM: Artificial Sequence
<220> FEATURE:
<223> OTHER INFORMATION: Synthetic

<400> SEQUENCE: 34

Met Ser Tyr Tyr His His His His His Asp Tyr Asp Ile Pro Thr
1               5                   10                  15

Thr Glu Asn Leu Tyr Phe Gln Gly Ala Gly Lys Ser Gln Pro Ala Ala
            20                  25                  30

Ser His Glu Asp Ile Thr Asp Glu Asn Gln Thr Val Lys Ser Gly Thr
        35                  40                  45

Ser Pro Ser Leu Lys Thr Val Leu Ser Ala Asp Gly Lys Arg Glu Trp
    50                  55                  60

Val Glu Asn Asn Thr Asn Ile Pro Thr Val Pro His Ala Ser Asp Ser
65                  70                  75                  80

Leu Ile Asp Thr Val Leu Tyr Thr Gly Leu Thr Glu Gly Val Ser Tyr
                85                  90                  95

Arg Leu Asp Ala Lys Leu Met Glu Ile Asn Pro Val Thr Gly Lys Val
            100                 105                 110

Ser Glu Thr Pro Val Ala Thr Gly Tyr Thr Glu Phe Thr Ala Lys Thr
        115                 120                 125

Ser Asp Gly Thr Ala Gln Val Thr Phe Asn Gly Ile Thr Gly Lys Leu
    130                 135                 140

Lys Ala Gly Tyr Lys Tyr Val Ala Tyr Glu Lys Met Thr Arg Pro Gly
145                 150                 155                 160

<210> SEQ ID NO 35
<211> LENGTH: 182
<212> TYPE: PRT
<213> ORGANISM: Artificial Sequence
<220> FEATURE:
<223> OTHER INFORMATION: Synthetic

<400> SEQUENCE: 35

Met Ser Tyr Tyr His His His His His Asp Tyr Asp Ile Pro Thr
1               5                   10                  15

Thr Glu Asn Leu Tyr Phe Gln Gly Ala Pro Asp Lys Pro Val Pro Pro
            20                  25                  30

Pro His Glu Asp Pro Lys Asp Pro Asn Gln Thr Val Val Ser Glu His
        35                  40                  45

Asn Pro Gly Ile Thr Thr Thr Leu Thr Asp Ala Gln Ala Ala Lys Gly
    50                  55                  60

Thr Asp Gly Lys Val Ile Ser Leu Thr Arg Asp Ala Gln Leu Lys Asp
65                  70                  75                  80

Val Val Arg Val Thr Gln Thr Gly Leu Ile Glu Gly Ala Lys Tyr His
                85                  90                  95

Val Phe Ser Lys Leu Val Asn Gln Ala Asn Pro Asp Gln Val Val Ser
            100                 105                 110

Ala Gly Met Gln Glu Phe Thr Ala Thr Gly Asp Gln Leu Arg Ser Val
        115                 120                 125

Thr Val Lys Phe Thr Val Pro Lys Glu Thr Leu Gln Glu Leu Ala Gly
    130                 135                 140

Ser Asp Pro Ser Ala Glu Phe Lys Leu Val Ala Tyr Glu Tyr Leu Ala
145                 150                 155                 160
```

```
Leu Asp Ser Asp Thr Asp Ile Val Asn Lys Glu Ala Thr Ser Glu Ile
                165                 170                 175

Glu Ala Val Gly Phe Lys
            180

<210> SEQ ID NO 36
<211> LENGTH: 176
<212> TYPE: PRT
<213> ORGANISM: Artificial Sequence
<220> FEATURE:
<223> OTHER INFORMATION: Synthetic

<400> SEQUENCE: 36

Met Ser Tyr Tyr His His His His His Asp Tyr Asp Ile Pro Thr
1               5                   10                  15

Thr Glu Asn Leu Tyr Phe Gln Gly Ala Gly Lys Thr Trp Ala Ala Thr
                20                  25                  30

His Ala Asp Pro Asn Asp Ala Gly Gln Thr Val Thr Val Lys Ala
                35                  40                  45

Pro Lys Ile Gly Thr Thr Leu Lys Tyr Gly Gln Ser Lys Thr Val Trp
50                  55                  60

Val Ala Asp Lys Val Glu Leu Thr Asp Thr Val Glu Tyr Phe Asn Leu
65                  70                  75                  80

Gln Pro Lys Thr Lys Tyr Thr Leu Ser Gly Asn Leu Met Gly Gly Thr
                85                  90                  95

Ser Ala Glu Ser Leu Ser Asp Thr Gly Val Lys Ala Thr Thr Glu Phe
                100                 105                 110

Thr Thr Pro Ala Ala Ala Asn Gly Ala Gln Thr Val Ser Gly Thr Ala
                115                 120                 125

Val Val Lys Phe Thr Val Pro Arg Glu Val Leu Glu Arg Asn Glu Lys
                130                 135                 140

Leu Val Ala Tyr Glu Tyr Leu Thr Ile Asp Gly Asn Pro Val Ala Ser
145                 150                 155                 160

His Glu Asp Pro Lys Asp Glu Asn Gln Thr Val Thr Ser Lys Lys Pro
                165                 170                 175

<210> SEQ ID NO 37
<211> LENGTH: 331
<212> TYPE: PRT
<213> ORGANISM: Artificial Sequence
<220> FEATURE:
<223> OTHER INFORMATION: Synthetic

<400> SEQUENCE: 37

Met Ser Tyr Tyr His His His His His Asp Tyr Asp Ile Pro Thr
1               5                   10                  15

Thr Glu Asn Leu Tyr Phe Gln Gly Ala Asn Leu Pro Glu Val Lys Asp
                20                  25                  30

Gly Thr Leu Arg Thr Thr Val Ile Ala Asp Gly Val Asn Gly Ser Ser
                35                  40                  45

Glu Lys Glu Ala Leu Val Ser Phe Glu Asn Ser Lys Asp Gly Val Asp
                50                  55                  60

Val Lys Asp Thr Ile Asn Tyr Glu Gly Leu Val Ala Asn Gln Asn Tyr
65                  70                  75                  80

Thr Leu Thr Gly Thr Leu Met His Val Lys Ala Asp Gly Ser Leu Glu
                85                  90                  95

Glu Ile Ala Thr Lys Thr Thr Asn Val Thr Ala Gly Glu Asn Gly Asn
                100                 105                 110
```

Gly Thr Trp Gly Leu Asp Phe Gly Asn Gln Lys Leu Gln Val Gly Glu
            115                 120                 125

Lys Tyr Val Val Phe Glu Asn Ala Glu Ser Val Glu Asn Leu Ile Asp
        130                 135                 140

Thr Asp Lys Asp Tyr Asn Ser His Gly Lys Ala Glu Ala Ala Lys
145                 150                 155                 160

Glu Ala Ala Lys Glu Ala Ala Lys Glu Ala Ala Lys Glu
                165                 170                 175

Ala Ala Lys Ala Ala Ala Pro Thr Ser Ala Gly Gln Val Val Ala
            180                 185                 190

Thr His Ala Asp Pro Lys Ser Asp Asp Gln Thr Val Thr Val Gly Ser
        195                 200                 205

Leu Asp Thr Thr Ala Thr Asp Ala Ala Asp Gly Asn Lys His Ala Asp
        210                 215                 220

Asn Ala Ala Ala Val Thr Ile Asn Asp Lys Val Asp Tyr Ser Gly Leu
225                 230                 235                 240

Asn Leu Ala Ala Thr Tyr Pro Asp Gly Thr Leu Lys Ala Tyr Leu Val
                245                 250                 255

Arg Gly Glu Leu Met Asp Lys Ala Thr Gly Lys Pro Val Ala Gly Val
            260                 265                 270

Ala Pro Val Glu Arg Val Ile Gly Ala Ala Asn Ser Val Tyr Arg Val
        275                 280                 285

Gly Asp Gln Asn Arg Pro Val Glu Glu Ile Thr Ser Gly Ala Gly
        290                 295                 300

Ser Val Val Leu Ser Phe Gln Val Pro Ala Lys Leu Thr Gln Gly Lys
305                 310                 315                 320

Val Leu Val Ala Phe Glu Thr Val Tyr Glu Glu
                325                 330

<210> SEQ ID NO 38
<211> LENGTH: 330
<212> TYPE: PRT
<213> ORGANISM: Artificial Sequence
<220> FEATURE:
<223> OTHER INFORMATION: Synthetic

<400> SEQUENCE: 38

Met Ser Tyr Tyr His His His His His His Asp Tyr Asp Ile Pro Thr
1               5                   10                  15

Thr Glu Asn Leu Tyr Phe Gln Gly Ala Asn Leu Pro Glu Val Lys Asp
                20                  25                  30

Gly Thr Leu Arg Thr Thr Val Ile Ala Asp Gly Val Asn Gly Ser Ser
            35                  40                  45

Glu Lys Glu Ala Leu Val Ser Phe Glu Asn Ser Lys Asp Gly Val Asp
        50                  55                  60

Val Lys Asp Thr Ile Asn Tyr Glu Gly Leu Val Ala Asn Gln Asn Tyr
65                  70                  75                  80

Thr Leu Thr Gly Thr Leu Met His Val Lys Ala Asp Gly Ser Leu Glu
                85                  90                  95

Glu Ile Ala Thr Lys Thr Thr Asn Val Thr Ala Gly Glu Asn Gly Asn
            100                 105                 110

Gly Thr Trp Gly Leu Asp Phe Gly Asn Gln Lys Leu Gln Val Gly Glu
        115                 120                 125

Lys Tyr Val Val Phe Glu Asn Ala Glu Ser Val Glu Asn Leu Ile Asp
    130                 135                 140

```
Thr Asp Lys Asp Tyr Asn Ser His Gly Lys Ala Glu Ala Ala Ala Lys
145                 150                 155                 160

Glu Ala Ala Ala Lys Glu Ala Ala Lys Glu Ala Ala Ala Lys Glu
            165                 170                 175

Ala Ala Ala Lys Ala Ala Ala Pro Thr Ser Ala Gly Arg Glu Phe Leu
            180                 185                 190

Ile His His Asp Ile Asn Asp Asp Ala Gln Thr Val Tyr Thr Pro Ser
                195                 200                 205

Val Lys Thr Gln Ala Arg Val Asp Ser Glu Arg Asn Leu Leu Leu Ala
            210                 215                 220

Asp Lys Asp Ser Thr Ile Lys Asp Thr Val Thr Leu Ser Gly Leu Lys
225                 230                 235                 240

Thr Gly Glu Thr Tyr Val Leu Ser Gly Val Leu Met Asp Lys Ala Thr
                245                 250                 255

Gly Gln Pro Val Leu Gly Lys Asp Met Gln Ala Ile Thr Ala Val Ser
            260                 265                 270

Glu Pro Leu Lys Ala Glu Ser Gly Ala Phe Val Lys Thr Asp Ala Val
            275                 280                 285

Ser Phe Thr Val Pro Ala Gly Thr Val Lys Ala Asp Thr Glu Leu Val
            290                 295                 300

Val Phe Glu Lys Leu Trp Val Ala Asn Glu Val Thr Val Asp Ala Lys
305                 310                 315                 320

Thr Lys Thr Val Thr Pro Lys Asp Thr Lys
                325                 330

<210> SEQ ID NO 39
<211> LENGTH: 322
<212> TYPE: PRT
<213> ORGANISM: Artificial Sequence
<220> FEATURE:
<223> OTHER INFORMATION: Synthetic

<400> SEQUENCE: 39

Met Ser Tyr Tyr His His His His His His Asp Tyr Asp Ile Pro Thr
1               5                   10                  15

Thr Glu Asn Leu Tyr Phe Gln Gly Ala Asn Leu Pro Glu Val Lys Asp
                20                  25                  30

Gly Thr Leu Arg Thr Thr Val Ile Ala Asp Gly Val Asn Gly Ser Ser
            35                  40                  45

Glu Lys Glu Ala Leu Val Ser Phe Glu Asn Ser Lys Asp Gly Val Asp
        50                  55                  60

Val Lys Asp Thr Ile Asn Tyr Glu Gly Leu Val Ala Asn Gln Asn Tyr
65                  70                  75                  80

Thr Leu Thr Gly Thr Leu Met His Val Lys Ala Asp Gly Ser Leu Glu
                85                  90                  95

Glu Ile Ala Thr Lys Thr Thr Asn Val Thr Ala Gly Glu Asn Gly Asn
            100                 105                 110

Gly Thr Trp Gly Leu Asp Phe Gly Asn Gln Lys Leu Gln Val Gly Glu
        115                 120                 125

Lys Tyr Val Val Phe Glu Asn Ala Glu Ser Val Glu Asn Leu Ile Asp
    130                 135                 140

Thr Asp Lys Asp Tyr Asn Ser His Gly Lys Ala Glu Ala Ala Ala Lys
145                 150                 155                 160

Glu Ala Ala Ala Lys Glu Ala Ala Ala Lys Glu Ala Ala Ala Lys Glu
                165                 170                 175
```

Ala Ala Ala Lys Ala Ala Ala Pro Thr Ser Ala Gly Lys Ser Gln Pro
            180                 185                 190

Ala Ala Ser His Glu Asp Ile Thr Asp Glu Asn Gln Thr Val Lys Ser
            195                 200                 205

Gly Thr Ser Pro Ser Leu Lys Thr Val Leu Ser Ala Asp Gly Lys Arg
            210                 215                 220

Glu Trp Val Glu Asn Asn Thr Asn Ile Pro Thr Val Pro His Ala Ser
225                 230                 235                 240

Asp Ser Leu Ile Asp Thr Val Leu Tyr Thr Gly Leu Thr Glu Gly Val
                245                 250                 255

Ser Tyr Arg Leu Asp Ala Lys Leu Met Glu Ile Asn Pro Val Thr Gly
            260                 265                 270

Lys Val Ser Glu Thr Pro Val Ala Thr Gly Tyr Thr Glu Phe Thr Ala
            275                 280                 285

Lys Thr Ser Asp Gly Thr Ala Gln Val Thr Phe Asn Gly Ile Thr Gly
            290                 295                 300

Lys Leu Lys Ala Gly Tyr Lys Tyr Val Ala Tyr Glu Lys Met Thr Arg
305                 310                 315                 320

Pro Gly

<210> SEQ ID NO 40
<211> LENGTH: 344
<212> TYPE: PRT
<213> ORGANISM: Artificial Sequence
<220> FEATURE:
<223> OTHER INFORMATION: Synthetic

<400> SEQUENCE: 40

Met Ser Tyr Tyr His His His His His His Asp Tyr Asp Ile Pro Thr
1               5                   10                  15

Thr Glu Asn Leu Tyr Phe Gln Gly Ala Asn Leu Pro Glu Val Lys Asp
            20                  25                  30

Gly Thr Leu Arg Thr Thr Val Ile Ala Asp Gly Val Asn Gly Ser Ser
        35                  40                  45

Glu Lys Glu Ala Leu Val Ser Phe Glu Asn Ser Lys Asp Gly Val Asp
    50                  55                  60

Val Lys Asp Thr Ile Asn Tyr Glu Gly Leu Val Ala Asn Gln Asn Tyr
65                  70                  75                  80

Thr Leu Thr Gly Thr Leu Met His Val Lys Ala Asp Gly Ser Leu Glu
                85                  90                  95

Glu Ile Ala Thr Lys Thr Thr Asn Val Thr Ala Gly Glu Asn Gly Asn
            100                 105                 110

Gly Thr Trp Gly Leu Asp Phe Gly Asn Gln Lys Leu Gln Val Gly Glu
        115                 120                 125

Lys Tyr Val Val Phe Glu Asn Ala Glu Ser Val Glu Asn Leu Ile Asp
    130                 135                 140

Thr Asp Lys Asp Tyr Asn Ser His Gly Lys Ala Glu Ala Ala Ala Lys
145                 150                 155                 160

Glu Ala Ala Ala Lys Glu Ala Ala Ala Lys Glu Ala Ala Ala Lys Glu
                165                 170                 175

Ala Ala Ala Lys Ala Ala Ala Pro Thr Ser Ala Pro Asp Lys Pro Val
            180                 185                 190

Pro Pro Pro His Glu Asp Pro Lys Asp Pro Asn Gln Thr Val Val Ser
        195                 200                 205

Glu His Asn Pro Gly Ile Thr Thr Leu Thr Asp Ala Gln Ala Ala
    210                 215                 220

Lys Gly Thr Asp Gly Lys Val Ile Ser Leu Thr Arg Asp Ala Gln Leu
225                 230                 235                 240

Lys Asp Val Val Arg Val Thr Gln Thr Gly Leu Ile Glu Gly Ala Lys
                245                 250                 255

Tyr His Val Phe Ser Lys Leu Val Asn Gln Ala Asn Pro Asp Gln Val
                260                 265                 270

Val Ser Ala Gly Met Gln Glu Phe Thr Ala Thr Gly Asp Gln Leu Arg
            275                 280                 285

Ser Val Thr Val Lys Phe Thr Val Pro Lys Glu Thr Leu Gln Glu Leu
290                 295                 300

Ala Gly Ser Asp Pro Ser Ala Glu Phe Lys Leu Val Ala Tyr Glu Tyr
305                 310                 315                 320

Leu Ala Leu Asp Ser Asp Thr Asp Ile Val Asn Lys Glu Ala Thr Ser
                325                 330                 335

Glu Ile Glu Ala Val Gly Phe Lys
            340

<210> SEQ ID NO 41
<211> LENGTH: 176
<212> TYPE: PRT
<213> ORGANISM: Artificial Sequence
<220> FEATURE:
<223> OTHER INFORMATION: Synthetic

<400> SEQUENCE: 41

Met Ser Tyr Tyr His His His His His His Asp Tyr Asp Ile Pro Thr
1               5                   10                  15

Thr Glu Asn Leu Tyr Phe Gln Gly Ala Gly Lys Thr Trp Ala Ala Thr
            20                  25                  30

His Ala Asp Pro Asn Asp Ala Gly Gln Thr Val Thr Val Val Lys Ala
            35                  40                  45

Pro Lys Ile Gly Thr Thr Leu Lys Tyr Gly Gln Ser Lys Thr Val Trp
    50                  55                  60

Val Ala Asp Lys Val Glu Leu Thr Asp Thr Val Glu Tyr Phe Asn Leu
65                  70                  75                  80

Gln Pro Lys Thr Lys Tyr Thr Leu Ser Gly Asn Leu Met Gly Gly Thr
                85                  90                  95

Ser Ala Glu Ser Leu Ser Asp Thr Gly Val Lys Ala Thr Thr Glu Phe
            100                 105                 110

Thr Thr Pro Ala Ala Ala Asn Gly Ala Gln Thr Val Ser Gly Thr Ala
        115                 120                 125

Val Val Lys Phe Thr Val Pro Arg Glu Val Leu Glu Arg Asn Glu Lys
    130                 135                 140

Leu Val Ala Tyr Glu Tyr Leu Thr Ile Asp Gly Asn Pro Val Ala Ser
145                 150                 155                 160

His Glu Asp Pro Lys Asp Glu Asn Gln Thr Val Thr Ser Lys Lys Pro
                165                 170                 175

<210> SEQ ID NO 42
<211> LENGTH: 339
<212> TYPE: PRT
<213> ORGANISM: Artificial Sequence
<220> FEATURE:
<223> OTHER INFORMATION: Synthetic

<400> SEQUENCE: 42

```
Met Ser Tyr Tyr His His His His His Asp Tyr Asp Ile Pro Thr
1               5                   10                  15

Thr Glu Asn Leu Tyr Phe Gln Gly Ala Asp Thr Lys Gln Val Val Lys
            20                  25                  30

His Glu Asp Lys Asn Asp Lys Ala Gln Thr Leu Val Val Glu Lys Pro
        35                  40                  45

Thr Gly Ser Gly Ser Gly Ala Glu Thr Val Val Asn Gly Ala Lys Leu
    50                  55                  60

Thr Val Thr Lys Asn Leu Asp Leu Val Asn Ser Asn Ala Leu Ile Pro
65                  70                  75                  80

Asn Thr Asp Phe Thr Phe Lys Ile Glu Pro Asp Thr Val Asn Glu
                85                  90                  95

Asp Gly Asn Lys Phe Lys Gly Val Ala Leu Asn Thr Pro Met Thr Lys
            100                 105                 110

Val Thr Tyr Thr Asn Ser Asp Lys Gly Gly Ser Asn Thr Lys Thr Ala
        115                 120                 125

Glu Phe Asp Phe Ser Glu Val Thr Phe Glu Lys Pro Gly Val Tyr Tyr
    130                 135                 140

Tyr Lys Val Thr Glu Glu Lys Ile Asp Lys Val Pro Gly Val Ser Tyr
145                 150                 155                 160

Asp Thr Thr Ser Tyr Thr Val Gln Val His Val Leu Trp Asn Glu Glu
                165                 170                 175

Gln Gln Lys Pro Val Ala Thr Tyr Ile Val Gly Tyr Lys Glu Gly Ser
            180                 185                 190

Lys Val Pro Ile Gln Phe Lys Asn Ser Leu Asp Ser Thr Thr Leu Thr
        195                 200                 205

Val Lys Lys Lys Val Ser Gly Thr Gly Gly Asp Arg Ser Lys Asp Phe
210                 215                 220

Asn Phe Gly Leu Thr Leu Lys Ala Asn Gln Tyr Tyr Lys Ala Ser Glu
225                 230                 235                 240

Lys Val Met Ile Glu Lys Thr Thr Lys Gly Gly Gln Ala Pro Val Gln
                245                 250                 255

Thr Glu Ala Ser Ile Asp Gln Leu Tyr His Phe Thr Leu Lys Asp Gly
            260                 265                 270

Glu Ser Ile Lys Val Thr Asn Leu Pro Val Gly Val Asp Tyr Val Val
        275                 280                 285

Thr Glu Asp Asp Tyr Lys Ser Glu Lys Tyr Thr Thr Asn Val Glu Val
290                 295                 300

Ser Pro Gln Asp Gly Ala Val Lys Asn Ile Ala Gly Asn Ser Thr Glu
305                 310                 315                 320

Gln Glu Thr Ser Thr Asp Lys Asp Met Thr Ile Thr Phe Thr Asn Lys
                325                 330                 335

Lys Phe Glu

<210> SEQ ID NO 43
<211> LENGTH: 337
<212> TYPE: PRT
<213> ORGANISM: Artificial Sequence
<220> FEATURE:
<223> OTHER INFORMATION: Synthetic

<400> SEQUENCE: 43

Met Ser Tyr Tyr His His His His His Asp Tyr Asp Ile Pro Thr
1               5                   10                  15
```

Thr Glu Asn Leu Tyr Phe Gln Gly Ala Asp Thr Lys Gln Val Val Lys
            20                  25                  30

His Glu Asp Lys Asn Asp Lys Ala Gln Thr Leu Val Val Glu Lys Pro
        35                  40                  45

Thr Gly Ser Gly Ser Gly Ala Glu Thr Ala Gly Val Ser Glu Asn Ala
    50                  55                  60

Lys Leu Ile Val Lys Lys Thr Phe Asp Ser Tyr Thr Asp Asn Glu Val
65                  70                  75                  80

Leu Met Pro Lys Ala Asp Tyr Thr Phe Lys Val Glu Ala Asp Ser Thr
                85                  90                  95

Ala Ser Gly Lys Thr Lys Asp Gly Leu Glu Ile Lys Pro Gly Ile Val
            100                 105                 110

Asn Gly Leu Thr Glu Gln Ile Ile Ser Tyr Thr Asn Thr Asp Lys Pro
        115                 120                 125

Asp Ser Lys Val Lys Ser Thr Glu Phe Asp Phe Ser Lys Val Val Phe
    130                 135                 140

Pro Gly Ile Gly Val Tyr Arg Tyr Ile Val Ser Glu Lys Gln Gly Asp
145                 150                 155                 160

Val Glu Gly Ile Thr Tyr Asp Thr Lys Lys Trp Thr Val Asp Val Tyr
                165                 170                 175

Val Gly Asn Lys Glu Gly Gly Phe Glu Pro Lys Phe Ile Val Ser
            180                 185                 190

Lys Glu Gln Gly Thr Asp Val Lys Lys Pro Val Asn Phe Asn Asn Ser
        195                 200                 205

Phe Ala Thr Thr Ser Leu Lys Val Lys Asn Val Ser Gly Asn Thr
    210                 215                 220

Gly Glu Leu Gln Lys Glu Phe Asp Phe Thr Leu Thr Leu Asn Glu Ser
225                 230                 235                 240

Thr Asn Phe Lys Lys Asp Gln Ile Val Ser Leu Gln Lys Gly Asn Glu
                245                 250                 255

Lys Phe Glu Val Lys Ile Gly Thr Pro Tyr Lys Phe Lys Leu Lys Asn
            260                 265                 270

Gly Glu Ser Ile Gln Leu Asp Lys Leu Pro Val Gly Ile Thr Tyr Lys
        275                 280                 285

Val Asn Glu Met Glu Ala Asn Lys Asp Gly Tyr Lys Thr Thr Ala Ser
    290                 295                 300

Leu Lys Glu Gly Asp Gly Gln Ser Lys Met Tyr Gln Leu Asp Met Glu
305                 310                 315                 320

Gln Lys Thr Asp Glu Ser Ala Asp Glu Ile Val Val Thr Asn Lys Arg
                325                 330                 335

Asp

<210> SEQ ID NO 44
<211> LENGTH: 335
<212> TYPE: PRT
<213> ORGANISM: Artificial Sequence
<220> FEATURE:
<223> OTHER INFORMATION: Synthetic

<400> SEQUENCE: 44

Met Ser Tyr Tyr His His His His His His Asp Tyr Asp Ile Pro Thr
1               5                   10                  15

Thr Glu Asn Leu Tyr Phe Gln Gly Ala Asp Thr Lys Gln Val Val Lys
            20                  25                  30

His Glu Asp Lys Asn Asp Lys Ala Gln Thr Leu Val Val Glu Lys Pro

```
            35                  40                  45
Thr Gly Ser Gly Ser Gly Ala Glu Thr Ala Gly Val Val Thr Gly Lys
 50                  55                  60

Thr Leu Pro Ile Thr Lys Ser Met Ile Tyr Thr Asp Asn Glu Ile Leu
 65                  70                  75                  80

Met Pro Lys Thr Thr Phe Thr Phe Thr Ile Glu Pro Asp Thr Thr Ala
                 85                  90                  95

Ser Gly Lys Thr Lys Asp Gly Leu Glu Ile Lys Ser Gly Glu Thr Thr
                100                 105                 110

Gly Leu Thr Thr Lys Ala Ile Val Ser Tyr Asp Asn Thr Asp Lys Glu
            115                 120                 125

Ser Ala Lys Asn Lys Thr Ser Asn Phe Asn Phe Glu Thr Val Thr Phe
130                 135                 140

Ser Gly Ile Gly Ile Tyr Arg Tyr Thr Val Ser Glu Gln Asn Asp Gly
145                 150                 155                 160

Ile Glu Gly Ile Gln Tyr Asp Gly Lys Lys Trp Thr Val Asp Val Tyr
                165                 170                 175

Val Gly Asn Lys Glu Gly Gly Phe Glu Pro Lys Tyr Val Val Ser
                180                 185                 190

Lys Glu Val Asn Ser Asp Val Lys Lys Pro Ile Arg Phe Glu Asn Ser
            195                 200                 205

Phe Lys Thr Thr Ser Leu Lys Ile Glu Lys Gln Val Thr Gly Asn Thr
210                 215                 220

Gly Glu Leu Gln Lys Asp Phe Asn Phe Thr Leu Ile Leu Glu Ala Ser
225                 230                 235                 240

Ala Leu Tyr Glu Lys Gly Gln Val Val Lys Ile Ile Gln Asp Gly Gln
                245                 250                 255

Thr Lys Asp Val Val Ile Gly Gln Glu Tyr Lys Phe Thr Leu His Asp
                260                 265                 270

His Gln Ser Ile Met Leu Ala Lys Leu Pro Ile Gly Ile Ser Tyr Lys
            275                 280                 285

Leu Thr Glu Asp Lys Ala Asp Gly Tyr Thr Thr Thr Ala Thr Leu Lys
290                 295                 300

Glu Gly Glu Ile Asp Ala Lys Glu Tyr Val Leu Gly Asn Leu Gln Lys
305                 310                 315                 320

Thr Asp Glu Ser Ala Asp Glu Ile Val Val Thr Asn Lys Arg Asp
                325                 330                 335

<210> SEQ ID NO 45
<211> LENGTH: 337
<212> TYPE: PRT
<213> ORGANISM: Artificial Sequence
<220> FEATURE:
<223> OTHER INFORMATION: Synthetic

<400> SEQUENCE: 45

Met Ser Tyr Tyr His His His His His His Asp Tyr Asp Ile Pro Thr
 1               5                  10                  15

Thr Glu Asn Leu Tyr Phe Gln Gly Ala Asp Thr Lys Gln Val Val Lys
                20                  25                  30

His Glu Asp Lys Asn Asp Lys Ala Gln Thr Leu Val Val Glu Lys Pro
            35                  40                  45

Thr Gly Ser Gly Ser Gly Ala Glu Thr Ala Gly Val Ile Asp Gly Ser
 50                  55                  60

Thr Leu Val Val Lys Lys Thr Phe Pro Ser Tyr Thr Asp Asp Lys Val
```

```
                65                  70                  75                  80
Leu Met Pro Lys Ala Asp Tyr Thr Phe Lys Val Glu Ala Asp Asp Asn
                85                  90                  95

Ala Lys Gly Lys Thr Lys Asp Gly Leu Asp Ile Lys Pro Gly Val Ile
            100                 105                 110

Asp Gly Leu Glu Asn Thr Lys Thr Ile His Tyr Gly Asn Ser Asp Lys
        115                 120                 125

Thr Thr Ala Lys Glu Lys Ser Val Asn Phe Asp Phe Ala Asn Val Lys
    130                 135                 140

Phe Pro Gly Val Gly Val Tyr Arg Tyr Thr Val Ser Glu Val Asn Gly
145                 150                 155                 160

Asn Lys Ala Gly Ile Ala Tyr Asp Ser Gln Gln Trp Thr Val Asp Val
                165                 170                 175

Tyr Val Val Asn Arg Glu Asp Gly Gly Phe Glu Ala Lys Tyr Ile Val
            180                 185                 190

Ser Thr Glu Gly Gly Gln Ser Asp Lys Lys Pro Val Leu Phe Lys Asn
        195                 200                 205

Phe Phe Asp Thr Thr Ser Leu Lys Val Thr Lys Lys Val Thr Gly Asn
    210                 215                 220

Thr Gly Glu His Gln Arg Ser Phe Ser Phe Thr Leu Leu Leu Thr Pro
225                 230                 235                 240

Asn Glu Cys Phe Glu Lys Gly Gln Val Val Asn Ile Leu Gln Gly Gly
                245                 250                 255

Glu Thr Lys Lys Val Val Ile Gly Glu Glu Tyr Ser Phe Thr Leu Lys
            260                 265                 270

Asp Lys Glu Ser Val Thr Leu Ser Gln Leu Pro Val Gly Ile Glu Tyr
        275                 280                 285

Lys Val Thr Glu Glu Asp Val Thr Lys Asp Gly Tyr Lys Thr Ser Ala
    290                 295                 300

Thr Leu Lys Asp Gly Asp Val Thr Asp Gly Tyr Asn Leu Gly Asp Ser
305                 310                 315                 320

Lys Thr Thr Asp Lys Ser Thr Asp Glu Ile Val Val Thr Asn Lys Arg
                325                 330                 335

Asp

<210> SEQ ID NO 46
<211> LENGTH: 339
<212> TYPE: PRT
<213> ORGANISM: Artificial Sequence
<220> FEATURE:
<223> OTHER INFORMATION: Synthetic

<400> SEQUENCE: 46

Met Ser Tyr Tyr His His His His His His Asp Tyr Asp Ile Pro Thr
1               5                   10                  15

Thr Glu Asn Leu Tyr Phe Gln Gly Ala Gly Gly Glu Glu Pro Phe Val
            20                  25                  30

Pro Gly Asn Gly Asp Thr Pro Ser Leu Lys Thr Thr Val Lys Ala Ala
        35                  40                  45

Ser Ser Thr Ala Ser Ser Glu Ala Ala Lys Leu Thr Ala Ser Glu
    50                  55                  60

Ala Ala Lys Gly Ala Ser Val Val Asp Thr Ile Asp Tyr Ala Asn Leu
65                  70                  75                  80

Tyr Gly Gly Lys Gln Tyr Glu Val Thr Ala Arg Leu Met Pro Val Lys
                85                  90                  95
```

```
Asp Gly Val Val Thr Gly Asp Pro Leu Val Thr Val Thr Val Arg Arg
            100                 105                 110

Thr Ala Asp Leu Ser Gly Ser Gly Ser Trp Thr Val Pro Leu Gly Thr
            115                 120                 125

Val Glu Gly Leu Glu Lys Asp Thr Ser Tyr Val Val Phe Glu Lys Ala
            130                 135                 140

Val Ser Ile Asp Asn Leu Val Asp Arg Asp Gly Asp Gly Asn Ser His
145                 150                 155                 160

Gly Lys Ala Glu Ala Ala Lys Glu Ala Ala Lys Glu Ala Ala
            165                 170                 175

Ala Lys Glu Ala Ala Lys Glu Ala Ala Lys Ala Ala Pro
            180                 185                 190

Thr Ser Ala Gly Gln Val Val Ala Thr His Ala Asp Pro Lys Ser Asp
            195                 200                 205

Asp Gln Thr Val Thr Val Gly Ser Leu Asp Thr Thr Ala Thr Asp Ala
            210                 215                 220

Ala Asp Gly Asn Lys His Ala Asp Asn Ala Ala Ala Val Thr Ile Asn
225                 230                 235                 240

Asp Lys Val Asp Tyr Ser Gly Leu Asn Leu Ala Ala Thr Tyr Pro Asp
            245                 250                 255

Gly Thr Leu Lys Ala Tyr Leu Val Arg Gly Glu Leu Met Asp Lys Ala
            260                 265                 270

Thr Gly Lys Pro Val Ala Gly Val Ala Pro Val Glu Arg Val Ile Gly
            275                 280                 285

Ala Ala Asn Ser Val Tyr Arg Val Gly Asp Gln Asn Arg Pro Val Glu
            290                 295                 300

Glu Glu Ile Thr Ser Gly Ala Gly Ser Val Val Leu Ser Phe Gln Val
305                 310                 315                 320

Pro Ala Lys Leu Thr Gln Gly Lys Val Leu Val Ala Phe Glu Thr Val
            325                 330                 335

Tyr Glu Glu

<210> SEQ ID NO 47
<211> LENGTH: 334
<212> TYPE: PRT
<213> ORGANISM: Artificial Sequence
<220> FEATURE:
<223> OTHER INFORMATION: Synthetic

<400> SEQUENCE: 47

Met Ser Tyr Tyr His His His His His His Asp Tyr Asp Ile Pro Thr
1               5                   10                  15

Thr Glu Asn Leu Tyr Phe Gln Gly Ala Thr Val Thr Asp Gln Asp Lys
            20                  25                  30

Tyr Val Asn Pro Lys Gly Glu Leu Lys Thr Thr Val Glu Ala Asp Gly
            35                  40                  45

Gln Ser Ser Thr Thr Glu Lys Ser Val Glu Val Thr Glu Asn Lys Asp
        50                  55                  60

Gly Val Lys Val Val Asp Thr Ile Lys Tyr Lys Gly Leu Val Glu Gly
65                  70                  75                  80

Lys Asp Tyr Thr Val Thr Gly Gln Leu Tyr Glu Val Lys Asp Gly Lys
            85                  90                  95

Ile Val Gly Glu Ala Lys Ala Thr Lys Thr Glu Thr Lys Lys Ala Asp
            100                 105                 110
```

```
Lys Asp Glu Gly Asn Trp Asn Leu Asp Phe Gly Thr Val Lys Gly Leu
            115                 120                 125

Glu Ala Gly Lys Ser Tyr Val Val Tyr Glu Thr Ala Thr Ser Leu Glu
        130                 135                 140

Asn Leu Val Asp Thr Asp Asn Asp Lys Ser His Gly Lys Ala Glu
145                 150                 155                 160

Ala Ala Ala Lys Glu Ala Ala Lys Glu Ala Ala Lys Glu Ala
                165                 170                 175

Ala Ala Lys Glu Ala Ala Lys Ala Ala Pro Thr Ser Ala Gly
            180                 185                 190

Arg Glu Phe Leu Ile His His Asp Ile Asn Asp Asp Ala Gln Thr Val
            195                 200                 205

Tyr Thr Pro Ser Val Lys Thr Gln Ala Arg Val Asp Ser Glu Arg Asn
210                 215                 220

Leu Leu Leu Ala Asp Lys Asp Ser Thr Ile Lys Asp Thr Val Thr Leu
225                 230                 235                 240

Ser Gly Leu Lys Thr Gly Glu Thr Tyr Val Leu Ser Gly Val Leu Met
                245                 250                 255

Asp Lys Ala Thr Gly Gln Pro Val Leu Gly Lys Asp Met Gln Ala Ile
            260                 265                 270

Thr Ala Val Ser Glu Pro Leu Lys Ala Glu Ser Gly Ala Phe Val Lys
        275                 280                 285

Thr Asp Ala Val Ser Phe Thr Val Pro Ala Gly Thr Val Lys Ala Asp
            290                 295                 300

Thr Glu Leu Val Val Phe Glu Lys Leu Trp Val Ala Asn Glu Val Thr
305                 310                 315                 320

Val Asp Ala Lys Thr Lys Thr Val Thr Pro Lys Asp Thr Lys
                325                 330

<210> SEQ ID NO 48
<211> LENGTH: 327
<212> TYPE: PRT
<213> ORGANISM: Artificial Sequence
<220> FEATURE:
<223> OTHER INFORMATION: Synthetic

<400> SEQUENCE: 48

Met Ser Tyr Tyr His His His His His His Asp Tyr Asp Ile Pro Thr
1               5                   10                  15

Thr Glu Asn Leu Tyr Phe Gln Gly Ala Arg Val Thr Asn Lys Lys Ile
                20                  25                  30

Val Ser Ser Leu Gln Thr Thr Val Glu Ala Asp Gly Gln Ser Ser Thr
            35                  40                  45

Ala Glu Lys Ser Ala Glu Val Thr Glu Asn Lys Asp Gly Val Asn Val
        50                  55                  60

Val Asp Thr Ile His Tyr Lys Gly Leu Ile Pro Lys Gln Lys Tyr Glu
65                  70                  75                  80

Val Val Gly Ile Leu Tyr Glu Val Lys Asp Gly Lys Leu Val Asp Pro
                85                  90                  95

Asn Lys Pro Ile Thr Ile Ser Asn Gly Thr Gly Glu Tyr Thr Val Ser
            100                 105                 110

Asp Ser Gly Glu Gly Glu Trp Lys Leu Asn Phe Gly Lys Ile Asp Gly
        115                 120                 125

Val Glu Ala Arg Lys Ser Tyr Val Val Tyr Glu Glu Val Thr Ser Val
    130                 135                 140
```

```
Glu Asn Leu Val Asp Thr Asp Asn Asp Gly Asn Ser His Gly Lys Ala
145                 150                 155                 160

Glu Ala Ala Ala Lys Glu Ala Ala Lys Glu Ala Ala Lys Glu
                165                 170                 175

Ala Ala Ala Lys Glu Ala Ala Lys Ala Ala Ala Pro Thr Ser Ala
            180                 185                 190

Gly Lys Ser Gln Pro Ala Ala Ser His Glu Asp Ile Thr Asp Glu Asn
            195                 200                 205

Gln Thr Val Lys Ser Gly Thr Ser Pro Ser Leu Lys Thr Val Leu Ser
            210                 215                 220

Ala Asp Gly Lys Arg Glu Trp Val Glu Asn Asn Thr Asn Ile Pro Thr
225                 230                 235                 240

Val Pro His Ala Ser Asp Ser Leu Ile Asp Thr Val Leu Tyr Thr Gly
                245                 250                 255

Leu Thr Glu Gly Val Ser Tyr Arg Leu Asp Ala Lys Leu Met Glu Ile
                260                 265                 270

Asn Pro Val Thr Gly Lys Val Ser Glu Thr Pro Val Ala Thr Gly Tyr
                275                 280                 285

Thr Glu Phe Thr Ala Lys Thr Ser Asp Gly Thr Ala Gln Val Thr Phe
                290                 295                 300

Asn Gly Ile Thr Gly Lys Leu Lys Ala Gly Tyr Lys Tyr Val Ala Tyr
305                 310                 315                 320

Glu Lys Met Thr Arg Pro Gly
                325

<210> SEQ ID NO 49
<211> LENGTH: 344
<212> TYPE: PRT
<213> ORGANISM: Artificial Sequence
<220> FEATURE:
<223> OTHER INFORMATION: Synthetic

<400> SEQUENCE: 49

Met Ser Tyr Tyr His His His His His His Asp Tyr Asp Ile Pro Thr
1               5                   10                  15

Thr Glu Asn Leu Tyr Phe Gln Gly Ala Asn Leu Pro Glu Val Lys Asp
                20                  25                  30

Gly Thr Leu Arg Thr Thr Val Ile Ala Asp Gly Val Asn Gly Ser Ser
            35                  40                  45

Glu Lys Glu Ala Leu Val Ser Phe Glu Asn Ser Lys Asp Gly Val Asp
50                  55                  60

Val Lys Asp Thr Ile Asn Tyr Glu Gly Leu Val Ala Asn Gln Asn Tyr
65                  70                  75                  80

Thr Leu Thr Gly Thr Leu Met His Val Lys Ala Asp Gly Ser Leu Glu
                85                  90                  95

Glu Ile Ala Thr Lys Thr Thr Asn Val Thr Ala Gly Glu Asn Gly Asn
                100                 105                 110

Gly Thr Trp Gly Leu Asp Phe Gly Asn Gln Lys Leu Gln Val Gly Glu
            115                 120                 125

Lys Tyr Val Val Phe Glu Asn Ala Glu Ser Val Glu Asn Leu Ile Asp
            130                 135                 140

Thr Asp Lys Asp Tyr Asn Ser His Gly Lys Ala Glu Ala Ala Lys
145                 150                 155                 160

Glu Ala Ala Ala Lys Glu Ala Ala Lys Glu Ala Ala Lys Glu
                165                 170                 175
```

```
Ala Ala Ala Lys Ala Ala Ala Pro Thr Ser Ala Pro Asp Lys Pro Val
            180                 185                 190

Pro Pro Pro His Glu Asp Pro Lys Asp Pro Asn Gln Thr Val Val Ser
        195                 200                 205

Glu His Asn Pro Gly Ile Thr Thr Thr Leu Thr Asp Ala Gln Ala Ala
    210                 215                 220

Lys Gly Thr Asp Gly Lys Val Ile Ser Leu Thr Arg Asp Ala Gln Leu
225                 230                 235                 240

Lys Asp Val Val Arg Val Thr Gln Thr Gly Leu Ile Glu Gly Ala Lys
                245                 250                 255

Tyr His Val Phe Ser Lys Leu Val Asn Gln Ala Asn Pro Asp Gln Val
            260                 265                 270

Val Ser Ala Gly Met Gln Glu Phe Thr Ala Thr Gly Asp Gln Leu Arg
        275                 280                 285

Ser Val Thr Val Lys Phe Thr Val Pro Lys Glu Thr Leu Gln Glu Leu
    290                 295                 300

Ala Gly Ser Asp Pro Ser Ala Glu Phe Lys Leu Val Ala Tyr Glu Tyr
305                 310                 315                 320

Leu Ala Leu Asp Ser Asp Thr Asp Ile Val Asn Lys Glu Ala Thr Ser
                325                 330                 335

Glu Ile Glu Ala Val Gly Phe Lys
            340

<210> SEQ ID NO 50
<211> LENGTH: 176
<212> TYPE: PRT
<213> ORGANISM: Artificial Sequence
<220> FEATURE:
<223> OTHER INFORMATION: Synthetic

<400> SEQUENCE: 50

Met Ser Tyr Tyr His His His His His His Asp Tyr Asp Ile Pro Thr
1               5                   10                  15

Thr Glu Asn Leu Tyr Phe Gln Gly Ala Gly Lys Thr Trp Ala Ala Thr
            20                  25                  30

His Ala Asp Pro Asn Asp Ala Gly Gln Thr Val Thr Val Val Lys Ala
        35                  40                  45

Pro Lys Ile Gly Thr Thr Leu Lys Tyr Gly Gln Ser Lys Thr Val Trp
    50                  55                  60

Val Ala Asp Lys Val Glu Leu Thr Asp Thr Val Glu Tyr Phe Asn Leu
65                  70                  75                  80

Gln Pro Lys Thr Lys Tyr Thr Leu Ser Gly Asn Leu Met Gly Gly Thr
                85                  90                  95

Ser Ala Glu Ser Leu Ser Asp Thr Gly Val Lys Ala Thr Thr Glu Phe
            100                 105                 110

Thr Thr Pro Ala Ala Ala Asn Gly Ala Gln Thr Val Ser Gly Thr Ala
        115                 120                 125

Val Val Lys Phe Thr Val Pro Arg Glu Val Leu Glu Arg Asn Glu Lys
    130                 135                 140

Leu Val Ala Tyr Glu Tyr Leu Thr Ile Asp Gly Asn Pro Val Ala Ser
145                 150                 155                 160

His Glu Asp Pro Lys Asp Glu Asn Gln Thr Val Thr Ser Lys Lys Pro
                165                 170                 175

<210> SEQ ID NO 51
<211> LENGTH: 295
```

```
<212> TYPE: PRT
<213> ORGANISM: Artificial Sequence
<220> FEATURE:
<223> OTHER INFORMATION: Synthetic

<400> SEQUENCE: 51

Met Ser Tyr Tyr His His His His His His Asp Tyr Asp Ile Pro Thr
1               5                   10                  15

Thr Glu Asn Leu Tyr Phe Gln Gly Gly Gly Asp Glu Leu Gln Thr Gly
            20                  25                  30

Ser His Glu Asp Pro Arg Asp Ser Ser Gln Thr Val Thr Val Ala Ser
        35                  40                  45

Asp Pro Gly Ser Gly Ser Gly Ala Met Val Ser Lys Gly Glu Glu Leu
    50                  55                  60

Phe Thr Gly Val Val Pro Ile Leu Val Glu Leu Asp Gly Asp Val Asn
65                  70                  75                  80

Gly His Lys Phe Ser Val Ser Gly Glu Gly Glu Gly Asp Ala Thr Tyr
                85                  90                  95

Gly Lys Leu Thr Leu Lys Phe Ile Cys Thr Thr Gly Lys Leu Pro Val
            100                 105                 110

Pro Trp Pro Thr Leu Val Thr Thr Leu Thr Tyr Gly Val Gln Cys Phe
        115                 120                 125

Ser Arg Tyr Pro Asp His Met Lys Gln His Asp Phe Phe Lys Ser Ala
    130                 135                 140

Met Pro Glu Gly Tyr Val Gln Glu Arg Thr Ile Phe Phe Lys Asp Asp
145                 150                 155                 160

Gly Asn Tyr Lys Thr Arg Ala Glu Val Lys Phe Glu Gly Asp Thr Leu
                165                 170                 175

Val Asn Arg Ile Glu Leu Lys Gly Ile Asp Phe Lys Glu Asp Gly Asn
            180                 185                 190

Ile Leu Gly His Lys Leu Glu Tyr Asn Tyr Asn Ser His Asn Val Tyr
        195                 200                 205

Ile Met Ala Asp Lys Gln Lys Asn Gly Ile Lys Val Asn Phe Lys Ile
    210                 215                 220

Arg His Asn Ile Glu Asp Gly Ser Val Gln Leu Ala Asp His Tyr Gln
225                 230                 235                 240

Gln Asn Thr Pro Ile Gly Asp Gly Pro Val Leu Leu Pro Asp Asn His
                245                 250                 255

Tyr Leu Ser Thr Gln Ser Ala Leu Ser Lys Asp Pro Asn Glu Lys Arg
            260                 265                 270

Asp His Met Val Leu Leu Glu Phe Val Thr Ala Ala Gly Ile Thr Leu
        275                 280                 285

Gly Met Asp Glu Leu Tyr Lys
    290                 295

<210> SEQ ID NO 52
<211> LENGTH: 295
<212> TYPE: PRT
<213> ORGANISM: Artificial Sequence
<220> FEATURE:
<223> OTHER INFORMATION: Synthetic

<400> SEQUENCE: 52

Met Ser Tyr Tyr His His His His His His Asp Tyr Asp Ile Pro Thr
1               5                   10                  15

Thr Glu Asn Leu Tyr Phe Gln Gly Gly Gly Asp Lys Lys His Glu Val
            20                  25                  30
```

```
Glu His Lys Asp Pro Lys Asp Lys Ser Gln Thr Phe Val Val Lys Pro
            35                  40                  45

Lys Thr Pro Gly Ser Gly Ser Ala Met Val Ser Lys Gly Glu Glu Leu
        50                  55                  60

Phe Thr Gly Val Val Pro Ile Leu Val Glu Leu Asp Gly Asp Val Asn
65                  70                  75                  80

Gly His Lys Phe Ser Val Ser Gly Glu Gly Glu Gly Asp Ala Thr Tyr
                85                  90                  95

Gly Lys Leu Thr Leu Lys Phe Ile Cys Thr Thr Gly Lys Leu Pro Val
            100                 105                 110

Pro Trp Pro Thr Leu Val Thr Thr Leu Thr Tyr Gly Val Gln Cys Phe
        115                 120                 125

Ser Arg Tyr Pro Asp His Met Lys Gln His Asp Phe Phe Lys Ser Ala
130                 135                 140

Met Pro Glu Gly Tyr Val Gln Glu Arg Thr Ile Phe Phe Lys Asp Asp
145                 150                 155                 160

Gly Asn Tyr Lys Thr Arg Ala Glu Val Lys Phe Glu Gly Asp Thr Leu
                165                 170                 175

Val Asn Arg Ile Glu Leu Lys Gly Ile Asp Phe Lys Glu Asp Gly Asn
            180                 185                 190

Ile Leu Gly His Lys Leu Glu Tyr Asn Tyr Asn Ser His Asn Val Tyr
        195                 200                 205

Ile Met Ala Asp Lys Gln Lys Asn Gly Ile Lys Val Asn Phe Lys Ile
210                 215                 220

Arg His Asn Ile Glu Asp Gly Ser Val Gln Leu Ala Asp His Tyr Gln
225                 230                 235                 240

Gln Asn Thr Pro Ile Gly Asp Gly Pro Val Leu Leu Pro Asp Asn His
                245                 250                 255

Tyr Leu Ser Thr Gln Ser Ala Leu Ser Lys Asp Pro Asn Glu Lys Arg
            260                 265                 270

Asp His Met Val Leu Leu Glu Phe Val Thr Ala Ala Gly Ile Thr Leu
        275                 280                 285

Gly Met Asp Glu Leu Tyr Lys
290                 295

<210> SEQ ID NO 53
<211> LENGTH: 296
<212> TYPE: PRT
<213> ORGANISM: Artificial Sequence
<220> FEATURE:
<223> OTHER INFORMATION: Synthetic

<400> SEQUENCE: 53

Met Ser Tyr Tyr His His His His His His Asp Tyr Asp Ile Pro Thr
1               5                   10                  15

Thr Glu Asn Leu Tyr Phe Gln Gly Gly Gly Asp Lys Lys Gln Glu Val
            20                  25                  30

Glu His Lys Asp Pro Lys Asp Lys Ser Gln Thr Phe Val Val Lys Pro
        35                  40                  45

Lys Thr Pro Gly Ser Gly Ser Gly Ala Met Val Ser Lys Gly Glu Glu
    50                  55                  60

Leu Phe Thr Gly Val Val Pro Ile Leu Val Glu Leu Asp Gly Asp Val
65                  70                  75                  80

Asn Gly His Lys Phe Ser Val Ser Gly Glu Gly Glu Gly Asp Ala Thr
                85                  90                  95
```

```
Tyr Gly Lys Leu Thr Leu Lys Phe Ile Cys Thr Thr Gly Lys Leu Pro
            100                 105                 110

Val Pro Trp Pro Thr Leu Val Thr Thr Leu Thr Tyr Gly Val Gln Cys
        115                 120                 125

Phe Ser Arg Tyr Pro Asp His Met Lys Gln His Asp Phe Phe Lys Ser
    130                 135                 140

Ala Met Pro Glu Gly Tyr Val Gln Glu Arg Thr Ile Phe Phe Lys Asp
145                 150                 155                 160

Asp Gly Asn Tyr Lys Thr Arg Ala Glu Val Lys Phe Glu Gly Asp Thr
                165                 170                 175

Leu Val Asn Arg Ile Glu Leu Lys Gly Ile Asp Phe Lys Glu Asp Gly
            180                 185                 190

Asn Ile Leu Gly His Lys Leu Glu Tyr Asn Tyr Asn Ser His Asn Val
        195                 200                 205

Tyr Ile Met Ala Asp Lys Gln Lys Asn Gly Ile Lys Val Asn Phe Lys
    210                 215                 220

Ile Arg His Asn Ile Glu Asp Gly Ser Val Gln Leu Ala Asp His Tyr
225                 230                 235                 240

Gln Gln Asn Thr Pro Ile Gly Asp Gly Pro Val Leu Leu Pro Asp Asn
                245                 250                 255

His Tyr Leu Ser Thr Gln Ser Ala Leu Ser Lys Asp Pro Asn Glu Lys
            260                 265                 270

Arg Asp His Met Val Leu Leu Glu Phe Val Thr Ala Ala Gly Ile Thr
        275                 280                 285

Leu Gly Met Asp Glu Leu Tyr Lys
    290                 295

<210> SEQ ID NO 54
<211> LENGTH: 294
<212> TYPE: PRT
<213> ORGANISM: Artificial Sequence
<220> FEATURE:
<223> OTHER INFORMATION: Synthetic

<400> SEQUENCE: 54

Met Ser Tyr Tyr His His His His His His Asp Tyr Asp Ile Pro Thr
1               5                   10                  15

Thr Glu Asn Leu Tyr Phe Gln Gly Ala Asp Thr Lys Gln Val Val Lys
            20                  25                  30

His Glu Asp Lys Asn Asp Lys Ala Gln Thr Leu Val Val Glu Lys Pro
        35                  40                  45

Thr Gly Ser Gly Ser Gly Ala Met Val Ser Lys Gly Glu Glu Leu Phe
    50                  55                  60

Thr Gly Val Val Pro Ile Leu Val Glu Leu Asp Gly Asp Val Asn Gly
65                  70                  75                  80

His Lys Phe Ser Val Ser Gly Glu Gly Glu Gly Asp Ala Thr Tyr Gly
                85                  90                  95

Lys Leu Thr Leu Lys Phe Ile Cys Thr Thr Gly Lys Leu Pro Val Pro
            100                 105                 110

Trp Pro Thr Leu Val Thr Thr Leu Thr Tyr Gly Val Gln Cys Phe Ser
        115                 120                 125

Arg Tyr Pro Asp His Met Lys Gln His Asp Phe Phe Lys Ser Ala Met
    130                 135                 140

Pro Glu Gly Tyr Val Gln Glu Arg Thr Ile Phe Phe Lys Asp Asp Gly
145                 150                 155                 160
```

```
Asn Tyr Lys Thr Arg Ala Glu Val Lys Phe Glu Gly Asp Thr Leu Val
            165                 170                 175

Asn Arg Ile Glu Leu Lys Gly Ile Asp Phe Lys Glu Asp Gly Asn Ile
        180                 185                 190

Leu Gly His Lys Leu Glu Tyr Asn Tyr Asn Ser His Asn Val Tyr Ile
        195                 200                 205

Met Ala Asp Lys Gln Lys Asn Gly Ile Lys Val Asn Phe Lys Ile Arg
    210                 215                 220

His Asn Ile Glu Asp Gly Ser Val Gln Leu Ala Asp His Tyr Gln Gln
225                 230                 235                 240

Asn Thr Pro Ile Gly Asp Gly Pro Val Leu Leu Pro Asn His Tyr
            245                 250                 255

Leu Ser Thr Gln Ser Ala Leu Ser Lys Asp Pro Asn Glu Lys Arg Asp
            260                 265                 270

His Met Val Leu Leu Glu Phe Val Thr Ala Ala Gly Ile Thr Leu Gly
        275                 280                 285

Met Asp Glu Leu Tyr Lys
    290

<210> SEQ ID NO 55
<211> LENGTH: 9
<212> TYPE: PRT
<213> ORGANISM: Artificial
<220> FEATURE:
<223> OTHER INFORMATION: Consensus sequence
<220> FEATURE:
<221> NAME/KEY: VARIANT
<222> LOCATION: (1)..(1)
<223> OTHER INFORMATION: H or E
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: VARIANT
<222> LOCATION: (6)..(6)
<223> OTHER INFORMATION: D or S
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: VARIANT
<222> LOCATION: (9)..(9)
<223> OTHER INFORMATION: Q or E

<400> SEQUENCE: 55

His Xaa Asp Xaa Xaa Asp Xaa Xaa Gln
1               5

<210> SEQ ID NO 56
<211> LENGTH: 9
<212> TYPE: PRT
<213> ORGANISM: Artificial
<220> FEATURE:
<223> OTHER INFORMATION: Consensus sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
```

```
<223> OTHER INFORMATION: Xaa can be any naturally occurring amino acid
<220> FEATURE:
<221> NAME/KEY: VARIANT
<222> LOCATION: (6)..(6)
<223> OTHER INFORMATION: D or S
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: VARIANT
<222> LOCATION: (9)..(9)
<223> OTHER INFORMATION: Q or E

<400> SEQUENCE: 56

His Xaa Asp Xaa Xaa Asp Xaa Xaa Gln
1               5

<210> SEQ ID NO 57
<211> LENGTH: 9
<212> TYPE: PRT
<213> ORGANISM: Artificial
<220> FEATURE:
<223> OTHER INFORMATION: Consensus sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: VARIANT
<222> LOCATION: (9)..(9)
<223> OTHER INFORMATION: Q or E

<400> SEQUENCE: 57

His Xaa Asp Xaa Xaa Ser Xaa Xaa Gln
1               5

<210> SEQ ID NO 58
<211> LENGTH: 9
<212> TYPE: PRT
<213> ORGANISM: Artificial
<220> FEATURE:
<223> OTHER INFORMATION: Consensus sequence
<220> FEATURE:
<221> NAME/KEY: VARIANT
<222> LOCATION: (1)..(1)
<223> OTHER INFORMATION: H or E
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(8)
<223> OTHER INFORMATION: Xaa can be any naturally occurring amino acid
<220> FEATURE:
<221> NAME/KEY: VARIANT
<222> LOCATION: (9)..(9)
<223> OTHER INFORMATION: Q or E

<400> SEQUENCE: 58

His Xaa Asp Xaa Xaa Xaa Xaa Xaa Gln
1               5
```

METHODS FOR PROTEIN LIGATION AND USES THEREOF

CROSS-REFERENCE TO RELATED PATENT APPLICATIONS

This application is a U.S. National Stage Application under 35 U.S.C. § 371 of International Patent Application No. PCT/NZ2017/050147, filed Nov. 16, 2017, which claims the benefit of priority under 35 U.S.C. Section 119(e) of New Zealand Patent Application number NZ 726413 filed Nov. 16, 2016, both of which are incorporated by reference in their entireties. The International Application was published on May 24, 2018, as International Publication No. WO 2018/093274 A1.

FIELD OF THE INVENTION

The present invention relates to protein ligation technologies, purified or recombinant peptides, methods for making peptides with covalent bonds including reversible covalent bonds such as reversible intermolecular covalent bonds, and uses thereof. In particular, this invention relates to intermolecular ester bonds, particularly reversible ester bonds between the hydroxyl and amide groups of amino acid side chains present in recombinant chimeric peptides and proteins and the use of such peptides and proteins in protein engineering.

BACKGROUND TO THE INVENTION

Protein ligation technologies are important tools in the field of molecular biology, and have wide application in a number of life science disciplines such as detection, purification and protein engineering technologies.

Until recently, protein ligation relied on weaker and non-permanent non-covalent interactions such as ionic bonds, hydrogen bonds, hydrophobic bonds and van der Waals forces. The recent characterisation of stabilising intramolecular covalent isopeptide bonds in the pili of Gram-positive bacteria has uncovered its potential as a new tool in protein ligation.

Isopeptide bonds are amide bonds which form between the amino acids side chains of lysine and asparagine or aspartate/aspartic acid. Isopeptide bonds have a number of advantages, including spontaneous formation, irreversible under biological conditions and resistance to most proteases. However, irreversibility of isopeptide system tends to limit the complexity and flexibility of protein complexes that can be generated using the isopeptide system.

The stable covalent isopeptide bonds can be used for the creation of protein structures for nanotechnology. The development of protein ligation technologies which enable the creation of complex protein structures is highly desirable.

As there are currently only two known isopeptide systems available, there is an ongoing need for new protein ligation technologies.

It is an object of the present invention to provide protein ligation technologies including reversible protein ligation technologies and uses thereof, which overcomes or at least ameliorates some of the abovementioned disadvantages or which at least provides the public with a useful choice.

Other objects of the invention may become apparent from the following description which is given by way of example only.

SUMMARY OF THE INVENTION

In one aspect the invention relates to recombinant polypeptides comprising one or more amino acid sequences comprising an immunoglobulin-like domain, wherein the Ig-like domain is split into a truncated protein and a peptide comprising the final β-strand of the Ig-like domain.

In another aspect the invention relates to a peptide tag and binding partner pair wherein
a) the peptide tag comprises one reactive residue capable of being involved in a spontaneously-formed ester bond within a β-clasp arrangement in a β-clasp containing protein, and wherein the peptide tag comprises at least 5 contiguous, for example 8, 10, 12, 14, or 16 amino acids of said β-clasp containing protein, and optionally does not comprise the entire amino acid sequence of the β-clasp containing protein;
b) said binding partner
   i. comprises a separate fragment of a β-clasp containing protein wherein said fragment comprises at least about 10, for example 20, 30, 40, 50 contiguous amino acids of said β-clasp containing protein or comprises a sequence which has at least 75%, for example at least 80%, at least 85%, at least 90% or at least 95% identity to said fragment, and
   ii. comprises the other reactive residue capable of being involved in the spontaneously-formed ester bond in a β-clasp containing protein and
said peptide tag and binding partner are capable of binding to each other by forming a spontaneously-formed ester bond.

For example, the invention relates to a peptide tag and binding partner pair wherein
a) the peptide tag comprises one reactive residue capable of being involved in a spontaneously-formed ester bond within a β-clasp arrangement in a β-clasp containing protein, and wherein the peptide tag comprises at least 5 contiguous amino acids of said β-clasp containing protein, and does not comprise the entire amino acid sequence of the β-clasp containing protein;
b) said binding partner
   i. comprises a separate fragment of a β-clasp containing protein wherein said fragment comprises at least about 10 contiguous amino acids of said β-clasp containing protein or comprises a sequence which has at least 75% identity to said fragment, and
   ii. comprises the other reactive residue capable of being involved in the spontaneously-formed ester bond in a β-clasp containing protein and
said peptide tag and binding partner are capable of binding to each other by forming a spontaneously-formed ester bond between the reactive residue present in the peptide tag and the reactive residue present in the binding partner,
and wherein the peptide tag is covalently linked to one or more heterologous amino acid sequences,
and wherein the binding partner is covalently linked to one or more heterologous amino acid sequences.

In another aspect the invention relates to a peptide tag and binding partner pair wherein
a) the peptide tag comprises at least about 10, for example at least 12, at least 14, at least 16, at least 18, at least 20, at least 22, or at least 24 amino acids capable of forming a β-sheet, wherein one of the amino acids is a reactive residue capable of spontaneously forming an ester bond in an β-clasp of an β-clasp containing protein, wherein the reactive residue is selected from the group comprising threonine, serine, glutamine, and glutamate/glutamic acid, and optionally wherein the peptide tag does not comprise the entire amino acid sequence of the β-clasp containing protein;

b) said binding partner
  i. comprises a separate fragment of a β-clasp containing protein, wherein said fragment comprises at least about 10, for example at least about 20, at least about 40, at least about 60, at least about 80, at least about 100, or at least about 120 contiguous amino acids of a β-clasp domain from a β-clasp containing protein or comprises a sequence which has at least 75% for example at least 80%, at least 85%, at least 90% or at least 95% identity to said fragment, and
  ii. comprises a reactive residue involved in a spontaneous ester bond in a β-clasp containing protein, wherein when the reactive residue in the peptide tag is threonine or serine, the reactive residue in the binding partner is glutamine or glutamate/glutamic acid, and wherein when the reactive residue in the peptide tag is glutamine or glutamate/glutamic acid, the reactive residue in the binding partner is threonine or serine; and
  said peptide tag and binding partner are capable of binding to each other by spontaneously forming an ester bond.

For example, the invention relates to a peptide tag and binding partner pair wherein
a) the peptide tag comprises at least about 10 amino acids capable of forming a β-sheet, wherein one of the amino acids is a reactive residue capable of spontaneously forming an ester bond in an β-clasp of an β-clasp containing protein, wherein the reactive residue is selected from the group comprising threonine, serine, glutamine, and glutamate/glutamic acid, and wherein the peptide tag does not comprise the entire amino acid sequence of the β-clasp containing protein;
b) said binding partner
  i. comprises a separate fragment of a β-clasp containing protein, wherein said fragment comprises at least about 10 contiguous amino acids of a β-clasp domain from a β-clasp containing protein or comprises a sequence which has at least 75% identity to said fragment, and
  ii. comprises a reactive residue involved in a spontaneous ester bond in a β-clasp containing protein, wherein when the reactive residue in the peptide tag is threonine or serine, the reactive residue in the binding partner is glutamine or glutamate/glutamic acid, and wherein when the reactive residue in the peptide tag is glutamine or glutamate/glutamic acid, the reactive residue in the binding partner is threonine or serine; and
c) said peptide tag and binding partner are capable of binding to each other by spontaneously forming an ester bond between the reactive residue present in the peptide tag and the reactive residue present in the binding partner,
  and wherein the peptide tag is covalently linked to one or more heterologous amino acid sequences,
  and wherein the binding partner is covalently linked to one or more heterologous amino acid sequences.

Those of skill in the art will appreciate that, where applicable, any of the embodiments described herein relate to any of the aspects described herein.

In various embodiments, the β-clasp containing protein is an Ig-like fold containing protein.

In various embodiments, one or more of the reactive residues capable of being involved in a spontaneously-formed ester bond within a β-clasp arrangement in a β-clasp containing protein is present in an Ig-like fold comprising two β-sheets in a (3-clasp from an Ig-like fold containing protein. In one example, each reactive residue is present in an Ig-like fold from an Ig-like fold containing protein.

In one embodiment, the Ig-like fold comprising two β-sheets in a β-clasp arrangement additionally has the first and last β-strands joined via the ester bond.

In various embodiments, the ester bond is an intermolecular ester bond.

In one embodiment, when the peptide tag comprises a reactive serine residue, the binding partner comprises a reactive glutamine or glutamate/glutamic acid residue, or wherein when the peptide tag comprises a reactive glutamine or glutamate/glutamic acid residue, the binding partner comprises a reactive serine residue.

In one embodiment, the ester bond formed between the two reactive residues is reversibly hydrolysable.

In one embodiment, the ester bond formed between the two reactive residues is reversibly hydrolysed when the pH is greater than 7.

In certain examples, the ester bond formed between the two reactive residues is reversibly hydrolysed when the pH is from about 7 to about 9, or from about 7.5 to about 9, or from about 8 to about 9. In one example, the ester bond is reversibly hydrolysed when the pH is about 8.

In various embodiments, the ester bond is capable of being formed when the peptide tag and binding partner are maintained under conditions comprising one or more of the following:
  a) a pH of about 7 or below,
  b) the presence of one or more molecular crowding agents,
  c) the presence of one or more divalent cations,
  d) the presence of glycerol,
  e) the presence of a zwitterionic buffering molecule,
  f) the presence of a buffering molecule comprising an alkyl linked sulfonic acid functionality, including an ethyl or propyl linked sulfonic acid functionality,
  g) the presence of a buffering molecule comprising a heterocyclic ring,
  h) the presence of a buffering molecule comprising a heterocyclic alkyl ring,
  i) the presence of a buffering molecule comprising a saturated heterocyclic alkyl ring,
  j) the presence of a buffering molecule comprising a saturated heterocyclic 6 membered ring,
  k) the presence of a buffering molecule as defined in each of e) to j) above,
  l) any combination of a) to k) above.

In one embodiment, the buffering molecule is selected from the group comprising MES, MOPS, and HEPES.

In one embodiment, said Ig-like fold containing protein is adhesin protein Cpe0147 from *Clostridium perfringens* or a protein with at least 75%, for example at least 80%, at least 85%, at least 90% or at least 95% identity thereto which is capable of spontaneously forming one or more ester bonds.

In one embodiment, said Ig-like fold containing protein comprises one or more of the Ig-like domains from one or more adhesin protein domains from *Mobiluncus mulieris*, such as the LPXTG-motif cell wall anchor domain protein, protein ID EFM47174.1), or a protein with at least 80%, at least 85%, at least 90% or at least 95% identity thereto which is capable of spontaneously forming one or more ester bonds.

In one embodiment, the peptide tag comprises 10 or more, for example 12 or more, 14 or more, 16 or more, 20 or more, 22 or more contiguous amino acids of the sequence set out in SEQ ID NO. 1 and corresponding to amino acids 565-587 of adhesin protein Cpe0147 from *Clostridium perfringens* or a sequence with at least 75%, for example at least 80%, at least 85%, at least 90% or at least 95% identity thereto.

In one embodiment, the binding partner comprises 10 or more, for example 20 or more, 40 or more, 60 or more, 80 or more, 100 or more contiguous amino acids of the sequence set out in SEQ ID NO. 1 and corresponding to amino acids 439-563 of adhesin protein Cpe0147 from *Clostridium perfringens* or a sequence with at least 75% identity thereto.

In one embodiment, the peptide tag is less than 50 amino acids in length.

In another aspect the invention relates to a peptide tag comprising at least about 10 contiguous amino acids of an Ig-like fold domain from an Ig-like fold domain containing protein, wherein the at least about 10 contiguous amino acids are capable of forming a β-sheet, and wherein one of the amino acids is a reactive residue capable of spontaneously forming an intermolecular ester bond in an Ig-like fold of an Ig-like fold containing protein selected from the group comprising threonine, serine, glutamine, and glutamate/glutamic acid, and wherein the peptide tag does not comprise the entire amino acid sequence of the Ig-like fold containing protein.

In another aspect the invention relates to a peptide tag comprising at least about 10 contiguous amino acids of an Ig-like fold domain from an Ig-like fold domain containing protein, wherein the at least about 10 contiguous amino acids are capable of forming a β-sheet, and wherein one of the amino acids is a reactive residue capable of spontaneously forming an intermolecular ester bond in an Ig-like fold of an Ig-like fold containing protein selected from the group comprising threonine, serine, glutamine, and glutamate/glutamic acid, and wherein the peptide tag comprises a heterologous amino acid sequence.

In one embodiment, the peptide tag comprises at least 8 contiguous amino acids from a heterologous protein.

In one embodiment, the peptide tag comprises 10 or more contiguous amino acids of the sequence set out in SEQ ID NO. 1 and corresponding to amino acids 565-587 of adhesin protein Cpe0147 from *Clostridium perfringens* or a sequence with at least 75% identity thereto.

In another embodiment, the peptide tag comprising a glutamine or glutamate/glutamic acid reactive residue, wherein the glutamine or glutamate/glutamic acid reactive residue is present in an amino acid sequence HXDXXDXX[Q/E], (SEQ ID NO.30).

In another embodiment, the glutamine or glutamate/glutamic acid reactive residue is present in an amino acid sequence [H/E]XDXX[D/S]XX[Q/E], (SEQ ID NO. 55).

In another embodiment, the glutamine or glutamate/glutamic acid reactive residue is present in an amino acid sequence HXDXX[D/S]XX[Q/E], (SEQ ID NO. 57).

In one embodiment, the glutamine or glutamate/glutamic acid reactive residue is present in an amino acid sequence HXDXXSXX[Q/E] (SEQ ID NO. 57).

In another embodiment, the glutamine or glutamate/glutamic acid reactive residue is present in an amino acid sequence [H/E]XD [Q/E], (SEQ ID NO. 58).

In a further aspect the invention relates to a binding partner comprising a fragment of an Ig-like fold containing protein, wherein said fragment comprises at least about 10 contiguous amino acids of an Ig-like fold domain from an Ig-like fold containing protein or comprises a sequence which has at least 75% identity to said fragment, and wherein the fragment comprises a reactive residue capable of spontaneously forming an intermolecular ester bond in an Ig-like fold of an Ig-like fold containing protein, the reactive amino acid residue being selected from the group comprising threonine, serine, glutamine, and glutamate/glutamic acid.

In one embodiment, the binding partner comprises a heterologous amino acid sequence. In one embodiment, the binding partner comprises at least 8 contiguous amino acids from a heterologous protein.

In one embodiment, the binding partner is a fragment of SEQ ID NO. 1.

In another embodiment, the binding partner comprises 10 or more contiguous amino acids of the sequence set out in SEQ ID NO. 1 and corresponding to amino acids 439-563 of adhesin protein Cpe0147 from *Clostridiumperfringens* or a sequence with at least 75% identity thereto, excluding the sequence of SEQ ID NO. 1.

In various embodiments, the peptide tag and/or the binding partner comprises 10 or more contiguous amino acids of the amino acid sequence of any one of SEQ ID NO.s 1-4 or 21-30.

In various embodiments, the peptide tag and/or the binding partner comprises at least about 15, at least about 20, at least about 25, at least about 30, at least about 35, or at least about 40 or more contiguous amino acids of the amino acid sequence of any one of SEQ ID NO.s 1-4 or 21-30.

In various embodiments, the peptide tag and/or the binding partner comprises 10 or more contiguous amino acids of the amino acid sequence of any one of SEQ ID NO.s 31-58. In various examples, the peptide tag and/or the binding partner comprises 10 or more contiguous amino acids of the amino acid sequence of any one of SEQ ID NO.s 31-58, and comprises at least one amino acid from two or more of the domains present in said amino acid sequence as identified in one of Tables 37 to 41.

In various embodiments, the peptide tag and/or the binding partner comprises at least about 15, at least about 20, at least about 25, at least about 30, at least about 35, or at least about 40 or more contiguous amino acids of the amino acid sequence of any one of SEQ ID NO.s 31-58. In various examples, the peptide tag and/or the binding partner comprises at least about 15, at least about 20, at least about 25, at least about 30, at least about 35, or at least about 40 or more contiguous amino acids of the amino acid sequence of any one of SEQ ID NO.s 31-58, and comprises at least one amino acid from two or more of the domains present in said amino acid sequence as identified in one of Tables 37 to 41.

In various embodiments, the peptide tag, the binding partner, or both the peptide tag and the binding partner comprise two or more reactive residues capable of spontaneously forming an ester bond, wherein the reactive residue is selected from the group comprising threonine, serine, glutamine, and glutamate/glutamic acid.

In one aspect the invention relates to a peptide tag and binding partner pair wherein said peptide tag and/or said binding partner is conjugated to a nucleic acid molecule, protein, peptide, small-molecule organic compound (including fluorophore), metal-ligand complex, polysaccharide, nanoparticle, nanotube, polymer or a combination thereof. For example, the peptide tag and/or binding partner comprises a heterologous amino acid sequence.

In one embodiment, the invention relates to a chimeric protein comprising a peptide tag and one or more heterologous amino acid sequences.

In one embodiment, the invention relates to a chimeric protein wherein the reactive residue in the peptide tag is serine.

In one embodiment, the invention relates to a chimeric protein wherein the reactive residue in the peptide tag is threonine.

In one embodiment, the invention relates to a chimeric protein comprising a binding partner and one or more heterologous amino acid sequences.

In one embodiment, the invention relates to a chimeric protein wherein the reactive residue in the binding partner is serine.

In one embodiment, the invention relates to a chimeric protein wherein the reactive residue in the binding partner is threonine.

In one aspect the invention relates to a chimeric protein comprising
 a) two or more peptide tags, or
 b) two or more binding partners, or
 c) at least one peptide tag, and at least one binding partner.

In one embodiment, the chimeric protein comprises one or more heterologous amino acid sequences.

In one embodiment, only one of peptide tags or binding partners present in the chimeric protein comprises a serine as the reactive residue.

In one embodiment, each of peptide tags or binding partners present in the chimeric protein comprises a serine as the reactive residue.

In one embodiment, only one of peptide tags or binding partners present in the chimeric protein comprises a threonine as the reactive residue.

In one embodiment, each of peptide tags or binding partners present in the chimeric protein comprises a threonine as the reactive residue.

In one embodiment, only one of peptide tags or binding partners present in the chimeric protein comprises a threonine, glutamine, or glutamate/glutamic acid as the reactive residue.

In one embodiment, wherein each of the peptide tags or binding partners present in the chimeric protein comprises a threonine, glutamine, or glutamate/glutamic acid as the reactive residue.

In one embodiment, the chimeric protein is branched.

In one embodiment, each branch of the branched protein comprises at least one peptide tag or binding partner.

In another aspect the invention relates to a multimeric protein complex comprising two or more chimeric proteins.

In one embodiment, at least one of the chimeric proteins comprises a heterologous amino acid sequence comprising an enzyme, an antigen, a structural protein, an antibody, a cytokine, or a receptor.

In one embodiment, the multimeric protein complex comprises two or more chimeric proteins, wherein at least one of the chimeric proteins comprises a heterologous amino acid sequence comprising an enzyme, and at least one of the chimeric proteins comprises a different heterologous amino acid sequence comprising an enzyme.

In another aspect the invention relates to a multimeric protein complex comprising one or more components selected from the group comprising: a peptide tag as herein described, a binding partner as herein described, a chimeric protein as herein described, and a heterologous amino acid sequence, such as a heterologous amino acid sequence comprising an enzyme, an antigen, a structural protein, an antibody, a cytokine, or a receptor.

In one embodiment, the multimeric protein complex comprises one or more components selected from the group comprising: a trunk domain as herein described, a branch domain as herein described, a cargo as herein described, and a cargo protein as herein described.

In one embodiment, the multimeric protein complex comprises two or more trunk domains. In various examples, the multimeric protein complex comprises two or more trunk domains capable of being assembled and covalently linked in a predetermined manner.

In certain embodiments, two or more of the trunk domains each comprise at least part of one or more Ig-like folds, thereby to provide specific complementation between a first trunk domain comprising a first part of an Ig-like fold and a second trunk domain comprising a complementary part of the Ig-like fold and specific binding of and formation of an ester bond between the two trunk domains.

In certain embodiments, each of the trunk domains forming the multimeric protein complex is complementary to and/or binds specifically to one or more other trunk domains, for example in a predetermined manner. In certain examples, specific binding between two trunk domains is provided by complementarity between binding domains present on each of the trunk domains, for example, one trunk domain comprises, for example, at least a part of the first or last β-strand of a β-sheet usually present in a β-clasp arrangement, and a second trunk domain comprises at least a complementary part of the β-strand or the β-sheet thereby to recapitulate the β-clasp arrangement on binding of the first and second trunk domains.

In certain embodiments, the trunk domains do not bind to other components of the multimeric protein complex, such as other trunk domains, other than those to which they are complementary. For example, the multimeric protein comprises two or more trunk domains wherein one of the trunk domains comprises at least one part of a first Ig-like domain from an Ig-like domain-containing protein and at least one part of a second Ig-like domain from an Ig-like domain-containing protein, and another of the trunk domains comprises at least a part of either the first Ig-like domain or the second Ig-like domain, thereby complementing and recapitulating the first or second Ig-like domain on binding between the two trunk domains.

In certain examples, the multimeric protein comprises two or more trunk domains which collectively comprise two or more Ig-like domains which are adjacent one another in the native sequence of the Ig-like domain-containing protein from which the domains are derived. In certain examples, two or more of the trunk domains each comprise at least a part of one Ig-like domain and at least a part of an Ig-like domain which is adjacent to the one Ig-like domain in the Ig-like domain-containing protein. In one example, the part of the Ig-like domain is the first or last β-strand of a β-sheet usually present in a β-clasp arrangement in an Ig-like domain of an Ig-like domain-containing protein.

In various embodiments, the multimeric protein complex comprises one or more protein components comprising 10 or more contiguous amino acids of the amino acid sequence of any one of SEQ ID NO.s 1-4 or 21-30.

In various embodiments, the multimeric protein complex comprises one or more protein components comprising at least about 15, at least about 20, at least about 25, at least about 30, at least about 35, or at least about 40 or more contiguous amino acids of the amino acid sequence of any one of SEQ ID NO.s 1-4 or 21-30.

In various embodiments, the multimeric protein complex comprises one or more protein components comprising 10 or more contiguous amino acids of the amino acid sequence of any one of SEQ ID NO.s 31-58. In various examples, the multimeric protein complex comprises one or more protein components comprising 10 or more contiguous amino acids of the amino acid sequence of any one of SEQ ID NO.s 31-58, and comprises at least one amino acid from two or more of the domains present in said amino acid sequence as identified in one of Tables 37 to 41.

In various embodiments, the multimeric protein complex comprises one or more protein components comprising at least about 15, at least about 20, at least about 25, at least about 30, at least about 35, or at least about 40 or more contiguous amino acids of the amino acid sequence of any one of SEQ ID NO.s 31-58. In various examples, the multimeric protein complex comprises one or more protein components comprising at least about 15, at least about 20, at least about 25, at least about 30, at least about 35, or at least about 40 or more contiguous amino acids of the amino acid sequence of any one of SEQ ID NO.s 31-58, and comprises at least one amino acid from two or more of the domains present in said amino acid sequence as identified in one of Tables 37 to 41.

In another aspect the invention relates to a method of forming a covalently linked multimeric protein complex, the method comprising
  a) providing a peptide tag or a chimeric protein, wherein the chimeric protein comprises at least one peptide tag,
  b) providing a binding partner or a chimeric protein, wherein the chimeric protein comprises at least one binding partner,
  c) contacting the peptide tag or chimeric protein of step a) and the binding partner or chimeric protein of step b) under conditions suitable for the spontaneous formation of an intermolecular ester bond,
  d) optionally repeating steps a) to c) one or more times for example 2 or more, 4 or more, 6 or more times,
  thereby forming a covalently linked multimeric protein complex.

In one embodiment, the method of forming a covalently linked multimeric protein complex comprises
  a) providing a peptide tag as herein described or a chimeric protein comprising at least one peptide tag as herein described,
  b) providing a binding partner as herein described or a chimeric protein comprising at least one binding partner as herein described,
  c) contacting the peptide tag or chimeric protein of step a) and the binding partner or chimeric protein of step b) under conditions suitable for the spontaneous formation of an intermolecular ester bond,
  thereby forming a covalently linked multimeric protein complex.

In one embodiment, the method of forming a covalently linked multimeric protein complex comprises, when one or more of the reactive residues present in the peptide tag, the binding partner, or one or more of the chimeric proteins is serine, glutamine, or glutamate/glutamic acid, maintaining the multimeric protein complex at a pH of greater than 7.

In one embodiment, the method of forming a covalently linked multimeric protein complex optionally comprises, when one or more of the reactive residues present in the peptide tag, the binding partner, or one or more of the chimeric proteins is serine, glutamine, or glutamate/glutamic acid, maintaining the multimeric protein complex at a pH of greater than 7, or maintaining the multimeric protein complex under conditions suitable for the hydrolysis of a covalent bond formed between a serine residue and a glutamine or glutamate/glutamic acid residue.

In one embodiment, the method of forming a covalently linked multimeric protein complex additionally comprises
  e) providing a peptide tag or a chimeric protein, wherein the chimeric protein comprises at least one peptide tag, and/or
  f) providing a binding partner or a chimeric protein, wherein the chimeric protein comprises at least one binding partner,
  g) contacting the peptide tag or chimeric protein of step e) and/or the peptide tag or chimeric protein of step f) with the multimeric protein complex under conditions suitable for the spontaneous formation of an intermolecular ester bond,
  h) optionally repeating steps e) to g) one or more times, for example 2 or more, 4 or more, 6 or more times, and/or
  i) optionally maintaining the multimeric protein complex at a pH of greater than 7, or
  j) any combination of h) and i).

In various embodiments, the conditions suitable for the formation of an intermolecular ester bond comprise one or more of the following:
  a) a pH of about 7 or below,
  b) presence of one or more molecular crowding agents,
  c) the presence of one or more divalent cations,
  d) the presence of glycerol,
  e) the presence of a zwitterionic buffering molecule,
  f) the presence of a buffering molecule comprising an alkyl linked sulfonic acid functionality, including an ethyl or propyl linked sulfonic acid functionality,
  g) the presence of a buffering molecule comprising a heterocyclic ring,
  h) the presence of a buffering molecule comprising a heterocyclic alkyl ring,
  i) the presence of a buffering molecule comprising a saturated heterocyclic alkyl ring,
  j) the presence of a buffering molecule comprising a saturated heterocyclic 6 membered ring,
  k) the presence of a buffering molecule as defined in each of e) to j) above,
  l) any combination of any two or more of a) to k) above.

In one embodiment, the buffering molecule is selected from the group comprising MES, MOPS, and HEPES.

In another aspect the invention relates to a method of hydrolysing one or more reversible covalent bonds in a covalently linked multimeric protein complex, the method comprising
  a) providing a covalently linked multimeric protein complex, the protein complex comprising
    i at least one peptide tag as herein described or a chimeric protein comprising at least one peptide tag as herein described, and
    ii at least one binding partner as herein described or a chimeric protein comprising at least one binding partner as herein described,
    wherein one or more of the reactive residues present in the peptide tag, the binding partner, or one or more of the chimeric proteins is serine, glutamine, or glutamate/glutamic acid,
  b) maintaining the protein complex at a pH of greater than about 7 for a period sufficient to hydrolyse the covalent bond between the serine and the glutamine or glutamate/glutamic acid, or maintaining the multimeric protein complex under conditions suitable for the hydrolysis of the covalent bond formed between a serine residue and a glutamine or glutamate/glutamic acid residue,
  thereby hydrolysing the one or more reversible covalent bonds in the multimeric protein complex.

In one embodiment, when one or more of the reactive residues present in the peptide tag, the binding partner, or one or more of the chimeric proteins is serine, the other reactive residue is glutamine, or glutamate/glutamic acid.

In various embodiments, the contacting or maintaining is for a period sufficient to allow the ester bond to form or be hydrolysed, as applicable.

In various embodiments, the conditions suitable for the hydrolysis of an intermolecular ester bond between a serine and a glutamine or glutamate/glutamic acid comprise one or more of the following:
   a) a pH of about 7 or above, for example a pH of from about 8 to about 9,
   b) the presence or absence of one or more molecular crowding agents,
   c) the presence or absence of one or more divalent cations,
   d) the presence or absence of glycerol,
   e) the presence or absence of a zwitterionic buffering molecule,
   f) the presence or absence of a buffering molecule comprising an alkyl linked sulfonic acid functionality, including an ethyl or propyl linked sulfonic acid functionality,
   g) the presence or absence of a buffering molecule comprising a heterocyclic ring,
   h) the presence or absence of a buffering molecule comprising a heterocyclic alkyl ring,
   i) the presence or absence of a buffering molecule comprising a saturated heterocyclic alkyl ring,
   j) the presence or absence of a buffering molecule comprising a saturated heterocyclic 6 membered ring,
   k) the presence or absence of a buffering molecule as defined in each of e) to j) above,
   l) any combination of any two or more of a) to k) above.

In one embodiment, the buffering molecule is selected from the group comprising MES, MOPS, and HEPES.

In one embodiment, the maintenance is at a pH of from about 8 to about 9.

In one embodiment, the maintenance is in the absence of one or more divalent cations.

In one embodiment, the maintenance is in the absence of one or more molecular crowding agents, and/or in the absence of glycerol.

In various embodiments, the contacting or maintaining is for a period of less than about 1 hour. In certain embodiments, the contacting or maintaining is for a period of less than about 30 minutes, or of less than about 20 minutes, less than about 10 minutes, or less than about 5 minutes.

In other embodiments, the contacting or maintaining is for a period of more than 1 hour, for example, more than 2, 3, 4, 5, or 6 hours. Longer periods are contemplated, including overnight. As those skilled in the art will appreciate, the Examples presented herein establish that both the formation of, and when the reactive residues so allow the hydrolysis of, the ester bond(s) occurs rapidly, and generally shorter reaction times are desired. In certain embodiments, for example when substantially all or all of the reactive residues present in the population of peptide tags, binding partners, binding pairs, or chimeric proteins present in a given reaction must be reacted, the contacting or maintaining may be for a longer period of several or more hours.

In another aspect the invention relates to the use of a peptide tag and binding partner pair or of one or more chimeric proteins, in the preparation of a covalently linked multimeric protein complex.

In one embodiment, the use of a peptide tag and binding partner pair or of one or more chimeric proteins wherein when said peptide tag comprises a reactive serine residue, said binding partner comprises a reactive glutamine or glutamate/glutamic acid residue, or when said peptide tag comprises a reactive glutamine or glutamate/glutamic acid residue, said binding partner comprises a reactive serine residue.

In one embodiment, the use of a peptide tag and binding partner pair or of one or more chimeric proteins wherein said peptide tag is from 5 to 50 amino acids in length.

In another aspect the invention relates to a nucleic acid molecule encoding a peptide tag and binding partner pair, a peptide tag, a binding partner, or a chimeric protein.

In another aspect the invention relates to a vector comprising a nucleic acid molecule encoding a peptide tag and binding partner pair, a peptide tag, a binding partner, or a chimeric protein.

In another aspect the invention relates to a cell comprising a nucleic acid molecule encoding a peptide tag and binding partner pair, a peptide tag, a binding partner, or a chimeric protein or a vector comprising a nucleic acid molecule encoding a peptide tag and binding partner pair, a peptide tag, a binding partner, or a chimeric protein.

In various embodiments, the invention relates to the use of a peptide tag, binding partner, a peptide tag and binding partner pair, a chimeric protein, or a nucleic acid molecule, vector, or cell as described above, in an application selected from the group comprising biocatalysis, biomaterial synthesis, chemical production, filtration, isolation or separation of one or more target molecules (for example from a complex mixture), bioremediation, nanoparticle synthesis, sensing, identification and/or localisation of target molecules, display of molecules including optically active molecules, surface coating, therapeutic biomaterials, biological scaffolds, tissue engineering, physical reinforcement, and delivery of one or more active agents.

In another aspect the invention relates to a peptide tag and binding partner pair wherein
   a) the peptide tag comprises one reactive residue capable of being involved in a spontaneously-formed ester bond within a β-clasp in a β-clasp containing protein, and wherein the peptide tag comprises a glutamine or glutamate/glutamic acid reactive residue, wherein the glutamine or glutamate/glutamic acid reactive residue is present in an amino acid sequence HXDXXDXX[Q/E], and optionally does not comprise the entire amino acid sequence of the β-clasp containing protein;
   b) said binding partner
      i. comprises a separate fragment of a β-clasp containing protein wherein said fragment comprises at least about 10, for example 20, 30, 40, 50 contiguous amino acids of said β-clasp containing protein or comprises a sequence which has at least 75%, for example at least 80%, at least 85%, at least 90% or at least 95% identity to said fragment, and
      ii. comprises the other reactive residue capable of being involved in the spontaneously-formed ester bond in said β-clasp containing protein and
   said peptide tag and binding partner are capable of binding to each other by forming a spontaneously-formed ester bond.

In another aspect the invention relates to a peptide tag and binding partner pair wherein
   c) the peptide tag comprises one reactive residue capable of being involved in a spontaneously-formed ester bond within a β-clasp in a β-clasp containing protein, and wherein the peptide tag comprises a glutamine or glutamate/glutamic acid reactive residue, wherein the glutamine or glutamate/glutamic acid reactive residue is present in an amino acid sequence [H/E]XDXX[D/S]XX[Q/E] (SEQ ID NO. 55), and optionally does not comprise the entire amino acid sequence of the β-clasp containing protein;
d) said binding partner
iii. comprises a separate fragment of a β-clasp containing protein wherein said fragment comprises at least about 10, for example 20, 30, 40, 50 contiguous amino acids of said β-clasp containing protein or comprises a sequence which has at least 75%, for example at least 80%, at least 85%, at least 90% or at least 95% identity to said fragment, and
iv. comprises the other reactive residue capable of being involved in the spontaneously-formed ester bond in said β-clasp containing protein and
said peptide tag and binding partner are capable of binding to each other by forming a spontaneously-formed ester bond.

In one embodiment, the glutamine or glutamate/glutamic acid reactive residue is present in an amino acid sequence HXDXX[D/S]XX[Q/E] (SEQ ID NO. 56). In another embodiment, the glutamine or glutamate/glutamic acid reactive residue is present in an amino acid sequence HXDXXSXX[Q/E] (SEQ ID NO. 57).

In one embodiment, the glutamine or glutamate/glutamic acid reactive residue is present in an amino acid sequence [H/E]XD [Q/E], (SEQ ID NO. 58).

In a further aspect the invention relates to a peptide binding pair comprising a first peptide binding partner and a second peptide binding partner, wherein when contacted the peptide binding partners are capable of spontaneously forming an intermolecular ester bond, wherein
a) one binding partner comprises a reactive residue selected from the group consisting of threonine, and serine, and
b) the other binding partner comprises a reactive residue selected from the group consisting of glutamine and glutamate/glutamic acid,
and when contacted, the first and second binding partners form a β-clasp, for example an Ig-like fold, containing a serine protease active site-like arrangement additionally comprising one or more accessory amino acid residues that facilitate spontaneous intermolecular ester bond formation.

In another aspect the invention relates to a first peptide binding partner and a second peptide binding partner, wherein when contacted the peptide binding partners are capable of spontaneously forming an intermolecular ester bond, wherein
a) one binding partner comprises a reactive residue selected from the group consisting of threonine, and serine, and
b) the other binding partner comprises a reactive residue selected from the group consisting of glutamine and glutamate/glutamic acid,
and when contacted, the first and second binding partners form a β-clasp, for example an Ig-like fold, containing a serine protease active site-like arrangement additionally comprising one or more accessory amino acid residues that facilitate spontaneous intermolecular ester bond formation.

In another aspect the invention relates to a peptide binding pair, wherein when contacted the peptide binding pair form a serine protease active site-like structure capable of spontaneously forming an intermolecular ester bond between two reactive amino acid residues, wherein one binding partner comprises one reactive residue selected from the group consisting of threonine, and serine, and the other binding partner comprises one reactive residue selected from the group consisting of glutamine and glutamate/glutamic acid, and wherein the reactive amino acid residues present in the active site have the following relative atom locations in the Protein Data Bank conventional orthogonal coordinate system:
a) Cβ (CB) Thr/Ser: 0, 0, 0;
b) Cδ (CD) Gln/Glu: 0.02±0.08, 1.91±0.08, −1.61±0.08.

In various embodiments one or both of the binding partners comprises one or more amino acid residues that facilitate spontaneous intermolecular ester bond formation.

In one embodiment, one or more of the amino acid residues that facilitate spontaneous intermolecular ester bond formation are present in a beta-strand forming sequence within the peptide binding partner.

In one embodiment, one or more of the amino acid residues that facilitate spontaneous intermolecular ester bond formation are present in a beta-strand forming amino acid sequence together with a reactive residue.

In one embodiment, the binding partner comprising the glutamine or glutamate/glutamic acid reactive amino acid residue comprises a histidine amino acid residue that facilitates spontaneous intermolecular ester bond formation.

In one embodiment, the binding partner comprising the glutamine or glutamate/glutamic acid reactive amino acid residue comprises a histidine amino acid residue that facilitates spontaneous intermolecular ester bond formation wherein both the reactive residue and the histidine are present in the same beta-strand of the binding partner.

In one embodiment, the binding partner comprising the glutamine or glutamate/glutamic acid reactive amino acid residue comprises a histidine amino acid residue that facilitates spontaneous intermolecular ester bond formation and wherein the histidine is within 10 amino acids in the primary amino acid sequence of the glutamine or glutamate/glutamic acid reactive residue.

In one embodiment, the histidine that facilitates spontaneous intermolecular ester bond formation and the glutamine or glutamate/glutamic acid are in a beta-strand forming amino acid sequence of one of the binding partners and are within 8 amino acids in the primary amino acid sequence of the peptide binding partner.

In one embodiment, the glutamine or glutamate/glutamic acid reactive residue present in the binding partner comprising the glutamine or glutamate/glutamic acid reactive residue is present in an amino acid sequence HXDXXDXX[Q/E], (SEQ ID NO. 30).

In one embodiment, the glutamine or glutamate/glutamic acid reactive residue present in the binding partner comprising the glutamine or glutamate/glutamic acid reactive residue is present in an amino acid sequence [H/E]XDXX[D/S]XX[Q/E] (SEQ ID NO. 55).

In one embodiment, the glutamine or glutamate/glutamic acid reactive residue present in the binding partner comprising the glutamine or glutamate/glutamic acid reactive residue is present in an amino acid sequence HXDXX[D/S]XX[Q/E] (SEQ ID NO. 56). In another embodiment, the glutamine or glutamate/glutamic acid reactive residue present in the binding partner comprising the glutamine or glutamate/glutamic acid reactive residue is present in an amino acid sequence HXDXXSXX[Q/E] (SEQ ID NO. 57). In another embodiment, the glutamine or glutamate/glutamic acid reactive residue present in the binding partner comprising the glutamine or glutamate/glutamic acid reactive residue is present in an amino acid sequence [H/E]XD[Q/E], (SEQ ID NO. 58).

In one embodiment, the binding partner comprising the glutamine or glutamate/glutamic acid reactive amino acid residue comprises a histidine amino acid residue that facilitates spontaneous intermolecular ester bond formation wherein the histidine is within about 6, about 5.5, about 5, about 4.5, about 4, about 3.5, about 3, about 2.5 or about 2 Angstrom of the glutamine or glutamate/glutamic acid reactive residue.

In one embodiment, when the binding partners are contacted, the closest atom of histidine that facilitates spontaneous intermolecular ester bond formation is within about 5, about 4.5, about 4, about 3.5, about 3, about 2.5 or about 2 Angstrom of the closest atom of threonine or serine reactive residue.

In one embodiment, the histidine residue that facilitates spontaneous intermolecular ester bond formation is present on the same binding partner as the threonine or serine reactive residue.

In one embodiment, one of the amino acid residue that facilitate spontaneous formation of the intermolecular ester bond is a histidine residue sufficiently close to the threonine or serine reactive residue so as to be capable of forming a hydrogen bond.

In one embodiment, the closest approach between the histidine residue and the threonine or serine reactive residue is less than about 5 Angstrom, less than about 4 Angstrom, less than about 3.5 Angstrom, less than about 3.4 Angstrom, less than about 3.2 Angstrom, or less than about 3 Angstrom.

In one embodiment, one of the amino acid residue that facilitate spontaneous formation of the intermolecular ester bond is a histidine residue capable of forming a hydrogen bond with the threonine or serine reactive residue.

In one embodiment, the distance between the histidine residue and the threonine or serine reactive residue is less than about 5 Angstrom, less than about 4 Angstrom, less than about 3.5 Angstrom, less than about 3.2 Angstrom, or less than about 3 Angstrom.

In various embodiments, one of the accessory amino acid residue that facilitate spontaneous formation of the intermolecular ester bond is an aspartic acid residue capable of forming a hydrogen bond with the glutamine and glutamate/glutamic acid reactive residue.

In one embodiment, the aspartic acid accessory residue is present on the same binding partner as the glutamine or glutamate/glutamic acid reactive residue.

In one embodiment, the aspartic acid accessory residue is present on the same binding partner as the threonine or serine reactive residue.

In one embodiment, a glutamate/glutamic acid or glutamine residue and an aspartic acid residue facilitate formation of the spontaneously-formed intermolecular ester bond.

In one embodiment, the glutamate/glutamic acid or glutamine residue that facilitates spontaneous formation of the intermolecular ester bond is on the same binding partner as the aspartic acid facilitating residue.

In one embodiment, the reactive amino acid residues present in the active site have the following relative atom locations in the Protein Data Bank conventional orthogonal coordinate system:
a) $C\beta$ (CB) Thr/Ser: 0, 0, 0;
b) $C\delta$ (CD) Gln/Glu: 0.02±0.08, 1.91±0.08, −1.61±0.08.

In one embodiment, the serine protease active site-like structure also comprises one or more accessory amino acids, wherein the reactive amino acid residues present in the active site have the following relative atom locations in the Protein Data Bank conventional orthogonal coordinate system:
a) $C\beta$ (CB) Thr/Ser: 0, 0, 0;
b) $C\delta$ (CD) Gln/Glu: 0.02, 1.91. −1.61
and wherein the one or more accessory amino acid residues present in the active site have when present the following $C\gamma$ (CG) locations relative to the reactive Thr/Ser $C\beta$ location:
c) His: 1.35, 3.67, 3.34
d) Asp: −3.45, −0.89, −2.19,
and wherein the standard deviation for distances between the atoms are:
e) 0.08 for $C\beta$ (CB) Thr to $C\delta$ (CD) Gln,
f) 0.25 for $C\beta$ (CB) Thr to $C\gamma$ (CG) His,
g) 0.04 for $C\beta$ (CB) Thr to $C\gamma$ (CG) Asp.

In another aspect the invention relates to a peptide binding pair comprising a first peptide binding partner and a second peptide binding partner, wherein when contacted the peptide binding partners are capable of spontaneously forming an intermolecular ester bond, wherein
a) one binding partner comprises a reactive residue selected from the group consisting of threonine, and serine, and
b) the other binding partner comprises a reactive residue selected from the group consisting of glutamine and glutamate/glutamic acid,
and when contacted, the first and second binding partners form a serine protease active site-like structure.

In another aspect the invention relates to a first peptide binding partner and a second peptide binding partner, wherein when contacted the peptide binding partners are capable of spontaneously forming an intermolecular ester bond, wherein
a) one binding partner comprises a reactive residue selected from the group consisting of threonine, and serine, and
b) the other binding partner comprises a reactive residue selected from the group consisting of glutamine and glutamate/glutamic acid,
and when contacted, the first and second binding partners form a serine protease active site-like structure.

In another aspect the invention relates to a peptide binding pair or a first peptide binding partner and a second peptide binding partner wherein the serine protease active site-like structure comprising reactive amino acid residues present in the active site having the following relative atom locations in the Protein Data Bank conventional orthogonal coordinate system:
a) $C\beta$ (CB) Thr/Ser: 0, 0, 0;
b) $C\delta$ (CD) Gln/Glu: 0.02, 1.91, −1.61
and wherein the serine protease active site-like structure comprises accessory amino acid residues present in the active site having the following $C\gamma$ (CG) locations relative to the reactive Thr/Ser $C\beta$ (CB) location:
c) His: 1.35, 3.67, 3.34
d) Asp: −3.45, −0.89, −2.19,
and wherein the standard deviation for distances between the atoms are:
e) 0.08 for $C\beta$ (CB) Thr to $C\delta$ (CD) Gln,
f) 0.25 for $C\beta$ (CB) Thr to $C\gamma$ (CG) His,
g) 0.04 for $C\beta$ (CB) Thr to $C\gamma$ (CG) Asp.

In one embodiment, the distance of $C\beta$ (CB) of the threonine or serine reactive amino acid residue is between about 2.2 Angstrom and about 3 Angstrom of $C\delta$ (CD) of the glutamine/glutamate/glutamic acid reactive amino acid residue.

In one embodiment, the distance of Cβ (CB) of the threonine or serine reactive amino acid residue is between 2.49 and 2.65 Angstrom of Cδ (CD) of the glutamine/glutamate/glutamic acid reactive amino acid residue.

In one embodiment, the distance of Cβ (CB) of the threonine or serine reactive amino acid residue is between about 4.5 and about 6.0 Angstrom of Cγ (CG) of the histidine amino acid residue that facilitate spontaneous intermolecular ester bond formation.

In one embodiment, the distance of Cβ (CB) of the threonine or serine reactive amino acid residue is between 4.86 and 5.60 Angstrom of Cγ (CG) of the histidine amino acid residue that facilitate spontaneous intermolecular ester bond formation.

In one embodiment, the distance of Cβ (CB) of the threonine or serine reactive amino acid residue is between about 3.5 and about 4.5 Angstrom of Cγ (CG) of the aspartic acid amino acid residue that facilitate spontaneous intermolecular ester bond formation.

In one embodiment, the distance of Cβ (CB) of the threonine or serine reactive amino acid residue is between 4.07 and 4.18 Angstrom of Cγ (CG) of the aspartic acid amino acid residue that facilitate spontaneous intermolecular ester bond formation.

In one embodiment, the minimum distance of Cβ (CB) of the threonine or serine reactive amino acid residue to
  a) Cδ (CD) of the glutamine/glutamate/glutamic acid reactive amino acid residue is about 2.2 Angstrom, and
  b) Cγ (CG) of the histidine amino acid residue that facilitate spontaneous intermolecular ester bond formation is about 4.5 Angstrom, and
  c) Cγ (CG) of the aspartic acid amino acid residue that facilitate spontaneous intermolecular ester bond formation is about 3.5 Angstrom,
  and wherein the maximum distance of Cβ (CB) of the threonine or serine reactive amino acid residue to
  d) Cδ (CD) of the glutamine/glutamate/glutamic acid reactive amino acid residue is about 3 Angstrom, and
  e) Cγ (CG) of the histidine amino acid residue that facilitate spontaneous intermolecular ester bond formation is about 6 Angstrom, and
  f) Cγ (CG) of the aspartic acid amino acid residue that facilitate spontaneous intermolecular ester bond formation is about 4.5 Angstrom.

In one embodiment, the minimum distance of Cβ (CB) of the threonine or serine reactive amino acid residue to
  a) Cδ (CD) of the glutamine/glutamate/glutamic acid reactive amino acid residue is 2.49 Angstrom, and
  b) Cγ (CG) of the histidine amino acid residue that facilitate spontaneous intermolecular ester bond formation is 4.86 Angstrom, and
  c) Cγ (CG) of the aspartic acid amino acid residue that facilitate spontaneous intermolecular ester bond formation is 4.07 Angstrom,
  and wherein the maximum distance of Cβ (CB) of the threonine or serine reactive amino acid residue to
  d) Cδ (CD) of the glutamine/glutamate/glutamic acid reactive amino acid residue is 2.65 Angstrom, and
  e) Cγ (CG) of the histidine amino acid residue that facilitate spontaneous intermolecular ester bond formation is 5.60 Angstrom, and
  f) Cγ (CG) of the aspartic acid amino acid residue that facilitate spontaneous intermolecular ester bond formation is 4.18 Angstrom.

In one embodiment, the Ig-like domain comprises an Ig-like domain derived from Gram-positive bacterium.

In various embodiments, the first peptide binding partner, the second peptide binding partner, or both the first and the second peptide binding partner comprise at least 10 contiguous amino acids from any one of SEQ ID No. 1-4 and 20-30 herein.

In various embodiments, the first peptide binding partner, the second peptide binding partner, or both the first and the second peptide binding partner comprise at least 10 contiguous amino acids from any one of SEQ ID No.s 31 to 58 herein.

In one embodiment, the Ig-like domain comprises a *Clostridium* protein or protein fragment.

In one embodiment, the Ig-like domain comprises a *Mobiluncus* protein or protein fragment.

In one embodiment, the Ig-like domain comprises a *Clostridium perfringens* protein or fragment thereof.

In one embodiment, the Ig-like domain comprises a *Mobiluncus mulieris* protein or fragment thereof.

In one embodiment, the Ig-like domain is encoded within the AC1_0147 gene of the *Clostridium perfringens* genome. The corresponding amino acid sequence for the gene product is given in Uniprot entry B1R775.

In one embodiment, the Ig-like domain is encoded within the HMPREF0580_0271 gene of the *Mobiluncus mulieris* genome. The corresponding amino acid sequence for the gene product is given in Uniprot entry E0QN07.

In one embodiment, the Ig-like domain is that of Cpe0147, the amino acid sequence of which is presented here as SEQ ID No. 1-4.

In one embodiment, the Ig-like domain is that of *Mobiluncus mulieris* LPXTG-motif cell wall anchor domain protein, the amino acid sequences of which are presented here as SEQ ID No. 21-30.

In one embodiment, the Ig-like domain is that of *Mobiluncus mulieris* LPXTG-motif cell wall anchor domain protein, and is present in an amino acid sequence comprising 10 or more contiguous amino acids from the amino acid sequences of any one of SEQ ID NO.s 31 to 58.

In one embodiment, the Ig-like domain comprises a) truncated protein having at least about 80% amino acid sequence identity to the polypeptide sequence of the Ig-like domain of Cpe0147 (amino acids 439 to 563) [SEQ ID No. 2], and/or
b) a peptide having at least about 80% amino acid sequence identity to the polypeptide sequence of the Ig-like domain of Cpe0147 (amino acids 565 to 587) [SEQ ID No. 3].

In one embodiment, the Ig-like domain comprises a) a protein having at least about 80% amino acid sequence identity to the amino acid sequence of an Ig-like domain of *Mobiluncus mulieris* LPXTG-motif cell wall anchor domain protein;
b) a protein having at least about 80% amino acid sequence identity to the amino acid sequence of an Ig-like domain present in any one of the amino acid sequences presented here as SEQ ID No. 21-30; and/or
c) a protein having at least about 80% amino acid sequence identity to the amino acid sequence of an Ig-like domain present in any one of the amino acid sequences presented here as SEQ ID No. 31-58.

In one embodiment, the Ig-like domain comprises a) a protein having at least about 90%, at least 95%, at least 98%, or at least 99% amino acid sequence identity to the amino acid sequence of an Ig-like domain of *Mobiluncus mulieris* LPXTG-motif cell wall anchor domain protein;

b) a protein having at least about 90%, at least 95%, at least 98%, or at least 99% amino acid sequence identity to the amino acid sequence of an Ig-like domain present in any one of the amino acid sequences presented here as SEQ ID No. 21-30; and/or c) a protein having at least about 90%, at least 95%, at least 98%, or at least 99% amino acid sequence identity to the amino acid sequence of an Ig-like domain present in any one of the amino acid sequences presented here as SEQ ID No. 31-58.

In one embodiment, the truncated protein further comprises the final β strand of the preceding Ig-like domain at the N-terminus.

In one embodiment, the Ig-like domain further comprises at its N-terminus at least 5 contiguous amino acids from the final β-strand of the preceding Ig-like domain. For example, the Ig-like domain further comprises at its N-terminus at least 5 contiguous amino acids from the final β-strand of the Ig-like domain preceding it in the native sequence from which the Ig-like domain is derived.

In one embodiment, the truncated protein further comprises the final β-strand of the preceding Ig-like domain comprising amino acids 416 to 438 (DTKQVVKHEDKNDKAQTLIVEKP [SEQ ID No.4]) of the full length Cpe0147 protein at the N-terminus.

In one embodiment, the truncated protein further comprising the final β-strand of the preceding Ig-like domain at the N-terminus is self-polymerising.

In one embodiment, the self-polymerising protein further comprises a branch domain which covalently captures proteins.

In one embodiment, the self-polymerising protein further comprises a branch domain which covalently captures cargo enzymes.

In one embodiment, the cargo enzymes form part of an enzymatic pathway.

In one embodiment, an ester bond forms between the truncated protein and a peptide.

In one embodiment, an ester bond forms between the first β-strand of the truncated protein and a peptide comprising the final β-strand of the Ig-like domain of Cpe0147.

In one embodiment, the ester bond is hydrolysable.

In one embodiment, the truncated protein comprises an amino acid substitution at position 450.

In one embodiment, the truncated protein comprises an amino acid substitution from threonine to serine at position 450.

Other aspects of the invention may become apparent from the following description which is given by way of example only and with reference to the accompanying drawings.

As used herein the term "and/or" means "and" or "or", or both.

As used herein "(s)" following a noun means the plural and/or singular forms of the noun.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

The term "comprising" as used in this specification means "consisting at least in part of". When interpreting statements in this specification which include that term, the features, prefaced by that term in each statement or claim, all need to be present but other features can also be present. Related terms such as "comprise" and "comprised" are to be interpreted in the same manner.

This invention may also be said broadly to consist in the parts, elements and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth.

BRIEF DESCRIPTION OF THE DRAWINGS

The invention will now be described by way of example only and with reference to the drawings in which:

FIG. 1 shows a ribbon diagram of a single domain from the *Clostridium perfringens* Cpe0147 adhesin, highlighting the last strand of the Ig-like protein domain (in blue) and the metal binding sites (red spheres). A stabilizing intermolecular ester bond linking the first and last strands of the protein is shown in stick form and in close-up (insert). The spontaneously-formed ester bond forms spontaneously between the side chains of a threonine and glutamine amino acid as shown in the chemical scheme.

FIG. 2 depicts the results of assays showing intermolecular ester bond formation between a peptide comprising the last β-strand (residues 565-587) and the truncated Cpe0147 protein. FIG. 2A shows the effect of buffer components on ester bond formation. After the removal of both glycerol and $CaCl_2$), little bond formation is observed. In the presence of calcium, ~40% of the protein is converted, while in the presence of glycerol, conversion is ~70%. A stylized conceptual diagram of the protein-peptide complex is shown with a linking ester bond (heavy black line). FIG. 2B shows the time course of bond formation under optimized buffer conditions. Ester bond formation nears completion in less than 15 min.

FIG. 3 shows the protein ligation potential of a split Cpe0147 domain. FIG. 3A shows small angle X-ray scattering analysis (SAXS)-derived ab initio envelope of the ligated assembly of construct A, an MBP-$Cpe0147^{439-563}$ fusion, and construct B, a $Cpe0147^{565-587}$-eGFP fusion. Crystal structures of the component parts have been fitted to the A-B envelope. FIG. 3B shows the SDS-PAGE analysis of a time course of ester bond formation between construct A, a maltose-binding protein-$Cpe0147^{439-563}$ adduct, and construct B, a $Cpe0147^{565-587}$-green fluorescent protein adduct. The time course shows >90% completion after a period of 20 hr. A stylized conceptual diagram of the A-B cross-linked assembly is shown to the right. FIG. 3C shows a plot of ester bond conversion normalized to 100% completion at 20 hr. Ester bond formation was plotted with GraphPad Prism and fitted to an exponential two phase association model. FIG. 3D shows in vivo assembly of nanochains in *E. coli* from a self-polymerizing Cpe0147 construct (a.a. 416-563) carrying maltose-binding protein as cargo. SDS-PAGE analysis shows the formation of many species with the largest greater than ~500 kDa in mass. A stylized conceptual diagram of the self-assembled nanochains is shown to the right.

FIG. 4 shows ester bond formation and hydrolysis triggered by a pH change in a T450S variant. FIG. 4A shows the reaction scheme of ester bond formation under low pH conditions and in the presence of $CaCl_2$) and glycerol. The bond can subsequently be hydrolysed by increasing the pH to above 8 and removing $CaCl_2$) and glycerol. The construct used (and illustrated to the right) is the same MBP/GFP cargo combination as that of FIG. 3A but with the substitution of serine for threonine 450 in Cpe0147. FIG. 4B shows the SDS-PAGE analysis of an ester bond formation time course (top) covering a 20 h period. The same time course is shown for the hydrolysis reaction (bottom). FIG. 4C shows a plot of ester bond formation and hydrolysis normalized to 100%. An exponential two phase exponential model was fitted with GraphPad Prism to both ester bond formation and hydrolysis data.

FIG. 5 shows the one-dimensional 1H nuclear magnetic resonance spectroscopic (NMR) analysis of Cpe0147 and variants. The methyl region (e.g. signal at −1 ppm) is diagnostic to the formation of the protein-peptide conjugate. The spectra were scaled according to the protein concentration to aid visualization. FIG. 5A shows the spectrum of a 600 μM $Cpe^{439-587}$ (bond-formed control). FIG. 5B shows the spectrum of 400 μM control $Cpe^{439-563}$, FIG. 5C shows the spectrum of mixed 50 μM $Cpe^{439-563}$+excess DTKQVVKHEDKNDKAQTLVVEKP [SEQ ID No. 3] peptide. The mixture was reacted in HEPES and glycerol (pH 7.0) for an hour to ensure the formation of the protein-peptide conjugate. The sample was then buffer-exchanged to remove the excess peptide. FIG. 5D show the spectrum of the peptide control 150 μM DTKQVVKHEDKNDKAQTLVVEKP [SEQ ID No. 3].

FIG. 6 shows the SDS-PAGE analysis of the effect of pH, molecular crowding agents, and $Ca^{2+}$ on ester bond formation. $Cpe^{439-563}$ was mixed with peptide ($Cpe^{565-587}$) comprising the last β-strand of the protein domain, and incubated for 180 min in a selection of buffer molecules (50 mM), molecular crowding agents, and calcium chloride (100 μM). SDS-PAGE gel lanes were as follows: (C) Control $Cpe^{439-563}$ without peptide; (1) $Cpe^{439-563}$+peptide in sodium acetate buffer, pH 5.0; (2) $Cpe^{439-563}$+peptide in sodium phosphate buffer, pH 6.0; (3) $Cpe^{439-563}$+peptide in MOPS buffer, pH 7.1; (4) $Cpe^{439-563}$+peptide in TRIS·HCl buffer, pH 8.0; (5) Cpe439-563+peptide in borate buffer pH 8.8; (6) Cpe439-563+peptide in glycerol (10% v/v); (7) Cpe439-563+peptide in sucrose (200 mM); (8) Cpe439-563+peptide in PEG 1k (10%).

FIG. 7 shows the SDS-PAGE buffer screen at neutral pH in the presence of glycerol and $CaCl_2$). $Cpe^{439-563}$ was mixed with peptide ($Cpe^{565-587}$) comprising the last β-strand of the protein domain, and incubated for 15 min in a selection of buffer molecules (50 mM), with a constant concentration of 20% (v/v) glycerol and 100 μM calcium chloride. SDS-PAGE gel lanes were as follows: (C) Control $Cpe^{439-563}$ without peptide; (1) $Cpe^{439-563}$+peptide in Bis-Tris propane buffer, pH 6.8; (2) Cpe439-563+peptide in HEPES buffer, pH 6.8; (3) Cpe439-563+peptide in sodium phosphate buffer, pH 6.8; (4) $Cpe^{439-563}$+peptide in MOPS buffer, pH 7.1.

FIG. 8 shows the SDS-PAGE analysis of the stability of Cpe0147 domain-2 in urea at alkaline pH. The intact domain $Cpe^{439-587}$ was incubated in increasing concentrations of urea in a TRIS·HCl, pH 9.0 buffer for 24 h. The wild type Cpe0147 domains with an intermolecular ester bond migrate further through an SDS-PAGE gel than the same protein that lacks an ester bond. The $Cpe^{439-587}$ construct is very stable to hydrolysis even in 50 mM TRIS·Cl pH 9.0, 6 M urea, with only a very small proportion where the ester bond is hydrolyzed as evident by the appearance of a faint higher mass band.

FIG. 9 shows the mass spectrometry analysis of Cpe0147-$T450S^{439-587}$ following trypsin digest. The spectra shows peaks corresponding to m/z fragments of the cross-linked complex and confirm the presence of the expected serine-glutamine side chain cross-link.

FIG. 10 shows the SDS-PAGE analysis of Cpe0147-$T450S^{439-587}$ stability over a pH range. $Cpe-T450S^{439-578}$ (250 μM concentration) was incubated for 20 h in various systems to analyze the effect of pH on ester bond stability or hydrolysis. The ester bond between Ser450 and Gln580 is stable at a pH below 7, and hydrolyses above pH 7. SDS-PAGE gel lanes were as follows: (1) $Cpe-T450S^{439-587}$ in MES buffer, pH 5.5; (2) $Cpe-T450S^{439-587}$ in MES buffer, pH 6.0; (3) $Cpe-T450S^{439-587}$ in MES buffer, pH 6.5; (4) $Cpe-T450S^{439-587}$ in HEPES buffer, pH 7.0; (5) $Cpe-T450S^{439-587}$ in HEPES buffer, pH 7.5; (6) $Cpe-T450S^{439-587}$ in TRIS·HCl buffer, pH 8.0; (7) $Cpe-T450S^{439-587}$ in TRIS·HCl buffer, pH 8.5; (8) $Cpe-T450S^{439-587}$ in TRIS·HCl buffer, pH 9.0.

FIG. 11 shows the 1D $^1H$ NMR end point analysis of the diagnostic methyl region of $Cpe0147-T450S^{439-287}$. Each protein sample (250 μM concentration), was incubated for 20 h (unless otherwise stated) in various systems to analyze the effect of pH on ester bond stability or hydrolysis. Signals at the methyl region (e.g. signal at −1 ppm) are indicative for the formation of the protein-peptide conjugate. As shown in the figure annotation, the samples, from top to bottom are: (1) $Cpe-T450S^{439-587}$ in TRIS·HCl buffer, pH 9.0; (2) $Cpe-T450S^{439-587}$ in TRIS·HCl buffer, pH 8.5; (3) $Cpe-T450S^{439-587}$ in TRIS·HCl buffer, pH 8.0; (4) $Cpe-T450S^{439-587}$ in HEPES buffer, pH 7.5; (5) $Cpe-T450S^{439-587}$ in HEPES buffer, pH 7.0; (6) $Cpe-T450S^{439-587}$ in MES buffer, pH 6.5; (7) $Cpe-T450S^{439-587}$ in MES buffer pH 6.0; (8) $Cpe-T450S^{439-587}$ in MES buffer, pH 5.5.

FIG. 12 shows the 1D $^1H$ NMR time course analysis of the diagnostic methyl region of Cpe-T450S 439-587 showing the formation of an ester bond and the protein stability of the T450S variant. The protein $Cpe-T450S^{439-587}$ (250 μM concentration) was incubated in TRIS·HCl buffer, pH 9.0 and the NMR spectra collected as different time points as annotated on the Figure.

FIG. 13 shows the SDS-PAGE analysis of repeated $Cpe0147-T450S^{439-587}$ ($Cpe-T450S^{439-587}$) ester bond formation and hydrolysis cycles. A single sample of $Cpe-T450S^{439-587}$ protein was cycled between buffers that either promote ester bond formation (50 mM MES pH 5.5, 0.1 mM calcium chloride and 20% (v/v) glycerol) or induce ester bond hydrolysis (50 mM TRIS·HCl pH 9.0). The same protein sample was cycled between the two buffers three times. Because of the slower hydrolysis step the sample was dialyzed for 24 h at each step to insure maximal reaction. SDS-PAGE gel lanes were as follows: (1) $Cpe-T450S^{439-587}$ in TRIS·HCl pH 7.0 buffer system, bond formed—as purified from *E. coli* by affinity chromatography and following a size exclusion chromatography step to isolate the single species; (2) $Cpe-T450S^{439-587}$ in TRIS·HCl pH 7.0 buffer system, mixed population as purified from *E. coli* by affinity chromatography; (3) Cpe-T450S$^{439-587}$ (from (2)) in MES buffer system, bond re-formed-1; (4) Cpe-T450S$^{439-587}$ (from (3)) in TRIS·HCl buffer system, bond re-hydrolysed-1; (5) Cpe-T450S$^{439-587}$ (from (4)) in MES buffer system, bond re-formed-2; (6) Cpe-T450S$^{439-587}$ (from (5)) in TRIS·HCl buffer system, bond re-hydrolysed-2; (7) Cpe-T450S$^{439-587}$ (from (6)) in MES buffer system, bond re-formed-3; (8) Cpe-T450S$^{439-587}$ (from (7)) in TRIS·HCl buffer system, bond re-hydrolysed-3.

FIG. 14 shows the small angle X-ray scattering analysis of the ligated assembly of construct A, an MBP-Cpe0147$^{439-563}$ fusion, and construct B, a Cpe0147$^{565-587}$-eGFP fusion. FIG. 14A shows the SEC-SAXS elution profile of the MBP-Cpe-GFP construct measured by small angle X-ray scattering intensity. Dashed lines represent the scattering data that was averaged to produce the scattering plot (shown in FIG. 14B). FIG. 14B shows the SAXS data plotted against scattering angle (log(I) vs q [Å$^{-1}$]; open circles, averaged and solvent-subtracted). Inset: Guinier plot of low angle data showing linearity (ln(I*C) vs q$^2$ [Å$^{-2}$]. The data shown in FIG. 14 was used to derive the ab initio envelope shown in FIG. 3A.

FIG. 15 shows the relative locations of the key reactive and accessory residues within the active site of the first Ig-like domain of the Cpe0147 protein as published in the Protein Data Bank (PDB ID 4NI6). The active site comprises threonine (or as described herein serine) and glutamine or glutamic acid or glutamate reactive residues and histidine and aspartic acid accessory residues.

FIG. 16 shows the spatial arrangement of the four active site amino acid residues comprising threonine and glutamine reactive residues with histidine and aspartic acid accessory residues require for intermolecular ester bond formation. Selected atom names are labelled. This figure was produced using Pymol and coordinates from Protein Data Bank file 4MKM.

FIG. 17 shows a structural overlay of nine Ig-like domains containing an intermolecular ester bond crosslinking the first and last beta-strand of the domain. FIG. 17A is an overall view of domains with Cα positions joined by black lines and the key reactive and accessory residues are shown as white stick models. FIG. 17B is a close up view of the threonine and glutamine reactive and histidine and aspartic acid accessory residue side chains in white ball-and-stick model with the backbone Cα positions joined by black lines.

FIG. 19 shows the multiple sequence alignment of nine *Mobiluncus mulieris* adhesin protein domains containing the key reactive and accessory residues. The reactive and accessory residues are highlighted.

Figure 21:
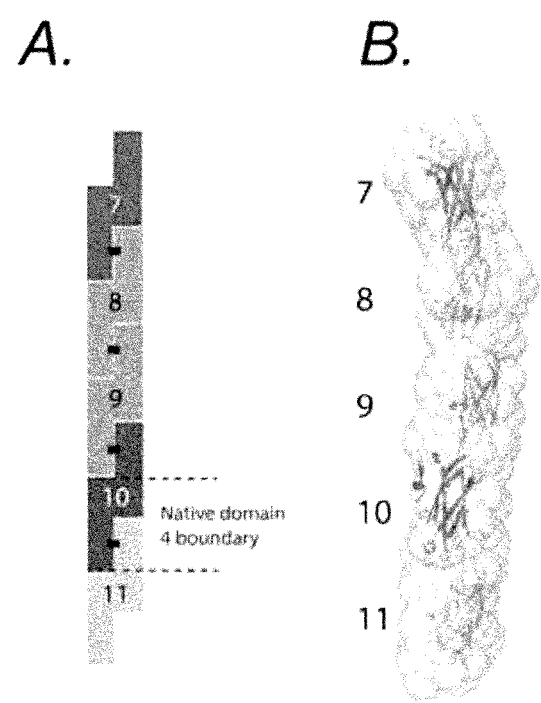

FIG. 21A shows a schematic diagram showing the modified boundaries of the ester bond cross-linking Mol domains. Each engineered Mol domain is staggered when compared to the native domain boundaries. The engineered constructs lack their own C-terminal beta-strand and instead have the C-terminal beta-strand of the preceding domain fused to the N-terminus. When mixed, adjacent domains bind through strand complementation and ligate together by spontaneous ester bond formation to reform a native-like domain structure. FIG. 21B shows the Mol 7-11 ligation product visualized by small-angle X-ray scattering (SAXS). A constructed ab initio envelope derived from the SAXS data, describes a molecule with maximum dimensions of ~220 Å, which fits very well with the atomic level X-ray crystal structures modelled as a 5 protein chain.

Figure 22:
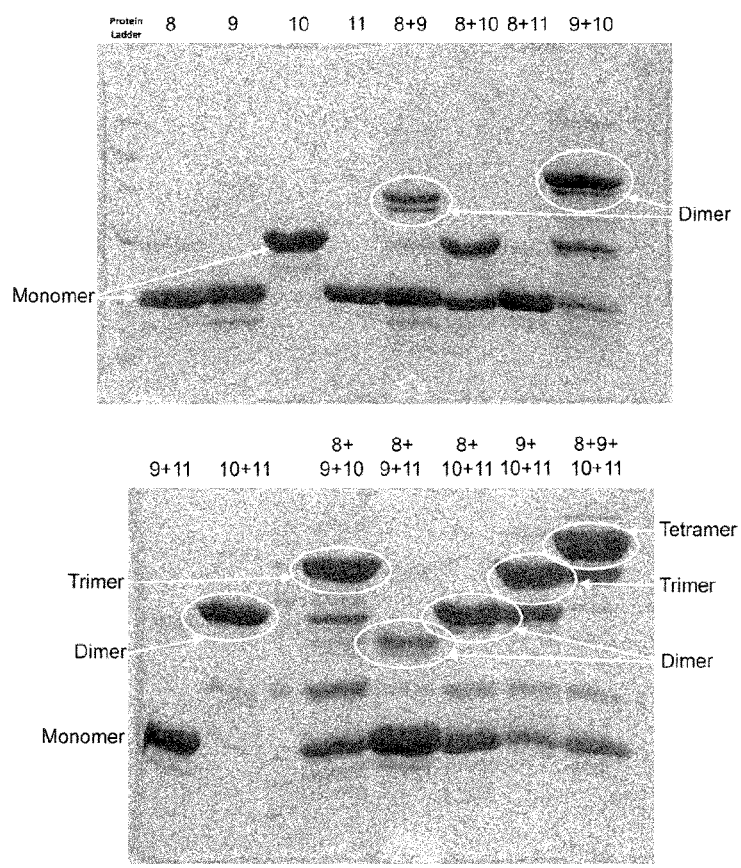

FIG. 22 shows SDS-PAGE analysis of ester bond formation between Mol domains. Samples of Mol8, Mol9, Mol10 and Mol11 were mixed in all possible combinations and analysed by SDS-PAGE after a 24 hour incubation. As can be seen, Mol domains form ester bonds in a specific order with no cross-reactivity between non-adjacent domains.

FIG. 23 shows the amino acid sequences of the engineered Ig-like domains of Mol7a, Mol8, Mol9, Mol10 and Mol11 proteins from *Mobiluncus mulieris* as described herein in Example 17. In each sequence, the HisTag and rTEV cleavage domain is shown in italics, the Mol trunk domain is shown in normal text, the strand complementation region is underlined, and the reactive and accessory residues are in bold.

Figure 24:
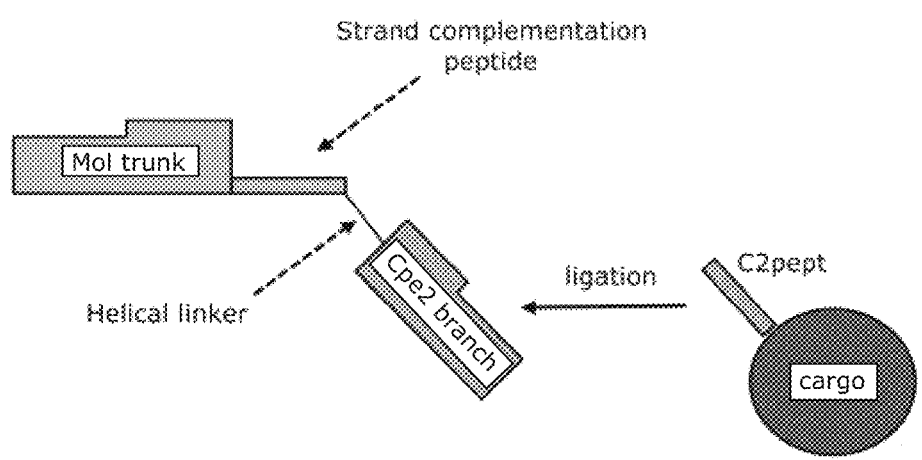

FIG. 24 shows a schematic diagram showing the engineered domain structure of the Cpe2-HL-Mol domains prepared as described in Example 18. Each construct consists of a Mol trunk domain with a Cpe2 branch domain fused to the N-terminus via a helical linker. The branch domain captures a C2pept-tagged cargo protein, which is covalently ligated to the construct by spontaneous ester bond formation.

Figure 25:
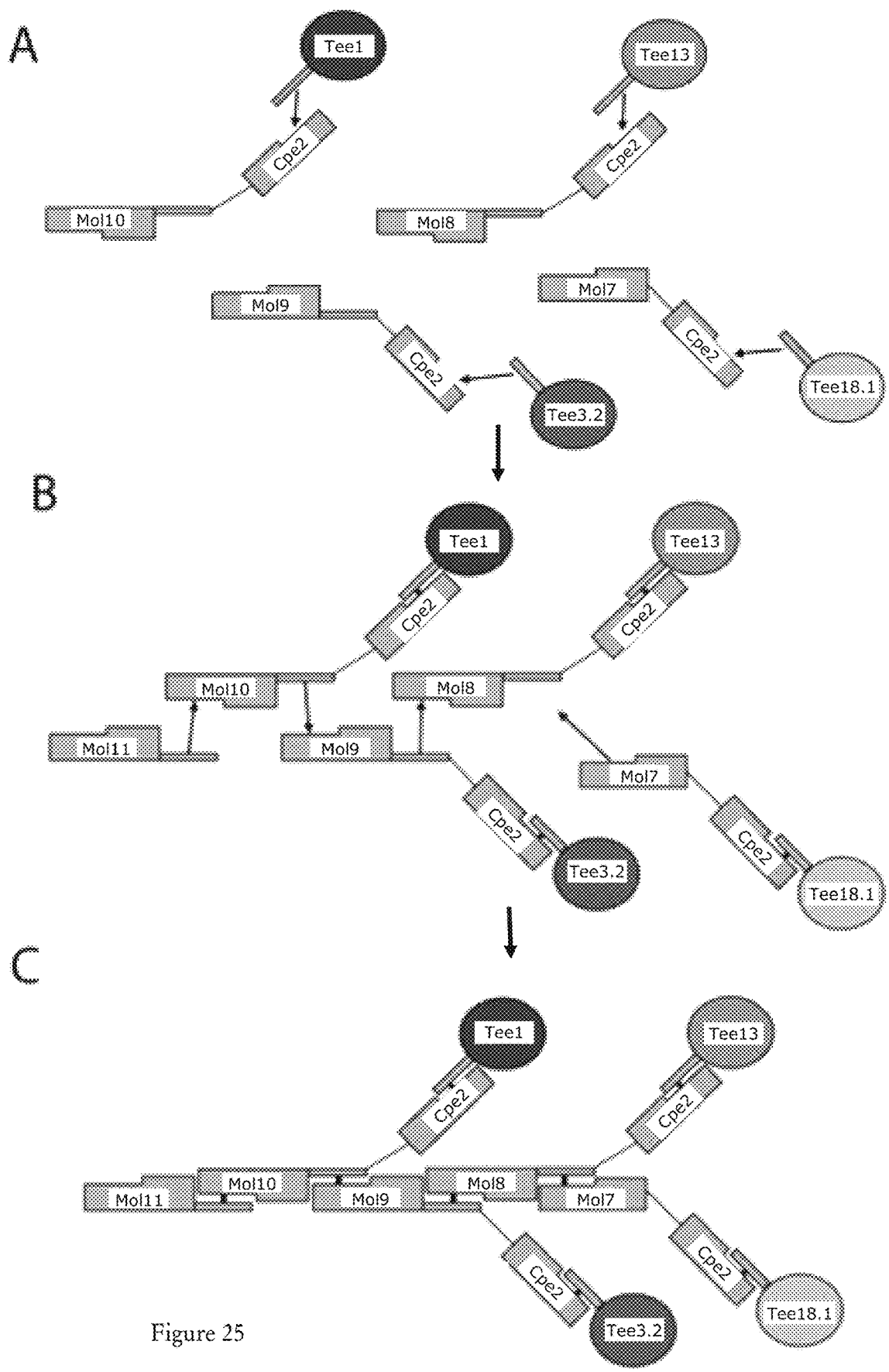

FIG. 25 shows a schematic diagram showing the process for assembly of an antigen-presenting scaffold tree as described in Example 18: (A) Each branch-trunk domain was ligated to a C2pept-tagged antigen separately. (B) Ligated antigen-branch-trunk constructs were mixed to form the tree-like structure with covalent linkages to the four individual T-antigens in a specified order. (C) Each assembled tree contains one copy of each of the four antigens.

Figure 26:
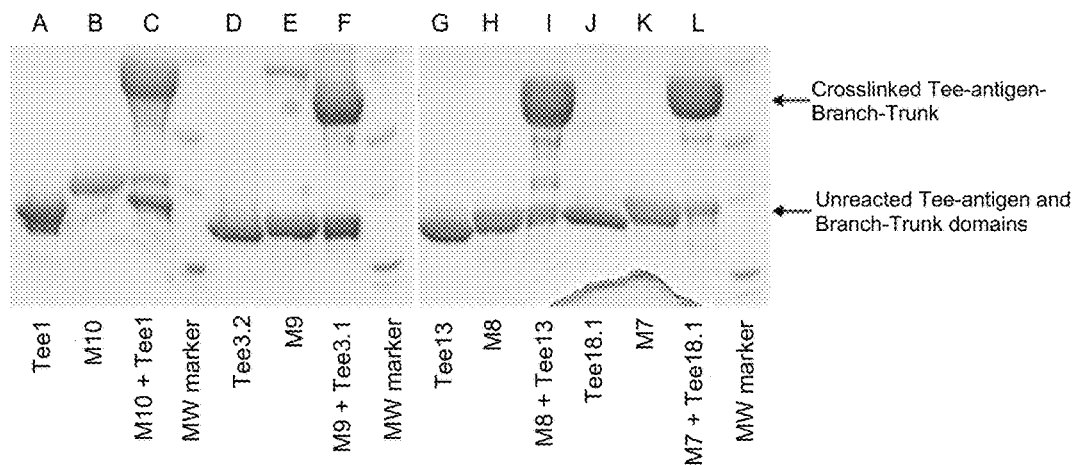

FIG. 26 shows SDS-PAGE analysis of reactions between branch-trunk constructs and their respective C2pept-T-antigen. A. T1 antigen. B. Cpe2-HL-Mol10 (M10). C. T1+Cpe2-HL-Mol10. D. T3.2 antigen. E. Cpe2-HL-Mol9 (M9). F. T3.2+Cpe2-HL-Mol9. G. T13 antigen. H. Cpe2-HL-Mol8 (M8). I. T13+Cpe2-HL-Mol8. J. T18.1 antigen. K. Cpe2-HL-Mol7 (M7). L. T1+Cpe2-HL-Mol7.

Figure 27:
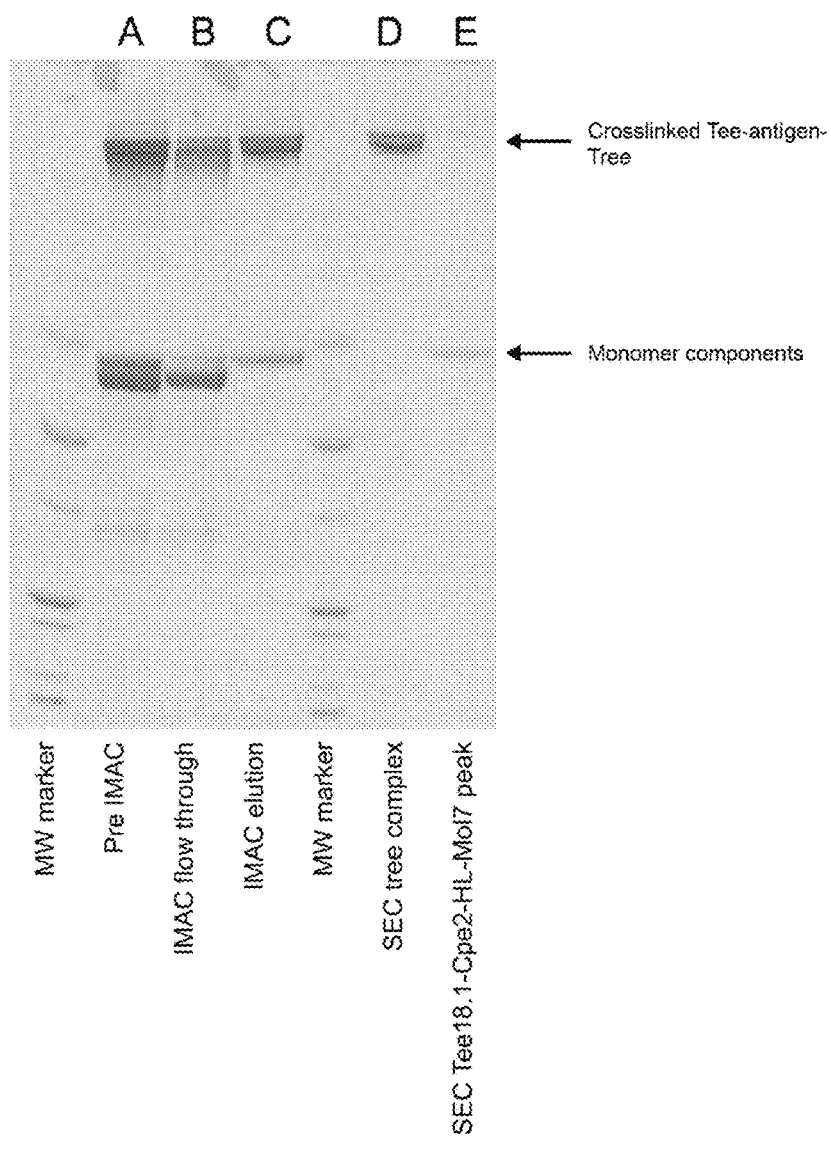

FIG. 27 shows SDS-PAGE analysis of tree assembly. A. All components of the tree ligate together to form a product that migrates at >250 kDa. B. IMAC flow through. Only T18.1 (ligated to Cpe2-HL-Mol7) has an intact His-tag. All partially formed complexes pass through the column, with only the fully-formed tree and monomeric T18.1-Cpe2-HL-Mol7 retained on the affinity column. C. IMAC elution. D. SEC purification of the IMAC eluted protein. The first peak contains fully-formed T-antigen trees. E. The second minor SEC peak contains monomeric T18.1-Cpe2-HL-Mol7.

FIG. 28 shows the amino acid sequences of the engineered Cpe2-Mol protein constructs as described herein in Example 18. In each sequence, the HisTag and rTEV cleavage domain is shown in italics, the Cpe2 branch domain is underlined, the helical linker domain is shown in underlined italics, and the Mol trunk domain is shown in normal text.

FIG. 29 shows the amino acid sequences of the engineered C2pept-T antigen protein constructs as described herein in Example 18. In each sequence, the HisTag and rTEV cleavage domain is shown in italics, the C2pept tag and linker domain is underlined, and the T antigen sequence is shown in normal text.

Figure 30:
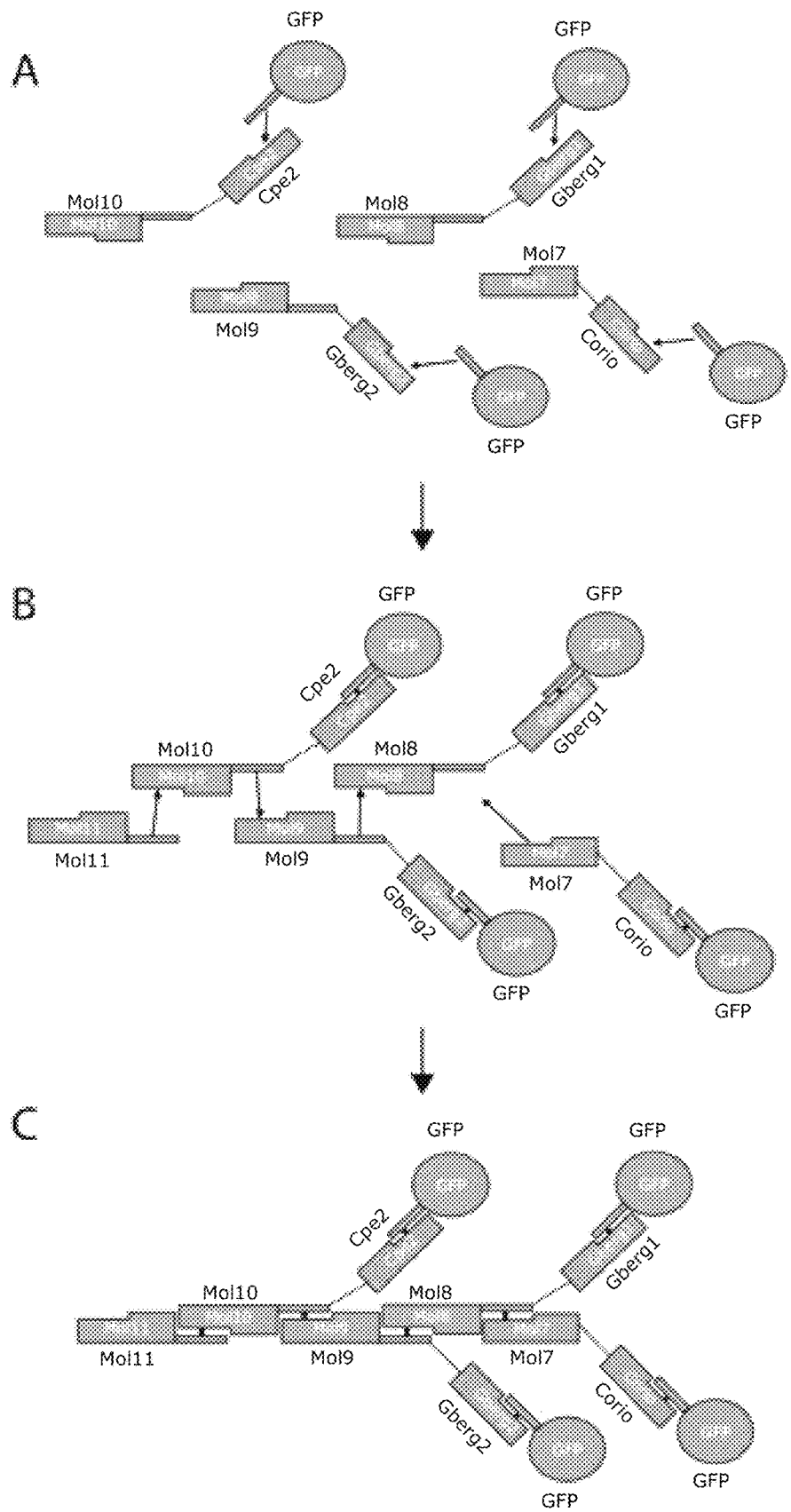

FIG. 30 shows process for assembly of a multimeric protein scaffold displaying eGFP. (A) All branch-trunks were ligated to peptide-tagged eGFP cargo separately. (B), (C) Ligated eGFP-branch-trunk constructs were mixed to form the tree-like structure.

Figure 31:
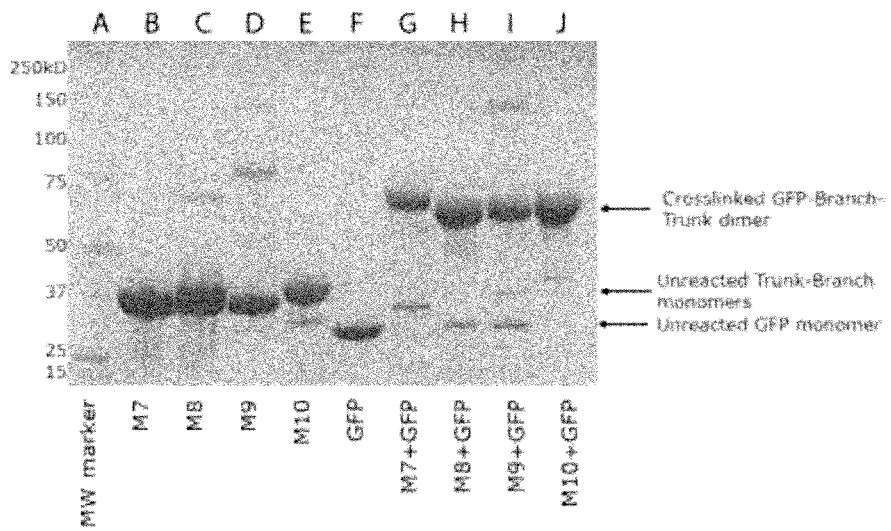

FIG. 31 shows SDS-PAGE analysis of ligation reactions between each branch-trunk construct and their respective pept-GFP cargo. A. Molecular mass ladder. B. Corio-HL-Mol7 protein. C. Gberg1-HL-Mol8 protein. D. Gberg2-HL-Mol9 protein. E. Cpe2-HL-Mol10 protein. F. C2pept-GFP cargo protein.* G. Corio-HL-Mol7+Coriopept-GFP. H. Gberg1-HL-Mol8+Gberg1pept-GFP. I. Gberg2-HL-Mol9+Gberg2pept-GFP. J. Cpe2-HL-Mol10+C2pept-GFP. * other peptide-GFP constructs are not shown for clarity but look nearly identical to this sample.

Figure 32:
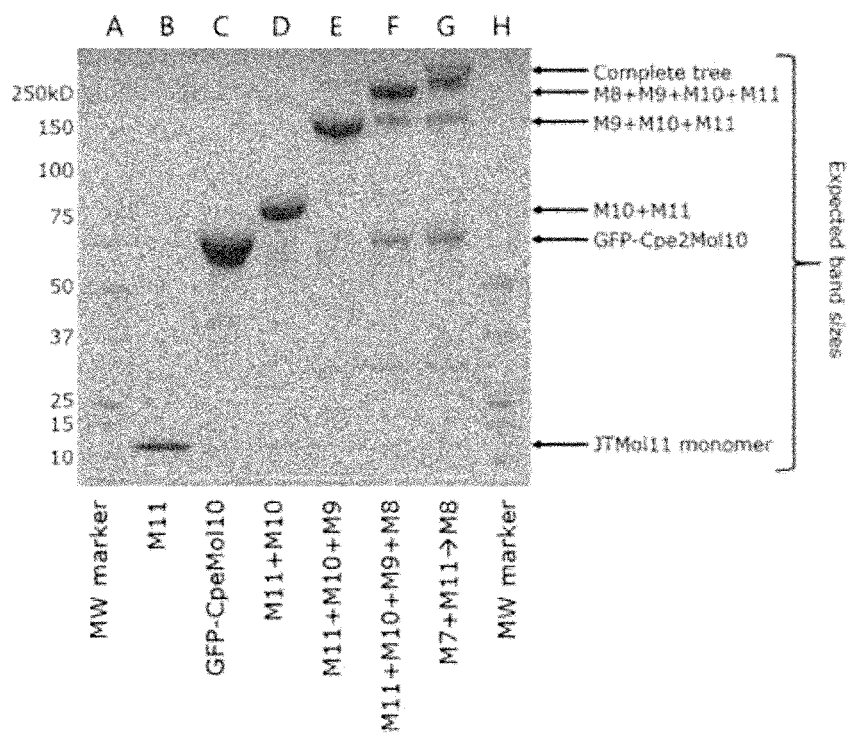

FIG. 32 shows SDS-PAGE analysis of eGFP-tree assembly showing an increase in the mass of the ligated product as additional GFP-branch-HL-trunk domains are added. A. Molecular mass ladder. B. Mol11 protein (M11). C. GFP-Cpe2-HL-Mol10 complex (M10). D. Ligation of Mol11 and GFP-Cpe2-HL-Mol10 complex (M11+M10). E. Ligation of M11+M10+GFP-Gberg2-Mol9 (M9) gives the expected ~150 kDa product. F. Reaction between M11+M10+M9+GFP-Gberg1-HL-Mol8 (M8) results in a hetero-tetrameric species of ~250 kDa. G. Complete tree assembly, as illustrated in FIG. 7C, M11+M10+M9+M8+GFP-Corio-HL-Mol7 (M7). H. Molecular mass ladder.

FIG. 33 shows the amino acid sequences of the engineered Cpe-like/Mol protein constructs as described herein in Example 19. In each sequence, the HisTag and rTEV cleavage domain is shown in italics, the Cpe-like branch domain is underlined, the helical linker domain is shown in underlined italics, and the Mol trunk domain is shown in normal text.

FIG. 34 shows the amino acid sequences of the engineered Cpe-like/GFP protein constructs as described herein in Example 19. In each sequence, the HisTag and rTEV cleavage domain is shown in italics, the C2pept tag and linker is underlined, and the GFP domain is shown in normal text.

Figure 35:
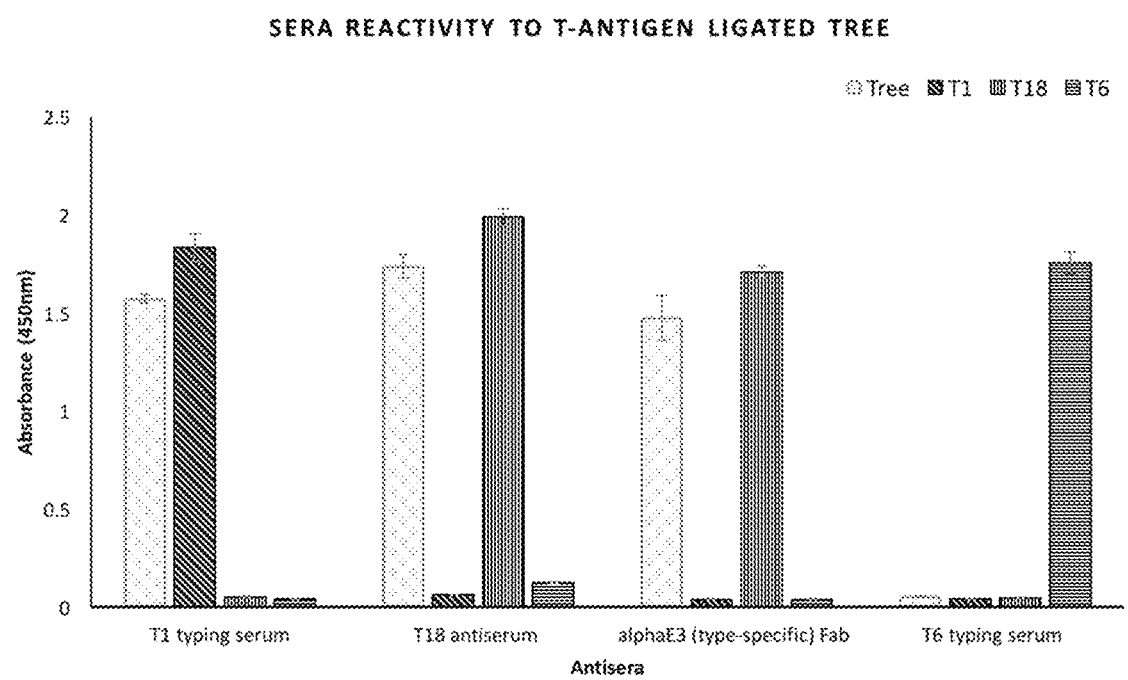

FIG. 35 is a graph showing the results of ELISA analysis of the immunogenicity of recombinant T antigens and of the T antigen-containing multivalent multimeric protein complex, as described herein in Example 20.

DETAILED DESCRIPTION OF THE INVENTION

The present invention provides methods for the formation of spontaneously-formed ester bond cross-links between amino acid side chains, particularly spontaneously-formed, reversible ester bond cross-links between amino acid side chains of different proteins, thereby enabling the ligation of two or more proteins or protein-containing binding partners. Accordingly, the present invention addresses the need for protein ligation technology and particularly ligation which is reversible, by exploiting the unique characteristics of ester bonds. This technology enables complex protein assemblies to be engineered with a fine degree of control.

In certain aspects the present invention relates to recombinant polypeptides comprising one or more amino acid sequences comprising an immunoglobulin (Ig) like domain, wherein the Ig-like domain is split into a truncated protein and a peptide comprising the final β-strand of the Ig-like domain. In particular, certain embodiments of the invention relate to reversible spontaneously-formed ester bond between the truncated protein, a derivative or fragment thereof and the peptide, a derivative or fragment thereof.

In other aspects the invention relates to one or more truncated Ig-like domains comprising one or more heterologous amino acid sequences, wherein when two or more such truncated Ig-like domains are contacted with one another the Ig-like domains undergo self-polymerisation.

In certain embodiments a heterologous amino acid sequence is referred to herein as a "cargo", for example, as a "cargo protein", or a "cargo enzyme".

The invention further relates to a truncated Ig-like domain comprising a plurality of attached cargo proteins, wherein the truncated Ig-like domain is reversibly self-polymerising. In certain embodiments, the self-polymerising Ig-like domains are from the same Ig-like domain-containing protein. In other embodiments, Ig-like domains from different Ig-like domain-containing proteins self-polymerise, or reversibly self-polymerise.

The truncated reversibly self-polymerising Ig-like domain provides for the controllable assembly of cargo proteins. For example, one or more truncated reversibly self-polymerising Ig-like domains provide for the controllable assembly of protein 'scaffolds' comprising one or more cargo proteins. In particular, the truncated reversibly self-polymerising Ig-like domain is useful for the controllable assembly of a plurality of enzymes. In some embodiments, the invention is useful for emulating natural enzymatic pathways for optimising enzyme yield.

Certain advantages of the invention include:
a) increased peptide stability,
b) highly controllable protein assembly process,
c) ease and efficiency of peptide and protein manufacture,
d) minimal cross-reactivity between non-adjacent or non-complementary binding pairs in multimeric protein complexes, and
e) reversible self-catalysing peptide cross-links.

Certain Definitions

The term "and/or" can mean "and" or "or".

The term "comprising" as used in this specification means "consisting at least in part of". When interpreting statements in this specification which include that term, the features, prefaced by that term in each statement, all need to be present but other features can also be present. Related terms such as "comprise" and "comprised" are to be interpreted in the same manner.

As used herein "purified" does not require absolute purity; rather, it is intended as a relative term where the material in question is more pure than in the environment it was previously in. In practice the material has typically, for example, been subjected to fractionation to remove various other components, and the resultant material has substantially retained its desired biological activity or activities. The term "substantially purified" refers to material that are at least 60% free, preferably at least about 75% free, and most preferably at least about 90% free, at least about 95% free, at least about 98% free, or more, from other components with which they may be associated during manufacture.

The term "α-amino acid" or "amino acid" refers to a molecule containing both an amino group and a carboxyl group bound to a carbon which is designated α-carbon. Suitable amino acids include, without limitation, both the D- and L-isomers of the naturally-occurring amino acids, as well as non-naturally occurring amino acids prepared by organic synthesis or other metabolic routes. Unless the context specifically indicates otherwise, the term amino acid, as used herein, is intended to include amino acid analogues.

In certain embodiments a protein, polypeptide, or peptide as contemplated herein comprises only natural amino acids. The term "naturally occurring amino acid" refers to any one of the twenty amino acids commonly found in peptides synthesized in nature, and known by the one letter abbreviations A, R, N, C, D, Q, E, G, H, I, L, K, M, F, P, S, T, W, Y and V. In other embodiments, a protein, polypeptide, or peptide as contemplated herein comprises one or more amino acid analogues.

The term "amino acid analogues" or "non-naturally occurring amino acid" refers to a molecule which is structurally similar to an amino acid and which can be substituted for an amino acid. Amino acid analogues include, without limitation, compounds which are structurally identical to an amino acid, as defined herein, except for the inclusion of one or more additional methylene groups between the amino and carboxyl group (e.g., α-amino β-carboxy acids), or for the substitution of the amino or carboxy group by a similarly reactive group (e.g. substitution of the primary amine with a secondary or tertiary amine, or substitution or the carboxy group with an ester).

Unless otherwise indicated, conventional techniques of molecular biology, microbiology, cell biology, biochemistry and immunology, which are within the skill of the art may be employed in practicing the methods described herein. Such techniques are explained fully in the literature, such as, Molecular Cloning: A Laboratory Manual, second edition (Sambrook et al., 1989); Oligonucleotide Synthesis (M. J. Gait, ed., 1984); Animal Cell Culture (R. I. Freshney, ed., 1987); Handbook of Experimental Immunology (D. M. Weir & C. C. Blackwell, eds.); Gene Transfer Vectors for Mammalian Cells G. M. Miller & M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); The Immunoassay Handbook (David Wild, ed., Stockton Press NY, 1994); Antibodies: A Laboratory Manual (Harlow et al., eds., 1987); and Methods of Immunological Analysis (R. Masseyeff, W. H. Albert, and N. A. Staines, eds., Weinheim: VCH Verlags gesellschaft mbH, 1993).

The term "peptide" and the like is used herein to refer to any polymer of amino acids residues of any length. The polymer can be linear or non-linear (e.g., branched), it can comprise modified amino acids or amino acids analogues. The term also encompasses amino acid polymers that have been modified naturally or by intervention, for example, by disulphide bond formation, glycosylation, lipidation, acetylation, phosphorylation, or any other modification or manipulation, for example conjugation with labelling or bioactive component.

A "fragment" as used herein with reference to a specified protein typically contemplates at least about 10 contiguous amino acids of the specified protein. For example, a fragment of an Ig-like fold domain from an Ig-like fold containing protein comprises 10 or more contiguous amino acids from said Ig-like fold domain. Similarly, a fragment of an amino acid sequence presented herein as one of SEQ ID NO.s 1 to 4, 21 to 30, or 31 to 58, comprises 10 or more contiguous amino acids from the specified sequence.

The term "truncated protein" is used herein to refer to protein derived from the truncation of the Ig-like domain of adhesin protein Cpe0147 (residues 439 to 563). Other uses of the term 'truncated protein' will be apparent from the context in which the term is used herein, for example, in reference to truncation of a different, specified protein.

As used herein the terms "branch" and/or "branch domain" when used with reference to a protein-containing component herein, such as a peptide tag, binding partner, chimeric protein, protein scaffold or protein complex, contemplates a polypeptide or protein domain that provides a ligating or linking moiety or function to join one or more cargoes or functionalities to one or more other protein components of a multimeric protein complex. Examples of branch domains are provided herein, for example in Examples 18 and 19, and are depicted in, for example, FIG. 20 (as components V, W, X, Y, and Z), and FIGS. 24, 25, and 30.

As exemplified herein, a branch or branch domain will in certain embodiments 'capture' and/or ligate to the one or more other protein components one or more cargoes or functionalities, such as one or more cargo proteins, via a peptide tag/peptide binding partner interaction and/or spontaneous covalent bond formation as herein described.

In certain specifically contemplated examples, the branch domain comprises either a) one reactive residue capable of being involved in a spontaneously-formed ester bond within a β-clasp arrangement in a β-clasp containing protein, and comprises at least 5 contiguous amino acids of said β-clasp containing protein, or b) comprises a fragment of a β-clasp containing protein wherein said fragment comprises at least about 10 contiguous amino acids of said β-clasp containing protein and comprises a reactive residue capable of being involved in the spontaneously-formed ester bond in a β-clasp containing protein. In one example, the branch domain comprises one part of the Cpe2-C2pept binding pair exemplified herein, where the complementary part of the Cpe2-C2pept binding pair is present on or comprises the cargo.

As used herein the term "cargo" contemplates a functionality that ultimately is to be present in or on or otherwise incorporated into a protein as described herein, such as a chimeric protein or multimeric protein complex as described herein. In certain embodiments, a cargo is attached to or to be attached to a peptide tag or a binding partner, or comprises a part of a chimeric protein or truncated protein, which in turn may be covalently bound to one or more other protein components to form multimeric protein complexes as herein provided. Such cargoes are also referred to herein as valencies, whereby a multivalent protein or protein complex contemplates the presence of multiple cargoes, which may be the same or may be different. It will be appreciated by those skilled in the art that in certain embodiments, a heterologous amino acid sequence comprises a cargo, and may thus provide a functionality or part of a functionality.

Particularly contemplated cargo proteins are enzymes, or parts of enzymes such as enzyme active sites or one or more subunits of a multimeric enzyme or enzyme complex.

As used herein the terms "trunk" and/or "trunk domain" when used with reference to a protein-containing component herein, such as a peptide tag, binding partner, chimeric protein, protein scaffold or protein complex, contemplates a polypeptide or protein domain that provides a scaffold moiety or function to which one or more further trunks or trunk domains, one or more branches or branch domains, one or more cargoes or functionalities, or one or more other protein components of a multimeric protein complex as herein described is covalently bound. Accordingly, a trunk or trunk domain can be thought of as a component of a core to or around which other components, including other trunk or trunk domains, are formed. Examples of trunk domains are provided herein, for example in Examples 18 and 19, and are depicted in, for example, FIG. 20 (as components 1, 2, 3, 4, and 5), and in FIGS. 24, 25, and 30.

As exemplified herein, a trunk or trunk domain will in certain embodiments ligate to the one or more other protein components, such as one or more other trunk or trunk domains, or one or more branches or branch domains, via a peptide tag/peptide binding partner interaction and/or spontaneous covalent bond formation as herein described.

In certain specifically contemplated examples, the trunk domain comprises either a) one reactive residue capable of being involved in a spontaneously-formed ester bond within a β-clasp arrangement in a β-clasp containing protein, and comprises at least 5 contiguous amino acids of said β-clasp containing protein, or b) comprises a fragment of a β-clasp containing protein wherein said fragment comprises at least about 10 contiguous amino acids of said β-clasp containing protein and comprises a reactive residue capable of being involved in the spontaneously-formed ester bond in a β-clasp containing protein. In one example, the trunk domain comprises an Ig-like domain or a part thereof, such as an Ig-like domain of a β-clasp containing protein, such as an Ig-like domain lacking its C-terminal β-strand or a part thereof. In another example, the trunk domain comprises an Ig-like domain or part thereof, in addition to a β-strand from another Ig-like domain, such as the final β-strand of another Ig-like domain, for example the final β-strand from the preceding Ig-like domain in the full length β-clasp domain of a β-clasp-containing protein. In one example, the trunk domain comprises at least a part of an Ig-like domain from Cpe0147 protein, and optionally has an additional part of another Ig-like domain from a β-clasp domain of a β-clasp-containing protein, including a part of another Ig-like domain from Cpe0147, such as the final β-strand of the preceding Ig-like domain in the full length Cpe0147 protein. In other examples, comparable trunk domains comprising one or more parts of one or more Ig-like domains such as the Mol polypeptides exemplified in Examples 6 to 16, or the Mol domains exemplified in Examples 17 to 20, are used.

The term "(s)" following a noun contemplates the singular or plural form, or both.

The invention consists in the foregoing and also envisages constructions of which the following gives examples only and in no way limit the scope thereof.

Cpe0147 Adhesin

Figure 15:
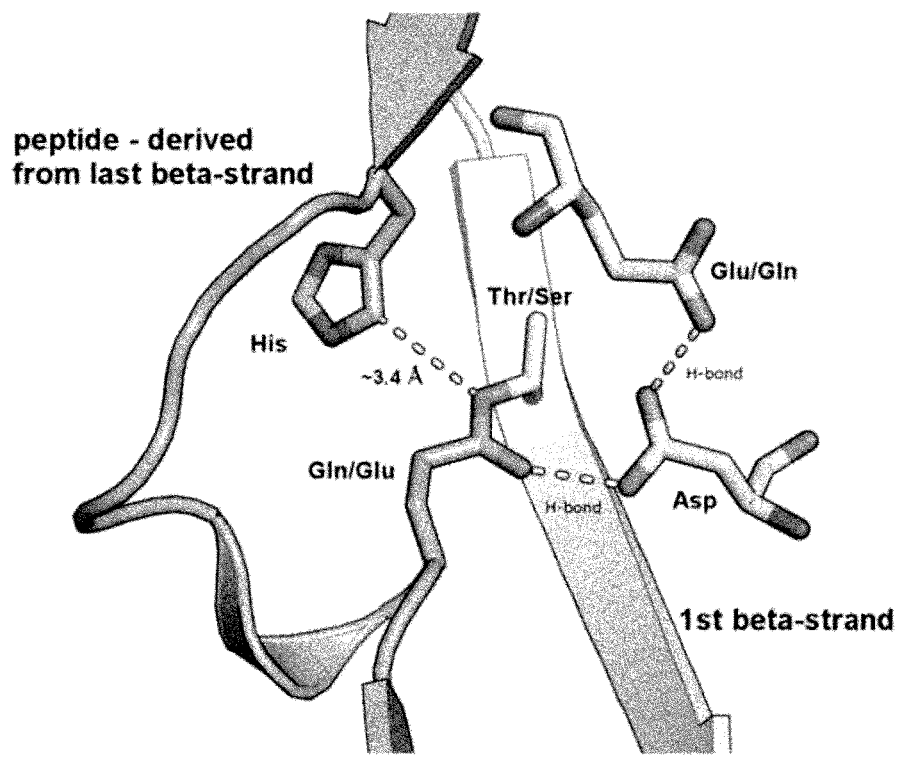
Figure 16:
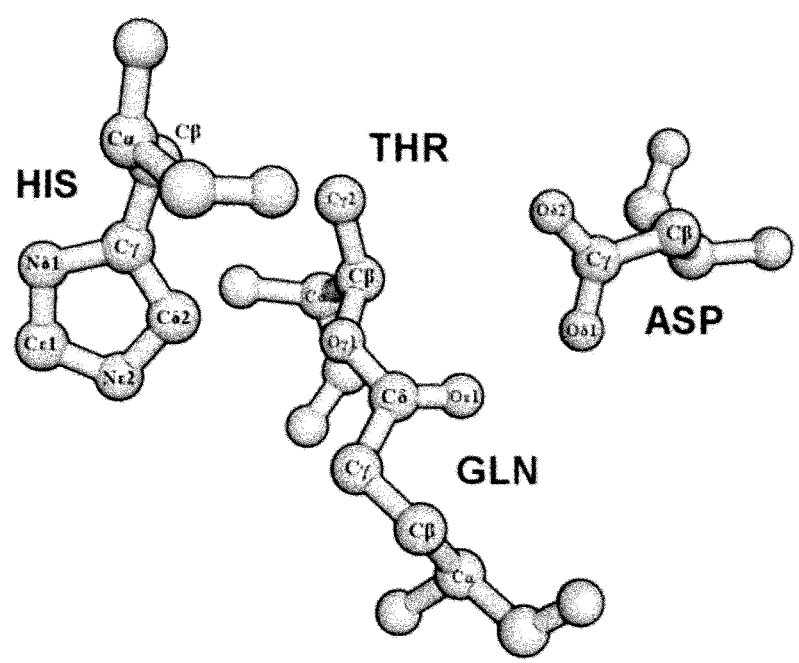
Figure 17:
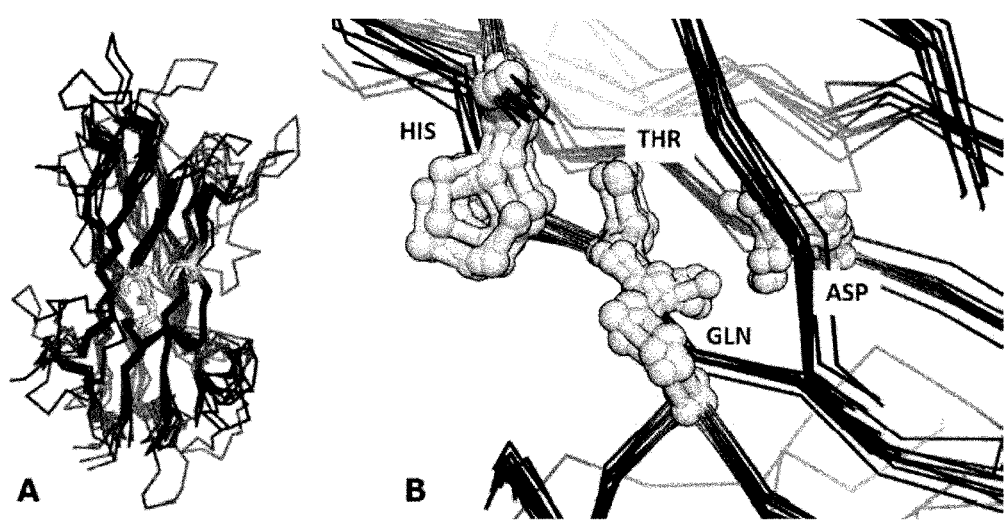
Figure 18:
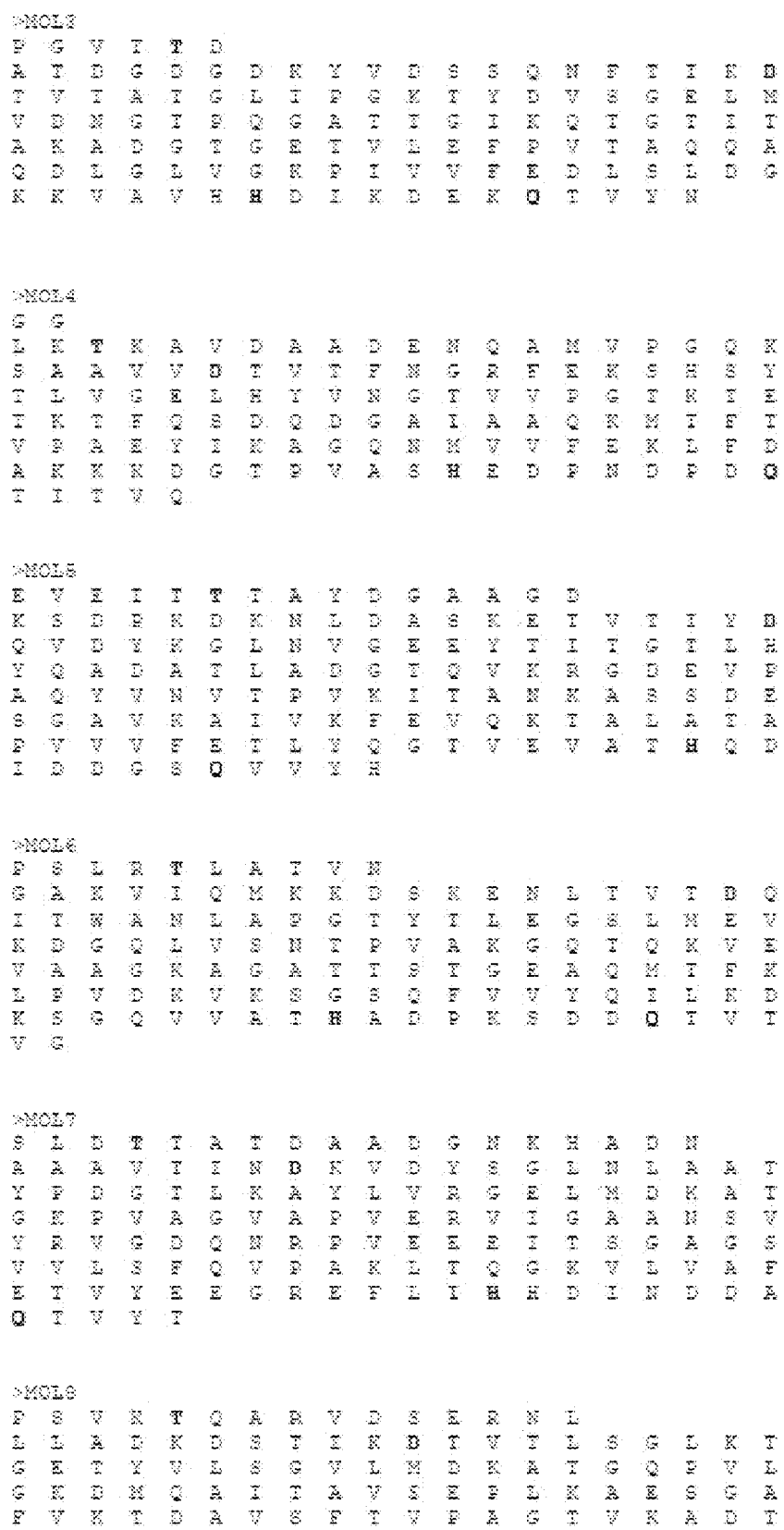
FIG. 18 shows the amino acid sequences of adhesin protein domains from *Mobiluncus mulieris* (LPXTG-motif cell wall anchor domain protein, protein ID EFM47174.1) capable of forming ester bond cross-links. The reactive and accessory residues are in bold.
Figure 18:
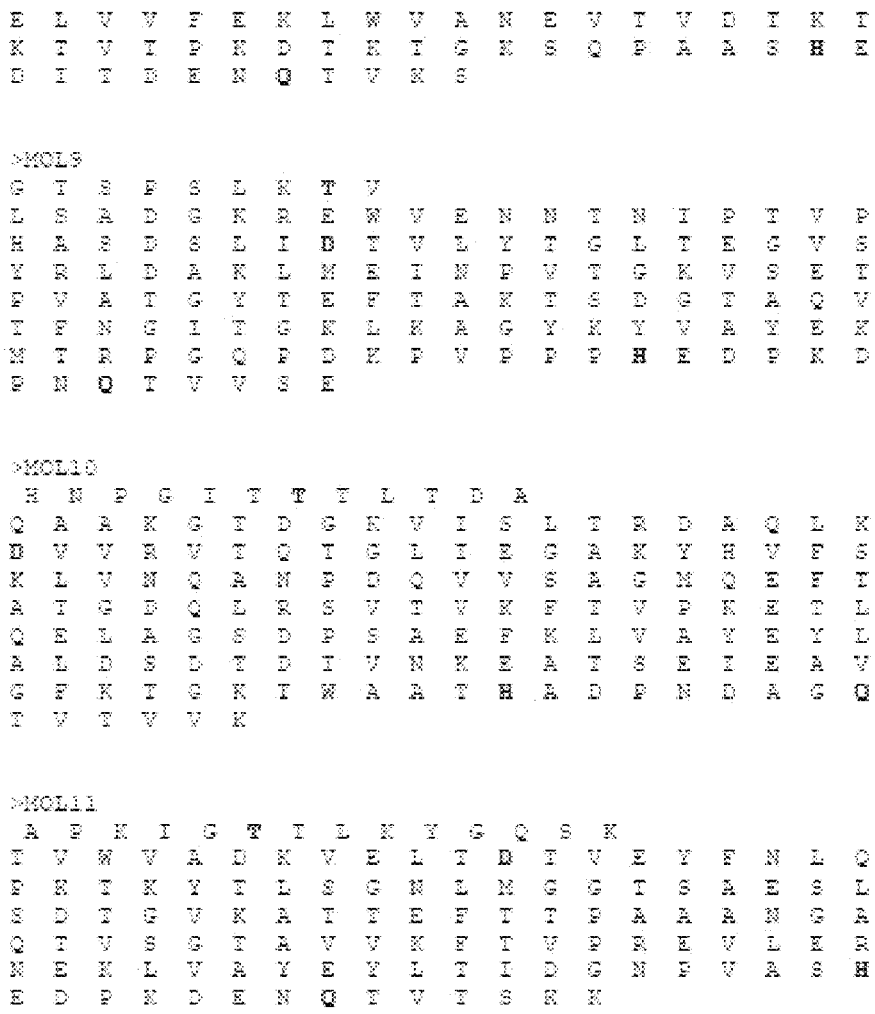

Microbial surface components recognising adhesive matrix molecules (MSCRAMMs) are a class of bacterial surface molecules which are very long, thin and subject to large mechanical shear stresses in protease-rich environments. MSCRAMMs are typically single polypeptides folded into many domains. In particular, the present invention takes advantage of MSCRAMM adhesin proteins derived from Gram-positive bacteria. In an exemplary embodiment of the invention, adhesin derived from *Clostridium perfringens* is used. Other examples of adhesins or related proteins derived from bacteria other than *C. perfringens* and useful as described herein are contemplated, including the proteins and bacterial species exemplified herein in the Examples.

Adhesins are important for mediating bacterial attachment to surfaces. Bioinformatic analysis of *Clostridium perfringens* adhesin (Cpe0147) predicts the structure to comprise an N-terminal adhesin domain attached to the cell wall by a shaft comprising 11 repeating domains and terminating with a C-terminal cell wall-anchoring motif (5'-LPKTG). The repeating domains have been predicted to each have an all β-strand IgG-like fold (Kwon, H.; Squire, C. J.; Young, P. G.; Baker, E. N., Autocatalytically generated Thr-Gln ester bond cross-links stabilize the repetitive Ig-domain shaft of a bacterial cell surface adhesin. *P Natl Acad Sci USA* 2014, 111 (4), 1367). Within each domain, the side chain of a threonine residue on the first β-strand is covalently linked to the side chain of a glutamine residue on the last β-strand by an ester bond.

Spontaneous Ester Bond Formation

Without wishing to be bound by any theory of mechanism, it is believed that, the ester bonds cross-links are spontaneously formed between hydroxyl and amide, or between hydroxyl and carboxylic acid/carboxylate groups on the amino acid side chains by nucleophilic attack of Thr-450 on Gln-580 (or Glu-580), proton abstraction by His-572, and bond polarisation by the Asp-480/Glu-547 pair. Comparable reactions are expected, again without wishing to be bound by any theory, in active sites comprising the reactive amino acid residues of other Ig-like domains capable of undergoing such spontaneous covalent bond formation as described herein.

The term "ester bond" as used herein, refers to a covalent bond between a hydroxyl group and an amide (with the elimination of an ammonia or water molecule), or between a hydroxyl group and carboxylic acid or carboxylate groups at least one which is not derived from a protein main chain. An ester bond may form intramolecularly within a single protein or intermolecularly between two peptide/protein or protein/protein molecules.

Typically, an ester bond may occur between, for example a threonine or a serine residue and a glutamine, glutamate/glutamic acid, asparagine or aspartate/aspartic acid. Each residue of the pair involved in the ester bond is referred to herein as a reactive residue. Thus, an ester bond may form between a threonine residue and a glutamine residue. Particularly, ester bonds can occur between the side chain hydroxyl of threonine and amide group of glutamine.

The term "peptide binding pair" as discussed herein refers to a binding partner having one reactive residue and a second binding partner having the second reactive residue. When contacted, the reactive residues from each binding partner form an ester bond cross-link. It will be appreciated that a polypeptide, such as a chimeric polypeptide contemplated herein, comprising one reactive residue capable of forming an ester bond with one binding partner will in certain embodiments comprise one or more other reactive residues capable of forming an ester bond with another binding partner, thereby having multiple binding partners. Representative examples of such polypeptides, capable of binding more than one binding partner, are presented herein in the Examples. Accordingly, a peptide binding pair does not exclude the binding of other binding partners to the peptides present in the pair, and those of skill in the art will appreciate that further binding partners may be attached to form further binding pairs, for example as part of a multimeric protein complex.

Ester bond formation between the reactive residues of the peptide binding pair may be facilitated by, for example an aspartic acid/aspartate and/or a histidine amino acid residue. Each residue facilitating the spontaneous ester bond formation is referred to herein as an accessory residue, as the residue facilitates the reaction but is unmodified by it. Thus, an aspartic acid and a histidine may facilitate the spontaneous ester bond formation between the reactive residue pair.

When the reactive residues are contacted, the reactive residues form an Ig-like fold containing a serine protease active site-like geometry. The serine protease active site-like structure comprising the reactive residues and accessory residues is referred to herein as the active site (see FIG. 15). Typically, the reactive and accessory residues of the active site comprises a spatial arrangement, for example as shown in FIG. 16.

The active site may comprise a threonine reactive residue in close proximity to the second reactive residue, for example a glutamine, glutamic acid or glutamate reactive residue, a first accessory residue, for example a histidine and a second accessory residue, for example an aspartic acid. For example, the Cβ atom of the threonine reactive residue may be within 2.40, 2.45, 2.50, 2.55, 2.60, 2.65, 2.70, 2.75, 2.80 or 2.85 Angstrom from the C6 of the reactive glutamine residue. For example, the Cβ atom of the threonine reactive residue may be within 4.50, 4.55, 4.60, 4.65, 4.70, 4.75, 4.80, 4.85, 4.90, 4.95, 5.00, 5.05, 5.15, 5.20, 5.25, 5.30, 5.35, 5.40, 5.45, 5.50, 5.55, 5.60, 5.65, or 5.70 Angstrom from the Cγ atom of the histidine accessory residue. For example, the Cβ atom of the threonine reactive residue may be within 4.00, 4.05, 4.10, 4.15, or 4.20 Angstrom from the Cγ atom of the aspartic acid accessory residue.

The term "spontaneously-formed" as used herein refers to a bond e.g. an ester or covalent bond which can form in a protein or between peptides or proteins (e.g. between 2 peptides or a peptide and a protein) without any other agent (e.g. an additional enzyme catalyst) being present and/or without chemical modification of the protein or peptide. A spontaneously-formed ester bond may form almost immediately after the production of a protein or after contact between peptide or protein binding partner e.g. within 1, 2, 3, 4, 5, 10, 15, 20, 25, or 30 minutes or within 1, 2, 4, 8, 12, 16 or 20 hours. The present inventors have established an amino acid substitution in the Ig-like fold of Cpe0147, Thr450>Ser, which preserves the spontaneously-formed ester bond between amino acid side chains, but renders ester bond formation reversible. Other amino acid substitutions which enable a reversible ester bond, such as serine homologues or derivatives including non-naturally occurring derivatives, are also contemplated.

The term "reversible" as used herein refers to a hydrolysable ester bond which can be hydrolysed when initiated by a trigger, for example, a pH change. Typically, a hydrolysable ester bond may form between a serine residue and a glutamine, glutamate, or glutamic acid residue. Particularly, ester bonds can occur between the side chain hydroxyl group of the serine residue and amide group of the glutamine residue.

In specifically contemplated embodiments, such as those exemplified by the Ser450 substitution in the Ig-like fold of Cpe1047, maintaining the complex in which the ester bond is present at a pH of about 7 or greater leads to hydrolysis of the serine-containing ester bond. Notably, other ester bonds which may be present in the complex and which are not reversible, for example, do not involve a serine-glutamine or a serine-glutamate/glutamic acid ester bond, are not hydrolysed. Those skilled in the art will recognise this specificity contributes to the directed construction of the multimeric protein complexes described and exemplified herein.

A reversible ester bond as contemplated herein will in certain embodiments be almost immediately hydrolysed after the protein complex, protein, polypeptide, or peptide in or between which the reversible ester bond is present is introduced into suitable conditions. For example, the bond is hydrolysed within 1, 2, 3, 4, 5, 10, 15, 20, 25, or 30 minutes or within 1, 2, 4, 8, 12, 16 or 20 hours. As exemplified in the Examples presented herein, pH is a significant determinant of reversibility of the serine-glutamine or a serine-glutamate/glutamic acid ester bonds described herein, where increasing the pH to 7 or above leads to hydrolysis. As outlined in the Examples, other factors, such as buffer conditions and buffering agents, the presence or absence of divalent cations, and/or the presence or absence of molecular crowding agents such as glycerol, can influence the kinetics and equilibrium of the hydrolysis reaction, and those skilled in the art can, using the description provided herein, identify reaction conditions to provide desired and/or optimal hydrolysis of reversible ester bonds present in the protein complexes described herein.

A "conservative amino acid substitution" is one in which an amino acid residue is replaced with another residue having a chemically similar or derivatised side chain. Families of amino acid residues having similar side chains, for example, have been defined in the art. These families include, for example, amino acids with basic side chains (e.g., lysine, arginine, histidine), acidic side chains (e.g., aspartate/aspartic acid, glutamate/glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Amino acid analogues (e.g., phosphorylated or glycosylated amino acids) are also contemplated in the present invention, as are peptides substituted with non-naturally occurring amino acids, including but not limited to N-alkylated amino acids (e.g. N-methyl amino acids), D-amino acids, β-amino acids, and γ-amino acids.

Peptide Motif

In addition to the Cpe0147, the inventors have identified other peptide/structures, including multiple adhesin protein domains from *Mobiluncus mulieris* [SEQ ID Nos. 21-29, 31], comprising reactive and accessory amino acid residues that are capable of spontaneous ester bond formation. A HxDxxDxxQ peptide sequence motif was identified containing the glutamine reactive residue and histidine accessory residue. The HxDxxDxxQ peptide sequence motif may, for example form one peptide of a peptide binding pair, a part of a chimeric protein as herein described, or a part of a protein component for or of a multimeric protein complex as herein described. A representative list of peptide/structures containing the HxDxxDxxQ peptide motif capable of spontaneous ester bond formation is shown in FIG. 19 and elsewhere herein. Further consensus peptide sequence motifs were identified, namely [H/E]xDxx[D/S]xx[Q/E] (SEQ ID NO. 55), HxDxx[D/S]xx[Q/E] (SEQ ID NO. 56), HXDXXSXX[Q/E] (SEQ ID NO. 57), and [H/E]XD [Q/E], (SEQ ID NO. 58). Again, the [H/E]xDxx[D/S]xx[Q/E] peptide sequence motif, and/or the HXDXX[D/S]XX[Q/E] peptide sequence motif, and/or the HXDXXSXX[Q/E] (SEQ ID NO. 57) peptide sequence motif, and/or the [H/E]XD [Q/E], (SEQ ID NO. 58) peptide sequence motif may, for example, form one peptide of a peptide binding pair, a part of a chimeric protein as herein described, or a part of a protein component for or of a multimeric protein complex as herein described.

Numerous representative engineered peptide binding pairs comprising reactive and accessory amino acid residues as above are exemplified herein in the Examples, wherein one or more of the reactive and accessory amino acid residues are present in one peptide (see, for example, the peptide sequences presented in Tables 42 and 44, and one or more of the other reactive and accessory amino acid residues comprising a binding pair are present in another peptide (see, for example, the peptide sequences presented in Tables 41 and 43). Furthermore, the Examples herein exemplify peptide binding pairs wherein one peptide comprises more than one set of reactive and accessory amino acid residues, to enable ligation to multiple binding partners. For example, certain peptide constructs presented in, for example, Example 18 and 19, comprise one set of reactive and accessory amino acids to enable ligation to a complementary 'trunk' domain (such as the Mo1 trunk domain depicted in FIG. 24 and identified in the amino acid sequences presented in Table 41), and a further set of reactive and accessory amino acids to enable ligation to a binding partner comprising a cargo protein (such as the C2pept-T protein construct depicted in FIG. 24 and identified in the amino acid sequences presented in Table 42).

Applications of the Technology

It will be appreciated that the present invention is useful in the fields of molecular biology, immunology, synthetic biology, nanotechnology and other related fields. For example, the present invention is useful in purification, detection and identification of peptides and/or proteins of interest, protein scaffolding for enhancing resilience and efficacy of enzymes.

Those skilled in the art will appreciate that the polypeptides of the invention are in certain embodiments suited for engineering self-assembling enzymatic complexes that emulate the natural efficiency of clustered multienzyme complexes. It will be appreciated that current protein scaffolds are restricted to small, two or three enzyme complexes with limited control of enzyme stoichiometry (Lee, H.; DeLoache, W. C.; Dueber, J. E., Spatial organization of enzymes for metabolic engineering. *Metab Eng* 2012, 14(3) 242-251, Horn, A. H. C.; Sticht, H., Synthetic protein scaffolds based on peptide motifs and cognate adaptor domains for improving metabolic productivity. *Frontiers in Bioengineering and Biotechnology*, 2015, 3(191), 1-7 and Chen, R. Chen, Q.; Kim, H.; Siu, K. H.; Sun, Q.; Tsai, S. L.; Chen, W., Biomolecular scaffolds for enhanced signalling and catalytic efficiency. *Curr Opin Biotech* 2014, 28, 59-68). All enzymes whether or not presently characterised, that form part of enzymatic pathways are contemplated.

In certain embodiments, the present invention are modular building blocks which co-localizes an enzymatic pathway in a specific arrangement. By selecting appropriate peptide tag/binding partner pairs, for example within trunk domains, multimeric protein complexes can be assembled in a directed manner, such that the cargo proteins or other functionalities can be positioned in a predetermined arrangement. In certain embodiments, such as is shown in the Examples, in particular in Examples 17-19, the appropriate selection of 5 different trunk domains enabled, unlike current technology, the complex assembly of each building block in a specific order of at least 5 domains, in the case of the trunk domains employed in Example 17 in a single reaction.

The constructs and methods described herein enable those skilled in the art to select and construct trunk domains that self-arrange in a specific order, whereby the trunk domains comprise at least part of one or more Ig-like folds, such that specific complementation between a first trunk domain comprising a first part of an Ig-like fold and a second trunk domain comprising a complementary part of the Ig-like fold leads to the specific binding of and formation of an ester bond between the two trunk domains. As those skilled in the art will appreciate, particularly in light of the examples provided herein such as those presented in Examples 17-19, the appropriate construction of one or more trunk domains having more than one part of an Ig-like fold enables such trunk domains to bind more than one other trunk domain, in turn enabling the directed binding of trunk domains in a predetermined order. For example, in certain embodiments, one trunk domain comprises, for example, at least a part of the first or last β-strand of a β-sheet usually present in a β-clasp arrangement, and a second trunk domain comprises at least a complementary part of the β-strand or the β-sheet thereby to recapitulate the β-clasp arrangement on binding of the first and second trunk domains.

In certain embodiments, multimeric protein complexes contemplated herein comprise a single trunk or branch domain to which a cargo or functionality is attached. In other embodiments, multimeric protein complexes contemplated herein comprise multiple trunk and/or branch domains, to any one or more of which one or more cargoes or functionalities are attached. Accordingly, in certain embodiments, multimeric protein complexes contemplated herein comprise at least 2, at least 3, at least 4, at least 5, or more than 5 protein components, such as 2, 3, 4, 5 or more than 5 trunk domains, branch domains, or cargo proteins. For example, multimeric protein complexes comprising 2, 3, 4, 5, or more than 5 trunk domains are specifically contemplated, as exemplified herein. Such multimeric protein complexes, including those exemplified herein, comprise additional protein components, for example 2, 3, 4, 5, or more than 5 branch domains, and/or 2, 3, 4, 5, or more than 5 cargo proteins.

As outlined above, it will be appreciated that unlike current technology, the present invention enables complex assembly of each building block in a specific order of at least 5 domains, commonly in a single reaction. In certain embodiments of the invention, a nanochain of five or more modular building blocks may be created. A nanochain of 10 or more building blocks are contemplated. It will also be appreciated that unlike current technology, the present invention enables complex assemblies to be made in a single reaction mixture.

In certain embodiments, the present invention is useful for purification, detection and identification applications, for example in the isolation of rare cells, including circulating tumour cells (CTC) (magnetic bead-affibody capture). Current technologies are typically limited by difficulty of capturing CTCs expressing low levels of tumour markers. It will be appreciated that the strong spontaneously-formed covalent bonds enabled by the present invention increases the sensitivity of diagnostics methods.

In certain embodiments, the invention is useful for investigating mechanical/physical characteristics of proteins, for example, by immobilisation onto atomic force microscopy (AFM) tips. It will be appreciated that the binding specificity of the present invention is suitable for studying mechanical properties of proteins compared with current approaches based on less specific disulphide bonds.

In certain embodiments, the invention is useful for enhancing the resilience and stability of enzymes, for example by circularisation of enzymes. It will be appreciated that increased enzyme resilience and stability enabled by the present invention is desired in many important applications such as biotransformation, biofuel production and molecular diagnostics.

In certain embodiments, the invention is useful for synthetic vaccine generation, for example in covalently attaching antigens to antibodies. Current technologies for synthetic vaccine generation are typically time consuming, costly and often limited by the size of the molecules expressed. The present invention enables generation of different protein subunits which can be assembled with high specificity at a lower cost and shorter time.

In certain embodiments, the invention is useful for therapeutic delivery of enzyme or proteins in outer membrane vesicles. It will be appreciated that using current technology, recombinant products are typically produced using a single microbial culture and purified for use. Accumulation of recombinant products within host expressing the product often leads to toxicity and limited yield. The present invention enables production of recombinant products in outer membrane vesicles reducing cellular toxicity and increases yield.

In certain embodiments, the invention is useful for constructing catalytic biofilms. The present invention enables engineering of biofilms to display functional peptides such as catalytic enzymes.

In certain embodiments, the invention is useful for protein expression and solubility analysis. It will be appreciated that current methods for expression and solubility analysis are typically very time consuming requiring many purification steps. The present invention enables rapid expression and solubility analysis by attachment of fluorescent labels to proteins of interest.

In certain embodiments, the invention is useful for producing protein based hydrogels. It will be appreciated that the present invention enables the synthesis of protein scaffolds that form spontaneously under physiological conditions.

In certain embodiments, the invention is useful for producing synthetic nanofibers. The present invention enables production of self-polymerising protein monomers.

It will be appreciated on reading this specification that multivalent protein structures can be assembled using various combinations of peptide binding pairs, where one binding partner comprises components of a spontaneously-reacting active site as described herein, and the other binding partner comprises the remaining components of a spontaneously-reacting active site, sufficient to recapitulate the active site and enable spontaneous bond formation. By appropriate selection of binding partners and active site components, binding specificity and selectivity can be achieved so as to enable the ordered construction of protein scaffolds carrying multiple functionalities. One representation of such a scaffold is shown herein in FIG. 20, where selective peptide binding partners recapitulate active sites to bring together different functional cargoes, co-locating these functionalities at a structural core itself formed via spontaneous ester bond formation as described herein. Both reversible and non-reversible bonds are formed, allowing the interchange of different functionalities, or replacement of functionalities, without necessarily resulting in the deconstruction of the structural core.

Figure 20:
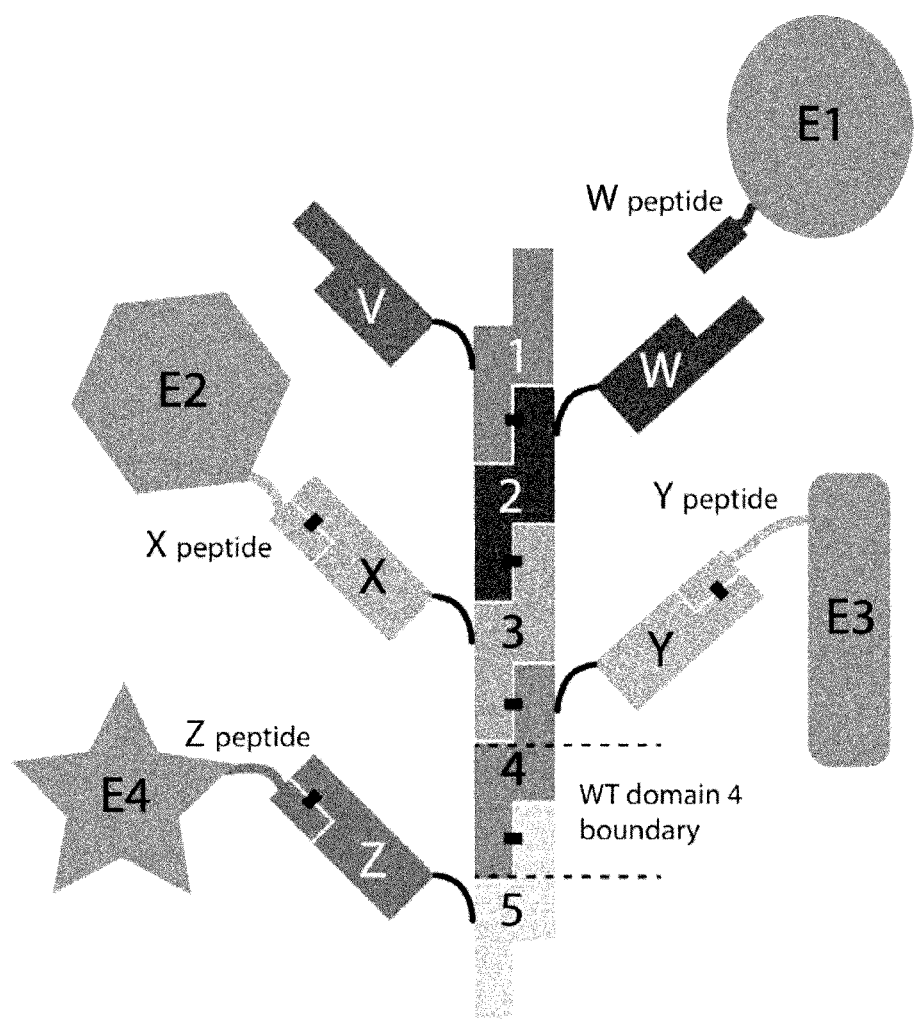
FIG. 20 shows a graphical representation of a multivalent protein scaffold comprising a 'trunk' of non-reversibly linked protein domains covalently linked via spontaneously-formed ester bonds, and 'limbs' comprising either non-reversibly linked or reversibly linked, selectively targeted domains comprising peptide binding partners carrying a functional domain as cargo.

A protein scaffold carrying multiple functionalities, such as that depicted in FIG. 20, and as exemplified in, for example, Examples 18 and 19, is also referred to herein as a multivalent multimeric protein complex. In certain embodiments, such scaffolds carry multiple copies of the same functionality, and so can be referred to as homovalent multimeric protein complexes or as multi-homovalent multimeric protein complexes. In other embodiments, such scaffolds carry multiple copies of the different functionalities, and so can be referred to as heterovalent multimeric protein complexes or as multi-heterovalent multimeric protein complexes.

Homovalent multimeric protein complexes, including multi-homovalent multimeric protein complexes, and heterovalent multimeric protein complexes, including multi-heterovalent multimeric protein complexes, including such complexes comprising one or more of the protein components specifically described and/or exemplified herein, including one or more protein components comprising 10 or more contiguous amino acids of the amino acid sequence of any one of SEQ ID NO.s 1-4 or 21-30, and/or comprising 10 or more contiguous amino acids of the amino acid sequence of any one of SEQ ID NO.s 31-58, such as 10 or more contiguous amino acids of the amino acid sequence of any one of SEQ ID NO.s 31-58, and comprises at least one amino acid from two or more of the domains present in said amino acid sequence as identified in one of Tables 37 to 41 herein, are specifically contemplated herein.

The following examples are intended to illustrate but not to limit the invention in any manner, shape, or form, either explicitly or implicitly. While they are typical of those that might be used, other procedures, methodologies, or techniques known to those skilled in the art may alternatively be used.

EXAMPLES

Methodology
Bacterial Strains, Plasmid and Oligonucleotides

*E. coli* strain DH5α was used for all DNA manipulation and the BL21 (ΔDE3) (Stratagene) strain was used for protein expression. Cultures were grown at 37° C. in 2×YT medium supplemented with ampicillin (100 µg/ml). The oligonucleotide primers used are listed in Table 1.
Cloning C2 Cpe0147 Constructs DNA encoding the Cpe0147 amino acid sequence 439-563 (for full sequence see Uniprot entry B1R775) was PCR amplified from the C2 construct previously reported in Kwon et al. (2014) using primers PYC2NtermFwd [SEQ ID No. 5] and PYC2NtermRev [SEQ ID No. 6]. Amplified PCR fragments were digested with EcoRI and KasI restriction endonucleases, and cloned into the expression vector pMBP-ProExHta (Invitrogen). pMBP-ProExHta, previously reported in Ting, Y. T.; Batot, G.; Baker, E. N.; Young, P. G. *Acta crystallographica. Section F, Structural biology communications* 2015, 71, 61, was generated by inserting the maltose binding protein (MBP) gene between the His$_6$-tag and the rTEV (recombinant Tobacco Etch Virus protease) cleavage site of pProExHta. The resulting vector, pMBP-Cpe0147$^{439-563}$, produces an N-terminal His$_6$-tagged MBP fusion protein followed by an rTEV cleavage site and the Cpe0147$^{439-563}$ truncated protein domain.

A second construct that lacks the cleavable rTEV recognition sequence was created by sub-cloning Cpe0147$^{439-563}$ into the vector pMBP3, previously described in Ting et al. 2015. The resulting vector, pMBP3L-Cpe0147$^{439-563}$, produces an N-terminal His$_6$-tagged MBP fusion protein followed by an -AGA- three residue linker and the Cpe0147$^{439-563}$ truncated protein domain.

A third, self-polymerising construct, was produced by the PCR amplification of Cpe0147 amino acid sequence 416-563 from the C2 construct using primers Fwdcomp1 [SEQ ID No. 7] and PYC2NtermRev [SEQ ID No. 6]. Amplified PCR fragments were digested with EcoRI and KasI restriction endonucleases, and were cloned into the expression vector pMBP-ProExHta to create the construct pMBP-Cpe0147$^{416-563}$Poly.

A construct comprising enhanced green fluorescent protein (eGFP) engineered with an N-terminal peptide tag derived from residues 565-587 of Cpe0147, was produced as follows. Customized, complementary 76 bp synthetic oligonucleotides CtermpeptF2 [SEQ ID No. 8] and CtermpeptR2 [SEQ ID No. 9]; Integrated DNA Technologies) encoding residues 565-587 of Cpe0147 were annealed by applying a temperature gradient from 100° C. to 20° C. The annealed product contained single-strand overhangs complementary to KasI and NcoI restriction endonuclease sites, and was inserted at the N-terminus of eGFP in the construct SP-GFP (Ting et al., 2015) between KasI and NcoI sites to create the construct pC2pept-GFP. This construct contains an N-terminal His$_6$-tag sequence followed by an rTEV cleavage site and the Cpe0147$^{565-587}$ peptide sequence fused to eGFP. All constructs were sequence verified at the DNA sequencing facility, School of Biological Sciences, University of Auckland.

Site-Directed Mutagenesis of Cpe0147

A T450S variant of pMBP3L-Cpe0147$^{439-563}$ was made by inverse PCR site-directed mutagenesis using the phosphorylated primers PYC2T13SFwd [SEQ ID No. 10] and PYC2T13SRev [SEQ ID No. 11] with pMBP3L-Cpe0147$^{439-563}$ as the template. Briefly, a high-fidelity DNA polymerase (iProof, Bio-Rad) was used for the PCR amplification of the pMBP3L-Cpe0147$^{439-563}$ plasmid to produce a linearized PCR product with the desired mutation at the 5' end of the sense primer. The methylated parental template without the T450S mutation was then removed from the non-methylated linear PCR product by DpnI digestion. Finally, the PCR product was re-circularized by intermolecular ligation. The resulting plasmid pMBP3L-Cpe0147-T450S$^{439-563}$ was transformed into E. coli DH5α cells, amplified, extracted and purified for sequence verification. A fully intact domain Cpe0147-T450S$^{439-587}$ was also engineered.

Protein Expression and Purification

The E. coli BL21 (20E3) cells harboring recombinant expression constructs were grown in 2×YT medium supplemented with ampicillin (100 µg/ml) at 37° C. in an orbital shaker (@180 rpm) to an optical density of OD$_{600}$=0.5-0.6. Protein expression was induced by the addition of isopropyl β-D-1-thiogalactopyranoside (IPTG) to a final concentration of 0.3 mM and cultures were left to incubate for an additional 16 h at 18° C. Cells were pelleted at 4000 g at 4° C. for 20 minutes, snap-frozen, and stored at −20° C.

Recombinant protein was purified from frozen cells, which were thawed and resuspended in lysis buffer [50 mM HEPES pH 7.0, 300 mM NaCl, 5% (v/v) glycerol, 10 mM imidazole] with the addition of Complete EDTA-free Protease Inhibitor Cocktail tablets (Roche) and lysed using a cell disruptor at 18,000 psi (Constant Systems). The insoluble protein fraction was removed by centrifugation (55,000 g at 4° C. for 30 minutes) and the soluble recombinant protein fraction loaded onto a 5 mL Protino NiNTA 5 column (Macherey-Nagel) for purification by immobilized metal affinity chromatography (IMAC). Recombinant protein was washed with Wash Buffer [50 mM HEPES pH 7, 300 mM NaCl, 20 mM imidazole] and eluted in a linear gradient with Elution Buffer (Wash Buffer with 500 mM imidazole).

For constructs with removable His- or His/MBP affinity tags, fractions from IMAC containing recombinant protein were dialyzed overnight against a >100×volume of dialysis buffer [20 mM HEPES pH7, 100 mM NaCl, 1 mM beta-mercaptoethanol] and the His6-tag or His-MBP concomitantly removed using recombinant TEV protease at a 1:50 molar ratio of rTEV to recombinant protein. Undigested protein and rTEV protease were removed by a second round of IMAC. Proteins with cleaved His-MBP tags were subjected to an additional purification by passage through an amylose resin (NEB) to remove contaminating cleaved MBP protein. Purified protein was concentrated and subjected to size-exclusion chromatography (SEC) on a Superdex 200 10/300 column (GE Healthcare) equilibrated with 10 mM HEPES pH7 and 100 mM NaCl. SEC-purified protein was concentrated to ~20 mg/ml and flash cooling in liquid nitrogen for subsequent storage at −80° C.

Peptide Synthesis

A synthetic peptide comprising Cpe0147$^{565-587}$, was prepared using the Fmoc/tBu solid phase methodology on a Tribute (Tucson, Az.) automated synthesizer on a 0.1 mmol scale using appropriately functionalized aminomethyl polystyrene resin. Briefly, the N-Fmoc group was removed with 20% piperidine in DMF (v/v) for 2×5 mins and the incoming Fmoc amino acid (0.5 mmol) was coupled with HATU (0.45 mmol) and DIPEA (1 mmol) in DMF for 20 mins. The peptide was released from the resin with 95% TFA, 2.5% TIPS and 2.5% water (v/v/v) for 3 h, precipitated with ether and recovered by centrifugation. Crude peptide was purified by reverse phase HPLC using an appropriate gradient based on its analytical profile and the mass confirmed by LC-MS.

Mass Spectrometry

Protein masses for Cpe0147$^{439-563}$-Cpe0147$^{565-587}$ products were confirmed by LC-MS using an Agilent 1120 Compact LC system with a Hewlett Packard Series 1100

TABLE 1

List of primers used.

| Primer name | Sequence | SEQ ID |
|---|---|---|
| PYC2NtermFwd | AAA GGC GCC AAT CTG CCT GAA GTG AAA GAT GG | 5 |
| PYC2NtermRev | TTT GAA TTC TCA GTT GTA ATC TTT ATC CGT ATC GAT | 6 |
| Fwdcomp1 | AAA GGC GCC GAT ACC AAA CAG GTG GTG AAA C | 7 |
| PYC2T13SFwd | (p)-AGC ACC GTT ATT GCA GAT GGC G | 10 |
| PYC2T13CRev | (p)-ACG CAG TGT ACC ATC TTT CAC | 11 |
| CtermpeptF2 | (p)-GCG CCG ACA CAA AAC AGG TTG TCA AAC ATG AGG ACA AAA ACG ACA AAG CAC AGA CAC TGG TGG TTG AAA AAC CGA C | 8 |
| CtermpeptR2 | (p)-CAT GGT CGG TTT TTC AAC CAC CAG TGT CTG TGC TTT GTC GTT TTT GTC CTC ATG TTT GAC AAC CTG TTT TGT GTC G | 9 |

(p) = 5' Phosphate

MSD mass spectrometer using ESI in the positive mode. LC-MS was performed using a Zorbax SB-300 C3 (5 µm; 3.0×150 mm) column (Agilent) and a linear gradient of 5% to 65% B over 21 mins (~3% B per minute) at a flow rate of 0.3 ml/min. The solvent system used was A (0.1% formic acid in $H_2O$) and B (0.1% formic acid in acetonitrile). Date was acquired in the m/z range of 400-2000 and the m/z values were deconvoluted to yield the monoisotopic mass. All other mass spectrometry experiments were performed by the Mass Spectrometry Centre, The University of Auckland, Auckland, New Zealand, using an LC-MS/MS, Q-Star XL Quadrupole-Time-of-Flight system.

Ester Bond Ligation Reactions

Initial protein purification of Cpe0147$^{439-563}$ was performed in a TRIS·HCl pH 8.0 buffering system. The initial experiments exploring the effect on pH and buffering systems contained residual TRIS·HCl (~2-5 mM) and NaCl (5 mM) from the diluted protein. For subsequent experiments protein was purified with a HEPES buffering system. Reactions for determining ester bond formation were performed with a protein concentration of 10 µM. Concentrated protein stored at −80° C. was thawed and diluted ~20 fold to 10 µM in the reaction buffer while the concentration of the other components was varied. All reactions were incubated at 20° C. unless otherwise stated. For time course experiments, samples were collected from a larger volume in the reaction tube and were stopped by adding SDS loading buffer and heating at 99° C. for ~3 min.

NMR Spectroscopy

NMR experiments were conducted using a Bruker 500 MHz instrument equipped with a BBFO probe. Conventional 5 mm NMR tubes (Norell) were used. Samples typically contained 90% $H_2O$ and 10% D20. Unless otherwise stated, all experiments were conducted at 300 K. Standard $^1H$ proton pulse sequence was used and water suppression was achieved by the excitation sculpting method with a 2 ms Squa100.1000 pulse. The pulse tip-angle calibration using the single-pulse nutation method (Bruker pulsecal routine)(Wu, P. S. C.; Otting, G. *J. Magn. Reson.* 2005, 176, 115) was undertaken for each sample.

Small-Angle X-Ray Scattering

Samples for small angle X-ray scattering were buffer exchanged into 10 mM HEPES pH 7.0, 100 mM NaCl with size exclusion chromatography (SEC). Data were collected at the Australian Synchrotron SAXS/WAXS beamline at a wavelength of 1.03 Å with a camera length of 1.6 m covering a momentum transfer range of $0.006 < q < 0.6$ Å$^{-1}$ ($q = 4\pi \sin(\theta)/\lambda$). Data were collected by SEC-SAXS and images were processed using scatterBrain[4] and PRIMUS[5]. SAXS data were further analyzed using programs in the ASTAS package including ab initio modeling produced in GASBOR and DAMMIF and with consensus models generated with DAMAVER (Petoukhov, M. V.; Franke, D.; Shkumatov, A. V.; Tria, G.; Kikhney, A. G.; Gajda, M.; Gorba, C.; Mertens, H. D.; Konarev, P. V.; and Svergun, D. I. *J Appl Crystallogr.* 2012, 45, 342).

Small angle X-ray scattering of the ligated MBP-Cpe-GFP assembly was undertaken to determine a low-resolution envelope of the structure. Data were collected every 2 seconds by SEC-SAXS from 25 µl of 12 mg/ml protein injected onto a Superdex S200 increase 5/150 GL column (GE Healthcare Life Sciences). Images representing the central peak of the SEC elution profile (images 120-130) were used for analysis, as shown in the scattering curve (FIG. 14A). The buffer subtracted scattering curve along with the Guinier plot (inset) is shown in FIG. 14B. SAX scattering parameters and statistics are shown in Table 2.

TABLE 2

Small Angle X-ray scattering parameters and statistics.

| Data collection parameters | |
| --- | --- |
| Beamline[a] | AS SAX/WAX |
| Wavelength (Å) | 1.03320 |
| Detector | 1M Pilatus detector |
| Camera length (mm) | 1575 |
| SEC column | S200 increase 5/150 GL |
| q range (Å$^{-1}$) | 0.006-0.6 |
| Sample capillary flow rate (ml/min) | 0.5 |
| Exposure time/images (s) | 2 |
| Number of images used | 10 |
| Sample concentration (mg/ml) | 12 |
| Sample volume (µl) | 25 |
| Temperature (K) | 283 |
| Structural parameters | |
| I(0) (cm$^{-1}$) (from P(r)) | 0.05 |
| Rg (Å) (from P(r)) | 47.2 |
| I(0) (cm$^{-1}$) (from Guinier) | 0.05 |
| Rg (Å) (from Guinier) | 45.4 |
| $D_{max}$ (Å) | 176.7 |
| Porod volume estimate (Å$^3$) | 134714 |
| MW calc from sequence (kDa) | 84.7 |
| MW calc from Porod volume (kDa) | 84.2 |
| Software | |
| Primary data collection | ScatterBrain |
| Data processing | ScatterBrain |
| Data analysis | Primus, ATSAS |

[a]Full details of the beamline specifications are available at the Australian Synchrotron website.

X-Ray Crystallography of Three Domain Constructs of *Mobiluncus mulieris* Adhesin Cloning of three-domain ester bond constructs of *Mobiluncus mulieris* strain BV 64-5 [ATCC® 35240™] was achieved by PCR amplification from genomic DNA and restriction cloning. Four overlapping three-domain ester bond constructs were PCR amplified from *M. mulieris* genomic DNA (ATCC® 35240™) using the gene specific primer pairs listed in Table 3. Briefly, a high-fidelity DNA polymerase (iProof, Bio-Rad) with GC-rich buffer was used for the PCR amplification of the 3-domain constructs from 0.5 ng genomic DNA. Amplified PCR fragments were digested with the KasI and XhoI restriction endonucleases and cloned into the expression vector pProExHta (Invitrogen) to create the constructs; Mol3-5, Mol5-7, Mol7-9, and Mol9-11. The resulting plasmids were sequence-verified and transformed into *E. coli* BL21 (DE3) cells for protein expression.

The *E. coli* BL21 (20E3) cells harboring recombinant expression constructs were grown in 2×YT medium supplemented with ampicillin (100 µg/ml) at 37° C. in an orbital shaker (@180 rpm) to an optical density of $OD_{600}$=0.5-0.6. Protein expression was induced by the addition of isopropyl β-D-1-thiogalactopyranoside (IPTG) to a final concentration of 0.3 mM and cultures were left to incubate for an additional 16 h at 18° C. Cells were pelleted at 4000 g at 4° C. for 20 minutes, snap-frozen, and stored at −20° C.

Recombinant protein was purified from frozen cells, which were thawed and resuspended in lysis buffer [50 mM HEPES pH 7.0, 300 mM NaCl, 5% (v/v) glycerol, 10 mM imidazole] with the addition of Complete EDTA-free Protease Inhibitor Cocktail tablets (Roche) and lysed using a cell disruptor at 18,000 psi (Constant Systems). The insoluble protein fraction was removed by centrifugation (55,000 g at 4° C. for 30 minutes) and the soluble recombinant protein fraction loaded onto a 5 mL Protino NiNTA 5 column (Macherey-Nagel) for purification by immobilized metal affinity chromatography (IMAC). Recombinant protein was washed with Wash Buffer [50 mM HEPES pH 7, 300 mM NaCl, 20 mM imidazole] and eluted in a linear gradient with Elution Buffer (Wash Buffer with 500 mM imidazole).

Fractions from IMAC containing recombinant protein were dialyzed overnight against a >100×volume of dialysis buffer [20 mM HEPES pH7, 100 mM NaCl, 1 mM beta-mercaptoethanol] and the His6-tag concomitantly removed using recombinant TEV protease at a 1:50 molar ratio of rTEV to recombinant protein. Undigested protein and rTEV protease were removed by a second round of IMAC. Purified protein was concentrated and subjected to size-exclusion chromatography (SEC) on a Superdex 200 10/300 column (GE Healthcare) equilibrated with 10 mM HEPES pH7 and 100 mM NaCl. SEC-purified protein was concentrated to ~200-400 mg/ml, and in the case of Mol5-7 concentrated to 750 mg/ml, and flash cooling in liquid nitrogen for subsequent storage at −80° C.

Selenomethionine-labelled Mol7-9 protein was produced using a modified protocol based on the inhibition of methionine biosynthesis (Doublie S, Carter C. (1992) Preparation of Selenomethionyl Protein Crystals. Oxford University Press. New York). Briefly, 2×YT media was substituted with M9 minimal media and the cells were grown as in the above protocol described for the expression of native protein. Once OD600 reached 1.5, 100 mg/l each of lysine, phenylalanine and threonine and 50 mg/leach of isoleucine, leucine and valine were added to the cultures. An abundance of L-selenomethionine (60 mg/1) was then added and the cells were grown for an additional 15 min at 37° C. prior to induction with 0.1 mM IPTG at 18° C. for 16 h.

Purified recombinant proteins were subjected to sitting-drop vapour diffusion crystallization screening trials at 290 K using a locally compiled crystallization screen. Initial crystallization conditions were optimised by hanging-drop vapour diffusion format with 1 µl protein solution mixed with an equal volume of well solution. The crystallization conditions, protein concentration and cryoprotection solution for each of the constructs is listed in Tables 4 and 5.

X-ray diffraction data were collected at the Australian Synchrotron (MX1 and MX2). Data were processed and scaled with XDS (Kabsch, W. (2010). XDS. Acta Cryst. D66, 125-132) and POINTLESS/AIMLESS (Evans, P. R. & Murshudov, G. N. (2013) Acta Cryst. D69, 1204-1214). The structure of Smet-Mol7-9 was solved by SAD phasing. Phase determination, density modification and model building used SHELX-CDE (A short history of SHELX. Sheldrick, G. M. (2008). Acta Cryst. A64, 112-122) Model building was completed with COOT (Emsley, P., Lohkamp, B., Scott, W. G. & Cowtan, K. (2010). Acta Cryst. D66, 486-501). The SeMet-Mol7-9 structure was refined with REFMAC (Murshudov G. N., Skubák P., Lebedev A. A., Pannu N. S., Steiner R. A., Nicholls R. A., Winn M. D., Long, F. & Vagin, A. A. (2011). Acta Cryst. D67, 355-367). The Mol7-9 native structure and the Mol9-11, Mol5-7 and Mol3-5 structures were solved by molecular replacement using the overlapping domain of each previously solved structure and refined using REFMAC. Final validation used MOLPROBITY (Chen V. B., Arendall W. B. 3$^{rd}$, Headd J. J., Keedy D. A., Immormino R. M., Kapral, G. J., Murray, L. W., Richardson, J. S. & Richardson, D. C. (2010). Acta Cryst. D66, 12-21.).

TABLE 3

List of primers used to amplify *Mobiluncus mulieris* strain BV 64-5 [ATCC ® 35240 ™].

| Primer name | Sequence | SEQ ID |
|---|---|---|
| MOB 3-5 FWD | AAA GGCGCC CCCGGTGTCACCACGGATGCCACCG | 12 |
| MOB 3-5 REV | AAA CTCGAG TCA CAGGCTCGGGTGGTACACGACCTGGG | 13 |
| MOB 5-7 FWD | AAA GGCGCC GTGCAAGAGGTAGAGATTACCACCACGGCC | 14 |
| MOB 5-7 REV | AAA CTCGAG TCA ACTCGGGGTGTAAACCGTCTGGGCGTCATC | 15 |
| MOB 7-9 FWD | AAA GGCGCC GTTGGTTCTCTGGATACCACCGCTACCGATG | 16 |
| MOB 7-9 RRV | AAA CTCGAG TCA ATGCTCCGACACCACCGTTTGGTTCGGATC | 17 |
| MOB 9-11 FWD | AAA GGCGCC GGCACGAGCCCGTCTCTAAAGACCGTG | 18 |
| MOB 9-11 REV | AAA CTCGAG TCA AGGCTTCTTGGACGTAACCGTCTGGTTTTCATCC | 19 |

TABLE 4

The crystallization conditions and protein concentration for each of the constructs.

| Construct | Protein concentration | Crystallization condition |
|---|---|---|
| MOB 3-5 | 140 mg/ml | 20% PEG 3350, 0.2M ammonium formate |
| MOB 5-7 | 750 mg/ml | 6% PEG 20K, 22% PEG 550, 0.03M MgCl$_2$, 0.03M CaCl$_2$, 0.1M MES/imidazole pH 6.5 |
| MOB 7-9 | 270 mg/ml | 4% PEG 8K, 8% PEG 1K, 0.2M MgCl$_2$ |
| MOB 9-11 | 360 mg/ml | 8% MPEG 5K, 0.2M citric acid pH 5.1 |
| MOB 7-9 Smet | 250 mg/ml | 12% PEG 8K, 6% PEG 1K, 0.2M MgCl$_2$ |

TABLE 5

Cryoprotection solution for each of the constructs.

| Construct | Crystallization Cryo |
|---|---|
| MOB 3-5 | 20% PEG 3350, 0.2M ammonium formate, 20% glycerol |
| MOB 5-7 | 6% PEG 20K, 22% PEG 550, 0.03M MgCl$_2$, 0.03M CaCl$_2$, 0.1M MES/imidazole pH 6.5 |
| MOB 7-9 | 4% PEG 8K, 8% PEG 1K, 0.2M MgCl$_2$, 20% glycerol |

TABLE 5-continued

Cryoprotection solution for each of the constructs.

| Construct | Crystallization Cryo |
|---|---|
| MOB 9-11 | 8% MPEG 5K, 0.2M citric acid pH 5.1, 20% glycerol |
| MOB 7-9 Smet | 12% PEG 8K, 6% PEG 1K, 0.2M MgCl$_2$, 20% glycerol |

Example 1

Figure 1:
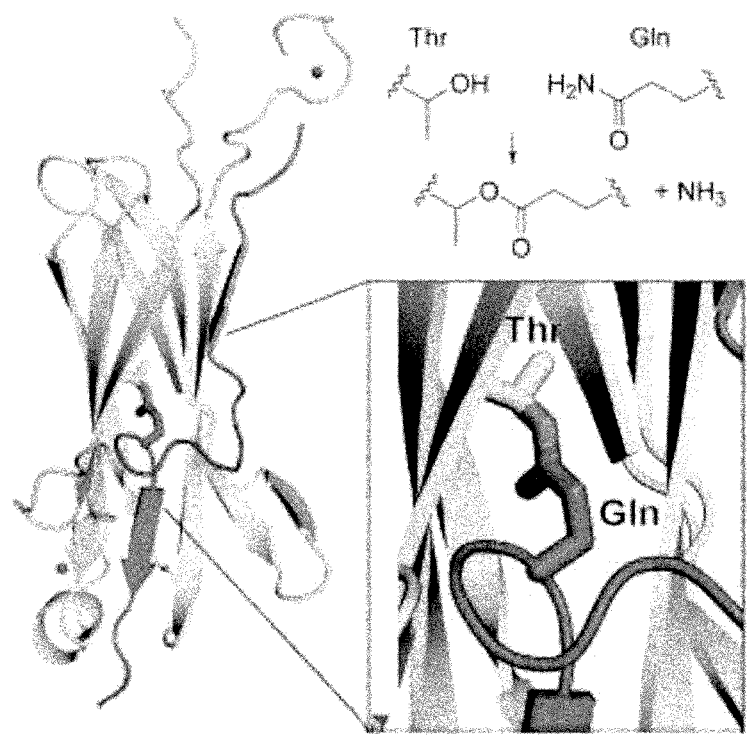
Figure 2:
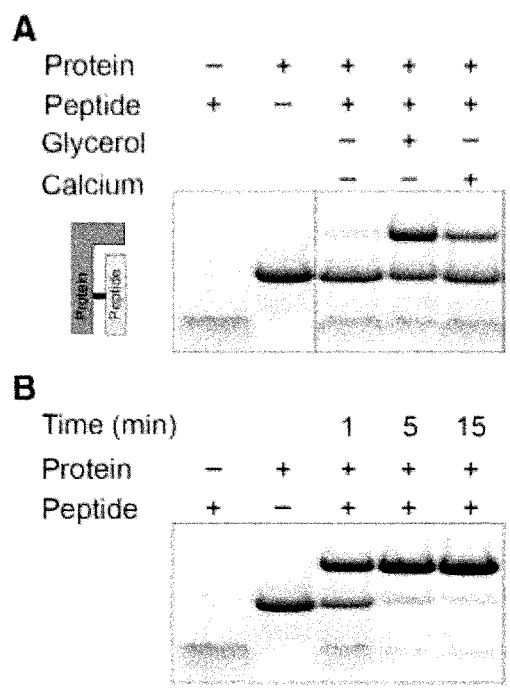
Figure 5:
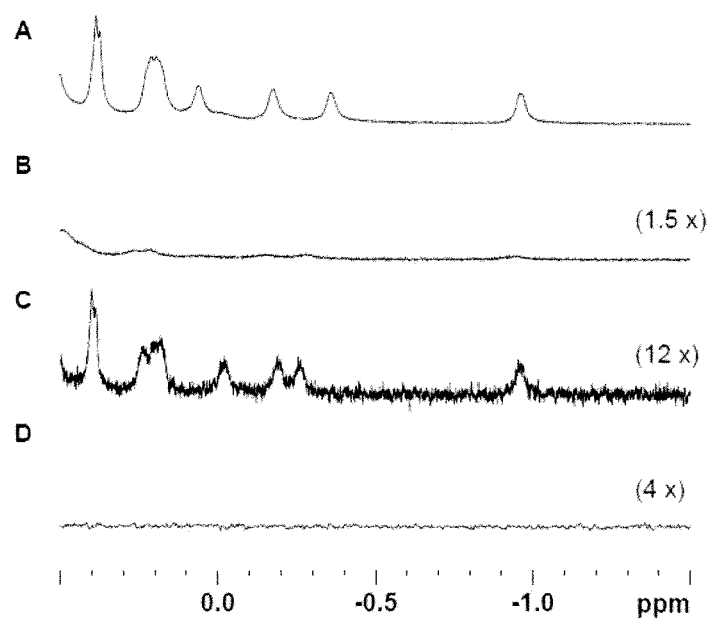

This example demonstrates the spontaneous formation of ester bond between Cpe0147$^{439-563}$ truncated protein domain and Cpe0147$^{565-587}$ peptide.
Method The Ig-like domain, encompassing Cpe0147 residues 439-587, is split into two parts; a truncated protein comprising the sequence 439-563 and a peptide comprising the final β-strand of the domain, residues 565-587 (DTKQVVKHEDKNDKAQTLVVEKP [SEQ ID No. 3]). The truncated protein was produced recombinantly in E. coli as a maltose binding protein (MBP) construct, with the MBP tag subsequently removed, while the complementary C-terminal peptide was chemically synthesized.
Results When mixed together, the N-terminal truncation and the peptide spontaneously form a covalent ester bond linkage that is evident in SDS-PAGE analysis (FIGS. 2A and 5). The mass of the complex was confirmed by mass spectrometry as 17129.2±1.4 Da (calculated 17131.6 Da). The rate of ester bond formation in this system was optimized by modifying the incubation conditions from an initial TRIS·HCl pH 8.0 system, with significant increases in bond formation rate achieved by including molecular crowding agents, divalent cations and specific pH buffering molecules (FIG. 2A). The optimized reaction buffer comprises 50 mM HEPES pH7.0, 10 mM NaCl, 100 CaCl$_2$ and 20% glycerol. Using this reaction buffer with 10 μM of protein, and at a protein:peptide ratio of 1:2, the ester bond formation reaction nears completion in as little as 5 min (FIG. 2B). The rate of bond formation is similar over a temperature range of 4° C.-28° C., allowing experiments to be incubated on ice or in a refrigerator.

Figure 6:
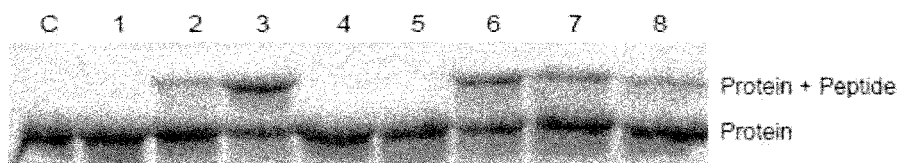
Figure 7:
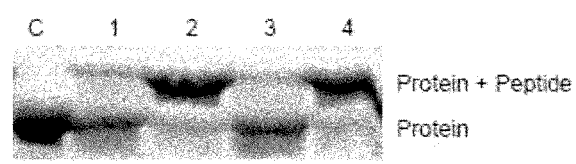
Figure 8:
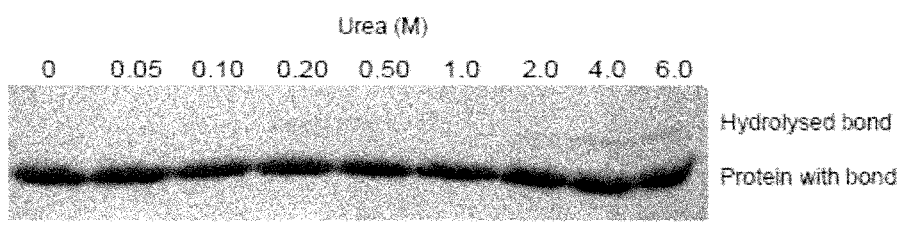

Interestingly, a pH/buffer screen suggests that the particular buffer molecule used has a greater impact on bond formation than the pH of the solution itself (FIGS. 6 and 7). The most efficient buffering molecules, MES, MOPS and HEPES, are all zwitterionic and contain a saturated, heterocyclic 6 membered ring with an alkyl (ethyl or propyl) linked sulfonic acid functionality.

Example 2

This example demonstrates covalent cross-linking between two proteins.
Method

Figure 3:
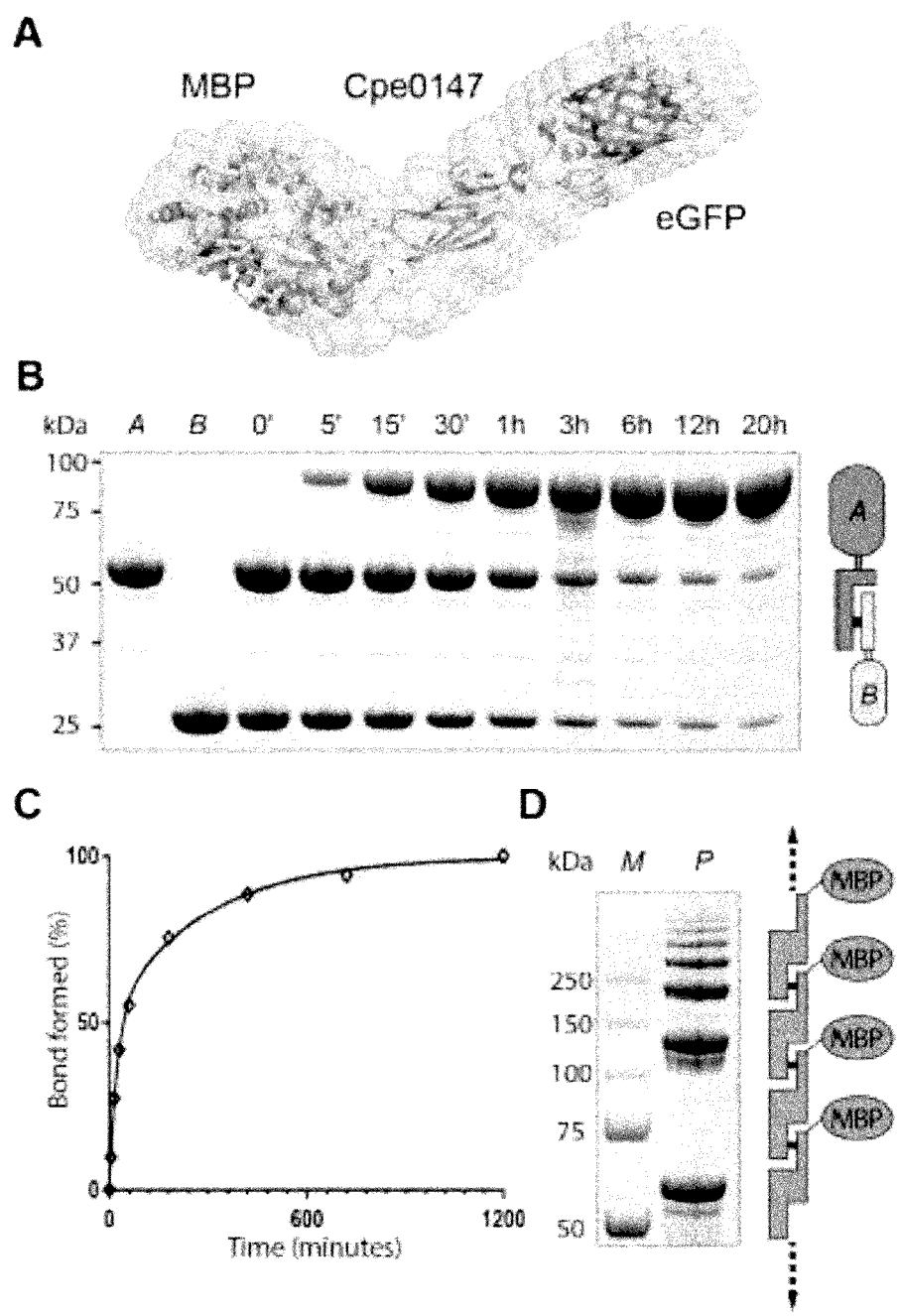

The N-terminally MBP-tagged Cpe0147 truncated protein was paired with an enhanced green fluorescent protein (eGFP) engineered with an N-terminal peptide tag derived from residues 565-587 of the Cpe0147 adhesin protein.
Results Incubation of Cpe0147$^{439-563}$ truncated protein domain with Cpe0147$^{565-587}$ peptide sequence fused to eGFP in the previously optimized buffer system produces a dimeric, irreversibly cross-linked assembly with a mass of 84,580 Da. The MBP-Cpe0147-eGFP ligation product was visualized by small-angle X-ray scattering (SAXS). A constructed ab initio envelope (FIG. 3A) and particle distribution functions derived from the SAXS data, describe a molecule with maximum dimensions of ~176 Å, which fits very well with the known sizes of the individual components of the ligated assembly. A time course illustrated in FIGS. 3B and 3C shows ester bond formation approaches 50% at a time point of ~1 h and ~90% conversion at 6 h.

Example 3

This example demonstrates the in vivo self-polymerisation of Cpe0147$^{439-563}$ truncated protein domain.
Method The Ig-like domain of Cpe0147 was engineered as a self-polymerizing construct to form nanochains comprising a central Cpe0147-derived stalk displaying MBP-cargo protein along the entire length (FIG. 3D, right). The truncated second domain of Cpe0147, lacking its C-terminal β-strand, had its N-terminus extended to include the final β-strand of the preceding Ig-like domain in the full length Cpe0147 protein (residues 416-438, DTKQVVKHEDKNDKAQTLIVEKP [SEQ ID No. 4]). The His$_6$-tagged MBP cargo protein was fused to this N-terminal extension, and the protein was expressed and isolated from the crude bacterial lysate using immobilized metal affinity chromatography resin.
Results SDS-PAGE analysis shows a diagnostic laddering pattern indicative of polymerization, with a mixture of species ranging from ~56 kDa (monomer) to >500 kDa molecular mass (FIG. 3D). This result shows that the ester bond technology developed in vitro is transferable to experiments in vivo with cross-links forming and stable to both proteolysis and hydrolysis inside the bacteria.

Example 4

This example demonstrates a reversible ester bond.
Method

Figure 4:
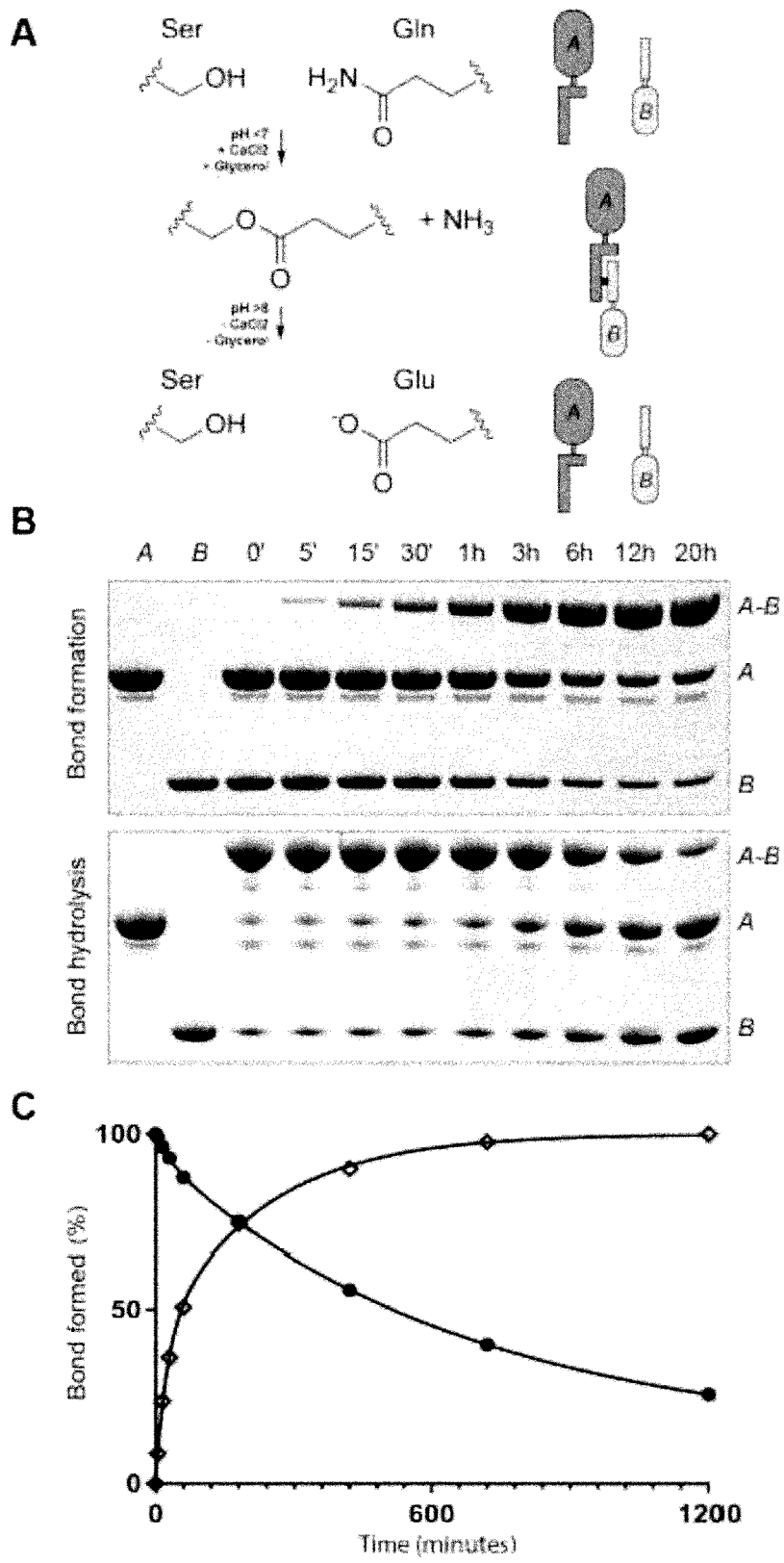
Figure 9:
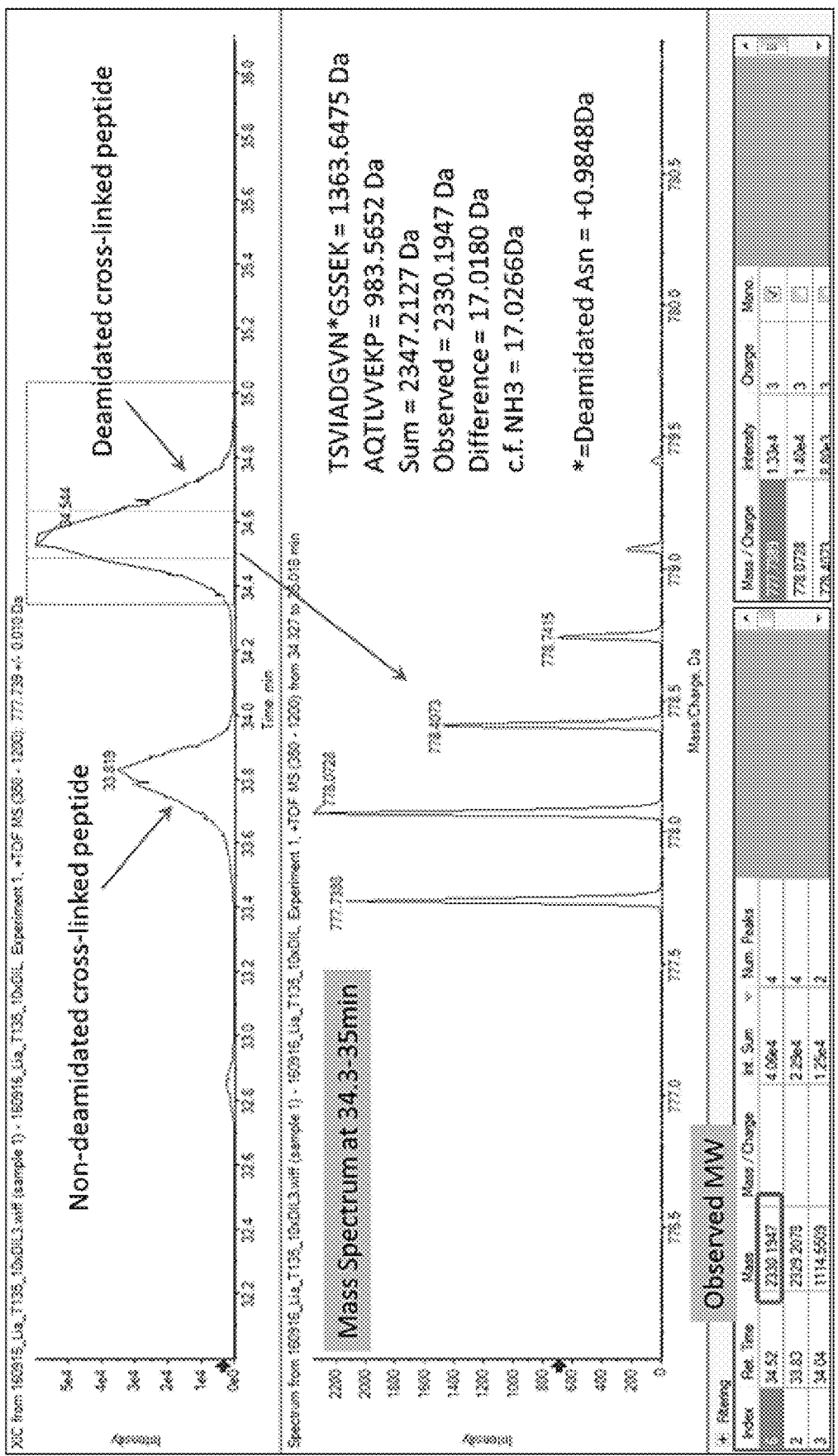
Figure 9:
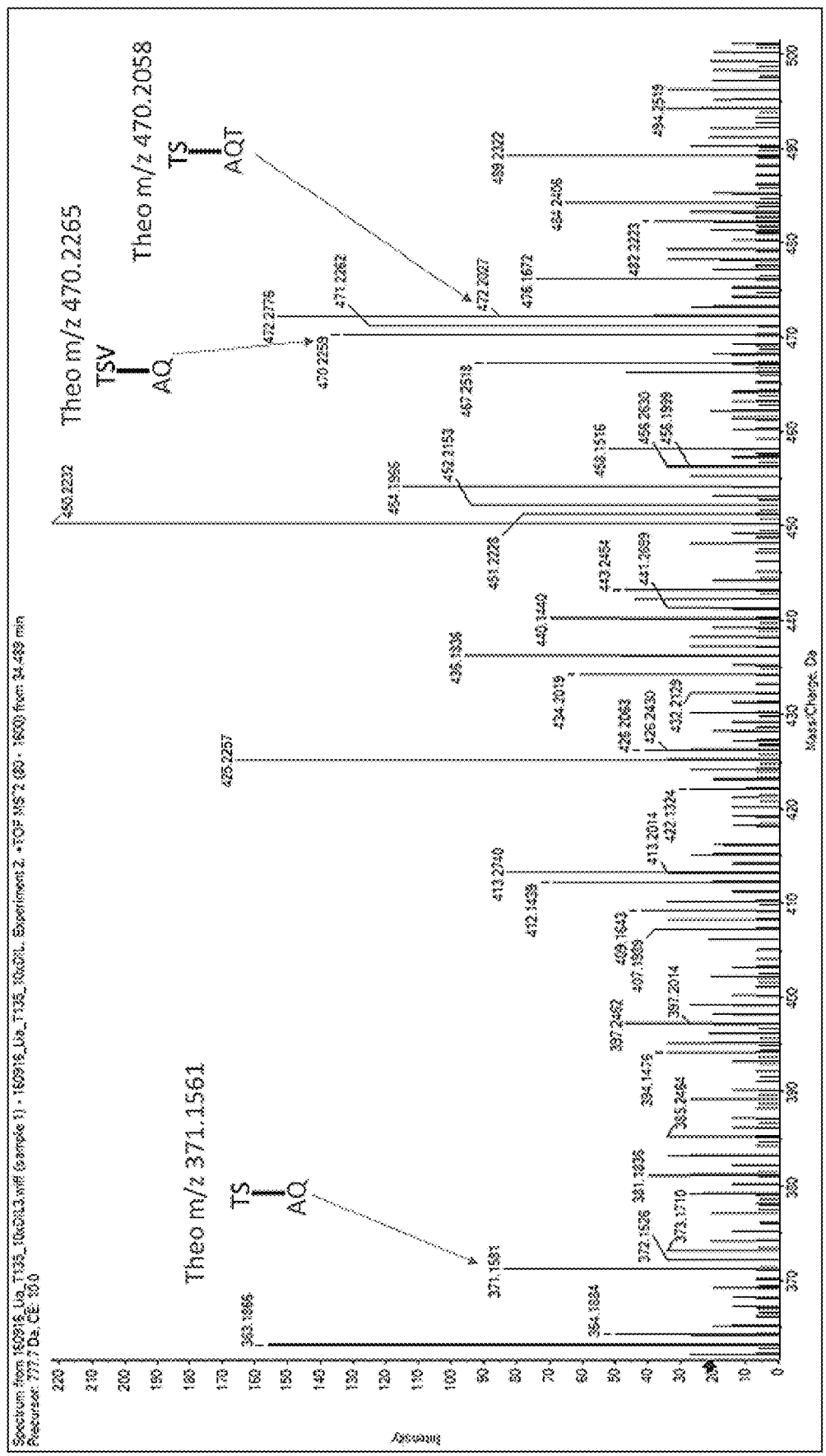
Figure 10:
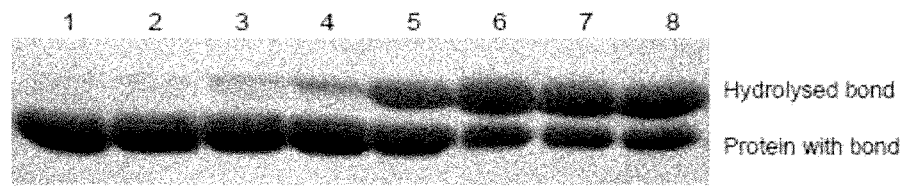
Figure 11:
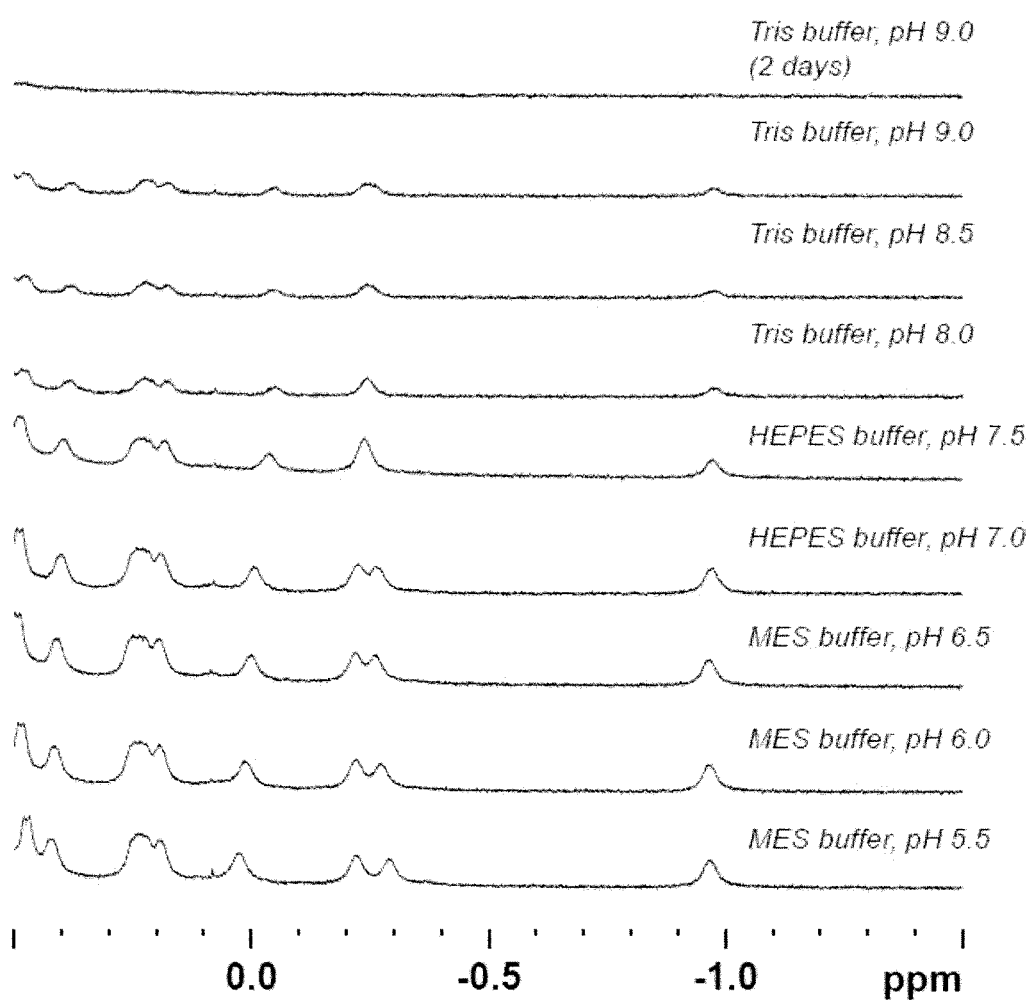
Figure 12:
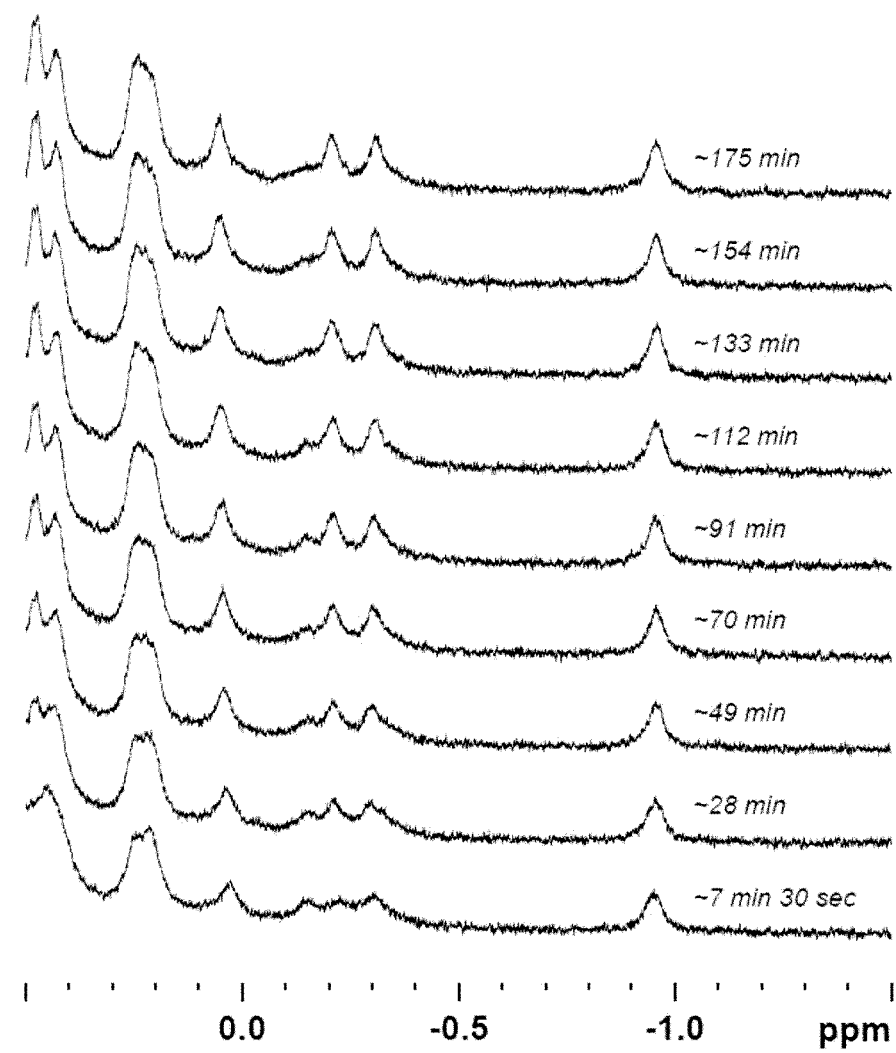

The cross-linking Thr-Gln pair was replaced with a Ser-Gln pair (T450S variant). The formation of a Ser-Gln crosslink under the previously optimized buffer system using the T450S variant of the Ig-like domain 2 of Cpe0147, was first confirmed by tryptic digest and mass spectrometry (FIG. 9). In this same system, the hydrolysis reactivity was assessed by SDS-PAGE and $^1$H-NMR (FIGS. 10 to 12) and optimized before application to a T450S variant of the inventor's three protein, MBP cargo system (FIG. 4).
Results Under low pH conditions and in the presence of CaCl$_2$) and glycerol, this construct forms ester bonds that are stable and that do not hydrolyze (FIGS. 4A and 4B). However, increasing the pH to between 8 and 9 and removing the CaCl$_2$) and glycerol, promotes ester bond hydrolysis leaving a Glu amino acid in place of the wild type Gln (FIGS. 4A and 4B).

The time courses of ester bond formation and hydrolysis, illustrated in FIG. 4C can, like the wild type system, be fitted to two-phase exponential models; for bond formation an association model and for hydrolysis a decay model. Ester bond formation in the T450S system, like the wild type equivalent, shows >50% conversion at ~1 h suggesting they are near equivalent in their ligation potential. Hydrolysis is slower than bond formation with ~20% intact ester bond remaining after 20 h.

Figure 13:
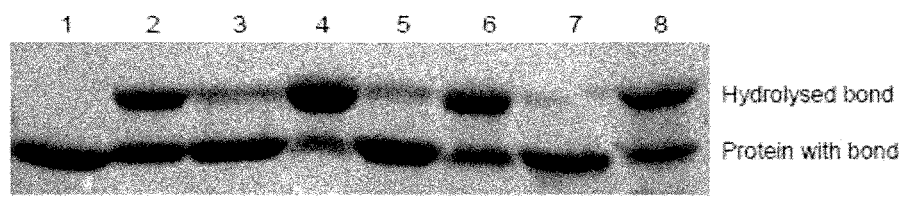

Following hydrolysis, the separated MBP and eGFP constructs can be re-ligated simply by switching the buffer to our low pH optimized condition which initiates ester bond formation. The implication here is that the wild type Gln can be replaced with a Glu in the active site and still form an ester bond. Intriguingly, the process of bond making and bond breaking can be completed through at least three cycles on the same sample (FIG. 13).

Example 5

This example demonstrates the peptide sequence, relative atom locations and interatomic distances of the essential residues in the active site of Cpe0147-domain 2.

TABLE 6

Peptide sequence of Cpe0147 - domain 2.

| Peptide and position | Sequence | SEQ ID |
|---|---|---|
| Cpe0147 - domain 2 439-587 | LPEVKDGTLRTTVIADGVNGSSEKEALVSFENSKDG VDVKDTINYEGLVANQNYTLTGTLMHVKADGSLEE IATKTTNVTAGENGNGTWGLDFGNQKLQVGEKYV VFENAESVENLIDTDKDYNLDTKQVVKHEDKNDK AQTLVVEKP | 1 |

The coordinates of the atoms of threonine, aspartic acid, histidine and glutamine residues are listed in Table 7 below.

TABLE 7

Relative atom locations of essential residues for spontaneous intermolecular ester bond formation.

| | | Atom | Residue type | Chain | Residue number | X coordinate | Y coordinate | Z coordinate | Occupancy | Temperature factor | Atom type |
|---|---|---|---|---|---|---|---|---|---|---|---|
| Cpe0147-domain 2 | 1193 | N | THR | A | 160 | 2.211 | −0.667 | 0.879 | 1.00 | 32.76 | N |
| | 1194 | CA | THR | A | 160 | 1.188 | −0.952 | −0.122 | 1.00 | 32.66 | C |
| | 1195 | C | THR | A | 160 | 1.706 | −0.934 | −1.570 | 1.00 | 35.12 | C |
| | 1196 | O | THR | A | 160 | 2.670 | −0.230 | −1.893 | 1.00 | 33.46 | O |
| | 1197 | CB | THR | A | 160 | 0.000 | 0.000 | 0.000 | 1.00 | 37.84 | C |
| | 1198 | OG1 | THR | A | 160 | 0.408 | 1.307 | −0.446 | 1.00 | 41.05 | O |
| | 1199 | CG2 | THR | A | 160 | −0.621 | 0.056 | 1.388 | 1.00 | 32.20 | C |
| | 1409 | N | ASP | A | 190 | −5.567 | −3.182 | −4.385 | 1.00 | 36.17 | N |
| | 1410 | CA | ASP | A | 190 | −4.390 | −2.782 | −3.609 | 1.00 | 32.95 | C |
| | 1411 | C | ASP | A | 190 | −3.907 | −3.947 | −2.748 | 1.00 | 36.79 | C |
| | 1412 | O | ASP | A | 190 | −4.726 | −4.618 | −2.146 | 1.00 | 35.26 | O |
| | 1413 | CB | ASP | A | 190 | −4.706 | −1.574 | −2.713 | 1.00 | 33.42 | C |
| | 1414 | CG | ASP | A | 190 | −3.453 | −0.882 | −2.188 | 1.00 | 36.02 | C |
| | 1415 | OD1 | ASP | A | 190 | −2.605 | −0.474 | −3.022 | 1.00 | 37.62 | O |
| | 1416 | OD2 | ASP | A | 190 | −3.354 | −0.685 | −0.962 | 1.00 | 37.50 | O |
| | 2126 | N | HIS | A | 282 | −1.293 | 4.493 | 5.905 | 1.00 | 31.69 | N |
| | 2127 | CA | HIS | A | 282 | −0.308 | 4.745 | 4.862 | 1.00 | 32.37 | C |
| | 2128 | C | HIS | A | 282 | −1.010 | 5.680 | 3.890 | 1.00 | 36.40 | C |
| | 2129 | O | HIS | A | 282 | −1.850 | 5.234 | 3.099 | 1.00 | 36.28 | O |
| | 2130 | CB | HIS | A | 282 | 0.162 | 3.454 | 4.201 | 1.00 | 33.33 | C |
| | 2131 | CG | HIS | A | 282 | 1.353 | 3.676 | 3.343 | 1.00 | 38.04 | C |
| | 2132 | ND1 | HIS | A | 282 | 2.583 | 3.981 | 3.888 | 1.00 | 40.88 | N |
| | 2133 | CD2 | HIS | A | 282 | 1.437 | 3.770 | 2.001 | 1.00 | 39.83 | C |
| | 2134 | CE1 | HIS | A | 282 | 3.397 | 4.159 | 2.861 | 1.00 | 40.97 | C |
| | 2135 | NE2 | HIS | A | 282 | 2.750 | 4.020 | 1.708 | 1.00 | 40.66 | N |
| | 2209 | N | GLN | A | 290 | 1.986 | 2.894 | −4.694 | 1.00 | 34.45 | N |
| | 2210 | CA | GLN | A | 290 | 0.536 | 3.078 | −4.538 | 1.00 | 32.16 | C |
| | 2211 | C | GLN | A | 290 | −0.125 | 3.900 | −5.636 | 1.00 | 35.86 | C |
| | 2212 | O | GLN | A | 290 | −1.346 | 4.120 | −5.565 | 1.00 | 33.51 | O |
| | 2213 | CB | GLN | A | 290 | 0.260 | 3.821 | −3.204 | 1.00 | 31.70 | C |
| | 2214 | CG | GLN | A | 290 | 0.818 | 3.147 | −1.975 | 1.00 | 31.37 | C |
| | 2215 | CD | GLN | A | 290 | 0.023 | 1.910 | −1.605 | 1.00 | 39.23 | C |
| | 2216 | OE1 | GLN | A | 290 | −0.719 | 1.304 | −2.384 | 1.00 | 32.11 | O |

Method

The peptide sequence for Cpe0147-domain 2 (residues 439-587) was obtained from Uniprot (entry B1R775).

The coordinate data of the atoms for each of the four essential residues for spontaneous intermolecular ester bond formation of Cpe0147-domain 2 was obtained from Protein Data Bank file 4MKM. The Protein Data Bank (PDB) conventional orthogonal coordinate system was used. The Cβ (CB) atom of the threonine reactive residue was chosen as the reference coordinate (0, 0, 0).

The interatomic distances were obtained by using the distance measurement tools within the software programme Pymol.

Cpe0147-Domain 2

Table 6 shows the peptide sequence of Cpe0147-domain 2. The essential reactive and accessory amino acids are in bold. The HxDxxDxxQ is underlined.

The interatomic distance (in Angstrom) of Cβ (CB) of threonine to Cδ (CD) of glutamine, Cγ (CG) of histidine and Cγ (CG) of aspartic acid is listed in table 8 below.

TABLE 8

Interatomic distances.

| | Cpe0147 - domain 2 |
|---|---|
| Thr CB to Gln CD | 2.49 |
| Thr CB to His CG | 5.15 |
| Thr CB to Asp CG | 4.18 |

Example 6

This example demonstrates the peptide sequence and the essential residues in the active site of T450S-Cpe0147-domain 2.

Method

The peptide sequence for Cpe0147-domain 2 (residues 439-587) was obtained from Uniprot (entry B1R775) and the threonine at amino acid position 450 replaced with a serine amino acid.

T450S-Cpe0147-Domain 2

Table 9 shows the peptide sequence of T450S-Cpe0147-domain 2. The essential reactive and accessory amino acids are in bold. The HxDxxDxxQ peptide sequence motif is underlined.

TABLE 9

| Peptide sequence of T450S-Cpe0147 – domain 2. | | |
|---|---|---|
| Peptide and position | Sequence | SEQ ID |
| T450S-Cpe0147 – domain 2 439-587 | LPEVKDGTLRSTVIADGVNGSSEKEALVSFENSKDG VDVKDTINYEGLVANQNYTLTGTLMHVKADGSLEE IATKTTNVTAGENGNGTWGLDFGNQKLQVGEKYV VFENAESVENLIDTDKDYNLDTKQVVKHED<ins>KNDK</ins> <ins>AQ</ins>TLVVEKP | 20 |

Example 7

This example demonstrates the peptide sequence, relative atom locations and interatomic distances of the essential residues in the active site of Mol3.

Method

The peptide sequence for Mol3 was obtained from Uniprot (entry E0QN07).

The coordinate data of the atoms for each of the four essential residues for spontaneous intermolecular ester bond formation of Mol3 was obtained from an unpublished X-ray crystal structure of a Mol3-Mol4-Mol5 construct (E0QN07 sequence 5430-5825). The Protein Data Bank (PDB) conventional orthogonal coordinate system was used. The Cβ (CB) atom of the threonine reactive residue was chosen as the reference coordinate (0, 0, 0).

The interatomic distances were obtained by using the distance measurement tools within the software programme Pymol.

Mol3

Table 10 shows the peptide sequence of Mol3. The essential reactive and accessory amino acids are in bold. The HxDxxDxxQ peptide sequence motif is underlined.

TABLE 10

| Peptide sequence of Mol3. | | |
|---|---|---|
| Peptide and position | Sequence | SEQ ID |
| Mol3 from E0QN07 5430-5553 | PGVTTD ATDGDGDKYVDSSQNFTIKD TVTATGLIPGKTYDVSGELM VDNGTPQGATTGIKQTGTIT AKADGTGETVLEFPVTAQQA QDLGLVGKPIVVFEDLSLDG KKVAVH<ins>HDIKDEKQ</ins>TVYN | 21 |

The coordinates of the atoms of threonine, aspartic acid, histidine and glutamine residues are listed in Table 11 below.

TABLE 11

| | | Atom | Residue type | Chain | Residue number | X coordinate | Y coordinate | Z coordinate | Occupancy | Temperature factor | Atom type |
|---|---|---|---|---|---|---|---|---|---|---|---|
| Mol3 | 1 | N | THR | A | 7 | 0.237 | 1.677 | 1.706 | 1.00 | 33.54 | N |
| | 2 | CA | THR | A | 7 | 0.222 | 1.462 | 0.290 | 1.00 | 37.70 | C |
| | 3 | C | THR | A | 7 | −0.863 | 2.270 | −0.399 | 1.00 | 41.11 | C |
| | 4 | O | THR | A | 7 | −1.707 | 2.846 | 0.282 | 1.00 | 41.48 | O |
| | 5 | CB | THR | A | 7 | 0.000 | 0.000 | 0.000 | 1.00 | 40.97 | C |
| | 6 | CG2 | THR | A | 7 | 0.797 | −0.938 | 0.865 | 1.00 | 42.06 | C |
| | 7 | OG1 | THR | A | 7 | −1.353 | −0.237 | 0.276 | 1.00 | 42.72 | O |
| | 9 | N | ASP | A | 28 | 0.505 | −0.819 | −7.497 | 1.00 | 35.39 | N |
| | 10 | CA | ASP | A | 28 | 0.485 | −0.550 | −6.062 | 1.00 | 35.04 | C |
| | 11 | C | ASP | A | 28 | 1.736 | 0.171 | −5.646 | 1.00 | 33.23 | C |
| | 12 | O | ASP | A | 28 | 2.792 | −0.375 | −5.791 | 1.00 | 31.66 | O |
| | 13 | CB | ASP | A | 28 | 0.420 | −1.857 | −5.261 | 1.00 | 34.95 | C |
| | 14 | CG | ASP | A | 28 | 0.019 | −1.618 | −3.836 | 1.00 | 34.09 | C |
| | 15 | OD1 | ASP | A | 28 | −0.902 | −0.840 | −3.634 | 1.00 | 30.49 | O |
| | 16 | OD2 | ASP | A | 28 | 0.563 | −2.244 | −2.918 | 1.00 | 43.42 | O |
| | 18 | N | HIS | A | 114 | 1.572 | −5.364 | 5.517 | 1.00 | 41.36 | N |
| | 19 | CA | HIS | A | 114 | 0.373 | −4.532 | 5.404 | 1.00 | 32.60 | C |
| | 20 | C | HIS | A | 114 | −0.668 | −5.379 | 4.744 | 1.00 | 33.25 | C |
| | 21 | O | HIS | A | 114 | −0.743 | −5.439 | 3.497 | 1.00 | 27.81 | O |
| | 22 | CB | HIS | A | 114 | 0.678 | −3.274 | 4.644 | 1.00 | 34.16 | C |
| | 23 | CG | HIS | A | 114 | −0.357 | −2.221 | 4.815 | 1.00 | 32.78 | C |
| | 24 | CD2 | HIS | A | 114 | −1.447 | −1.902 | 4.077 | 1.00 | 39.05 | C |
| | 25 | ND1 | HIS | A | 114 | −0.386 | −1.404 | 5.909 | 1.00 | 35.38 | N |
| | 26 | CE1 | HIS | A | 114 | −1.431 | −0.595 | 5.835 | 1.00 | 39.36 | C |
| | 27 | NE2 | HIS | A | 114 | −2.087 | −0.870 | 4.723 | 1.00 | 36.33 | N |
| | 29 | N | GLN | A | 122 | −5.755 | 0.651 | −0.506 | 1.00 | 22.69 | N |
| | 30 | CA | GLN | A | 122 | −5.228 | −0.488 | −1.249 | 1.00 | 27.25 | C |
| | 31 | C | GLN | A | 122 | −6.282 | −1.151 | −2.160 | 1.00 | 30.92 | C |

TABLE 11-continued

Relative atom locations of essential residues for spontaneous intermolecular ester bond formation.

| | Atom | Residue type | Chain | Residue number | X coordinate | Y coordinate | Z coordinate | Occupancy | Temperature factor | Atom type |
|---|---|---|---|---|---|---|---|---|---|---|
| 32 | O | GLN | A | 122 | −6.027 | −2.263 | −2.652 | 1.00 | 37.38 | O |
| 33 | CB | GLN | A | 122 | −4.702 | −1.532 | −0.275 | 1.00 | 27.08 | C |
| 34 | CG | GLN | A | 122 | −3.566 | −1.003 | 0.597 | 1.00 | 26.96 | C |
| 35 | CD | GLN | A | 122 | −2.274 | −1.241 | −0.107 | 1.00 | 25.59 | C |
| 36 | OE1 | GLN | A | 122 | −2.165 | −1.045 | −1.339 | 1.00 | 25.28 | O |

The interatomic distance (in Angstrom) of Cβ (CB) of threonine to Cδ (CD) of glutamine, Cγ (CG) of histidine and Cγ (CG) of aspartic acid is listed in table 12 below.

TABLE 12

Interatomic distances.

| | Mol3 |
|---|---|
| Thr CB to Gln CD | 2.59 |
| Thr CB to His CG | 5.31 |
| Thr CB to Asp CG | 4.16 |

Example 8

This example demonstrates the peptide sequence, relative atom locations and interatomic distances of the essential residues in the active site of Mol4.

Method

The peptide sequence for Mol4 was obtained from Uniprot (entry E0QN07).

The coordinate data of the atoms for each of the four essential residues for spontaneous intermolecular ester bond formation of Mol4 was obtained from an unpublished X-ray crystal structure of a Mol3-Mol4-Mol5 construct (E0QN07 sequence 5430-5825). The Protein Data Bank (PDB) conventional orthogonal coordinate system was used. The Cβ (CB) atom of the threonine reactive residue was chosen as the reference coordinate (0, 0, 0).

The interatomic distances were obtained by using the distance measurement tools within the software programme Pymol.

Mol4

Table 13 shows the peptide sequence of Mol4. The essential reactive and accessory amino acids are in bold. The HxDxxDxxQ peptide sequence motif is underlined.

TABLE 13

Peptide sequence of Mol4.

| Peptide and position | Sequence | SEQ ID |
|---|---|---|
| Mol4 from E0QN07 5554-5680 | G G L K T K A V D A A D E N Q A M V P G Q K S A A V V D T V T F N G R F E K S H S Y T L V G E L H Y V N G T V V P G T K T E T K T F Q S D Q D G A I A A Q K M T F T V P A E Y I K A G Q N M V V F E K L F D A K K K D G T P V A S <u>H E D P N D P D Q</u> T I T V Q | 22 |

The coordinates of the atoms of threonine, aspartic acid, histidine and glutamine residues are listed in Table 14 below.

TABLE 14

Relative atom locations of essential residues for spontaneous intermolecular ester bond formation.

| | | Atom | Residue type | Chain | Residue number | X coordinate | Y coordinate | Z coordinate | Occupancy | Temperature factor | Atom type |
|---|---|---|---|---|---|---|---|---|---|---|---|
| Mol4 | 1 | N | THR | A | 131 | 0.221 | 1.930 | 1.461 | 1.00 | 33.74 | N |
| | 2 | CA | THR | A | 131 | 0.104 | 1.497 | 0.088 | 1.00 | 36.50 | C |
| | 3 | C | THR | A | 131 | −1.092 | 2.062 | −0.639 | 1.00 | 34.44 | C |
| | 4 | O | THR | A | 131 | −2.144 | 2.305 | −0.055 | 1.00 | 32.42 | O |
| | 5 | CB | THR | A | 131 | 0.000 | 0.000 | 0.000 | 1.00 | 40.07 | C |
| | 6 | CG2 | THR | A | 131 | 1.120 | −0.722 | 0.781 | 1.00 | 42.85 | C |
| | 7 | OG1 | THR | A | 131 | −1.265 | −0.339 | 0.535 | 1.00 | 34.89 | O |
| | 9 | N | ASP | A | 154 | 0.752 | −0.619 | −7.662 | 1.00 | 38.88 | N |
| | 10 | CA | ASP | A | 154 | 0.806 | −0.284 | −6.238 | 1.00 | 40.90 | C |
| | 11 | C | ASP | A | 154 | 2.032 | 0.563 | −5.905 | 1.00 | 41.39 | C |
| | 12 | O | ASP | A | 154 | 3.156 | 0.247 | −6.311 | 1.00 | 39.05 | O |
| | 13 | CB | ASP | A | 154 | 0.742 | −1.547 | −5.382 | 1.00 | 44.36 | C |
| | 14 | CG | ASP | A | 154 | 0.235 | −1.284 | −3.951 | 1.00 | 48.17 | C |
| | 15 | OD1 | ASP | A | 154 | −0.946 | −0.907 | −3.780 | 1.00 | 55.41 | O |
| | 16 | OD2 | ASP | A | 154 | 1.002 | −1.500 | −2.972 | 1.00 | 50.04 | O |
| | 18 | N | HIS | A | 240 | 1.991 | −4.931 | 5.169 | 1.00 | 36.54 | N |
| | 19 | CA | HIS | A | 240 | 0.658 | −4.345 | 5.017 | 1.00 | 34.75 | C |
| | 20 | C | HIS | A | 240 | −0.220 | −5.373 | 4.289 | 1.00 | 33.79 | C |
| | 21 | O | HIS | A | 240 | 0.072 | −5.785 | 3.188 | 1.00 | 41.11 | O |
| | 22 | CB | HIS | A | 240 | 0.741 | −2.995 | 4.325 | 1.00 | 39.22 | C |
| | 23 | CG | HIS | A | 240 | −0.457 | −2.109 | 4.547 | 1.00 | 42.36 | C |
| | 24 | CD2 | HIS | A | 240 | −0.551 | −0.821 | 4.945 | 1.00 | 44.98 | C |

TABLE 14-continued

Relative atom locations of essential residues for spontaneous intermolecular ester bond formation.

|  | Atom | Residue type | Chain | Residue number | X coordinate | Y coordinate | Z coordinate | Occupancy | Temperature factor | Atom type |
|---|---|---|---|---|---|---|---|---|---|---|
| 25 | ND1 | HIS | A | 240 | -1.744 | -2.513 | 4.278 | 1.00 | 42.94 | N |
| 26 | CE1 | HIS | A | 240 | -2.582 | -1.533 | 4.558 | 1.00 | 43.45 | C |
| 27 | NE2 | HIS | A | 240 | -1.883 | -0.485 | 4.938 | 1.00 | 45.04 | N |
| 29 | N | GLN | A | 248 | -5.688 | 0.389 | -0.797 | 1.00 | 25.84 | N |
| 30 | CA | GLN | A | 248 | -5.213 | -0.808 | -1.500 | 1.00 | 28.94 | C |
| 31 | C | GLN | A | 248 | -6.290 | -1.524 | -2.361 | 1.00 | 31.66 | C |
| 32 | O | GLN | A | 248 | -6.060 | -2.615 | -2.925 | 1.00 | 31.79 | O |
| 33 | CB | GLN | A | 248 | -4.818 | -1.824 | -0.443 | 1.00 | 31.09 | C |
| 34 | CG | GLN | A | 248 | -3.705 | -1.339 | 0.437 | 1.00 | 31.22 | C |
| 35 | CD | GLN | A | 248 | -2.467 | -1.176 | -0.326 | 1.00 | 25.89 | C |
| 36 | OE1 | GLN | A | 248 | -2.236 | -1.875 | -1.294 | 1.00 | 30.46 | O |

The interatomic distance (in Angstrom) of Cβ (CB) of threonine to Cδ (CD) of glutamine, Cγ (CG) of histidine and Cγ (CG) of aspartic acid is listed in table 15 below.

TABLE 15

Interatomic distances.

|  | Mol4 |
|---|---|
| Thr CB to Gln CD | 2.75 |
| Thr CB to His CG | 5.03 |
| Thr CB to Asp CG | 4.16 |

Example 9

This example demonstrates the peptide sequence, relative atom locations and interatomic distances of the essential residues in the active site of Mol5.

Method

The peptide sequence for Mol5 was obtained from Uniprot (entry E0QN07).

The coordinate data of the atoms for each of the four essential residues for spontaneous intermolecular ester bond formation of Mol5 was obtained from an unpublished X-ray crystal structure of a Mol3-Mol4-Mol5 construct (E0QN07 sequence 5430-5825). The Protein Data Bank (PDB) conventional orthogonal coordinate system was used. The Cβ (CB) atom of the threonine reactive residue was chosen as the reference coordinate (0, 0, 0).

The interatomic distances were obtained by using the distance measurement tools within the software programme Pymol.

Mol5

Table 16 shows the peptide sequence of Mol5. The essential reactive and accessory amino acids are in bold. The HxDxxDxxQ peptide sequence motif is underlined.

TABLE 16

Peptide sequence of Mol5.

| Peptide and position | Sequence | SEQ ID |
|---|---|---|
| Mol5 from E0QN07 5681- 5825 | E V E I T T T A Y D G A A G D<br>K S D P K D K N L D A S K E T V T I Y D<br>Q V D Y K G L N V G E E Y T I T G T L H<br>Y Q A D A T L A D G T Q V K R G D E V P<br>A Q Y V N V T P V K I T A N K A S S D E<br>S G A V K A I V K F E V Q K T A L A T A<br>P V V V F E T L Y Q G T V E V A T <u>H Q D</u><br><u>I D D G S Q</u> V V Y H | 23 |

The coordinates of the atoms of threonine, aspartic acid, histidine and glutamine residues are listed in Table 17 below.

TABLE 17

Relative atom locations of essential residues for spontaneous intermolecular ester bond formation.

|  |  | Atom | Residue type | Chain | Residue number | X coordinate | Y coordinate | Z coordinate | Occupancy | Temperature factor | Atom type |
|---|---|---|---|---|---|---|---|---|---|---|---|
| Mol5 | 1 | N | THR | B | 10 | 0.325 | 1.794 | 1.605 | 1.00 | 17.87 | N |
|  | 2 | CA | THR | B | 10 | 0.212 | 1.510 | 0.184 | 1.00 | 17.43 | C |
|  | 3 | C | THR | B | 10 | -0.912 | 2.303 | -0.518 | 1.00 | 16.69 | C |
|  | 4 | O | THR | B | 10 | -1.880 | 2.726 | 0.113 | 1.00 | 15.96 | O |
|  | 5 | CB | THR | B | 10 | 0.000 | 0.000 | 0.000 | 1.00 | 17.71 | C |
|  | 6 | CG2 | THR | B | 10 | 1.096 | -0.823 | 0.609 | 1.00 | 18.64 | C |
|  | 7 | OG1 | THR | B | 10 | -1.226 | -0.373 | 0.641 | 1.00 | 17.12 | O |
|  | 9 | N | ASP | B | 39 | 1.125 | -0.307 | -7.429 | 1.00 | 14.50 | N |
|  | 10 | CA | ASP | B | 39 | 0.949 | -0.093 | -6.021 | 1.00 | 14.78 | C |
|  | 11 | C | ASP | B | 39 | 2.150 | 0.627 | -5.443 | 1.00 | 15.66 | C |

TABLE 17-continued

Relative atom locations of essential residues for spontaneous intermolecular ester bond formation.

| | Atom | Residue type | Chain | Residue number | X coordinate | Y coordinate | Z coordinate | Occupancy | Temperature factor | Atom type |
|---|---|---|---|---|---|---|---|---|---|---|
| 12 | O | ASP | B | 39 | 3.232 | 0.042 | −5.305 | 1.00 | 15.45 | O |
| 13 | CB | ASP | B | 39 | 0.740 | −1.411 | −5.293 | 1.00 | 14.69 | C |
| 14 | CG | ASP | B | 39 | 0.098 | −1.223 | −3.967 | 1.00 | 14.62 | C |
| 15 | OD1 | ASP | B | 39 | −0.966 | −0.539 | −3.903 | 1.00 | 14.86 | O |
| 16 | OD2 | ASP | B | 39 | 0.667 | −1.736 | −2.987 | 1.00 | 15.02 | O |
| 18 | N | HIS | B | 137 | 1.832 | −5.036 | 5.020 | 1.00 | 23.31 | N |
| 19 | CA | HIS | B | 137 | 0.574 | −4.310 | 5.040 | 1.00 | 22.65 | C |
| 20 | C | HIS | B | 137 | −0.451 | −5.176 | 4.343 | 1.00 | 23.54 | C |
| 21 | O | HIS | B | 137 | −0.476 | −5.285 | 3.110 | 1.00 | 22.59 | O |
| 22 | CB | HIS | B | 137 | 0.704 | −2.933 | 4.399 | 1.00 | 23.38 | C |
| 23 | CG | HIS | B | 137 | −0.506 | −2.071 | 4.581 | 1.00 | 24.12 | C |
| 24 | CD2 | HIS | B | 137 | −1.630 | −1.943 | 3.838 | 1.00 | 23.11 | C |
| 25 | ND1 | HIS | B | 137 | −0.645 | −1.198 | 5.640 | 1.00 | 25.07 | N |
| 26 | CE1 | HIS | B | 137 | −1.805 | −0.573 | 5.546 | 1.00 | 24.90 | C |
| 27 | NE2 | HIS | B | 137 | −2.425 | −1.010 | 4.461 | 1.00 | 24.22 | N |
| 29 | N | GLN | B | 145 | −5.944 | 0.750 | −0.789 | 1.00 | 14.31 | N |
| 30 | CA | GLN | B | 145 | −5.372 | −0.407 | −1.478 | 1.00 | 14.19 | C |
| 31 | C | GLN | B | 145 | −6.329 | −1.122 | −2.395 | 1.00 | 12.90 | C |
| 32 | O | GLN | B | 145 | −5.997 | −2.181 | −2.878 | 1.00 | 12.73 | O |
| 33 | CB | GLN | B | 145 | −4.872 | −1.385 | −0.442 | 1.00 | 14.29 | C |
| 34 | CG | GLN | B | 145 | −3.815 | −0.776 | 0.429 | 1.00 | 15.31 | C |
| 35 | CD | GLN | B | 145 | −2.473 | −0.725 | −0.265 | 1.00 | 15.46 | C |
| 36 | OE1 | GLN | B | 145 | −2.324 | −0.790 | −1.497 | 1.00 | 15.59 | O |

The interatomic distance (in Angstrom) of Cβ (CB) of threonine to Cδ (CD) of glutamine, Cγ (CG) of histidine and Cγ (CG) of aspartic acid is listed in table 18 below.

TABLE 18

Interatomic distances.

| | Mol5 |
|---|---|
| Thr CB to Gln CD | 2.59 |
| Thr CB to His CG | 5.05 |
| Thr CB to Asp CG | 4.15 |

Example 10

This example demonstrates the peptide sequence, relative atom locations and interatomic distances of the essential residues in the active site of Mol6.

Method

The peptide sequence for Mol6 was obtained from Uniprot (entry E0QN07).

The coordinate data of the atoms for each of the four essential residues for spontaneous intermolecular ester bond formation of Mol6 was obtained from an unpublished X-ray crystal structure of a Mol5-Mol6-Mol7 construct (E0QN07 sequence 5681-6100). The Protein Data Bank (PDB) conventional orthogonal coordinate system was used. The Cβ (CB) atom of the threonine reactive residue was chosen as the reference coordinate (0, 0, 0).

The interatomic distances were obtained by using the distance measurement tools within the software programme Pymol.

Mol6

Table 19 shows the peptide sequence of Mol6. The essential reactive and accessory amino acids are in bold. The HxDxxDxxQ peptide sequence motif is underlined.

TABLE 19

Peptide sequence of Mol6.

| Peptide and position | Sequence | SEQ ID |
|---|---|---|
| Mol6 from E0QN07 5826-5957 | P S L R T L A T V N G A K V I Q M K K D S K E N L T V T D Q I T W A N L A P G T Y T L E G S L M E V K D G Q L V S N T P V A K G Q T Q K V E V A A G K A G A T T S T G E A Q M T F K L P V D K V K S G S Q F V V Y Q I L K D K S G Q V V A T <u>H A D P K S D D Q</u> T V T V G | 24 |

The coordinates of the atoms of threonine, aspartic acid, histidine and glutamine residues are listed in Table 20 below.

TABLE 20

Relative atom locations of essential residues for spontaneous intermolecular ester bond formation.

| | | Atom | Residue type | Chain | Residue number | X coordinate | Y coordinate | Z coordinate | Occupancy | Temperature factor | Atom type |
|---|---|---|---|---|---|---|---|---|---|---|---|
| Mol6 | 1 | N | THR | B | 154 | 0.011 | 1.987 | 1.418 | 1.00 | 16.51 | N |
| | 2 | CA | THR | B | 154 | −0.086 | 1.529 | 0.059 | 1.00 | 16.14 | C |

TABLE 20-continued

Relative atom locations of essential residues for spontaneous intermolecular ester bond formation.

| | Atom | Residue type | Chain | Residue number | X coordinate | Y coordinate | Z coordinate | Occupancy | Temperature factor | Atom type |
|---|---|---|---|---|---|---|---|---|---|---|
| 3 | C | THR | B | 154 | −1.356 | 2.073 | −0.573 | 1.00 | 15.93 | C |
| 4 | O | THR | B | 154 | −2.313 | 2.380 | 0.132 | 1.00 | 16.35 | O |
| 5 | CB | THR | B | 154 | 0.000 | 0.000 | 0.000 | 1.00 | 16.49 | C |
| 6 | CG2 | THR | B | 154 | 1.212 | −0.573 | 0.724 | 1.00 | 16.12 | C |
| 7 | OG1 | THR | B | 154 | −1.159 | −0.519 | 0.645 | 1.00 | 17.71 | O |
| 9 | N | ASP | B | 178 | 0.041 | −0.697 | −7.584 | 1.00 | 14.03 | N |
| 10 | CA | ASP | B | 178 | 0.114 | −0.395 | −6.168 | 1.00 | 14.72 | C |
| 11 | C | ASP | B | 178 | 1.320 | 0.505 | −5.913 | 1.00 | 15.00 | C |
| 12 | O | ASP | B | 178 | 2.442 | 0.110 | −6.220 | 1.00 | 13.65 | O |
| 13 | CB | ASP | B | 178 | 0.232 | −1.694 | −5.341 | 1.00 | 14.32 | C |
| 14 | CG | ASP | B | 178 | −0.123 | −1.487 | −3.868 | 1.00 | 14.43 | C |
| 15 | OD1 | ASP | B | 178 | −1.206 | −0.920 | −3.581 | 1.00 | 13.91 | O |
| 16 | OD2 | ASP | B | 178 | 0.681 | −1.872 | −2.998 | 1.00 | 13.88 | O |
| 18 | N | HIS | B | 268 | 1.696 | −5.379 | 5.533 | 1.00 | 17.63 | N |
| 19 | CA | HIS | B | 268 | 0.498 | −4.573 | 5.294 | 1.00 | 17.43 | C |
| 20 | C | HIS | B | 268 | −0.553 | −5.479 | 4.671 | 1.00 | 16.51 | C |
| 21 | O | HIS | B | 268 | −0.493 | −5.789 | 3.478 | 1.00 | 16.41 | O |
| 22 | CB | HIS | B | 268 | 0.780 | −3.361 | 4.406 | 1.00 | 17.89 | C |
| 23 | CG | HIS | B | 268 | −0.314 | −2.348 | 4.429 | 1.00 | 19.44 | C |
| 24 | CD2 | HIS | B | 268 | −1.524 | −2.319 | 3.825 | 1.00 | 20.99 | C |
| 25 | ND1 | HIS | B | 268 | −0.237 | −1.203 | 5.178 | 1.00 | 21.14 | N |
| 26 | CE1 | HIS | B | 268 | −1.341 | −0.496 | 5.018 | 1.00 | 21.60 | C |
| 27 | NE2 | HIS | B | 268 | −2.144 | −1.160 | 4.214 | 1.00 | 21.28 | N |
| 29 | N | GLN | B | 276 | −5.974 | 0.084 | −0.325 | 1.00 | 12.48 | N |
| 30 | CA | GLN | B | 276 | −5.398 | −1.090 | −0.969 | 1.00 | 12.31 | C |
| 31 | C | GLN | B | 276 | −6.382 | −1.884 | −1.822 | 1.00 | 12.24 | C |
| 32 | O | GLN | B | 276 | −5.985 | −2.895 | −2.414 | 1.00 | 11.33 | O |
| 33 | CB | GLN | B | 276 | −4.776 | −2.041 | 0.058 | 1.00 | 12.64 | C |
| 34 | CG | GLN | B | 276 | −3.660 | −1.477 | 0.885 | 1.00 | 12.59 | C |
| 35 | CD | GLN | B | 276 | −2.563 | −0.842 | 0.051 | 1.00 | 13.42 | C |
| 36 | OE1 | GLN | B | 276 | −2.310 | −1.130 | −1.135 | 1.00 | 13.64 | O |

The interatomic distance (in Angstrom) of Cβ (CB) of threonine to Cδ (CD) of glutamine, Cγ (CG) of histidine and Cγ (CG) of aspartic acid is listed in table 21 below.

TABLE 21

Interatomic distances.

| | Mol6 |
|---|---|
| Thr CB to Gln CD | 2.7 |
| Thr CB to His CG | 5.02 |
| Thr CB to Asp CG | 4.15 |

Example 11

This example demonstrates the peptide sequence, relative atom locations and interatomic distances of the essential residues in the active site of Mol7.

Method

The peptide sequence for Mol7 was obtained from Uniprot (entry E0QN07).

The coordinate data of the atoms for each of the four essential residues for spontaneous intermolecular ester bond formation of Mol7 was obtained from an unpublished X-ray crystal structure of a Mol5-Mol6-Mol7 construct (E0QN07 sequence 5681-6100). The Protein Data Bank (PDB) conventional orthogonal coordinate system was used. The Cβ (CB) atom of the threonine reactive residue was chosen as the reference coordinate (0, 0, 0).

The interatomic distances were obtained by using the distance measurement tools within the software programme Pymol.

Mol7

Table 22 shows the peptide sequence of Mol7. The essential reactive and accessory amino acids are in bold. The HxDxxDxxQ peptide sequence motif is underlined.

TABLE 22

Peptide sequence of Mol7.

| Peptide and position | Sequence | SEQ ID |
|---|---|---|
| Mol7 from E0QN07 5958-6100 | S L D T T A T D A A D G N K H A D N A A A V T I N D K V D Y S G L N L A A T Y P D G T L K A Y L V R G E L M D K A T G K P V A G V A P V E R V I G A A N S V Y R V G D Q N R P V E E E I T S G A G S V V L S F Q V P A K L T Q G K V L V A F E T V Y E E G R E F L I H H D I N D D A Q T V Y T | 25 |

The coordinates of the atoms of threonine, aspartic acid, histidine and glutamine residues are listed in Table 23 below.

TABLE 23

Relative atom locations of essential residues for spontaneous intermolecular ester bond formation.

| | | Atom | Residue type | Chain | Residue number | X coordinate | Y coordinate | Z coordinate | Occupancy | Temperature factor | Atom type |
|---|---|---|---|---|---|---|---|---|---|---|---|
| Mol7 | 1 | N | THR | B | 285 | 0.064 | 1.998 | 1.432 | 1.00 | 16.63 | N |
| | 2 | CA | THR | B | 285 | −0.064 | 1.534 | 0.060 | 1.00 | 16.84 | C |
| | 3 | C | THR | B | 285 | −1.335 | 2.100 | −0.590 | 1.00 | 16.83 | C |
| | 4 | O | THR | B | 285 | −2.390 | 2.249 | 0.052 | 1.00 | 16.72 | O |
| | 5 | CB | THR | B | 285 | 0.000 | 0.000 | 0.000 | 1.00 | 17.18 | C |
| | 6 | CG2 | THR | B | 285 | 1.138 | −0.593 | 0.781 | 1.00 | 16.65 | C |
| | 7 | OG1 | THR | B | 285 | −1.170 | −0.511 | 0.614 | 1.00 | 17.83 | O |
| | 9 | N | ASP | B | 307 | 0.335 | −0.151 | −7.481 | 1.00 | 16.17 | N |
| | 10 | CA | ASP | B | 307 | 0.297 | −0.010 | −6.038 | 1.00 | 16.74 | C |
| | 11 | C | ASP | B | 307 | 1.514 | 0.835 | −5.648 | 1.00 | 16.96 | C |
| | 12 | O | ASP | B | 307 | 2.649 | 0.394 | −5.769 | 1.00 | 18.66 | O |
| | 13 | CB | ASP | B | 307 | 0.344 | −1.371 | −5.344 | 1.00 | 16.38 | C |
| | 14 | CG | ASP | B | 307 | −0.119 | −1.315 | −3.909 | 1.00 | 16.82 | C |
| | 15 | OD1 | ASP | B | 307 | −1.021 | −0.511 | −3.577 | 1.00 | 17.21 | O |
| | 16 | OD2 | ASP | B | 307 | 0.413 | −2.093 | −3.097 | 1.00 | 16.46 | O |
| | 18 | N | HIS | B | 412 | 1.936 | −4.634 | 5.460 | 1.00 | 15.81 | N |
| | 19 | CA | HIS | B | 412 | 0.666 | −3.987 | 5.318 | 1.00 | 16.00 | C |
| | 20 | C | HIS | B | 412 | −0.306 | −5.014 | 4.771 | 1.00 | 16.18 | C |
| | 21 | O | HIS | B | 412 | −0.364 | −5.252 | 3.547 | 1.00 | 15.52 | O |
| | 22 | CB | HIS | B | 412 | 0.783 | −2.755 | 4.424 | 1.00 | 16.62 | C |
| | 23 | CG | HIS | B | 412 | −0.427 | −1.883 | 4.465 | 1.00 | 17.57 | C |
| | 24 | CD2 | HIS | B | 412 | −1.545 | −1.871 | 3.700 | 1.00 | 18.43 | C |
| | 25 | ND1 | HIS | B | 412 | −0.593 | −0.891 | 5.400 | 1.00 | 17.73 | N |
| | 26 | CE1 | HIS | B | 412 | −1.754 | −0.293 | 5.206 | 1.00 | 18.09 | C |
| | 27 | NE2 | HIS | B | 412 | −2.351 | −0.868 | 4.179 | 1.00 | 18.86 | N |
| | 29 | N | GLN | B | 420 | −6.070 | 0.585 | −0.588 | 1.00 | 16.56 | N |
| | 30 | CA | GLN | B | 420 | −5.509 | −0.587 | −1.264 | 1.00 | 17.21 | C |
| | 31 | C | GLN | B | 420 | −6.491 | −1.391 | −2.116 | 1.00 | 17.36 | C |
| | 32 | O | GLN | B | 420 | −6.088 | −2.405 | −2.714 | 1.00 | 17.13 | O |
| | 33 | CB | GLN | B | 420 | −4.931 | −1.528 | −0.209 | 1.00 | 16.74 | C |
| | 34 | CG | GLN | B | 420 | −3.796 | −0.931 | 0.578 | 1.00 | 17.41 | C |
| | 35 | CD | GLN | B | 420 | −2.510 | −0.919 | −0.231 | 1.00 | 16.90 | C |
| | 36 | OE1 | GLN | B | 420 | −2.459 | −0.813 | −1.463 | 1.00 | 16.71 | O |

The interatomic distance (in Angstrom) of Cβ (CB) of threonine to Cδ (CD) of glutamine, Cγ (CG) of histidine and Cγ (CG) of aspartic acid is listed in table 24 below.

TABLE 24

Interatomic distances.

| | Mol7 |
|---|---|
| Thr CB to Gln CD | 2.68 |
| Thr CB to His CG | 4.86 |
| Thr CB to Asp CG | 4.13 |

Example 12

This example demonstrates the peptide sequence, relative atom locations and interatomic distances of the essential residues in the active site of Mol8.

Method

The peptide sequence for Mol8 was obtained from Uniprot (entry E0QN07).

The coordinate data of the atoms for each of the four essential residues for spontaneous intermolecular ester bond formation of Mol8 was obtained from an unpublished X-ray crystal structure of a Mol7-Mol8-Mol9 construct (E0QN07 sequence 5958-6383). The Protein Data Bank (PDB) conventional orthogonal coordinate system was used. The Cβ (CB) atom of the threonine reactive residue was chosen as the reference coordinate (0, 0, 0).

The interatomic distances were obtained by using the distance measurement tools within the software programme Pymol.

Mol8

Table 25 shows the peptide sequence of Mol8. The essential reactive and accessory amino acids are in bold. The HxDxxDxxQ peptide sequence motif is underlined.

TABLE 25

Peptide sequence of Mol8.

| Peptide and position | Sequence | SEQ ID |
|---|---|---|
| Mol8 from E0QN07 6101-6246 | P S V K T Q A R V D S E R N L<br>L L A D K D S T I K D T V T L S G L K T<br>G E T Y V L S G V L M D K A T G Q P V L<br>G K D M Q A I T A V S E P L K A E S G A<br>F V K T D A V S F T V P A G T V K A D T<br>E L V V F E K L W V A N E V T V D T K T<br>K T V T P K D T K T G K S Q P A A S <u>H E</u><br><u>D I T D E N Q</u> T V K S | 26 |

The coordinates of the atoms of threonine, aspartic acid, histidine and glutamine residues are listed in Table 26 below.

TABLE 26

Relative atom locations of essential residues for spontaneous intermolecular ester bond formation.

|  |  | Atom | Residue type | Chain | Residue number | X coordinate | Y coordinate | Z coordinate | Occupancy | Temperature factor | Atom type |
|---|---|---|---|---|---|---|---|---|---|---|---|
| Mol8 | 1 | N | THR | A | 152 | 0.293 | 1.796 | 1.630 | 1.00 | 11.45 | N |
|  | 2 | CA | THR | A | 152 | 0.146 | 1.509 | 0.213 | 1.00 | 11.34 | C |
|  | 3 | C | THR | A | 152 | −1.050 | 2.221 | −0.435 | 1.00 | 11.97 | C |
|  | 4 | O | THR | A | 152 | −2.087 | 2.462 | 0.210 | 1.00 | 11.54 | O |
|  | 5 | CB | THR | A | 152 | 0.000 | 0.000 | 0.000 | 1.00 | 10.89 | C |
|  | 6 | CG2 | THR | A | 152 | 1.076 | −0.805 | 0.650 | 1.00 | 11.06 | C |
|  | 7 | OG1 | THR | A | 152 | −1.226 | −0.419 | 0.616 | 1.00 | 11.03 | O |
|  | 9 | N | ASP | A | 173 | 0.739 | −0.153 | −7.599 | 1.00 | 13.80 | N |
|  | 10 | CA | ASP | A | 173 | 0.712 | 0.121 | −6.166 | 1.00 | 13.43 | C |
|  | 11 | C | ASP | A | 173 | 1.924 | 0.938 | −5.750 | 1.00 | 12.91 | C |
|  | 12 | O | ASP | A | 173 | 3.065 | 0.494 | −5.934 | 1.00 | 13.50 | O |
|  | 13 | CB | ASP | A | 173 | 0.660 | −1.178 | −5.372 | 1.00 | 13.48 | C |
|  | 14 | CG | ASP | A | 173 | 0.141 | −0.971 | −3.979 | 1.00 | 13.31 | C |
|  | 15 | OD1 | ASP | A | 173 | 0.921 | −0.599 | −3.092 | 1.00 | 13.65 | O |
|  | 16 | OD2 | ASP | A | 173 | −1.067 | −1.167 | −3.750 | 1.00 | 12.94 | O |
|  | 18 | N | HIS | A | 281 | 1.692 | −5.346 | 5.351 | 1.00 | 11.74 | N |
|  | 19 | CA | HIS | A | 281 | 0.440 | −4.632 | 5.291 | 1.00 | 12.22 | C |
|  | 20 | C | HIS | A | 281 | −0.568 | −5.524 | 4.571 | 1.00 | 11.72 | C |
|  | 21 | O | HIS | A | 281 | −0.593 | −5.614 | 3.338 | 1.00 | 11.49 | O |
|  | 22 | CB | HIS | A | 281 | 0.592 | −3.269 | 4.618 | 1.00 | 12.58 | C |
|  | 23 | CG | HIS | A | 281 | −0.628 | −2.427 | 4.760 | 1.00 | 13.08 | C |
|  | 24 | CD2 | HIS | A | 281 | −1.511 | −1.972 | 3.842 | 1.00 | 13.45 | C |
|  | 25 | ND1 | HIS | A | 281 | −1.119 | −2.047 | 5.989 | 1.00 | 13.82 | N |
|  | 26 | CE1 | HIS | A | 281 | −2.232 | −1.358 | 5.820 | 1.00 | 13.53 | C |
|  | 27 | NE2 | HIS | A | 281 | −2.495 | −1.303 | 4.527 | 1.00 | 12.99 | N |
|  | 29 | N | GLN | A | 289 | −5.843 | 0.359 | −0.505 | 1.00 | 11.93 | N |
|  | 30 | CA | GLN | A | 289 | −5.317 | −0.813 | −1.211 | 1.00 | 11.99 | C |
|  | 31 | C | GLN | A | 289 | −6.315 | −1.535 | −2.086 | 1.00 | 11.76 | C |
|  | 32 | O | GLN | A | 289 | −6.023 | −2.625 | −2.572 | 1.00 | 11.05 | O |
|  | 33 | CB | GLN | A | 289 | −4.750 | −1.821 | −0.212 | 1.00 | 11.97 | C |
|  | 34 | CG | GLN | A | 289 | −3.630 | −1.274 | 0.625 | 1.00 | 11.74 | C |
|  | 35 | CD | GLN | A | 289 | −2.394 | −0.942 | −0.175 | 1.00 | 12.21 | C |
|  | 36 | OE1 | GLN | A | 289 | −2.245 | −1.153 | −1.376 | 1.00 | 11.40 | O |

The interatomic distance (in Angstrom) of Cβ (CB) of threonine to Cδ (CD) of glutamine, Cγ (CG) of histidine and Cγ (CG) of aspartic acid is listed in table 27 below.

TABLE 27

Interatomic distances.

|  | Mol8 |
|---|---|
| Thr CB to Gln CD | 2.58 |
| Thr CB to His CG | 4.58 |
| Thr CB to Asp CG | 4.1 |

Example 13

This example demonstrates the peptide sequence, relative atom locations and interatomic distances of the essential residues in the active site of T6105S-Mol8.

Method

The peptide sequence for Mol8 was obtained from Uniprot (entry E0QN07) and the threonine at amino acid position 6105 replaced with a serine amino acid.

The coordinate data of the atoms for each of the four essential residues for spontaneous intermolecular ester bond formation of T6105S-Mol8 was obtained from an unpublished X-ray crystal structure of a Mol7-T6105S-Mol8-Mol9 construct (E0QN07 sequence 5958-6383). The wild type DNA sequence of Mol7-Mol8-Mol9 (E0QN07 sequence 5958-6383) was subjected to site-directed mutagenesis to produce a T6105S variant of Mol8. Mol7 and Mol9 domain sequences comprised wild type sequence. The Protein Data Banks (PDB) conventional orthogonal coordinate system was used. The Cβ (CB) atom of the serine reactive residue was chosen as the reference coordinate (0, 0, 0).

The interatomic distances were obtained by using the distance measurement tools within the software programme Pymol.

T6105S-Mol8

Table 28 shows the peptide sequence of T6105S-Mol8. The essential reactive and accessory amino acids are in bold. The HxDxxDxxQ peptide sequence motif is underlined.

TABLE 28

Peptide sequence of T6105S-Mol8.

| Peptide and position | Sequence | SEQ ID |
|---|---|---|
| T6105S-Mol8 from E0QN07 6101-6246 | P S V K S Q A R V D S E R N L L L A D K D S T I K D T V T L S G L K T G E T Y V L S G V L M D K A T G Q P V L G K D M Q A I T A V S E P L K A E S G A F V K T D A V S F T V P A G T V K A D T E L V V F E K L W V A N E V T V D T K T K T V T P K D T K T G K S Q P A A S <u>H E D I T D E N Q</u> T V K S | 27 |

The coordinates of the atoms of serine, aspartic acid, histidine and glutamine residues are listed in Table 29 below.

TABLE 29

Relative atom locations of essential residues for spontaneous intermolecular ester bond formation.

| | | Atom | Residue type | Chain | Residue number | X coordinate | Y coordinate | Z coordinate | Occupancy | Temperature factor | Atom type |
|---|---|---|---|---|---|---|---|---|---|---|---|
| T6105S- | 1 | N | SER | A | 152 | −0.316 | −2.311 | −0.669 | 1.00 | 24.09 | N |
| | 2 | CA | SER | A | 152 | 0.068 | −1.470 | 0.419 | 1.00 | 24.03 | C |
| | 3 | C | SER | A | 152 | −0.784 | −1.686 | 1.653 | 1.00 | 23.81 | C |
| | 4 | O | SER | A | 152 | −2.008 | −1.994 | 1.565 | 1.00 | 21.38 | O |
| | 5 | CB | SER | A | 152 | 0.000 | 0.000 | 0.000 | 1.00 | 20.00 | C |
| | 6 | OG | SER | A | 152 | −1.331 | 0.385 | −0.296 | 1.00 | 20.00 | O |
| | 7 | N | ASP | A | 173 | 3.082 | 3.229 | 6.073 | 1.00 | 22.28 | N |
| | 8 | CA | ASP | A | 173 | 2.618 | 2.398 | 4.992 | 1.00 | 20.70 | C |
| | 9 | CB | ASP | A | 173 | 2.183 | 3.261 | 3.833 | 1.00 | 21.48 | C |
| | 10 | CG | ASP | A | 173 | 1.266 | 2.547 | 2.910 | 1.00 | 22.16 | C |
| | 11 | OD2 | ASP | A | 173 | 1.776 | 2.009 | 1.932 | 1.00 | 21.07 | O |
| | 12 | OD1 | ASP | A | 173 | 0.045 | 2.458 | 3.193 | 1.00 | 22.48 | O |
| | 13 | C | ASP | A | 173 | 3.711 | 1.419 | 4.555 | 1.00 | 21.71 | C |
| | 14 | O | ASP | A | 173 | 4.816 | 1.808 | 4.150 | 1.00 | 22.34 | O |
| | 15 | N | HIS | A | 281 | −1.034 | 2.264 | −7.596 | 1.00 | 27.78 | N |
| | 16 | CA | HIS | A | 281 | −2.104 | 1.752 | −6.766 | 1.00 | 29.22 | C |
| | 17 | CB | HIS | A | 281 | −1.571 | 0.843 | −5.691 | 1.00 | 30.29 | C |
| | 18 | CG | HIS | A | 281 | −2.645 | 0.139 | −4.932 | 1.00 | 29.81 | C |
| | 19 | ND1 | HIS | A | 281 | −3.173 | −1.061 | −5.343 | 1.00 | 30.82 | N |
| | 20 | CE1 | HIS | A | 281 | −4.109 | −1.446 | −4.488 | 1.00 | 32.00 | C |
| | 21 | NE2 | HIS | A | 281 | −4.187 | −0.544 | −3.526 | 1.00 | 30.73 | N |
| | 22 | CD2 | HIS | A | 281 | −3.300 | 0.470 | −3.794 | 1.00 | 30.01 | C |
| | 23 | C | HIS | A | 281 | −2.864 | 2.925 | −6.154 | 1.00 | 31.03 | C |
| | 24 | O | HIS | A | 281 | −2.445 | 3.546 | −5.134 | 1.00 | 27.11 | O |
| | 25 | N | GLN | A | 289 | −5.392 | 0.299 | 2.528 | 1.00 | 21.99 | N |
| | 26 | CA | GLN | A | 289 | −4.815 | 1.638 | 2.409 | 1.00 | 23.21 | C |
| | 27 | CB | GLN | A | 289 | −4.674 | 2.057 | 0.931 | 1.00 | 21.32 | C |
| | 28 | CG | GLN | A | 289 | −3.886 | 1.101 | 0.067 | 1.00 | 21.10 | C |
| | 29 | CD | GLN | A | 289 | −2.403 | 1.005 | 0.483 | 1.00 | 21.15 | C |
| | 30 | OE1 | GLN | A | 289 | −1.851 | 1.720 | 1.340 | 1.00 | 20.69 | O |
| | 31 | C | GLN | A | 289 | −5.553 | 2.737 | 3.153 | 1.00 | 23.46 | C |
| | 32 | O | GLN | A | 289 | −5.191 | 3.906 | 2.987 | 1.00 | 24.32 | O |

The interatomic distance (in Angstrom) of Cβ (CB) of serine to Cδ (CD) of glutamine, Cγ (CG) of histidine and Cγ (CG) of aspartic acid is listed in table 30 below.

TABLE 30

Interatomic distances.

| | T6105S-Mol8 |
|---|---|
| Ser CB to Gln CD | 2.65 |
| Ser CB to His CG | 5.60 |
| Ser CB to Asp CG | 4.07 |

Example 14

This example demonstrates the peptide sequence, relative atom locations and interatomic distances of the essential residues in the active site of Mol10.

Method

The peptide sequence for Mol10 was obtained from Uniprot (entry E0QN07).

The coordinate data of the atoms for each of the four essential residues for spontaneous intermolecular ester bond formation of Mol10 was obtained from an unpublished X-ray crystal structure of a Mol9-Mol10-Mol11 construct (E0QN07 sequence 6247-6669). The Protein Data Bank (PDB) conventional orthogonal coordinate system was used. The Cβ (CB) atom of the threonine reactive residue was chosen as the reference coordinate (0, 0, 0).

The interatomic distances were obtained by using the distance measurement tools within the software programme Pymol.

Mol10

Table 31 shows the peptide sequence of Mol10. The essential reactive and accessory amino acids are in bold. The HxDxxDxxQ peptide sequence motif is underlined.

TABLE 31

Peptide sequence of Mol10.

| Peptide and position | Sequence | SEQ ID |
|---|---|---|
| Mol10 from E0QN07 6384-6541 | H N P G I T T T L T D A Q A A K G T D G K V I S L T R D A Q L K D V V R V T Q T G L I E G A K Y H V F S K L V N Q A N P D Q V V S A G M Q E F T A T G D Q L R S V T V K F T V P K E T L Q E L A G S D P S A E F K L V A Y E Y L A L D S D T D I V N K E A T S E I E A V G F K T G K T W A A T <u>H</u> A <u>D</u> P N <u>D</u> A G <u>Q</u> T V T V V K | 28 |

The coordinates of the atoms of threonine, aspartic acid, histidine and glutamine residues are listed in Table 32 below.

TABLE 32

Relative atom locations of essential residues for spontaneous intermolecular ester bond formation.

| | | Atom | Residue type | Chain | Residue number | X coordinate | Y coordinate | Z coordinate | Occupancy | Temperature factor | Atom type |
|---|---|---|---|---|---|---|---|---|---|---|---|
| Mol | 1 | N | THR | A | 146 | 0.097 | 1.989 | 1.463 | 1.00 | 21.29 | N |
| | 2 | CA | THR | A | 146 | 0.094 | 1.517 | 0.054 | 1.00 | 21.32 | C |
| | 3 | C | THR | A | 146 | −1.091 | 2.123 | −0.682 | 1.00 | 22.18 | C |
| | 4 | O | THR | A | 146 | −2.118 | 2.392 | −0.084 | 1.00 | 21.01 | O |
| | 5 | CB | THR | A | 146 | 0.000 | 0.000 | 0.000 | 1.00 | 21.82 | C |
| | 6 | CG2 | THR | A | 146 | 1.096 | −0.715 | 0.715 | 1.00 | 23.80 | C |
| | 7 | OG1 | THR | A | 146 | −1.242 | −0.384 | 0.577 | 1.00 | 25.23 | O |
| | 9 | N | ASP | A | 172 | 0.904 | −0.293 | −7.607 | 1.00 | 20.59 | N |
| | 10 | CA | ASP | A | 172 | 0.832 | −0.045 | −6.194 | 1.00 | 18.21 | C |
| | 11 | C | ASP | A | 172 | 2.093 | 0.709 | −5.754 | 1.00 | 21.29 | C |
| | 12 | O | ASP | A | 172 | 3.231 | 0.178 | −5.921 | 1.00 | 18.93 | O |
| | 13 | CB | ASP | A | 172 | 0.754 | −1.353 | −5.455 | 1.00 | 18.89 | C |
| | 14 | CG | ASP | A | 172 | 0.225 | −1.176 | −4.029 | 1.00 | 23.67 | C |
| | 15 | OD1 | ASP | A | 172 | −1.021 | −1.272 | −3.793 | 1.00 | 20.52 | O |
| | 16 | OD2 | ASP | A | 172 | 1.025 | −0.893 | −3.138 | 1.00 | 24.02 | O |
| | 18 | N | HIS | A | 283 | 1.713 | −4.889 | 4.998 | 1.00 | 22.82 | N |
| | 19 | CA | HIS | A | 283 | 0.453 | −4.170 | 4.988 | 1.00 | 22.33 | C |
| | 20 | C | HIS | A | 283 | −0.527 | −5.014 | 4.254 | 1.00 | 22.61 | C |
| | 21 | O | HIS | A | 283 | −0.378 | −5.241 | 3.058 | 1.00 | 20.75 | O |
| | 22 | CB | HIS | A | 283 | 0.500 | −2.795 | 4.387 | 1.00 | 23.27 | C |
| | 23 | CG | HIS | A | 283 | −0.774 | −2.015 | 4.579 | 1.00 | 26.16 | C |
| | 24 | CD2 | HIS | A | 283 | −1.731 | −1.663 | 3.703 | 1.00 | 25.08 | C |
| | 25 | ND1 | HIS | A | 283 | −1.165 | −1.472 | 5.798 | 1.00 | 25.84 | N |
| | 26 | CE1 | HIS | A | 283 | −2.330 | −0.848 | 5.656 | 1.00 | 24.78 | C |
| | 27 | NE2 | HIS | A | 283 | −2.665 | −0.912 | 4.381 | 1.00 | 25.17 | N |
| | 29 | N | GLN | A | 291 | −5.834 | 0.440 | −0.914 | 1.00 | 21.93 | N |
| | 30 | CA | GLN | A | 291 | −5.193 | −0.738 | −1.483 | 1.00 | 24.16 | C |
| | 31 | C | GLN | A | 291 | −6.123 | −1.545 | −2.382 | 1.00 | 21.62 | C |
| | 32 | O | GLN | A | 291 | −5.736 | −2.609 | −2.829 | 1.00 | 19.95 | O |
| | 33 | CB | GLN | A | 291 | −4.770 | −1.730 | −0.404 | 1.00 | 23.96 | C |
| | 34 | CG | GLN | A | 291 | −3.656 | −1.272 | 0.538 | 1.00 | 23.15 | C |
| | 35 | CD | GLN | A | 291 | −2.393 | −0.851 | −0.236 | 1.00 | 22.36 | C |
| | 36 | OE1 | GLN | A | 291 | −2.205 | −1.013 | −1.457 | 1.00 | 19.46 | O |

The interatomic distance (in Angstrom) of Cβ (CB) of threonine to Cδ (CD) of glutamine, Cγ (CG) of histidine and Cγ (CG) of aspartic acid is listed in table 33 below.

TABLE 33

Interatomic distances.

| | Mol10 |
|---|---|
| Thr CB to Gln CD | 2.55 |
| Thr CB to His CG | 5.06 |
| Thr CB to Asp CG | 4.2 |

Example 15

This example demonstrates the peptide sequence, relative atom locations and interatomic distances of the essential residues in the active site of Mol11.

Method

The peptide sequence for Mol11 was obtained from Uniprot (entry E0QN07).

The coordinate data of the atoms for each of the four essential residues for spontaneous intermolecular ester bond formation of Mol11 was obtained from an unpublished X-ray crystal structure of a Mol9-Mol10-Mol11 construct (E0QN07 sequence 6247-6669). The Protein Data Banks (PDB) conventional orthogonal coordinate system was used. The Cβ (CB) atom of the threonine reactive residue was chosen as the reference coordinate (0, 0, 0).

The interatomic distances were obtained by using the distance measurement tools within the software programme Pymol.

Mol11

Table 34 shows the peptide sequence of Mol11. The essential reactive and accessory amino acids are in bold. The HxDxxDxxQ peptide sequence motif is underlined.

TABLE 34

Peptide sequence of Mol11.

| Peptide and position | Sequence | SEQ ID |
|---|---|---|
| Mol11 from E0QN07 6542-6669 | A P K I G T T L K Y G Q S K T V W V A D K V E L T D T V E Y F N L Q P K T K Y T L S G N L M G G T S A E S L S D T G V K A T T E F T T P A A A N G A Q T V S G T A V V K F T V P R E V L E R N E K L V A Y E Y L T I D G N P V A S <u>H</u> <u>E D P K D E N Q</u> T V T S K K | 29 |

The coordinates of the atoms of threonine, aspartic acid, histidine and glutamine residues are listed in Table 35 below.

TABLE 35

Relative atom locations of essential residues for spontaneous intermolecular ester bond formation-Mol11

| | Atom | Residue type | Chain | Residue number | X coordinate | Y coordinate | Z coordinate | Occupancy | Temperature factor | Atom type |
|---|---|---|---|---|---|---|---|---|---|---|
| 1 | N | THR | A | 303 | 0.229 | 2.000 | 1.478 | 1.00 | 18.55 | N |
| 2 | CA | THR | A | 303 | 0.106 | 1.594 | 0.079 | 1.00 | 17.69 | C |
| 3 | C | THR | A | 303 | −1.062 | 2.266 | −0.650 | 1.00 | 17.48 | C |
| 4 | O | THR | A | 303 | −2.160 | 2.461 | −0.080 | 1.00 | 18.08 | O |
| 5 | CB | THR | A | 303 | 0.000 | 0.000 | 0.000 | 1.00 | 18.35 | C |
| 6 | CG2 | THR | A | 303 | 1.012 | −0.769 | 0.782 | 1.00 | 18.46 | C |
| 7 | OG1 | THR | A | 303 | −1.280 | −0.404 | 0.486 | 1.00 | 20.39 | O |
| 9 | N | ASP | A | 323 | 0.767 | −0.080 | −7.474 | 1.00 | 17.21 | N |
| 10 | CA | ASP | A | 323 | 0.742 | −0.035 | −6.018 | 1.00 | 17.43 | C |
| 11 | C | ASP | A | 323 | 1.939 | 0.770 | −5.579 | 1.00 | 16.91 | C |
| 12 | O | ASP | A | 323 | 3.075 | 0.280 | −5.543 | 1.00 | 20.98 | O |
| 13 | CB | ASP | A | 323 | 0.678 | −1.444 | −5.359 | 1.00 | 18.89 | C |
| 14 | CG | ASP | A | 323 | 0.129 | −1.386 | −3.936 | 1.00 | 19.81 | C |
| 15 | OD1 | ASP | A | 323 | −0.799 | −0.585 | −3.758 | 1.00 | 18.90 | O |
| 16 | OD2 | ASP | A | 323 | 0.606 | −2.132 | −3.007 | 1.00 | 19.63 | O |
| 18 | N | HIS | A | 411 | 1.693 | −4.552 | 5.258 | 1.00 | 17.21 | N |
| 19 | CA | HIS | A | 411 | 0.419 | −3.803 | 5.249 | 1.00 | 17.57 | C |
| 20 | C | HIS | A | 411 | −0.585 | −4.743 | 4.576 | 1.00 | 21.51 | C |
| 21 | O | HIS | A | 411 | −0.518 | −5.019 | 3.350 | 1.00 | 19.05 | O |
| 22 | CB | HIS | A | 411 | 0.528 | −2.494 | 4.505 | 1.00 | 18.90 | C |
| 23 | CG | HIS | A | 411 | −0.704 | −1.623 | 4.637 | 1.00 | 18.52 | C |
| 24 | CD2 | HIS | A | 411 | −1.680 | −1.262 | 3.770 | 1.00 | 18.46 | C |
| 25 | ND1 | HIS | A | 411 | −1.000 | −1.017 | 5.822 | 1.00 | 20.56 | N |
| 26 | CE1 | HIS | A | 411 | −2.092 | −0.285 | 5.673 | 1.00 | 23.69 | C |
| 27 | NE2 | HIS | A | 411 | −2.540 | −0.438 | 4.443 | 1.00 | 20.98 | N |
| 29 | N | GLN | A | 419 | −5.798 | 1.052 | −0.795 | 1.00 | 18.52 | N |
| 30 | CA | GLN | A | 419 | −5.271 | −0.153 | −1.427 | 1.00 | 19.82 | C |
| 31 | C | GLN | A | 419 | −6.287 | −0.875 | −2.286 | 1.00 | 18.39 | C |
| 32 | O | GLN | A | 419 | −5.983 | −1.926 | −2.861 | 1.00 | 20.28 | O |
| 33 | CB | GLN | A | 419 | −4.824 | −1.127 | −0.317 | 1.00 | 20.02 | C |
| 34 | CG | GLN | A | 419 | −3.700 | −0.681 | 0.530 | 1.00 | 19.80 | C |
| 35 | CD | GLN | A | 419 | −2.393 | −0.647 | −0.226 | 1.00 | 18.36 | C |
| 36 | OE1 | GLN | A | 419 | −2.296 | −0.598 | −1.470 | 1.00 | 18.86 | O |

The interatomic distance (in Angstrom) of Cβ (CB) of threonine to Cδ (CD) of glutamine, Cγ (CG) of histidine and Cγ (CG) of aspartic acid is listed in table 36 below.

TABLE 36

Interatomic distances.

| | Mol11 |
|---|---|
| Thr CB to Gln CD | 2.49 |
| Thr CB to His CG | 4.96 |
| Thr CB to Asp CG | 4.17 |

Example 16

This example demonstrates the peptide sequence, relative atom locations and interatomic distances of the essential residues in the active site of Mol9.

Method

The peptide sequence for Mol9 was obtained from Uniprot (entry E0QN07).

The coordinate data of the atoms for each of the four essential residues for spontaneous intermolecular ester bond formation of Mol9 was obtained from an unpublished X-ray crystal structure of a Mol9-Mol10-Mol11 construct (E0QN07 sequence 6247-6669). The Protein Data Banks (PDB) conventional orthogonal coordinate system was used. The Cβ (CB) atom of the threonine reactive residue was chosen as the reference coordinate (0, 0, 0).

The interatomic distances were obtained by using the distance measurement tools within the software programme Pymol.

Mol9

Table 37 shows the peptide sequence of Mol9. The essential reactive and accessory amino acids are in bold. The HxDxxDxxQ peptide sequence motif is underlined.

TABLE 37

Peptide sequence of Mol9.

| Peptide and position | Sequence | SEQ ID |
|---|---|---|
| Mol9 from E0QN07 6247-6383 | G T S P S L K T V L S A D G K R E W V E N N T N I P T V P H A S D S L I D T V L Y T G L T E G V S Y R L D A K L M E I N P V T G K V S E T P V A T G Y T E F T A K T S D G T A Q V T F N G I T G K L K A G Y K Y V A Y E K M T R P G Q P D K P V P P P H E D P K D P N Q T V V S E | 31 |

The coordinates of the atoms of serine, aspartic acid, histidine and glutamine residues are listed in Table 38 below.

TABLE 38

Relative atom locations of essential residues for spontaneous intermolecular ester bond formation-Mol9.

|   | Atom | Residue type | Chain | Residue number | X coordinate | Y coordinate | Z coordinate | Occupancy | Temperature factor | Atom type |
|---|------|------|---|------|--------|--------|--------|------|-------|---|
| 1 | N    | THR | A | 6254 | −1.474 | −1.086 |  1.715 | 1.00 | 26.99 | N |
| 2 | CA   | THR | A | 6254 | −1.306 |  0.052 |  0.793 | 1.00 | 25.35 | C |
| 3 | CB   | THR | A | 6254 |  0.000 |  0.000 |  0.000 | 1.00 | 24.17 | C |
| 4 | OG1  | THR | A | 6254 | −0.082 | −1.137 | −0.900 | 1.00 | 24.60 | O |
| 5 | CG2  | THR | A | 6254 |  1.226 | −0.197 |  0.833 | 1.00 | 22.81 | C |
| 6 | C    | THR | A | 6254 | −2.532 |  0.106 | −0.137 | 1.00 | 24.59 | C |
| 7 | O    | THR | A | 6254 | −3.113 | −0.928 | −0.507 | 1.00 | 22.88 | O |
| 8 | N    | ASP | A | 6283 | −0.671 |  6.909 | −3.265 | 1.00 | 21.90 | N |
| 9 | CA   | ASP | A | 6283 | −0.502 |  5.717 | −2.458 | 1.00 | 21.36 | C |
| 10 | CB  | ASP | A | 6283 |  0.774 |  4.891 | −2.781 | 1.00 | 21.23 | C |
| 11 | CG  | ASP | A | 6283 |  0.593 |  3.445 | −2.406 | 1.00 | 19.70 | C |
| 12 | OD1 | ASP | A | 6283 | −0.495 |  2.858 | −2.666 | 1.00 | 20.24 | O |
| 13 | OD2 | ASP | A | 6283 |  1.458 |  2.870 | −1.711 | 1.00 | 20.64 | O |
| 14 | C   | ASP | A | 6283 | −0.554 |  6.079 | −0.964 | 1.00 | 20.57 | C |
| 15 | O   | ASP | A | 6283 |  0.330 |  6.766 | −0.448 | 1.00 | 24.37 | O |
| 16 | N   | HIS | A | 6370 |  6.585 | −3.885 |  0.695 | 1.00 | 26.09 | C |
| 17 | CA  | HIS | A | 6370 |  5.388 | −4.415 |  0.195 | 1.00 | 24.44 | C |
| 18 | CB  | HIS | A | 6370 |  4.199 | −3.727 |  0.751 | 1.00 | 26.18 | C |
| 19 | CG  | HIS | A | 6370 |  2.943 | −4.373 |  0.347 | 1.00 | 26.11 | C |
| 20 | ND1 | HIS | A | 6370 |  2.589 | −5.620 |  0.812 | 1.00 | 32.01 | N |
| 21 | CE1 | HIS | A | 6370 |  1.426 | −5.956 |  0.300 | 1.00 | 32.92 | C |
| 22 | NE2 | HIS | A | 6370 |  1.025 | −4.981 | −0.497 | 1.00 | 29.37 | N |
| 23 | CD2 | HIS | A | 6370 |  1.985 | −4.009 | −0.524 | 1.00 | 25.39 | C |
| 24 | C   | HIS | A | 6370 |  5.453 | −4.228 | −1.313 | 1.00 | 25.81 | C |
| 25 | O   | HIS | A | 6370 |  5.232 | −3.145 | −1.836 | 1.00 | 23.66 | O |
| 26 | N   | GLN | A | 6378 | −3.321 | −2.170 | −4.282 | 1.00 | 21.15 | N |
| 27 | CA  | GLN | A | 6378 | −2.221 | −1.412 | −4.725 | 1.00 | 19.36 | C |
| 28 | CB  | GLN | A | 6378 | −0.909 | −2.103 | −4.452 | 1.00 | 21.66 | C |
| 29 | CG  | GLN | A | 6378 | −0.616 | −2.262 | −2.987 | 1.00 | 21.70 | C |
| 30 | CD  | GLN | A | 6378 | −0.538 | −0.926 | −2.256 | 1.00 | 22.43 | C |
| 31 | OE1 | GLN | A | 6378 | −0.505 |  0.227 | −2.773 | 1.00 | 21.93 | O |
| 32 | C   | GLN | A | 6378 | −2.317 | −1.123 | −6.273 | 1.00 | 18.51 | C |
| 33 | O   | GLN | A | 6378 | −1.430 | −0.516 | −6.820 | 1.00 | 18.86 | O |

The interatomic distance (in Angstrom) of Cβ (CB) of threonine to Cδ (CD) of glutamine, Cγ (CG) of histidine and Cγ (CG) of aspartic acid is listed in table 39 below.

TABLE 39

Interatomic distances.

|  | Mol9 |
|---|---|
| Thr CB to Gln CD | 2.50 |
| Thr CB to His CG | 5.28 |
| Thr CB to Asp CG | 4.24 |

Example 17

This example demonstrates preparation of a covalently linked multimeric protein complex having a 'trunk' structure through the spontaneous formation of ester bonds between engineered *Mobiluncus mulieris* (Mol) domains that ligate together in a specific order to form a stalk or trunk-like multimeric structure.

Method

The Ig-like domains of Mol7, Mol8, Mol9, Mol10 and Mol11 were modified whereby the domain boundaries of each individual construct were shifted such that the Mol7 to Mol10 constructs lacked their own final beta-strand, and each Mol construct was extended at the N-terminus to include the final beta-strand of the preceding Mol domain, also referred to herein as the strand complementation sequence. A His$_6$-tag and rTEV cleavage motif was fused to each N-terminal extension, and each protein was expressed and isolated from the crude bacterial lysate using immobilized metal affinity chromatography (IMAC) resin, and the His$_6$-tag was then removed with rTEV protease.

The amino acid sequences of the modified Mol constructs Mol7a-Mol11 used in this example are shown in Table 40 below and in FIG. 23. In each sequence, the HisTag and rTEV cleavage domain is shown in italics, the Mol trunk domain is shown in normal text, the strand complementation region is underlined, and the reactive and accessory residues are in bold. The Mol7a domain construct lacks an N-terminal strand complementation sequence, while the Mol11 domain construct is comprised of the native Mol11 domain with an N-terminal Mol10 strand complementation sequence.

TABLE 40

Peptide sequence of Mol constructs.

| Construct | Sequence | SEQ ID |
|---|---|---|
| Mol7a | *MSYYHHHHHHDYDIPTTENLYFQ*GAVGSLDTTATDAADG NKHADNAAAVTINDKVDYSGLNLAATYPDGTLKAYLVRG ELMDKATGKPVAGVAPVERVIGAANSVYRVGDQNRPVEE EITSGAGSVVLSFQVPAKLTQGKVLVAFETVYEE* | 32 |
| Mol8 | *MSYYHHHHHHDYDIPTTENLYFQ*GA<u>GREFLIHHDINDDA QTVYT</u>PSVKTQARVDSERNLLLADKDSTIKDTVTLSGLK TGETYVLSGVLMDKATGQPVLGKDMQAITAVSEPLKAES GAFVKTDAVSFTVPAGTVKADTELVVFEKLWVANEVTVD AKTKTVTPKDTK* | 33 |

TABLE 40-continued

Peptide sequence of Mol constructs.

| Construct | Sequence | SEQ ID |
|---|---|---|
| Mol9 | MSYYHHHHHHDYDIPTTENLYFQGAGKSQPAASHEDITD ENQTVKSGTSPSLKTVLSADGKREWVENNTNIPTVPHAS DSLIDTVLYTGLTEGVSYRLDAKLMEINPVTGKVSETPV ATGYTEFTAKTSDGTAQVTFNGITGKLKAGYKYVAYEKM TRPG* | 34 |
| Mol10 | MSYYHHHHHHDYDIPTTENLYFQGAPDKPVPPPHEDPKD PNQTVVSEHNPGITTTLTDAQAAKGTDGKVISLTRDAQL KDVVRVTQTGLIEGAKYHVFSKLVNQANPDQVVSAGMQE FTATGDQLRSVTVKFTVPKETLQELAGSDPSAEFKLVAY EYLALDSDTDIVNKEATSEIEAVGFK* | 35 |
| Mol11 | MSYYHHHHHHDYDIPTTENLYFQGAGKTWAATHADPNDA GQTVTVVKAPKIGTTLKYGQSKTVWVADKVELTDTVEYF NLQPKTKYTLSGNLMGGTSAESLSDTGVKATTEFTTPAA ANGAQTVSGTAVVKFTVPREVLERNEKLVAYEYLTIDGN PVASHEDPKDENQTVTSKKP* | 36 |

When mixed together each construct ligates to others in a specific order through strand complementation and ester bond formation (see FIG. 21A), to reform a structure comparable to the native domain structure, as shown in FIG. 21A and FIG. 21B.

The specificity of each construct was tested by adding equimolar amounts of the Mol domains in an optimized reaction buffer (50 mM HEPES pH 7.0, 10 mM NaCl, 100 μM CaCl$_2$) and 20% glycerol for 24 h. Bond formation was analysed by SDS-PAGE.

Results

SDS-PAGE analysis shows that an ester bond only forms between adjacent pairs (FIG. 22)—that is, the covalently bound protein construct recapitulates the Ig-like domain sequence present in the native protein. There is no ester bond formation between non-adjacent pairs. When all four constructs are mixed a covalent complex that is consistent with the sum of the four constructs is formed.

Discussion

This example demonstrates that multimeric protein complexes having a desired defined structure can be prepared via selection of appropriate complementarity between individual component constructs. Here, the selection of complementary amino acid sequences from the β-clasp domains of Mol Ig-like proteins enables the directed ligation and formation of a multimeric protein complex providing a trunk-like scaffold. Fur tigens were used, each expressed naturally by different strains of *S. pyogenes*, to yield four different C2pept-T protein constructs.

The amino acid sequences of these C2pept-T constructs are shown in Table 42 below and in FIG. 29. In each sequence, the HisTag and rTEV cleavage domain is shown in italics, the C2pept tag and linker is underlined, the helical linker domain is shown in underlined italics, and the Mol trunk domain is shown in normal text.

TABLE 42

Peptide sequence of C2pept-T constructs.

| Con-struct | Sequence | SEQ ID |
|---|---|---|
| C2pept-T1 | *MSYYHHHHHHDYDIPTTENLYFQ*GADTKQVVKHEDKNDK<br>AQTLVVEKPTGSGSGAETVVNGAKLTVTKNLDLVNSNAL<br>IPNTDFTFKIEPDTTVNEDGNKFKGVALNIPMTKVTYTN<br>SDKGGSNTKTAEFDFSEVTFEKPGVYYYKVTEEKIDKVP<br>GVSYDTTSYTVQVHVLWNEEQQKPVATYIVGYKEGSKVP<br>IQFKNSLDSTTLTVKKKVSGTGGDRSKDFNFGLTLKANQ<br>YYKASEKVMIEKTTKGGQAPVQTEASIDQLYHFTLKDGE<br>SIKVTNLPVGVDYVVTEDDYKSEKYTTNVEVSPQDGAVK<br>NIAGNSTEQETSTDKDMTITFTNKKFE | 42 |
| C2pept-T3.2 | *MSYYHHHHHHDYDIPTTENLYFQ*GADTKQVVKHEDKNDK<br>AQTLVVEKPTGSGSGAETAGVSENAKLIVKKTFDSYTDN<br>EVLMPKADYTFKVEADSTASGKTKDGLEIKPGIVNGLTE<br>QIISYTNTDKPDSKVKSTEFDFSKVVFPGIGVYRYIVSE<br>KQGDVEGITYDTKKWTVDVYVGNKEGGGFEPKFIVSKEQ<br>GTDVKKPVNFNNSFATTSLKVKKNVSGNTGELQKEFDFT<br>LTLNESTNFKKDQIVSLQKGNEKFEVKIGTPYKFKLKNG<br>ESIQLDKLPVGITYKVNEMEANKDGYKTTASLKEGDGQS<br>KMYQLDMEQKTDESADEIVVTNKRD | 43 |
| C2pept-T13 | *MSYYHHHHHHDYDIPTTENLYFQ*GADTKQVVKHEDKNDK<br>AQTLVVEKPTGSGSGAETAGVVTGKTLPITKSMIYTDNE<br>ILMPKTTFTFTIEPDTTASGKTKDGLEIKSGETTGLTTK<br>AIVSYDNTDKESAKNKTSNFNFETVTFSGIGIYRYTVSE<br>QNDGIEGIQYDGKKWTVDVYVGNKEGGGFEPKYVVSKEV<br>NSDVKKPIRFENSFKTTSLKIEKQVTGNTGELQKDFNFT<br>LILEASALYEKGQVVKIIQDGQTKDVVIGQEYKFTLHDH<br>QSIMLAKLPIGISYKLTEDKADGYTTTATLKEGEIDAKE<br>YVLGNLQKTDESADEIVVTNKRD | 44 |
| C2pept-T18 | *MSYYHHHHHHDYDIPTTENLYFQ*GADTKQVVKHEDKNDK<br>AQTLVVEKPTGSGSGAETAGVIDGSTLVVKKTFPSYTDD<br>KVLMPKADYTFKVEADDNAKGKTKDGLDIKPGVIDGLEN<br>TKTIHYGNSDKTTAKEKSVNFDFANVKFPGVGVYRYTVS<br>EVNGNKAGIAYDSQQWTVDVYVVNREDGGFEAKYIVSTE<br>GGQSDKKPVLFKNFFDTTSLKVIKKVIGNTGEHQRSFSF<br>TLLLTPNECFEKGQVVNILQGGETKKVVIGEEYSFTLKD<br>KESVTLSQLPVGIEYKVTEEDVTKDGYKTSATLKDGDVT<br>DGYNLGDSKTTDKSTDEIVVTNKRD | 45 |

The protein constructs were expressed and purified individually. Each component was expressed with a His6-tag and rTEV cleavage motif fused to the N-terminus of the construct (i.e., His6-rTEV-Cpe-like-HL-Mol and His6-rTEV-pept-T18.1). Recombinant proteins were isolated from the crude bacterial lysate using immobilized metal affinity chromatography, and the His6-tag subsequently removed with rTEV protease from all protein constructs with the exception of T18.1.

By way of outline, the multimeric protein complex was prepared as follows. Each Cpe2-HL-Mol construct was first ligated to the paired C2pept-T protein individually as depicted in FIG. 25A) such that a different T-antigen was ligated to each unique Cpe2-HL-Mol construct. These separate reactions were then mixed together as shown in FIG. 25B, whereby the trunk domains bind and ligate together in a specific order through strand complementation and spontaneous ester bond formation, as previously described in Example 16 above. This formed a multimeric protein complex having a tree-like structure that was covalently linked by ester bonds, and which displayed T-antigens at the branch termini, as shown in FIG. 25C.

Equimolar amounts of each Cpe2-HL-Mol construct was first ligated to the paired C2pept-T protein in separate reactions. Aliquots were removed for verification of bond formation by SDS-PAGE.

In the next step, all individually ligated T-protein-Cpe2-HL-Mol constructs were mixed together. After a 24 h incubation the multimeric protein complex was purified by IMAC to remove any partially formed scaffolds and any monomeric proteins. Only the T18.1 protein retained a His-tag and because all His-affinity tags on the other constructs were removed with rTEV protease, thus only complexes containing T18.1 were retained on the affinity column.

Results

SDS-PAGE analysis (FIG. 26) shows that when each C2pept-T protein cargo was mixed with the complementary Cpe2-HL-Mol construct an ester bond formed between the Cpe2 domain and C2pept-T protein. See, in particular, lanes C, F, I and L of FIG. 26, in which each high MW covalently-bound Cpe2-HL-Mol-C2pept-T protein can readily be seen at the position identified as "Crosslinked T-antigen-Branch-Trunk" in FIG. 26.

Representative results of the second ligation step, where the four Cpe2-HL-Mol-C2pept-T proteins were mixed together, incubated, then purified by IMAC, are shown in FIG. 27.

High molecular weight species were observed in the incubated sample prior to IMAC (FIG. 27, lane A), and also in the flow through and eluted fractions (FIG. 27, lanes B and C, respectively). The eluted protein from the IMAC purification contained two major species of protein as shown in FIG. 27, lane C. A major, high MW complex of >250 kDa, and a smaller MW complex of approximately 70 kDA were observed. These molecular weights correspond very well with the theoretical mass of the multivalent multimeric protein complex (i.e., the fully-formed multimeric protein complex depicted in FIG. 25C), at 290 kDa, and the theoretical mass of the monomeric T18.1-Cpe2-HL-Mol7 construct, at 69.1 kDa, respectively.

These two species were separated by size exclusion chromatography (SEC), as shown in FIG. 27 lanes D and E, respectively.

Discussion

This example demonstrates that multimeric protein complexes having a defined, desired structure and carrying different cargo proteins at pre-determined positions can be prepared via appropriate complementarity between individual component constructs. Here, the selection of complementary amino acid sequences from the β-clasp domains of Mol Ig-like proteins enables the directed ligation and formation of a multimeric protein complex providing a trunk-like scaffold, where each different 'trunk' component carries a specific functional protein cargo via further covalent linkage between specific Cpe2-C2pept binding partners.

In this instance, individual monovalent multimeric protein constructs ("trunk-branch-cargo" protein constructs), where each monovalent construct had a single, different antigen, were first prepared in separate reactions. This was followed by the formation of a desired multivalent multimeric protein complex having a defined structure by the combination of multiple monovalent multimeric protein constructs in a single second reaction. The structural relationship between the different functional activities present in the multivalent multimeric protein can readily be adapted by appropriate selection of complementarity between ligation partners, and by appropriate sequencing of ligation reactions.

Example 19

This example demonstrates the formation of a multimeric protein complex having a 'tree-like' structure with functional activities positioned in desired relationships to one another.

Here, Mol trunk domains were engineered to carry diverse Cpe-like branch domains derived from bacterial adhesins from species other than *Clostridium perfringens*, where each Cpe-like branch domain has a covalently linked peptide tag. Spontaneous formation of ester bonds between the Cpe-like branch domains and their specific peptide tagged cargo (here, enhanced green fluorescent protein, eGFP) enabled each component to be ligated together in a specific order to form a multivalent multimeric protein complex having a tree-like structure.

Method

Cpe-like domains were cloned from the following sources:

Geberg1—*Gemella bergeriae* ATCC 700627, ACCESSION AWVP01000087

Gberg2—*Gemella bergeriae* ATCC 700627, ACCESSION ERK56535

Corio—*Coriobacteriaceae bacterium* 68-1-3, ACCESSION NZ_CP009302

Ig-like domains of Mol7, Mol8, Mol9, Mol10 and Mol11 (as described in Example 18 above) were engineered with the Cpe-like domains fused to the N-terminus of the N-terminal strand complementation peptide of each domain via a helical linker (eg. Corio-HL-Mol, FIG. 30A). The amino acid sequences of the Cpe-like-HL-Mol constructs prepared in this example are shown in Table 43 below and in FIG. 33. In each sequence, the HisTag and rTEV cleavage domain is shown in italics, the Cpe-like branch domain is underlined, the helical linker domain is shown in underlined italics, and the Mol trunk domain is shown in normal text.

TABLE 43

Peptide sequence of Cpe-like-HL-Mol constructs.

| Construct | Sequence | SEQ ID |
|---|---|---|
| Corio-HL-Mol7b | MSYYHHHHHHDYDIPTTENLYFQGAGGEEPFVPGNGDTP<br>SLKTTVKAASSTASSEAAAKLTASEAAKGASVVDTIDYA<br>NLYGGKQYEVTARLMPVKDGVVTGDPLVTVTVRRTADLS<br>GSGSWTVPLGTVEGLEKDTSYVVFEKAVSIDNLVDRDGD<br>GNSHGKAEAAAKEAAAKEAAAKEAAAKEAAAKAAAPTSA<br>GQVVATHADPKSDDQTVTVGSLDTTATDAADGNKHADNA<br>AAVTINDKVDYSGLNLAATYPDGTLKAYLVRGELMDKAT<br>GKPVAGVAPVERVIGAANSVYRVGDQNRPVEEEITSGAG<br>SVVLSFQVPAKLTQGKVLVAFETVYEE | 46 |
| Gberg1-HL-Mol8 | MSYYHHHHHHDYDIPTTENLYFQGATVTDQDKYVNPKGE<br>LKTTVEADGQSSTTEKSVEVTENKDGVKVVDTIKYKGLV<br>EGKDYTVTGQLYEVKDGKIVGEAKATKTETKKADKDEGN<br>WNLDFGTVKGLEAGKSYVVYETATSLENLVDTDNDNKSH<br>GKAEAAAKEAAAKEAAAKEAAAKEAAAKAAAPTSAGREF<br>LIHHDINDDAQTVYTPSVKTQARVDSERNLLLADKDSTI<br>KDTVTLSGLKTGETYVLSGVLMDKATGQPVLGKDMQAIT<br>AVSEPLKAESGAFVKTDAVSFTVPAGTVKADTELVVFEK<br>LWVANEVTVDAKTKTVTPKDTK | 47 |
| Gberg2-HL-Mol9 | MSYYHHHHHHDYDIPTTENLYFQGARVTNKKIVSSLQTT<br>VEADGQSSTAEKSAEVTENKDGVNVVDTIHYKGLIPKQK<br>YEVVGILYEVKDGKLVDPNKPITISNGTGEYTVSDSGEG<br>EWKLNFGKIDGVEARKSYVVYEEVTSVENLVDTDNDGNS<br>HGKAEAAAKEAAAKEAAAKEAAAKEAAAKAAAPTSAGKS<br>QPAASHEDITDENQTVKSGTSPSLKTVLSADGKREWVEN<br>NTNIPTVPHASDSLIDTVLYTGLTEGVSYRLDAKLMEIN<br>PVTGKVSETPVATGYTEFTAKTSDGTAQVTFNGITGKLK<br>AGYKYVAYEKMTRPG | 48 |
| CpeC2-HL-Mol10 | MSYYHHHHHHDYDIPTTENLYFQGANLPEVKDGTLRTTV<br>IADGVNGSSEKEALVSFENSKDGVDVKDTINYEGLVANQ<br>NYTLTGTLMHVKADGSLEEIATKTTNVTAGENGNGTWGL<br>DFGNQKLQVGEKYVVFENAESVENLIDTDKDYNSHGKAE<br>AAAKEAAAKEAAAKEAAAKEAAAKAAAPTSAPDKPVPPP<br>HEDPKDPNQTVVSEHNPGITTTLTDAQAAKGTDGKVISL<br>TRDAQLKDVVRVTQTGLIEGAKYHVFSKLVNQANPDQVV<br>SAGMQEFTATGDQLRSVTVKFTVPKETLQELAGSDPSAE<br>FKLVAYEYLALDSDTDIVNKEATSEIEAVGFK | 49 |
| JT-Mol11 | MSYYHHHHHHDYDIPTTENLYFQGAGKTWAATHADPNDA<br>GQTVTVVKAPKIGTTLKYGQSKTVWVADKVELTDTVEYF<br>NLQPKTKYTLSGNLMGGTSAESLSDTGVKATTEFTTPAA<br>ANGAQTVSGTAVVKFTVPREVLERNEKLVAYEYLTIDGN<br>PVASHEDPKDENQTVTSKKP | 50 |

GFP cargo proteins were engineered, with each having a specific Cpe-like pept tag complementary to a Cpe-like domain as outlined above at its N-terminus, to yield four different Cpe-like pept-GFP protein constructs. The amino acid sequence of the four different Cpe-like pept-GFP constructs are shown in Table 44 below and in FIG. 34. In each sequence, the HisTag and rTEV cleavage domain is shown in italics, the Cpe-like pept tag and linker is underlined, and the GFP domain is shown in normal text.

TABLE 44

Peptide sequence of Cpe-like pept-GFP constructs.

| Construct | Sequence | SEQ ID |
|---|---|---|
| Coriopept-GFP | MSYYHHHHHHDYDIPTTENLYFQGGGDELQTGSHEDPRD<br>SSQTVTVASDPGSGSGAMVSKGEELFTGVVPILVELDGD<br>VNGHKFSVSGEGEGDATYGKLTLKFICTTGKLPVPWPTL<br>VTTLTYGVQCFSRYPDHMKQHDFFKSAMPEGYVQERTIF<br>FKDDGNYKTRAEVKFEGDTLVNRIELKGIDFKEDGNILG<br>HKLEYNYNSHNVYIMADKQKNGIKVNFKIRHNIEDGSVQ<br>LADHYQQNTPIGDGPVLLPDNHYLSTQSALSKDPNEKRD<br>HMVLLEFVTAAGITLGMDELYK | 51 |
| Gberg1pept-GFP | MSYYHHHHHHDYDIPTTENLYFQGGGDKKQEVEHKDPKD<br>KSQTFVVKPKTPGSGSGAMVSKGEELFTGVVPILVELDG<br>DVNGHKFSVSGEGEGDATYGKLTLKFICTTGKLPVPWPT | 52 |

TABLE 44-continued Peptide sequence of Cpe-like pept-GFP constructs.

| Construct | Sequence | SEQ ID |
|---|---|---|
| | LVTTLTYGVQCFSRYPDHMKQHDFFKSAMPEGYVQERTI<br>FFKDDGNYKTRAEVKFEGDTLVNRIELKGIDFKEDGNIL<br>GHKLEYNYNSHNVYIMADKQKNGIKVNFKIRHNIEDGSV<br>QLADHYQQNTPIGDGPVLLPDNHYLSTQSALSKDPNEKR<br>DHMVLLEFVTAAGITLGMDELYK | |
| Gberg2pept-GFP | *MSYYHHHHHHDYDIPTTENLYFQGGGDKKHEVEHKDPKD*<br>*KSQTFVVKPKTPGSGS*AMVSKGEELFTGVVPILVELDGD<br>VNGHKFSVSGEGEGDATYGKLTLKFICTTGKLPVPWPTL<br>VTTLTYGVQCFSRYPDHMKQHDFFKSAMPEGYVQERTIF<br>FKDDGNYKTRAEVKFEGDTLVNRIELKGIDFKEDGNILG<br>HKLEYNYNSHNVYIMADKQKNGIKVNFKIRHNIEDGSVQ<br>LADHYQQNTPIGDGPVLLPDNHYLSTQSALSKDPNEKRD<br>HMVLLEFVTAAGITLGMDELYK | 53 |
| C2pept-GFP | *MSYYHHHHHHDYDIPTTENLYFQGADTKQVVKHEDKNDK*<br>*AQTLVVEKPTGSGSG*AMVSKGEELFTGVVPILVELDGDV<br>NGHKFSVSGEGEGDATYGKLTLKFICTTGKLPVPWPTLV<br>TTLTYGVQCFSRYPDHMKQHDFFKSAMPEGYVQERTIFF<br>KDDGNYKTRAEVKFEGDTLVNRIELKGIDFKEDGNILGH<br>KLEYNYNSHNVYIMADKQKNGIKVNFKIRHNIEDGSVQL<br>ADHYQQNTPIGDGPVLLPDNHYLSTQSALSKDPNEKRDH<br>MVLLEFVTAAGITLGMDELYK | 54 |

The constructs were purified individually before mixing and assembly into multimeric protein scaffold complexes having a 'tree-like' structure. Each component was expressed with a His6-tag and rTEV cleavage motif fused to the N-terminus of the construct (ie. His6-rTEV-Cpe-like-HL-Mol and His6-rTEV-pept-GFP). Recombinant proteins were isolated from the crude bacterial lysate using immobilized metal affinity chromatography with the His6-tag subsequently removed with rTEV protease.

By way of outline, the multimeric protein complex was prepared as follows. Each Cpe-like-HL-Mol construct was first ligated to the paired Cpe-like pept-GFP protein individually as depicted in FIG. 30A such that a GFP functionality was ligated to each unique Cpe-like-HL-Mol construct (eg. Corio-pept-GFP). These separate reactions were then mixed together as shown in FIG. 30B, whereby the trunk domains bind and ligate together in a specific order through strand complementation and spontaneous ester bond formation. This formed a multivalent multimeric protein complex having a tree-like structure that was covalently linked by ester bonds, and which displayed GFP functionalities at the branch termini, as shown in FIG. 30C.

Equimolar amounts of each Cpe-like-HL-Mol construct was first ligated to the paired Cpe-like pept-GFP protein in separate reactions. After a 24 h incubation, the four individual GFP-Cpe-like-HL-Mol ligation assemblies were combined along with the capping Mol11 domain. Aliquots were removed for verification of bond formation by SDS-PAGE.

In the next step, individual reactions were mixed together to explore ligation product formation.

Results

SDS-PAGE analysis (FIG. 31) of individual reactions showed that when each Cpe-like pept-GFP cargo protein was mixed with its complementary Cpe-like-HL-Mol construct an ester bond was formed between the Cpe-like domain and pept-GFP protein. See the high MW species in lanes G, H, I and J of FIG. 31 at positions labelled "Cross-linked GFP-Branch dimer".

After a 24 h incubation the four individual GFP-Cpe-like-HL-Mol ligation assemblies were combined along with the capping Mol11 domain. The Mol trunk domains associated through strand complementation to form a multivalent multimeric protein complex having a 'tree-like' structure that is then covalently linked through ester bond formation to yield the covalently linked multimeric protein.

As can readily be seen in FIG. 32, when individual reactions were mixed, the ligation product increased in mass in a step-wise manner with the addition of each successive GFP-Cpe-like-HL-Mol complex. See, for example, lanes D, E, F, and G of FIG. 32. The final product was a complex of 9 individual proteins that are covalently ligated together in a specified order—see the high MW species in lane G at position labelled "Complete tree".

Discussion

This example demonstrates that multivalent multimeric protein complexes having a desired defined structure and carrying multiple cargo proteins at pre-determined positions can be prepared via appropriate complementarity between individual component constructs. Here, the selection of complementary amino acid sequences from the β-clasp domains of Ig-like proteins from different bacterial species enables the directed ligation and formation of a multimeric protein complex providing a trunk-like scaffold, where each different 'trunk' component carries a functional protein cargo via further covalent linkage between specific Cpe-like-Cpe-like pept binding partners.

In this instance, individual monovalent multimeric protein constructs ("trunk-branch-cargo" protein constructs), where each monovalent construct had a protein functionality, were first prepared in separate reactions. This was followed by the formation of a desired multivalent multimeric protein complex having a defined structure by the combination of multiple monovalent multimeric protein constructs in a multiple, stepwise reactions. The structural relationship between the functional activities present in the multivalent multimeric protein can readily be adapted by appropriate selection of complementarity between ligation partners, and by appropriate sequencing of ligation reactions.

Example 20

This example demonstrates the functional activity of multiple protein cargoes and the co-location of these protein functionalities via the formation of a multivalent multimeric protein complex having a 'tree-like' structure with functional activities positioned in desired relationships to one another.

Method

The immunogenicity of the multivalent T antigen-comprising multimeric protein complexes prepared as described in Example 18 were analysed by Western blot and ELISA.

Aliquots of multimeric protein complexes were electrophoresed by SDS-PAGE (as outlined above in Example 18 and as depicted in FIG. 27) and transferred to membranes for Western blot analysis using standard techniques. ELISA plates were coated with either individual recombinant T antigen protein or the complete multivalent multimeric protein complex (e.g., the species identified as "Crosslinked T-antigen tree" in FIG. 27, lane D). The plates were then incubated with antisera for T antigens: T1 typing sera is specific to T1 antigen, T6 typing sera is specific to T6 antigen, and T18 typing sera is specific to T18 antigen. A T18 specific monoclonal FAB, alphaE3, was also used and was reactive only with the recombinant T18 or T antigen tree. Recombinant T6 protein was used as a negative control, as this T antigen was not part of the multimeric protein.

Results

Western blot analysis (data not shown) established that the multivalent multimeric protein complex exhibited immunogenicity with T antisera, confirming that T antigens co-located with the multivalent multimeric protein complex.

The results of ELISA are shown in FIG. 35. T1 typing serum was bound by T1 recombinant protein and by the multivalent multimeric protein, but did not bind to T18 or T6 recombinant proteins. Similarly, both T18 typing serum and the T18-specific FAB alphaE3 bound to recombinant T18 protein and to the multivalent multimeric protein. No reactivity to the multivalent multimeric protein was shown by T6 typing serum, consistent with T6 antigen not being present on the multivalent multimeric protein.

Discussion

These results clearly demonstrate that the function of protein cargoes is maintained when present in a multivalent multimeric protein complex as herein described. The Western blot analysis reported above establishes the presence of the linear epitopes comprising the component T antigens in the protein complex. Furthermore, the ELISA, being performed under non-denaturing conditions, establishes that the antigens present in the multivalent multimeric complex retain their native conformation and immunogenic functionality.

This example demonstrates that the function of multiple protein cargoes—in this case the immunogenic function of each of the T antigen 'valencies'—is maintained and presented by the multivalent multimeric protein complexes as described herein. Hence, the directed ligation and formation of a multimeric protein complex providing a trunk-like scaffold, where each different 'trunk' component carries a functional protein cargo enables the presentation and co-location of multiple functionalities in a defined, structured manner.

INDUSTRIAL APPLICATION

The present invention provides peptide and protein ligation techniques to allow for the controlled assembly and disassembly of multimeric complexes, particularly covalently linked multimeric protein complexes. The present invention thus has application in a wide range of industries including the biomedical, pharmaceutical, diagnostic, engineering, agricultural, and horticultural sectors.

Where in the foregoing description reference has been made to elements or integers having known equivalents, then such equivalents are included as if they were individually set forth.

Although the invention has been described by way of example and with reference to particular embodiments, it is to be understood that modifications and/or improvements may be made without departing from the scope or spirit of the invention.

In addition, where features or aspects of the invention are described in terms of Markush groups, those skilled in the art will recognise that the invention is also thereby described in terms of any individual member or subgroup of members of the Markush group.

PUBLICATIONS

Kwon, H.; Squire, C. J.; Young, P. G.; Baker, E. N., Autocatalytically generated Thr-Gln ester bond cross-links stabilize the repetitive Ig-domain shaft of a bacterial cell surface adhesin. *P Natl Acad Sci USA* 2014, 111 (4), 1367.

Lee, H.; DeLoache, W. C.; Dueber, J. E., Spatial organization of enzymes for metabolic engineering. *Metab Eng* 2012, 14(3) 242-251

Horn, A. H. C.; Sticht, H., Synthetic protein scaffolds based on peptide motifs and cognate adaptor domains for improving metabolic productivity. *Frontiers in Bioengineering and Biotechnology,* 2015, 3(191), 1-7

Chen, R. Chen, Q.; Kim, H.; Siu, K. H.; Sun, Q.; Tsai, S. L.; Chen, W., Biomolecular scaffolds for enhanced signalling and catalytic efficiency. *Curr Opin Biotech* 2014, 28, 59-68

Ting, Y. T.; Batot, G.; Baker, E. N.; Young, P. G. *Acta crystallographica. Section F, Structural biology communications* 2015, 71, 61

Wu, P. S. C.; Otting, G. *J. Magn. Reson.* 2005, 176, 115

Petoukhov, M. V.; Franke, D.; Shkumatov, A. V.; Tria, G.; Kikhney, A. G.; Gajda, M.; Gorba, C.; Mertens, H. D.; Konarev, P. V.; and Svergun, D. I. *J Appl Crystallogr.* 2012, 45, 342.

Doublie S, Carter C. (1992) Preparation of Selenomethionyl Protein Crystals. Oxford University Press. New York.

Kabsch, W. (2010). XDS. Acta Cryst. D66, 125-132.

Evans, P. R. & Murshudov, G. N. (2013) Acta Cryst. D69, 1204-1214

A short history of SHELX". Sheldrick, G. M. (2008). Acta Cryst. A64, 112-122

Emsley, P., Lohkamp, B., Scott, W. G. & Cowtan, K. (2010). Acta Cryst. D66, 486-501.

Murshudov G. N., Skubak P., Lebedev A. A., Pannu N. S., Steiner R. A., Nicholls R. A., Winn M. D., Long, F. & Vagin, A. A. (2011). Acta Cryst. D67, 355-367.

Chen V. B., Arendall W. B. 3rd, Headd J. J., Keedy D. A., Immormino R. M., Kapral, G. J., Murray, L. W., Richardson, J. S. & Richardson, D. C. (2010). Acta Cryst. D66, 12-21.

The invention claimed is:

1. A peptide tag and binding partner pair wherein a) the peptide tag comprises at least about 10 contiguous amino acids of an Ig-like fold of a Cpe-like domain comprising two β-sheets in a β-clasp from a β-clasp containing protein, wherein one of the amino acids is a reactive residue capable of spontaneously forming an intermolecular ester bond in an Ig-like fold of a Cpe-like domain, and wherein the peptide tag does not comprise the entire amino acid sequence of the β-clasp containing protein; and b) said binding partner comprises a separate fragment of a β-clasp containing protein wherein said fragment comprises at least about 10 contiguous amino acids of a complementary part of an Ig-like fold of a Cpe-like domain from a Cpe-like domain containing protein, wherein one of the amino acids is a reactive residue capable of forming an intermolecular ester bond with the peptide tag;

and wherein either:

i) the reactive residue in (a) is serine or threonine, and the reactive residue in (b) is glutamine or glutamate/glutamic acid; or ii) the reactive residue in (a) is glutamine or glutamate/glutamic acid, and the reactive residue in (b) is serine or threonine;

and wherein said peptide tag and binding partner are covalently bound to each other only by an intermolecular ester bond between the reactive residues and wherein the peptide tag or the binding partner or both the peptide tag and the binding partner is covalently linked to one or more heterologous amino acid sequences.

2. The peptide tag and binding partner pair of claim 1 wherein the ester bond formed between the two reactive residues is reversibly hydrolysable.

3. The peptide tag and binding partner pair of claim 2 wherein the ester bond formed between the two reactive residues is reversibly hydrolysed when the pH is greater than 7.

4. The peptide tag and binding partner pair of claim 1 wherein said Ig-like fold domain is adhesin protein Cpe0147 from *Clostridium perfringens* or a protein with at least 75% identity thereto which is capable of spontaneously forming one or more ester bonds.

5. The peptide tag and binding partner pair of claim 1 wherein a) said peptide tag comprises 10 or more contiguous amino acids of the sequence set out in SEQ ID NO: 1 and corresponding to amino acids 565-587 of adhesin protein Cpe0147 from *Clostridium perfringens* or a sequence with at least 75% identity thereto; and/or b) said peptide tag is less than 50 amino acids in length; and/or c) said binding partner comprises 10 or more contiguous amino acids of the sequence set out in SEQ ID NO: 1 and corresponding to amino acids 439-563 of adhesin protein Cpe0147 from *Clostridium perfringens* or a sequence with at least 75% identity thereto.

6. The peptide tag and binding partner pair of claim 1 wherein one or both of the peptide tag and the binding partner comprises one or more amino acid residues that facilitate spontaneous intermolecular ester bond formation.

7. The peptide tag and binding partner pair of claim 6 wherein the one or more of the amino acid residues that facilitate spontaneous intermolecular ester bond formation are present in a beta-strand forming amino acid sequence together with a reactive residue.

8. The peptide tag and binding partner pair of claim 6 wherein the glutamine or glutamate/glutamic acid reactive residue is present in an amino acid sequence HXDXXDXX[Q/E] (SEQ ID NO: 30), or is present in an amino acid sequence [H/E]XDXX[D/S]XX[Q/E] (SEQ ID NO: 55), or is present in an amino acid sequence HXDXX[D/S]XX[Q/E] (SEQ ID NO: 56), or is present in an amino acid sequence HXDXXSXX[Q/E] (SEQ ID NO: 57), or is present in an amino acid sequence [H/E]XDXXXXX[Q/E], (SEQ ID NO: 58), wherein X is any amino acid.

9. The peptide tag and binding partner pair of claim 6 wherein the binding partner comprising the glutamine reactive amino acid residue or the glutamate/glutamic acid reactive amino acid residue comprises a histidine amino acid residue that facilitates spontaneous intermolecular ester bond formation, wherein the histidine is within about 6, about 5.5, about 5, about 4.5, about 4, about 3.5, about 3, about 2.5 or about 2 Angstrom of the glutamine or glutamate/glutamic acid reactive residue.

10. The peptide tag and binding partner pair of claim 9 wherein when the binding partners are contacted, the histidine that facilitates spontaneous intermolecular ester bond formation is within about 5, about 4.5, about 4, about 3.5, about 3, about 2.5 or about 2 Angstrom of the threonine and serine reactive residue.

11. The peptide tag and binding partner pair according to claim 6, wherein when contacted, the peptide tag and the binding partner form a serine protease active site-like structure, and wherein the serine protease active site-like structure comprises reactive amino acid residues present in the active site having the following relative atom locations in the Protein Data Bank conventional orthogonal coordinate system:

c) Cβ (CB) Thr/Ser: 0, 0, 0;

d) Cδ (CD) Gln/Glu: 0.02, 1.91, −1.61 and wherein the serine protease active site-like structure comprises accessory amino acid residues present in the active site having the following Cγ (CG) locations relative to the reactive Thr/Ser Cβ (CB) location:

e) His: 1.35, 3.67, 3.34 f) Asp: −3.45, −0.89, −2.19.

12. The peptide tag and binding partner pair of claim 1 wherein at least one of the heterologous amino acid sequences comprises an enzyme, an antigen, a structural protein, an antibody, a cytokine, or a receptor.

13. The peptide tag and binding partner pair of claim 1 wherein at least one of the heterologous amino acid sequences comprises an antigen.

14. The peptide tag and binding partner pair of claim 1 wherein at least one of the heterologous amino acid sequences comprises two or more antigens.

15. The peptide tag and binding partner pair of claim 1 wherein at least one of the heterologous amino acid sequences comprises at least 8 contiguous amino acids from a heterologous protein.

* * * * *